United States Patent
Kim et al.

(10) Patent No.: US 9,966,540 B2
(45) Date of Patent: May 8, 2018

(54) CONDENSED CYCLIC COMPOUND AND ORGANIC LIGHT-EMITTING DEVICE INCLUDING THE SAME

(71) Applicants: Samsung Display Co., Ltd., Yongin, Gyeonggi-Do (KR); Pusan National University Industry-University Cooperation Foundation, Busan (KR)

(72) Inventors: Jae-Hong Kim, Yongin (KR); Myeong-Suk Kim, Yongin (KR); Sung-Wook Kim, Yongin (KR); Jin-Soo Hwang, Yongin (KR); Hong-Suk Suh, Busan (KR)

(73) Assignees: Samsung Display Co., Ltd., Yongin-si (KR); Pusan National University Industry-University Cooperation Foundation, Busan (KR)

( * ) Notice: Subject to any disclaimer, the term of this patent is extended or adjusted under 35 U.S.C. 154(b) by 852 days.

(21) Appl. No.: 14/338,201

(22) Filed: Jul. 22, 2014

(65) Prior Publication Data

US 2015/0228911 A1    Aug. 13, 2015

(30) Foreign Application Priority Data

Feb. 13, 2014  (KR) ........................ 10-2014-0016791

(51) Int. Cl.
*H01L 51/00* (2006.01)
*C07D 487/04* (2006.01)

(52) U.S. Cl.
CPC ........ *H01L 51/0072* (2013.01); *C07D 487/04* (2013.01); *H01L 51/0067* (2013.01); *H01L 51/0069* (2013.01); *H01L 51/0081* (2013.01)

(58) Field of Classification Search
CPC ............. H01L 51/0072; H01L 51/0069; H01L 51/0067; H01L 51/5072; H01L 51/5056; H01L 51/5096; H01L 51/5092; H01L 51/5088
See application file for complete search history.

(56) References Cited

U.S. PATENT DOCUMENTS

| 5,942,340 | A | 8/1999 | Hu et al. |
| 2011/0037062 | A1 | 2/2011 | Fukumatsu et al. |
| 2012/0104943 | A1 | 5/2012 | Kato et al. |
| 2012/0298979 | A1 | 11/2012 | Ise et al. |

FOREIGN PATENT DOCUMENTS

| KR | 10-2006-0085471 | 7/2006 |
| KR | 10-2011-0007124 | 1/2011 |
| KR | 10-2011-0018340 | 2/2011 |

OTHER PUBLICATIONS

Rong Gu et al., Facile one-pot synthesis of 6-monosubstituted and 6,12-disubstituted 5,11-dihydroindolo [3,2-b] carbazoles and preparation of various functionalized derivatives; Journal of Organic Chemistry, (2007), 72(19), 7207-7213.*

* cited by examiner

*Primary Examiner* — Alexander R Pagano
*Assistant Examiner* — Ebenezer Sackey
(74) *Attorney, Agent, or Firm* — Lewis Roca Rothgerber Christie LLP

(57) ABSTRACT

A condensed cyclic compound is represented by Formula 1. An organic light-emitting device includes the condensed cyclic compound represented by Formula 1.

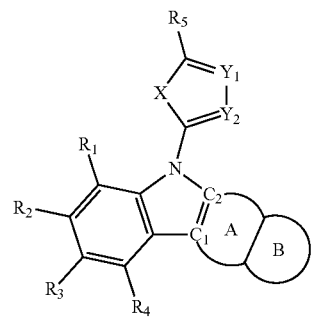

Formula 1

X, $Y_1$, $Y_2$, A, B, and $R_1$ of Formula 1 are described herein. An organic light-emitting device including an organic layer including the condensed cyclic compound may have low driving voltage, high efficiency, high brightness, and long lifespan.

20 Claims, 1 Drawing Sheet

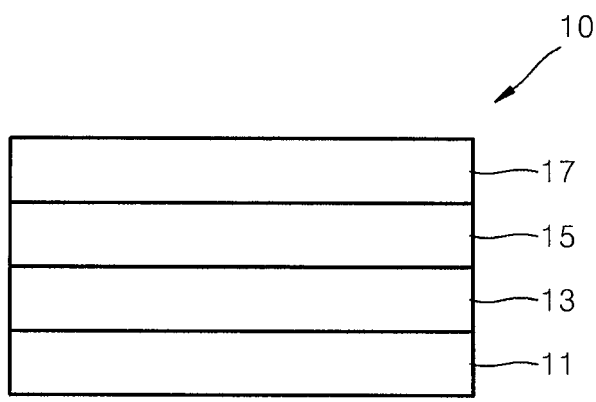

CONDENSED CYCLIC COMPOUND AND ORGANIC LIGHT-EMITTING DEVICE INCLUDING THE SAME

CROSS-REFERENCE TO RELATED APPLICATION

This application claims priority to and the benefit of Korean Patent Application No. 10-2014-0016791, filed on Feb. 13, 2014, in the Korean Intellectual Property Office, the disclosure of which is incorporated herein in its entirety by reference.

BACKGROUND

1. Field

Aspects of embodiments of the present disclosure relate to a condensed cyclic compound and an organic light-emitting device including the same.

2. Description of the Related Art

Organic light-emitting devices (OLEDs) are self-emitting devices that have wide viewing angles, high contrast ratios, short response times, and excellent brightness, driving voltage, and response speed characteristics, and produce full-color images.

An OLED may include a first electrode on a substrate, and a hole transport region, an emission layer, an electron transport region, and a second electrode, which are sequentially on the first electrode. Holes provided from the first electrode may move toward the emission layer through the hole transport region, and electrons provided from the second electrode may move toward the emission layer through the electron transport region. Carriers, such as holes and electrons, are recombined in the emission layer to produce excitons. These excitons change (or transition) from an excited state to a ground state, thereby generating light.

As a material for a green emission layer and a red emission layer, a compound having a structure in which a 6-membered hetero ring is connected to a carbazole derivative may be used (utilized).

SUMMARY

One or more aspects of embodiments of the present disclosure are directed toward a novel condensed cyclic compound and an organic light-emitting device including the same.

An embodiment of the present disclosure provides a condensed cyclic compound represented by Formula 1:

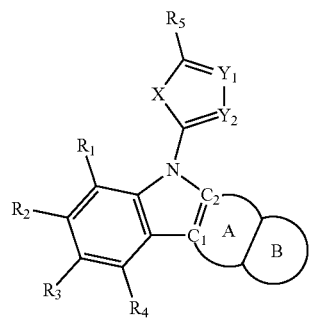

Formula 1 where in Formula 1,

X is an oxygen atom (O) or a sulfur (S) atom;

$Y_1$ and $Y_2$ are each independently a nitrogen (N) atom or $-CR_6$;

$C_1$ and $C_2$ are each a carbon (C) atom;

ring A is a benzene ring represented by Formula 1A, where 3 to 6 in Formula 1A are reference numbers and two of the reference numbers 3 to 6 correspond to respective carbon atoms included in ring B;

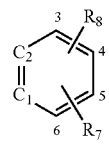

Formula 1A the ring B is an indole ring represented by Formula 1B, where 7 and 8 in Formula 1B are reference numbers, each of which corresponds to a carbon atom included in ring A;

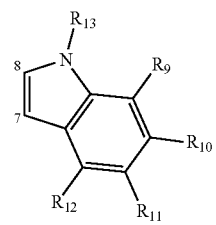

Formula 1B $R_1$ to $R_{13}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, a monovalent $C_6$-$C_{30}$ non-aromatic condensed polycyclic group, $-Si(Q_1)(Q_2)(Q_3)$, and $-B(Q_4)(Q_5)$, at least one substituent of the substituted $C_1$-$C_{10}$ alkyl group, the substituted $C_2$-$C_{10}$ alkenyl group, the substituted $C_2$-$C_{10}$ alkynyl group, the substituted $C_1$-$C_{10}$ alkoxy group, the substituted $C_3$-$C_{10}$ cycloalkyl group, the substituted $C_3$-$C_{10}$ cycloalkenyl group, the substituted $C_3$-$C_{10}$ heterocycloalkyl group, the substituted $C_3$-$C_{10}$ heterocycloalkenyl group, the substituted $C_6$-$C_{30}$ aryl group, the substituted $C_2$-$C_{30}$ heteroaryl group, the substituted $C_6$-$C_{30}$ aryloxy group, and the substituted $C_6$-$C_{30}$ arylthio group is selected from:

a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group;

a $C_1$-$C_{30}$ alkyl group, a $C_2$-$C_{30}$ alkenyl group, a $C_2$-$C_{30}$ alkynyl group, and a $C_1$-$C_{30}$ alkoxy group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_2$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —$N(Q_{21})(Q_{22})$, —$Si(Q_{23})(Q_{24})(Q_{25})$, and —$B(Q_{26})(Q_{27})$; and —$Si(Q_{31})(Q_{32})(Q_{33})$ and —$B(Q_{34})(Q_{35})$, and $Q_1$ to $Q_5$, $Q_{11}$ to $Q_{17}$, $Q_{21}$ to $Q_{27}$, and $Q_{31}$ to $Q_{35}$ are each independently selected from a hydrogen atom, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

According to another embodiment of the present disclosure, an organic light-emitting device includes: a first electrode; a second electrode facing the first electrode; and an organic layer between the first and second electrodes and including an emission layer, the organic layer including at least one of the condensed cyclic compound.

BRIEF DESCRIPTION OF THE DRAWINGS

The above and/or other aspects of the present disclosure will become apparent and more readily appreciated by reference to the following description when considered together with the accompanying drawing, which is a schematic view of an organic light-emitting device according to an embodiment of the present disclosure.

DETAILED DESCRIPTION

Reference will now be made to certain embodiments of the present disclosure, an example of which is illustrated in the accompanying drawing. As those skilled in the art would recognize, the described embodiments may be modified in many ways and, therefore, should not be construed as limiting. Accordingly, the embodiments are described below, by referring to the figures, merely to explain aspects of the present description. Expressions such as "at least one," when preceding a list of elements, modify the entire list of elements and do not modify the individual elements of the list.

A condensed cyclic compound according to an embodiment of the present disclosure is represented by Formula 1:

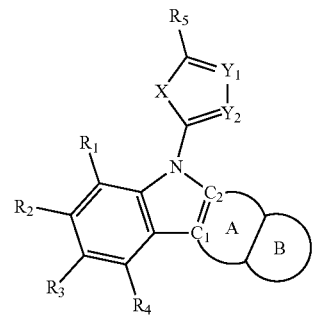

Formula 1 where in Formula 1,

X is an oxygen atom (O) or a sulfur (S) atom;

$Y_1$ and $Y_2$ may be each independently a nitrogen (N) atom or —$CR_6$;

$C_1$ and $C_2$ may be each a carbon (C) atom;

ring A may be a benzene ring represented by Formula 1A, where 3 to 6 in Formula 1A are reference (or indication) numbers and two of the reference numbers 3 to 6 correspond to respective carbon atoms included in ring B. For example, the reference numbers 3 to 6 may be used (utilized) to distinguish a binding site in Formula 1A.

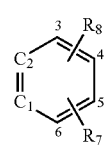

Formula 1A the ring B may be an indole ring represented by Formula 1B, where 7 and 8 in Formula 1B are reference (or indication) numbers, each of which corresponds to a carbon atom included in the ring A. For example, the reference numbers 7 and 8 may be used to distinguish a binding site in Formula 1B, and a binding region between the reference numbers 7 and 8 may be condensed into the ring A.

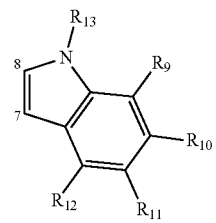

Formula 1B $R_1$ to $R_{13}$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, a monovalent $C_6$-$C_{30}$ non-aromatic condensed polycyclic group (non-aromatic condensed polycyclic group), —Si($Q_1$)($Q_2$)($Q_3$), and —B($Q_4$)($Q_5$).

Here, at least one substituent of the substituted $C_1$-$C_{10}$ alkyl group, the substituted $C_2$-$C_{10}$ alkenyl group, the substituted $C_2$-$C_{10}$ alkynyl group, the substituted $C_1$-$C_{10}$ alkoxy group, the substituted $C_3$-$C_{10}$ cycloalkyl group, the substituted $C_3$-$C_{10}$ cycloalkenyl group, the substituted $C_3$-$C_{10}$ heterocycloalkyl group, the substituted $C_3$-$C_{10}$ heterocycloalkenyl group, the substituted $C_6$-$C_{30}$ aryl group, the substituted $C_2$-$C_{30}$ heteroaryl group, the substituted $C_6$-$C_{30}$ aryloxy group, and the substituted $C_6$-$C_{30}$ arylthio group may be selected from:

a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group;

a $C_1$-$C_{30}$ alkyl group, a $C_2$-$C_{30}$ alkenyl group, $C_2$-$C_{30}$ alkynyl group, and a $C_1$-$C_{30}$ alkoxy group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{11}$)($Q_{12}$), —Si($Q_{13}$)($Q_{14}$)($Q_{15}$), and —B($Q_{16}$)($Q_{17}$);

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_2$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —N($Q_{21}$)($Q_{22}$), —Si($Q_{23}$)($Q_{24}$)($Q_{25}$), and —B($Q_{26}$)($Q_{27}$); and —Si($Q_{31}$)($Q_{32}$)($Q_{33}$) and —B($Q_{34}$)($Q_{35}$).

Here, $Q_1$ to $Q_5$, $Q_{11}$ to $Q_{17}$, $Q_{21}$ to $Q_{27}$, and $Q_{31}$ to $Q_{35}$ may be each independently selected from a hydrogen atom, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

The ring B may be condensed into one of a binding region between the reference (or indication) numbers 3 and 4 of the ring A, a binding region between the reference (or indication) numbers 4 and 5 of the ring A, and a binding region between the reference (or indication) numbers 5 and 6 of the ring A. For example, the ring B may be condensed to include the carbon atoms corresponding to the reference numbers 3 and 4, the carbon atoms corresponding to the reference numbers 4 and 5, or the carbon atoms corresponding to the references numbers 5 and 6 of the Ring A.

In some embodiments, the rings A and B

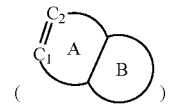

may include a group (e.g., be formed of a compound) represented by any one of Formulae 2A to 2F:

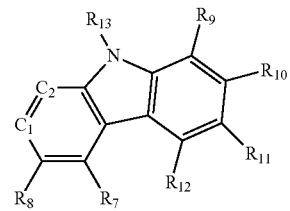

<Formula 2A>

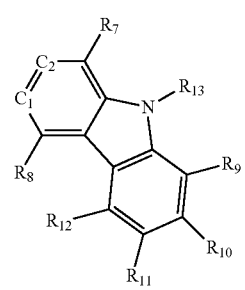

<Formula 2B>

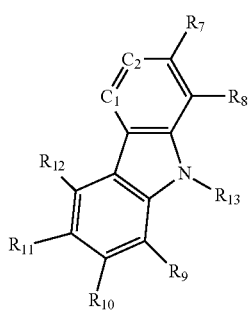
<Formula 2C>

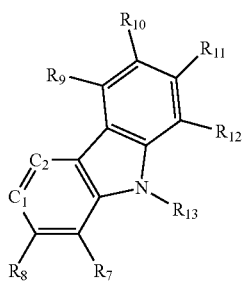
<Formula 2D>

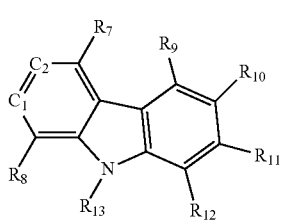
<Formula 2E>

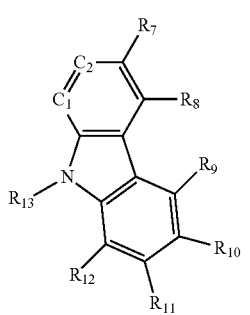
<Formula 2F> where in Formulae 2A to 2F, $R_7$ to $R_{13}$ may be each independently selected from a hydrogen atom, a substituted or unsubstituted $C_6$-$C_{30}$ aryl group, and a substituted or unsubstituted $C_2$-$C_{30}$ heteroaryl group, and at least one substituent of the substituted $C_6$-$C_{30}$ aryl group and the substituted $C_2$-$C_{30}$ heteroaryl group may be selected from a $C_6$-$C_{30}$ aryl group and a $C_2$-$C_{30}$ heteroaryl group.

In Formulae 2A to 2F, $R_{13}$ may not be a hydrogen atom. For example, $R_{13}$ may be selected from a substituted or unsubstituted $C_6$-$C_{30}$ aryl group, and a substituted or unsubstituted $C_2$-$C_{30}$ heteroaryl group, and at least one substituent of the substituted $C_6$-$C_{30}$ aryl group and the substituted $C_2$-$C_{30}$ heteroaryl group may be selected from a $C_6$-$C_{30}$ aryl group and a $C_2$-$C_{30}$ heteroaryl group.

In Formulae 2A to 2F, $R_1$ to $R_{13}$ may be each independently selected from a hydrogen atom, a methyl group, an ethyl group, a propyl group, a butyl group, a pentyl group, a hexyl group, a heptyl group, an octyl group, a nonyl group, a decyl group, a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl function, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyranyl group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group;

a methyl group, an ethyl group, a propyl group, a butyl group, a pentyl group, a hexyl group, a heptyl group, an octyl group, a nonyl group, and a decyl group, each substituted with at least one selected from a deuterium atom, a halogen atom, a hydroxyl group, a cyano group, a nitro group, and an amino group; and a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl function, a fluoranthenyl group, a pyrenyl group, a benzofluorenyl group, a naphthacenyl group, a chrysenyl group, a triphenylenyl group, a terphenyl group, a perylenyl group, an picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, pyranyl group, a thiophenyl group, a thiazolyl group, an isothiazolyl group, a thiopyranyl group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group, each substituted with at least one selected from a deuterium atom, a halogen atom, a hydroxyl group, a cyano group, a nitro group, an amino group, a carboxylic acid group or a salt thereof, a sulfonic acid group or a salt thereof, and a phosphoric acid group or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, $C_3$-$C_{10}$ heterocycloalkenyl group, a $C_6$-$C_{30}$ aryl group, a $C_4$-$C_{30}$ heteroaryl group, a $C_5$-$C_{30}$ aryloxy group, a $C_5$-$C_{30}$ arylthio group, and —Si($Q_{31}$)($Q_{32}$)($Q_{33}$) (where, $Q_{31}$ to $Q_{33}$ may be each independently selected from a hydrogen atom, a $C_1$-$C_{10}$ alkyl group, a $C_1$-$C_{10}$ alkoxy group, and a $C_6$-$C_{20}$ aryl group), where $R_5$ and $R_{13}$ may not be a hydrogen.

For example, $R_1$ to $R_4$ and $R_6$ to $R_{12}$ may be each independently selected from a hydrogen atom and a compound represented by one of Formulae 3A to 3C, and $R_5$ and $R_{13}$ may be each independently selected from a compound represented by one of Formulae 3A to 3C:

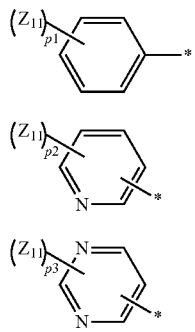

where in Formulae 3A to 3C, $Z_{11}$ may be selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{30}$ aryl group, a $C_4$-$C_{30}$ heteroaryl group, and —Si($Q_{31}$)($Q_{32}$)($Q_{33}$) (where $Q_{31}$ to $Q_{33}$ may be each independently selected from a hydrogen atom, a $C_1$-$C_{10}$ alkyl group, a $C_1$-$C_{10}$ alkoxy group, and a $C_6$-$C_{20}$ aryl group), and p1 may be selected from an integer of 1 to 5,
p2 may be selected from an integer of 1 to 4,
p3 may be selected from an integer of 1 to 3, and
* may be (or correspond to) a binding site.

For example, $R_1$ to $R_4$ and $R_6$ to $R_{12}$ may be each independently selected from a hydrogen and a compound represented by one of Formulae 4A to 4M, and $R_5$ and $R_{13}$ may be each independently selected from a compound represented by one of Formulae 4A to 4M.

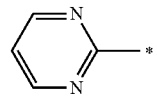

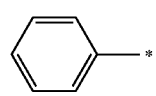

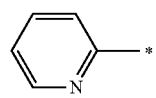

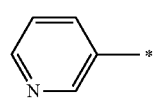

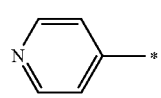

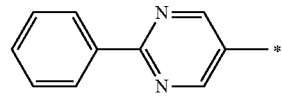

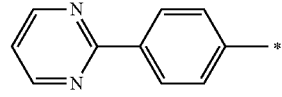

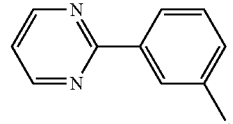

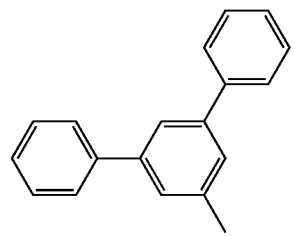

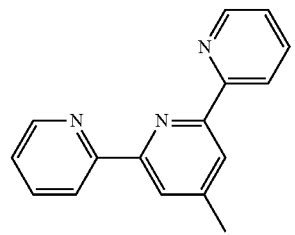

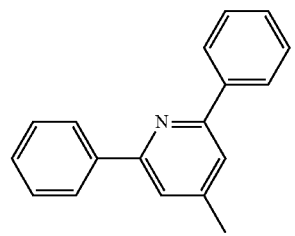

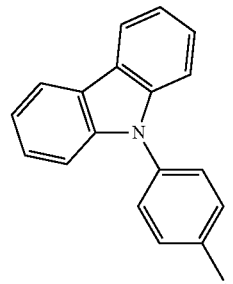

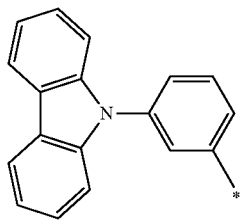

<4M>

According to an embodiment, in Formula 1, X may be a sulfur (S) atom, $Y_1$ may be a nitrogen (N) atom, and $Y_2$ may be $-CR_6$.

According to another embodiment of the present disclosure, in Formula 1, X may be a S atom, $Y_1$ may be $-CR_6$, and $Y_2$ may be a N atom.

According to another embodiment of the present disclosure, in Formula 1, X may be an oxygen (O) atom, $Y_1$ may be a N atom, and $Y_2$ may be $-CR_6$.

According to another embodiment, in Formula 1, X may be an O atom, $Y_1$ is $-CR_6$, and $Y_2$ may be a N atom.

In some embodiments, the condensed cyclic compound of Formula 1 may be represented by Formulae 1-1 to 1-6:

Formula 1-1

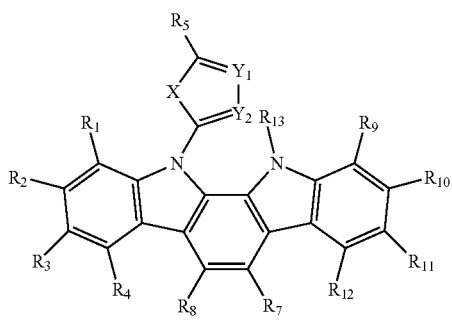

Formula 1-2

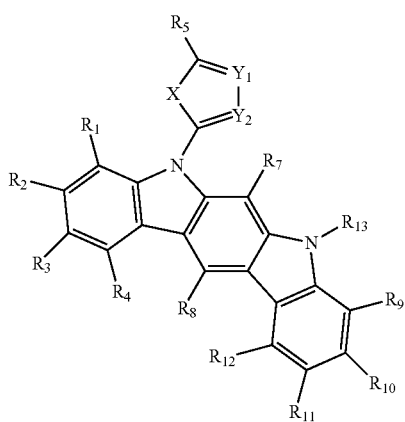

Formula 1-3

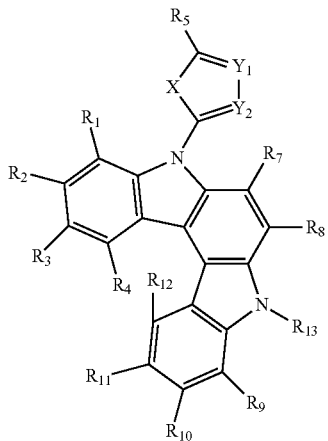

Formula 1-4

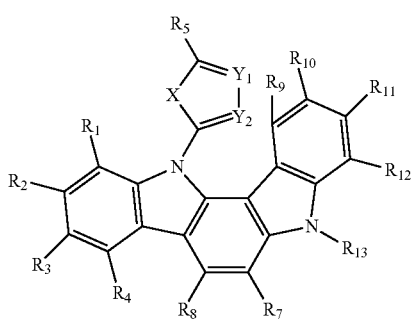

Formula 1-5

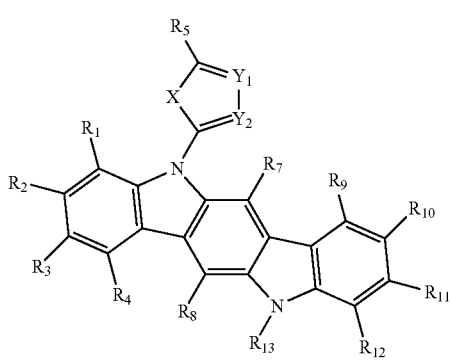

Formula 1-6

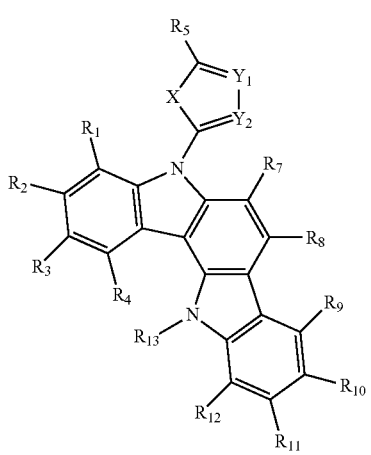

In Formulae 1-1 to 1-6, X, $Y_1$, and $Y_2$ may be understood by referring to the description thereof with respect to Formula 1.

In Formulae 1-1 to 1-6, $R_1$ to $R_4$ and $R_6$ to $R_{12}$ may be each independently selected from a phenyl group, a pyridyl group, and a pyrimidinyl group, each substituted with at least one selected from a hydrogen atom, a phenyl group, a pyridyl group, and a pyrimidinyl group; and a phenyl group, a pyridyl group, a pyrimidinyl group, and a carbazolyl group.

$R_5$ and $R_{13}$ may be each independently selected from a phenyl group, a pyridyl group, and a pyrimidinyl group, each substituted with at least one selected from a phenyl group, a pyridyl group, and a pyrimidinyl group; and a phenyl group, a pyridyl group, a pyrimidinyl group, and a carbazolyl group.

The condensed cyclic compound of Formula 1 may be any one of Compounds 1 to 159:

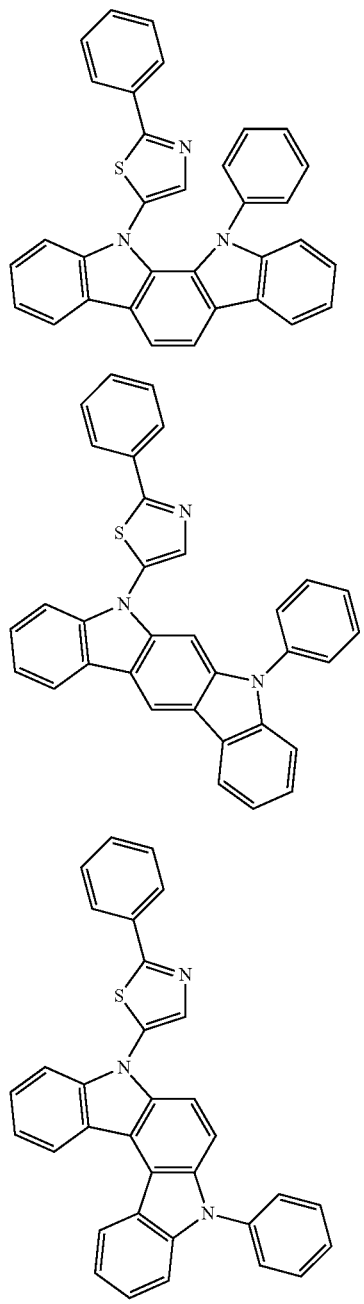

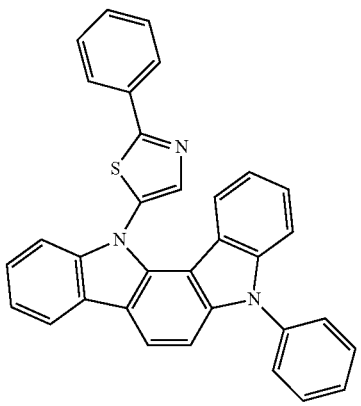

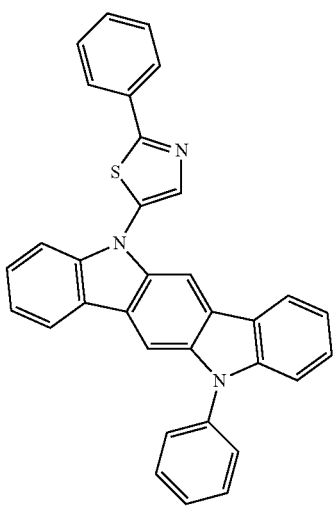

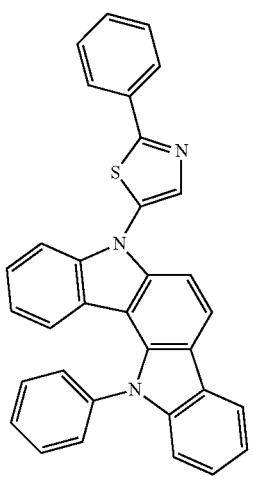

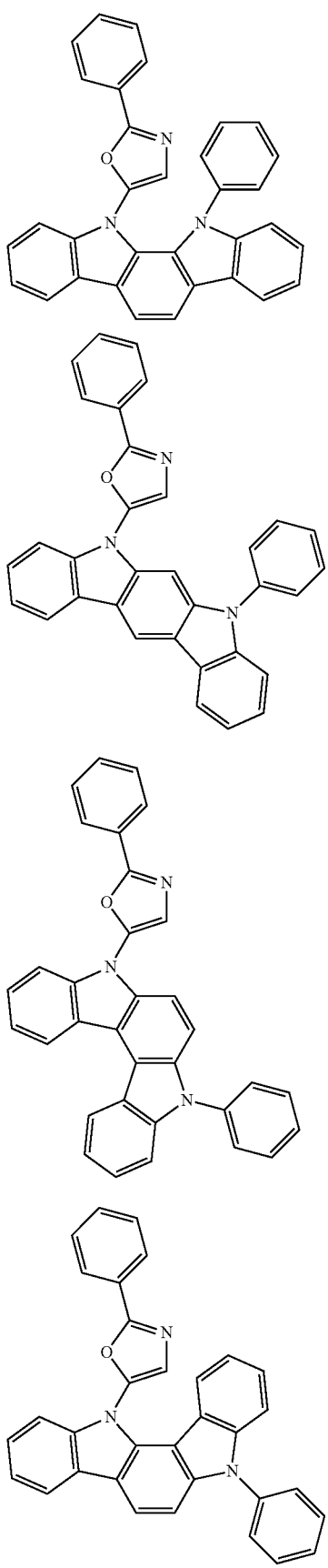
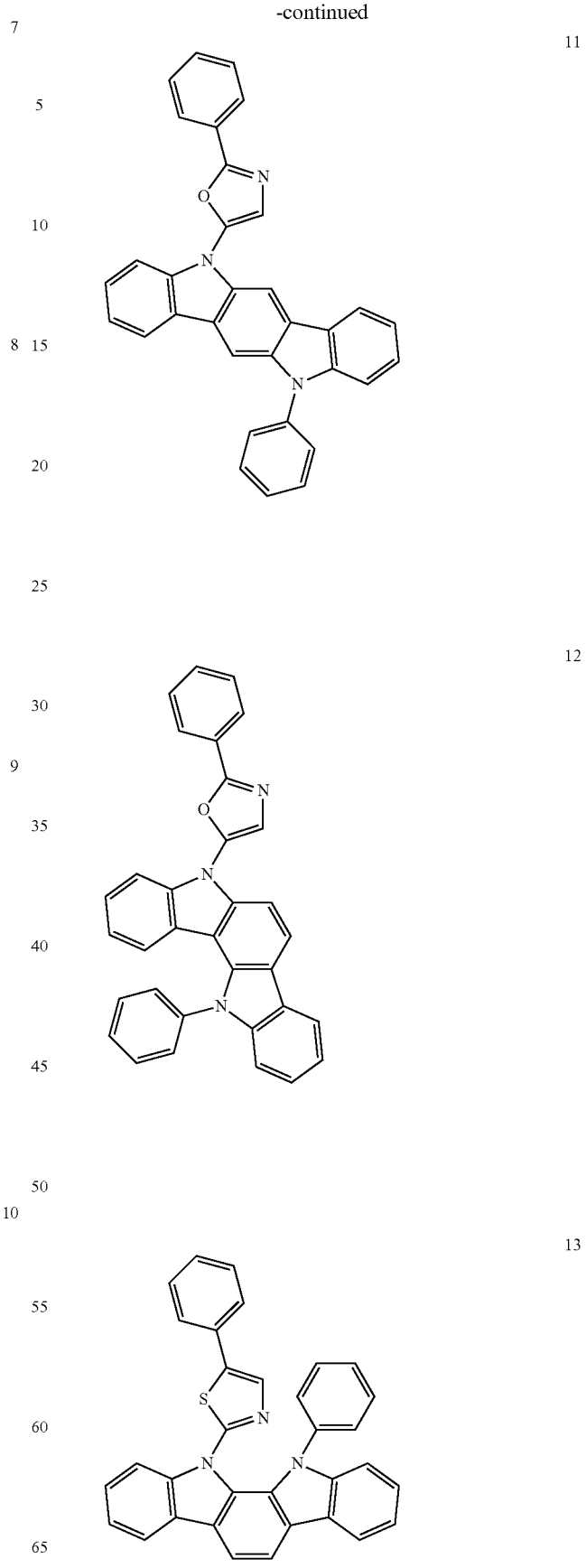

14
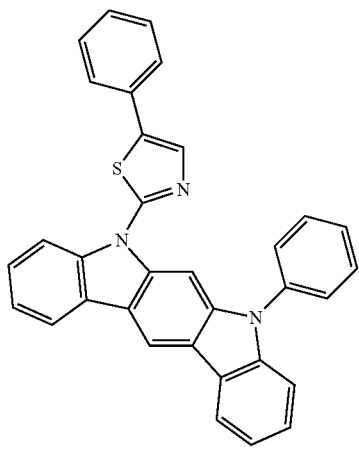
15
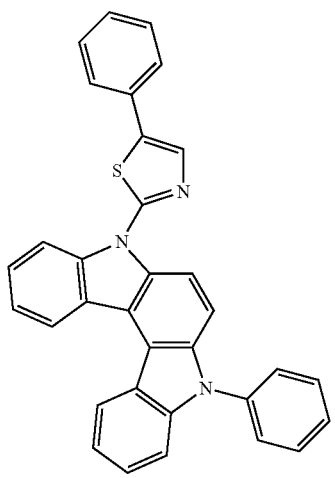
16
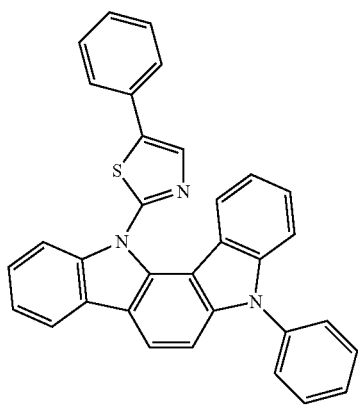
5
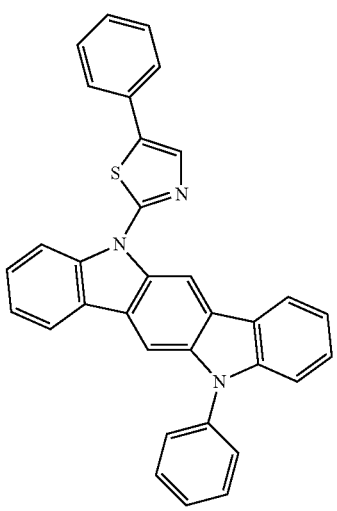
17
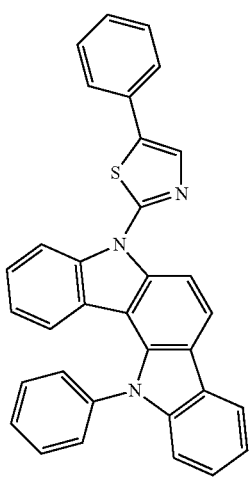
18
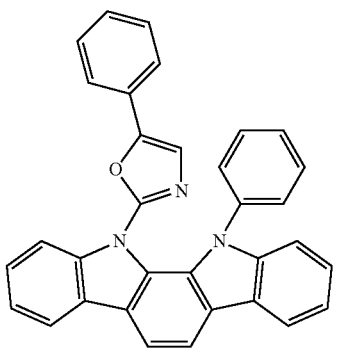
19

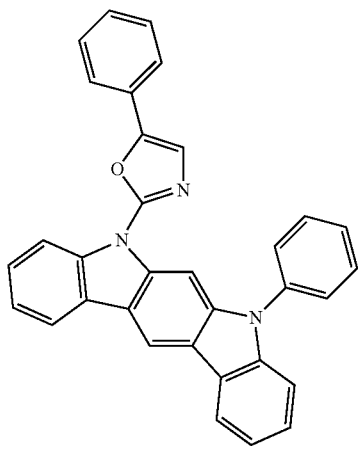
19
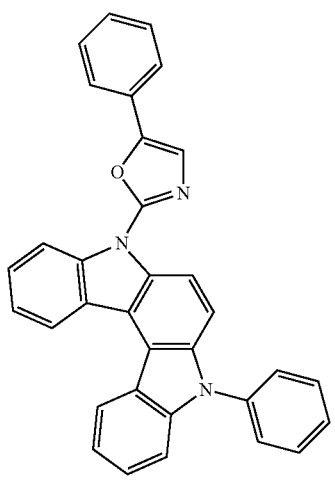
21
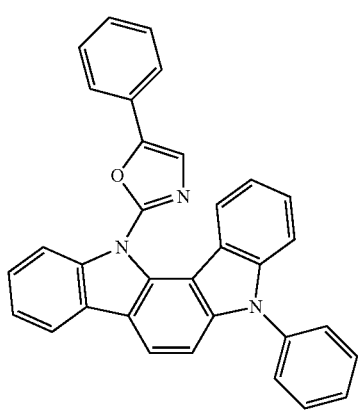
22
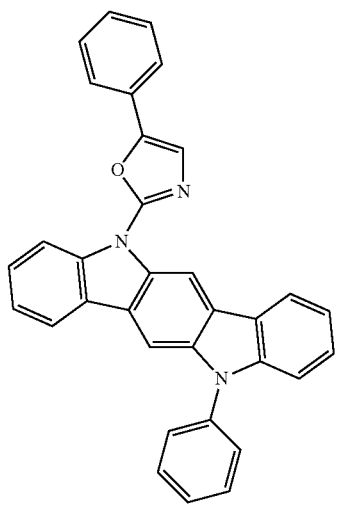
20
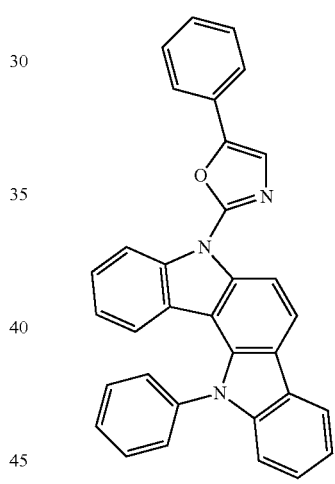
23
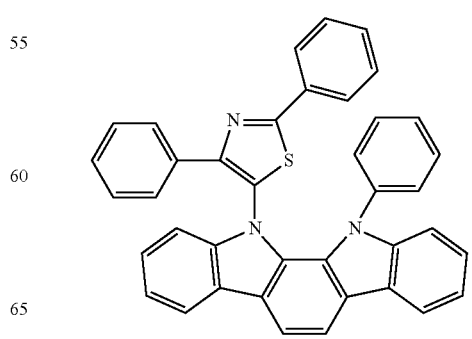
25

26
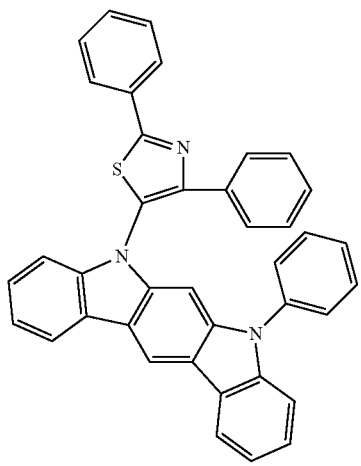
27
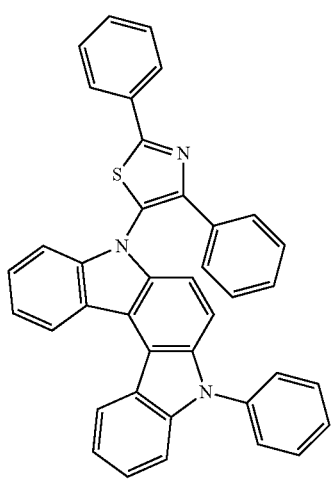
28
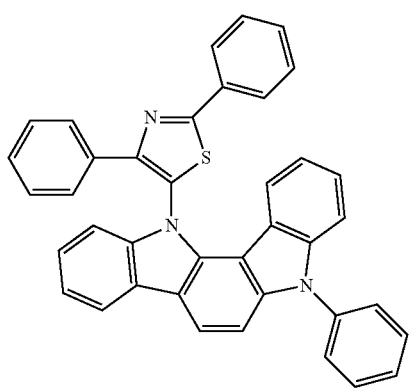
29
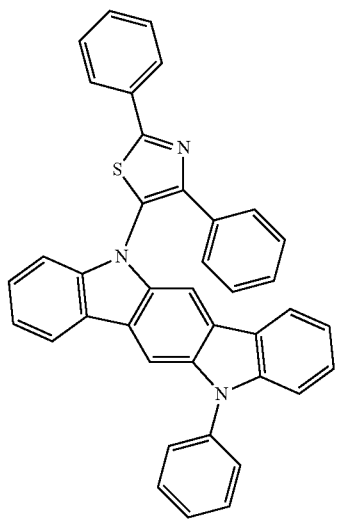
30
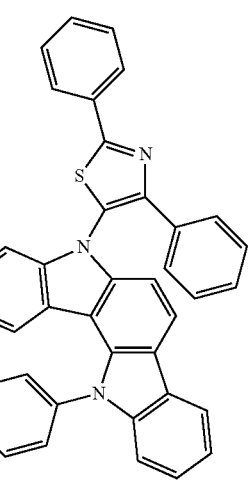
31
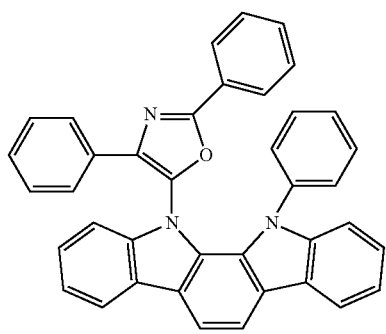

32
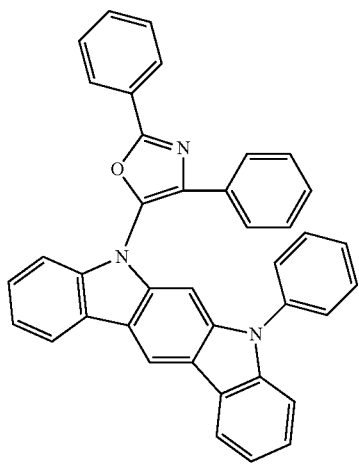
33
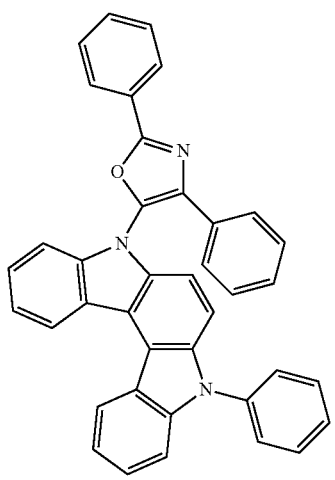
34
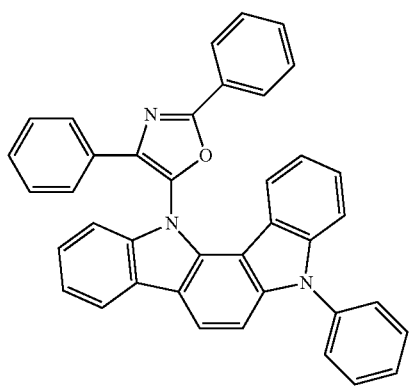
35
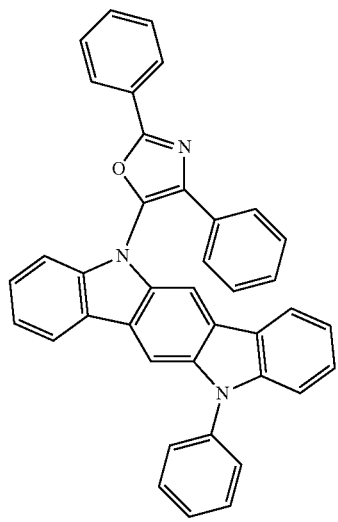
36
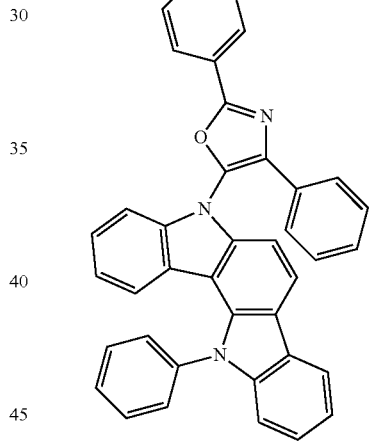
37
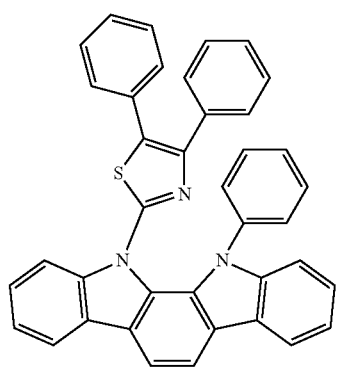

38
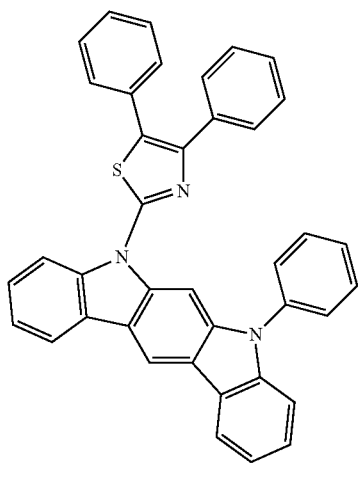
39
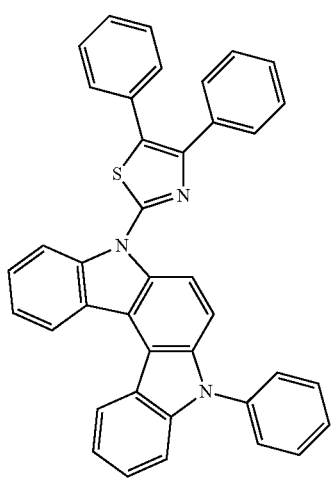
40
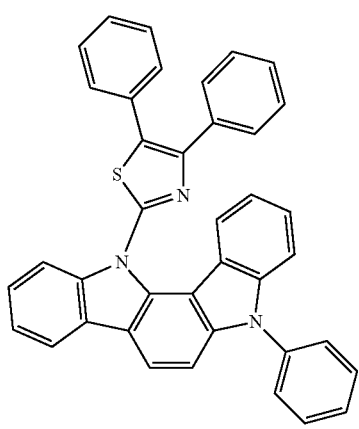
41
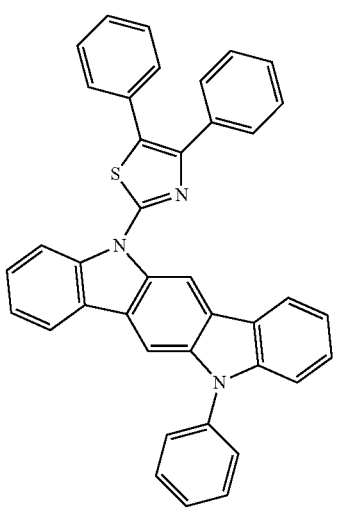
42
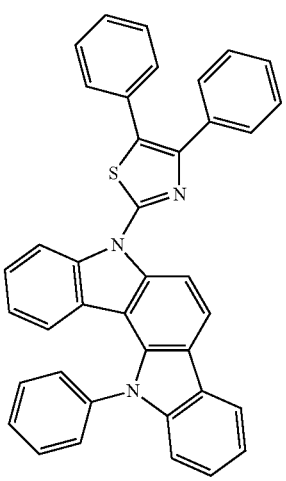
43
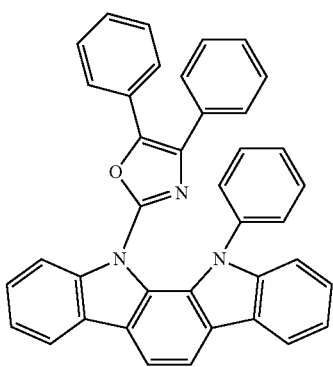

44
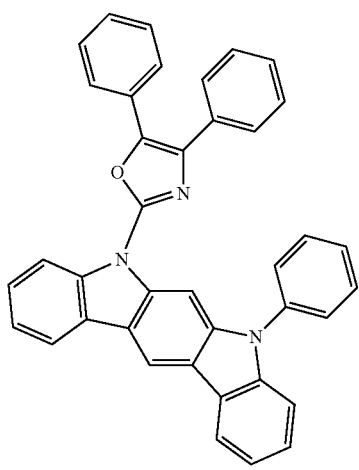
45
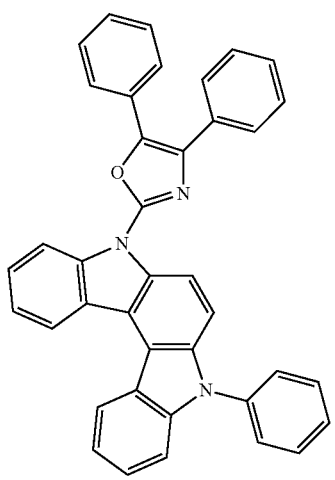
46
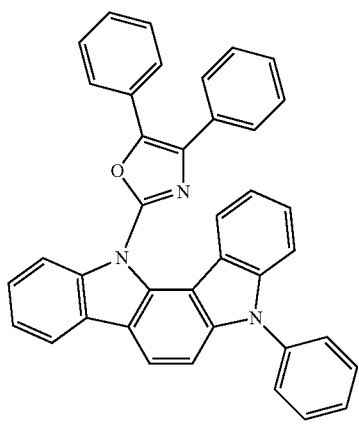
47
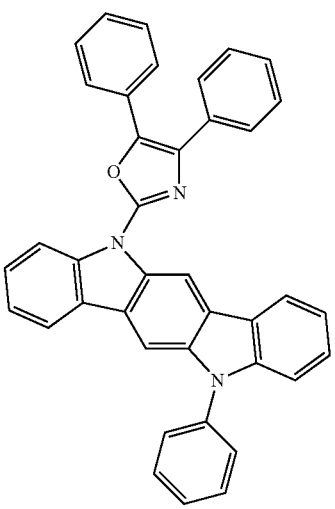
48
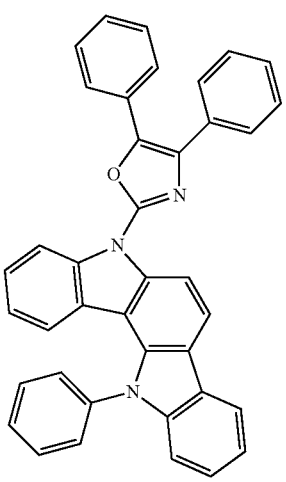
49
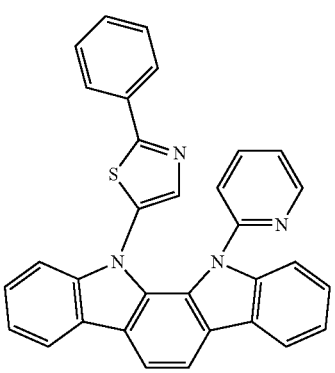

50
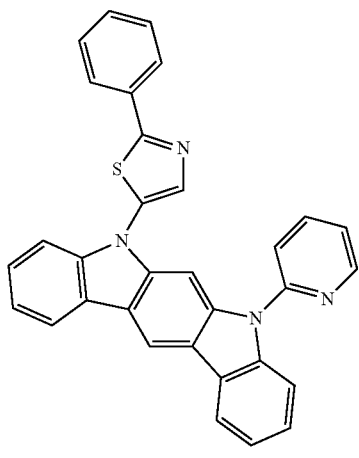
51
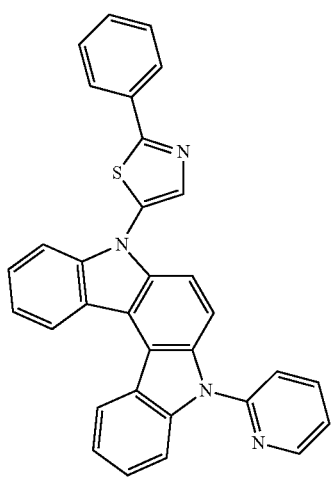
52
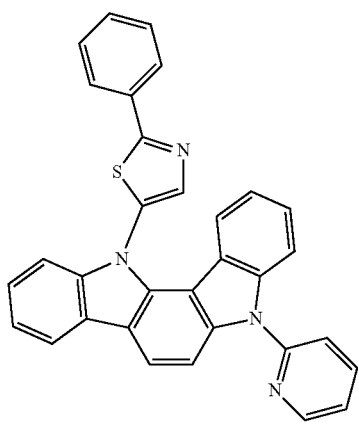
53
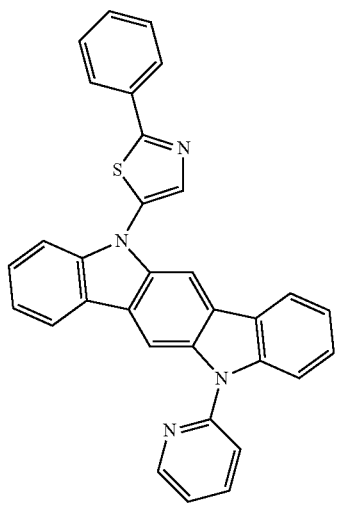
54
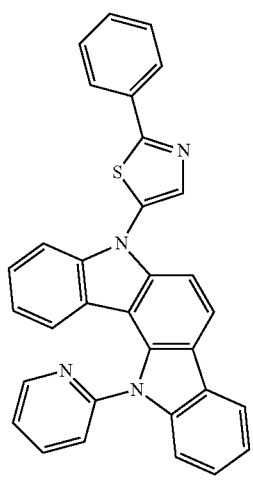
55
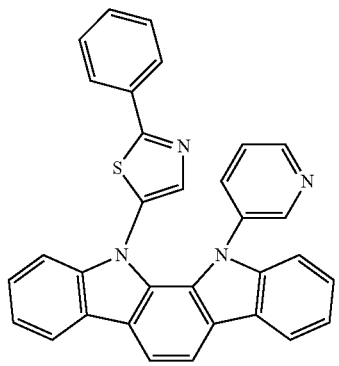

56
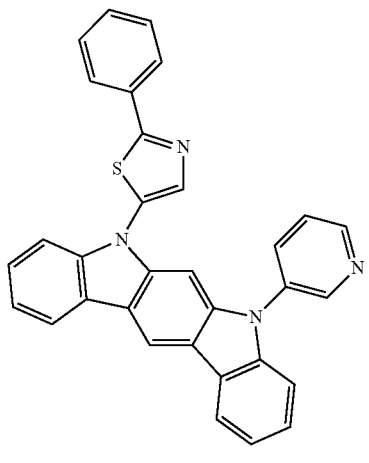
57
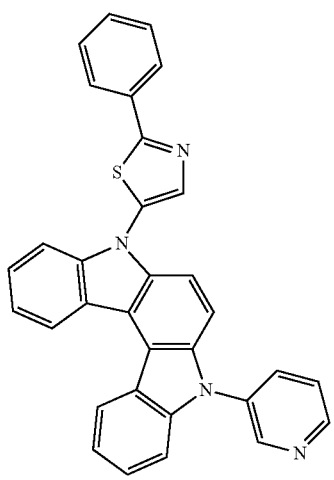
58
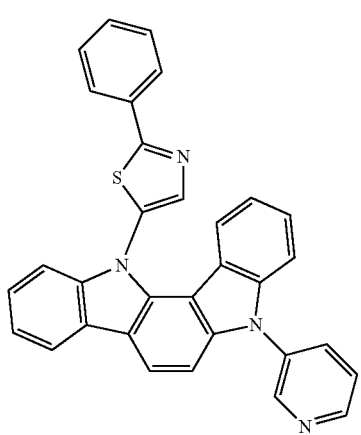
59
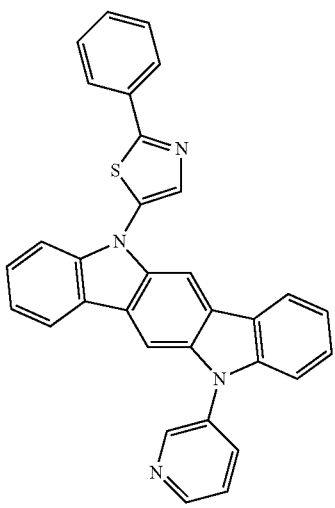
60
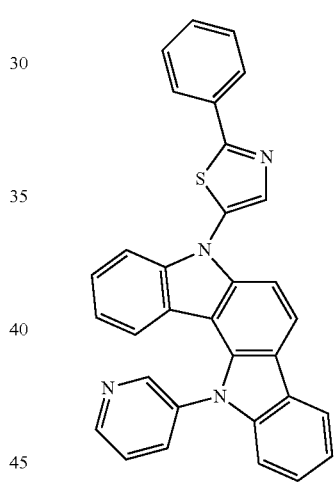
61
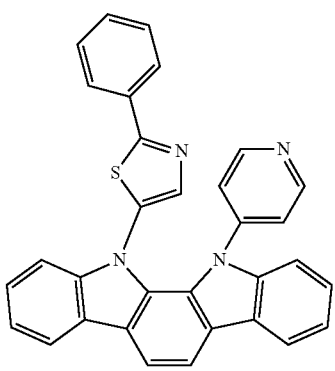

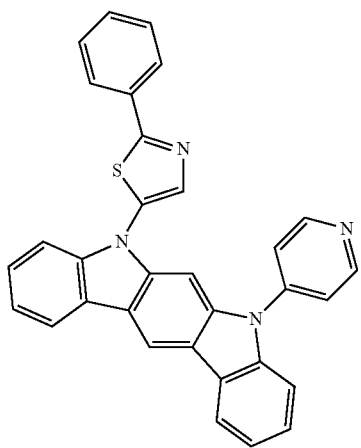
62
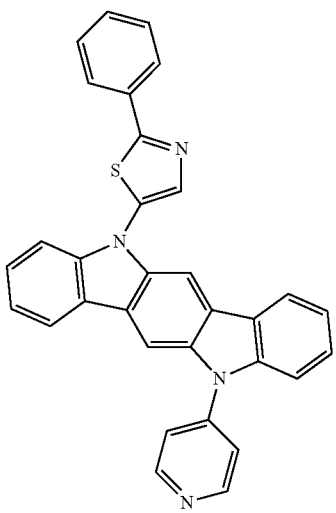
65
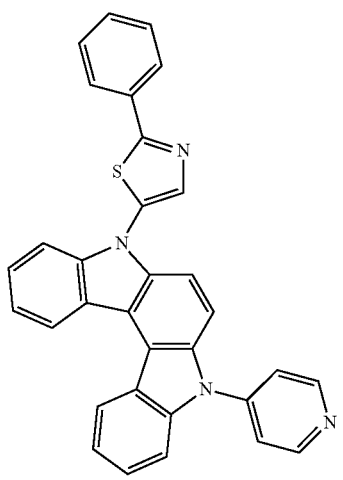
63
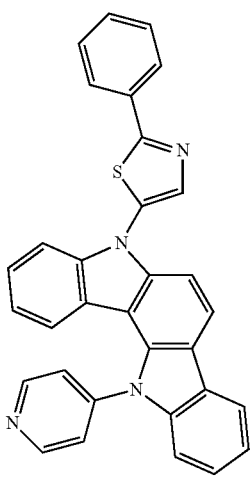
66
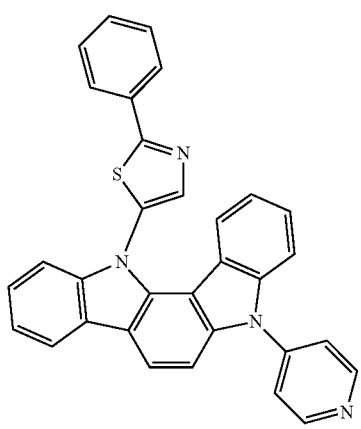
64
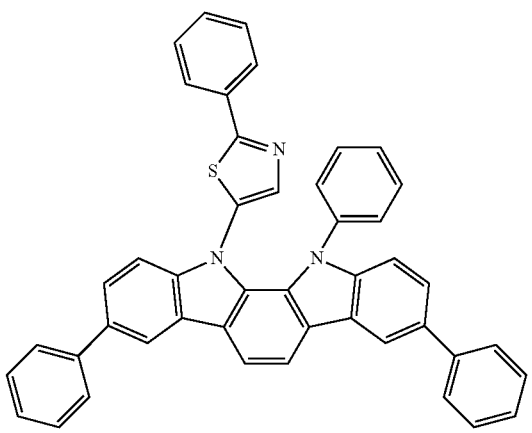
67

68
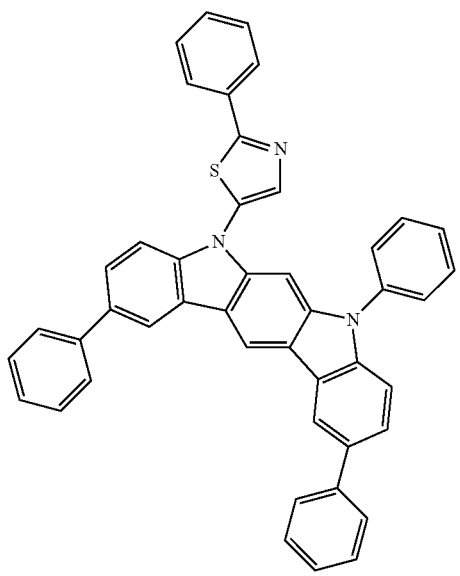
69
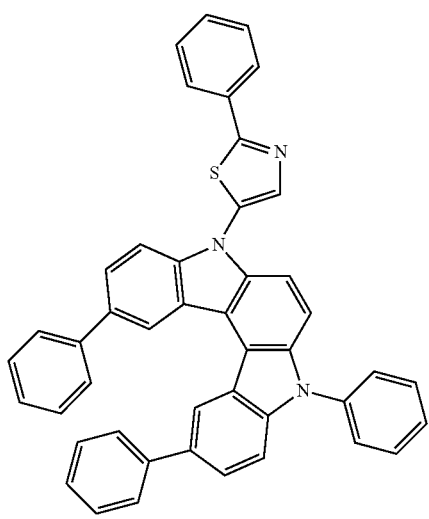
70
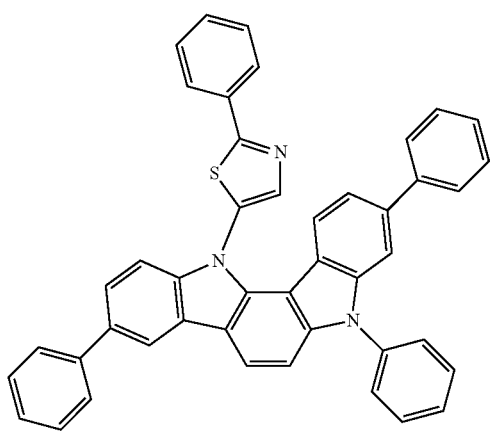
71
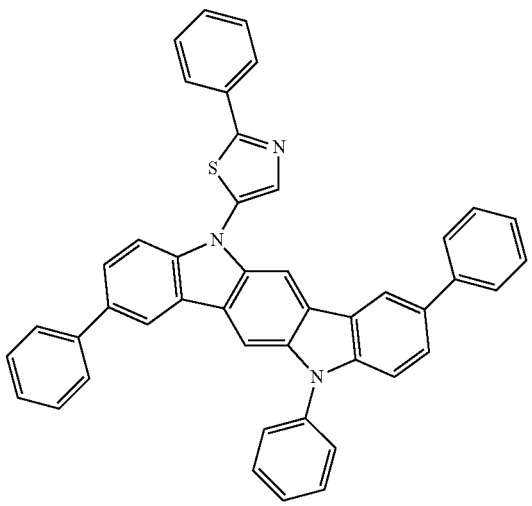
72
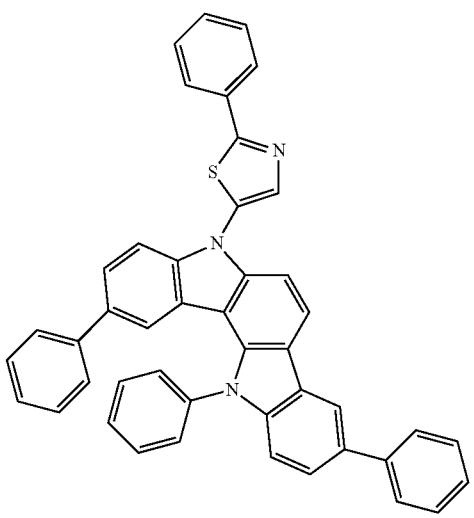
73
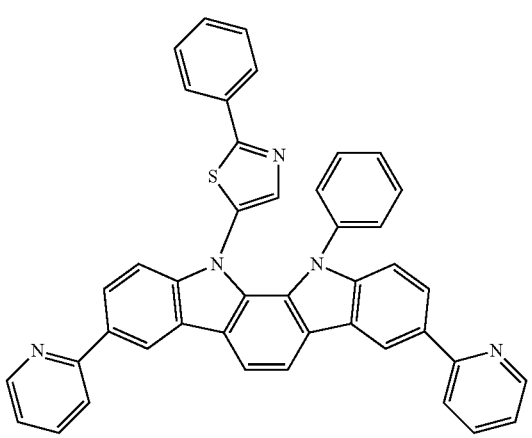

74
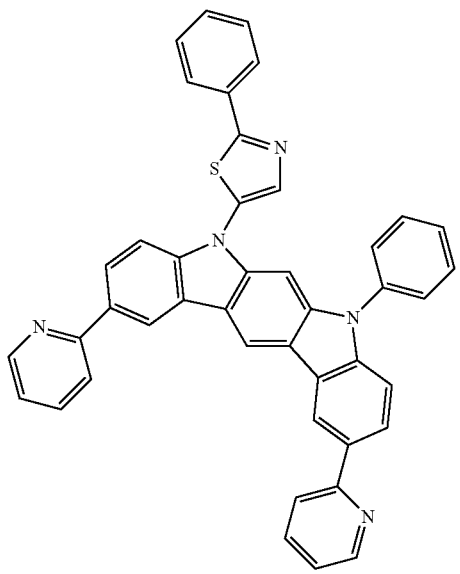
75
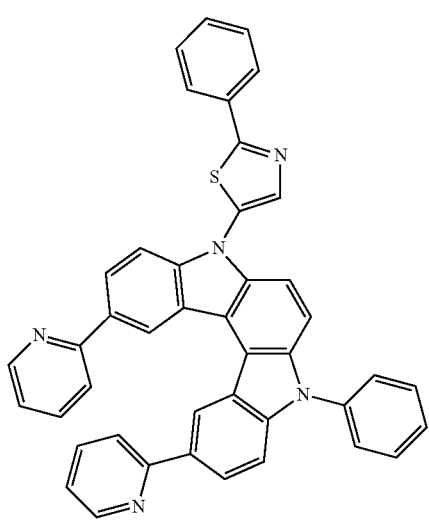
76
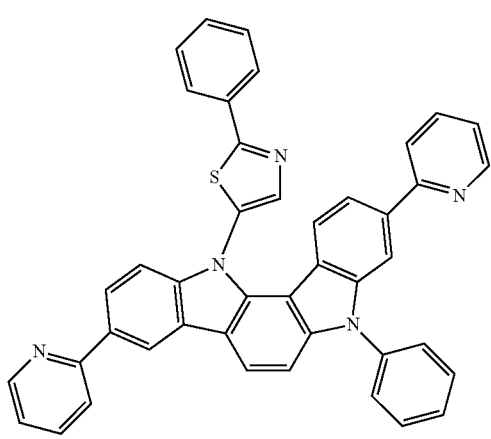
77
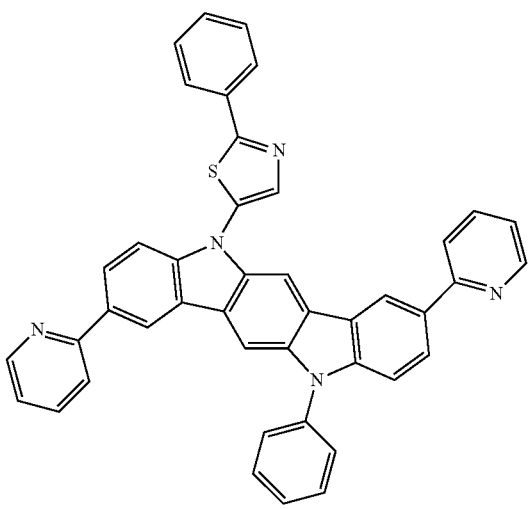
78
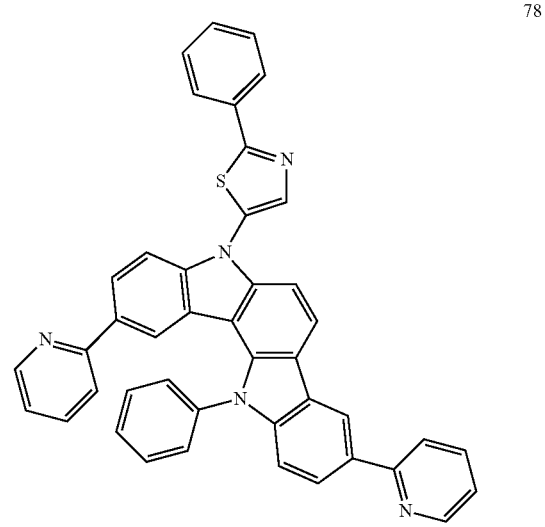
79
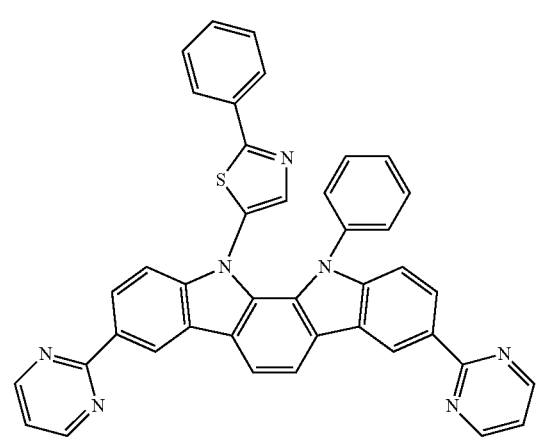

80
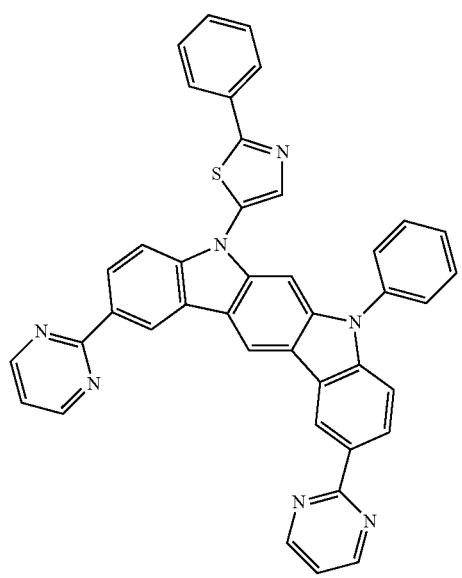
81
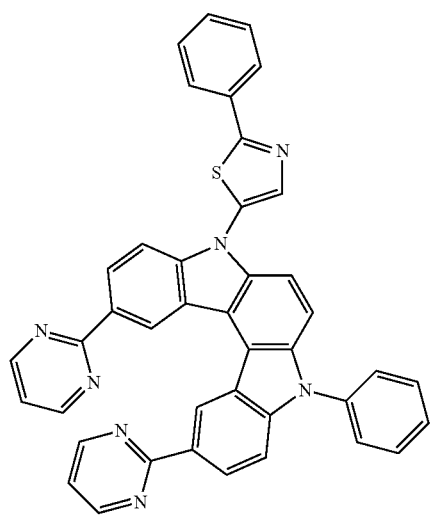
82
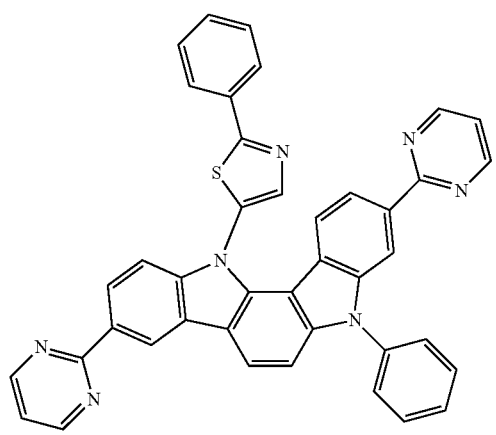
83
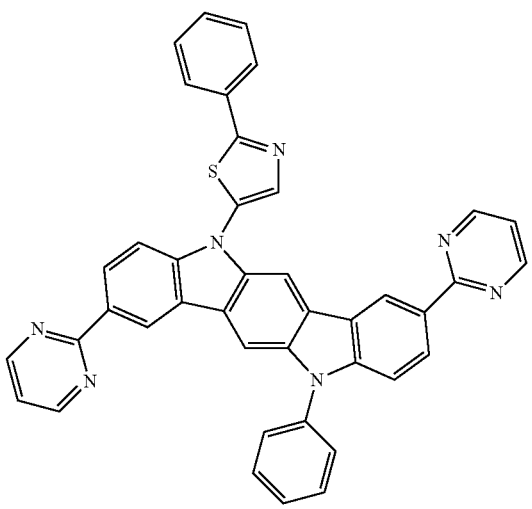
84
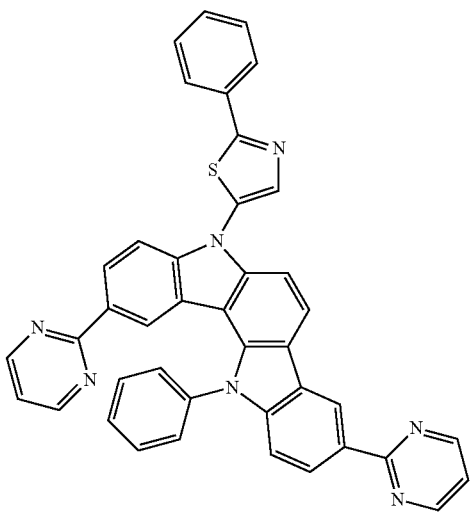
85
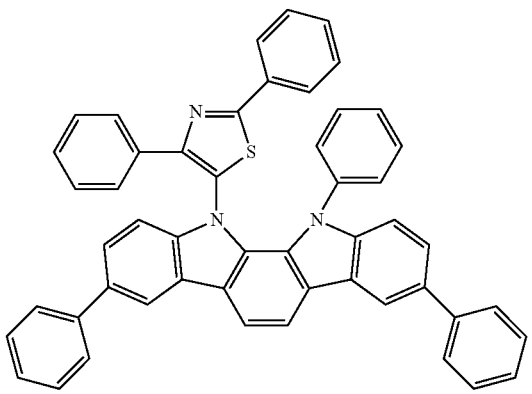

86
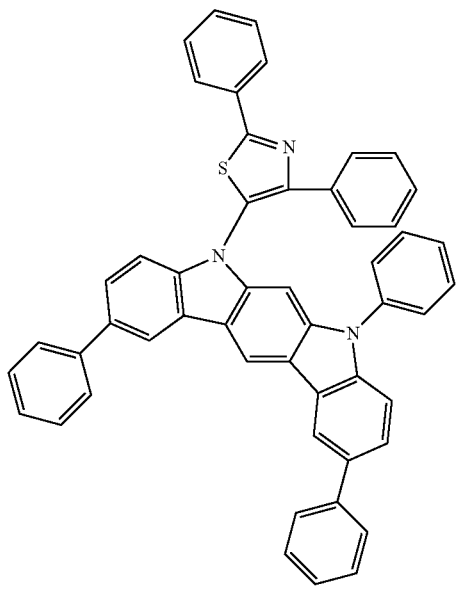
87
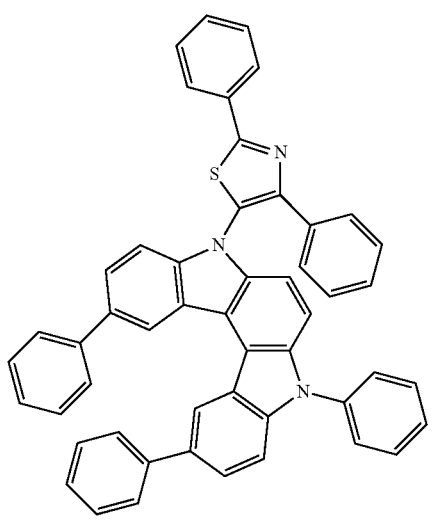
88
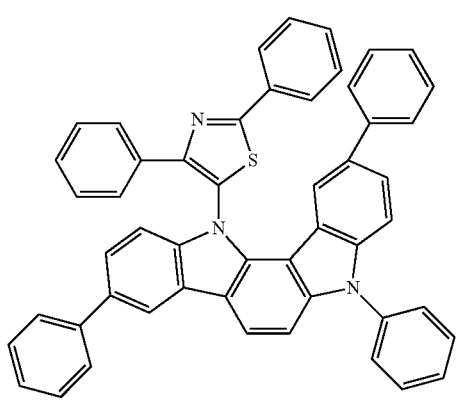
89
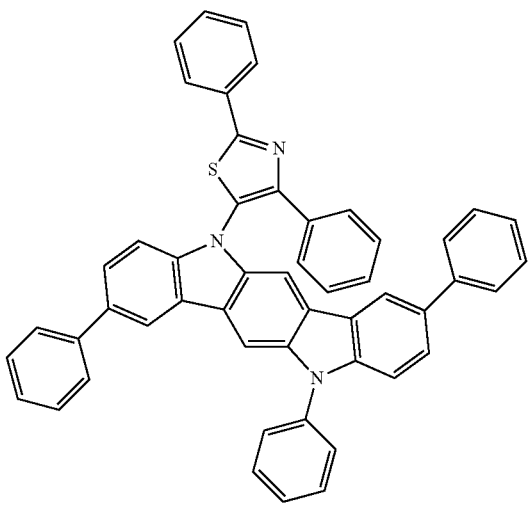
90
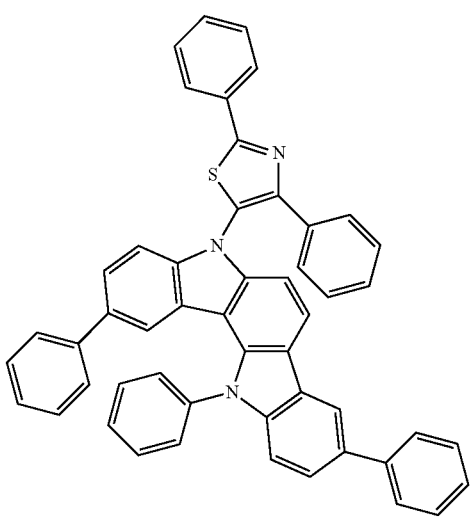
91
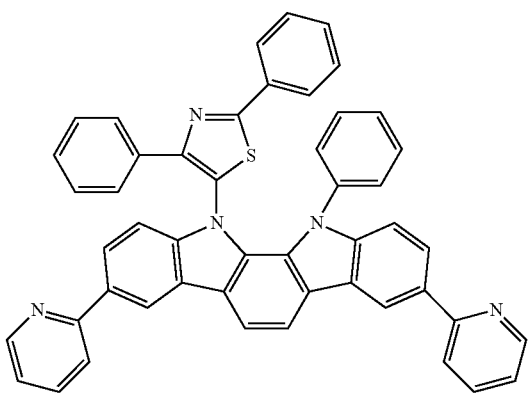

92
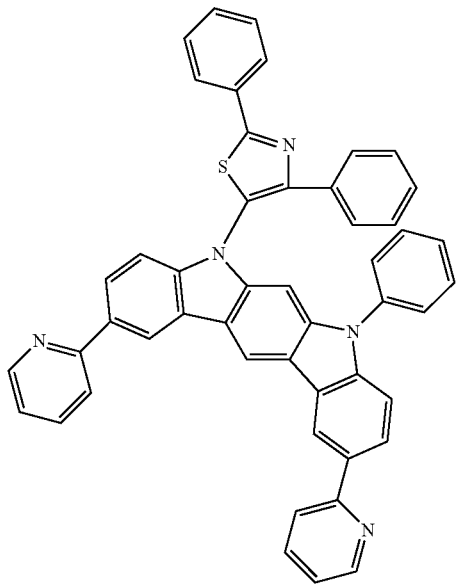
93
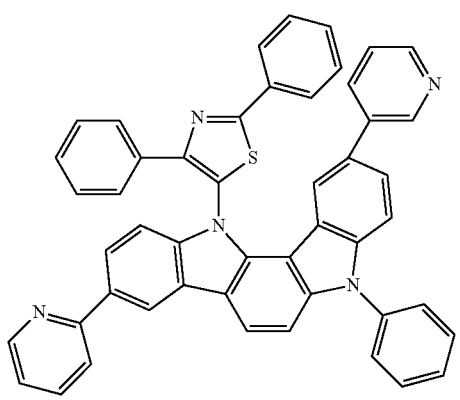
95
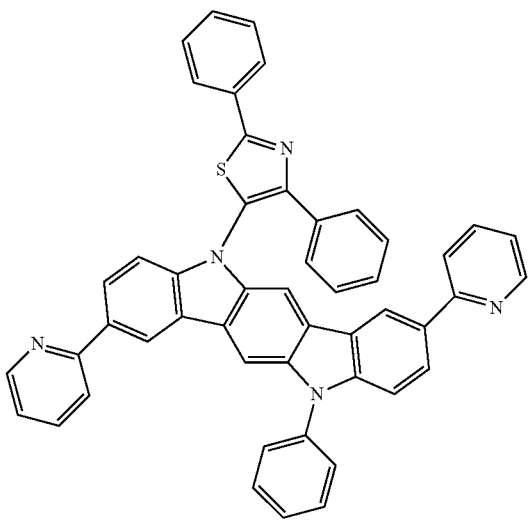
96
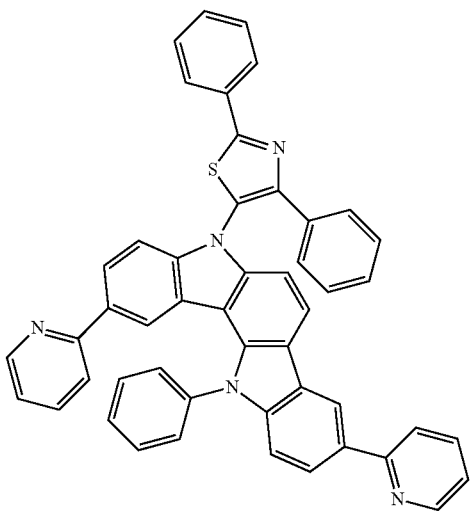
97
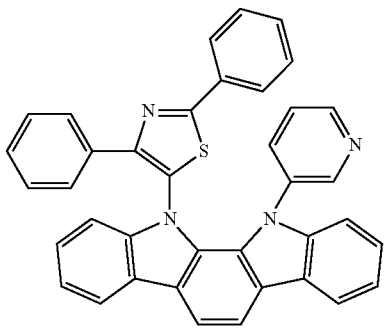

98
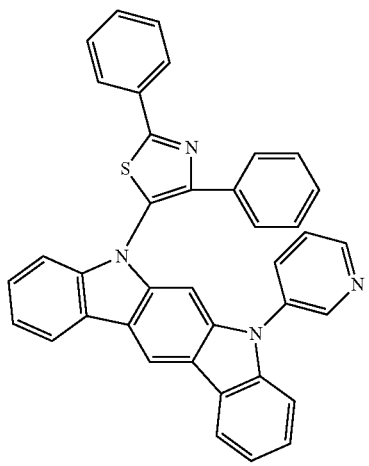
99
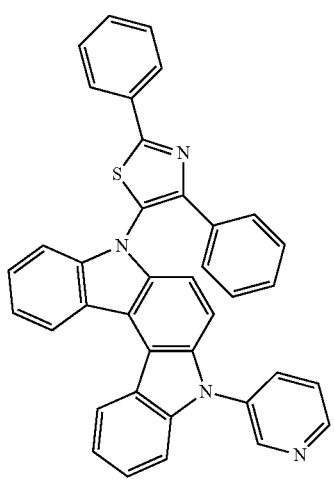
100
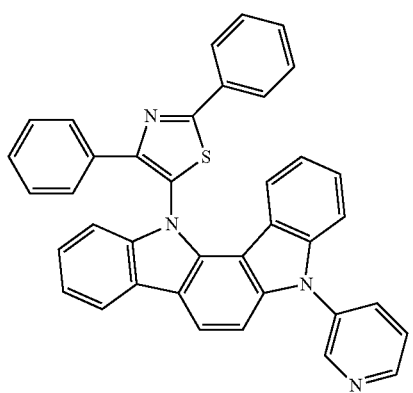
101
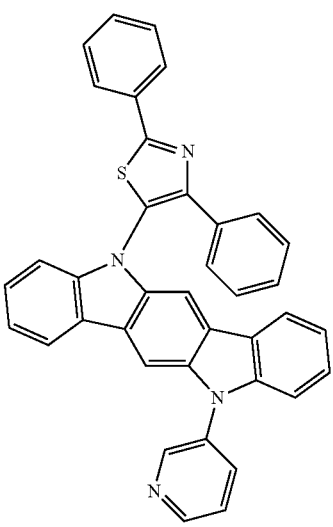
102
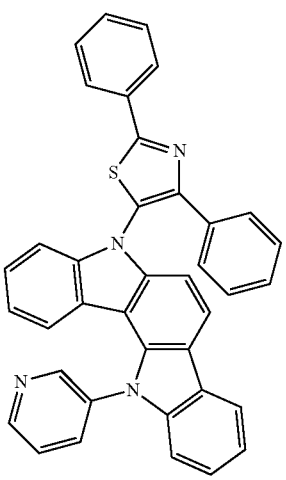
103
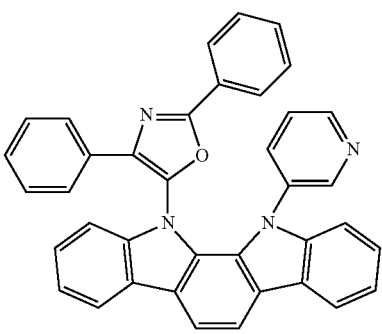

104
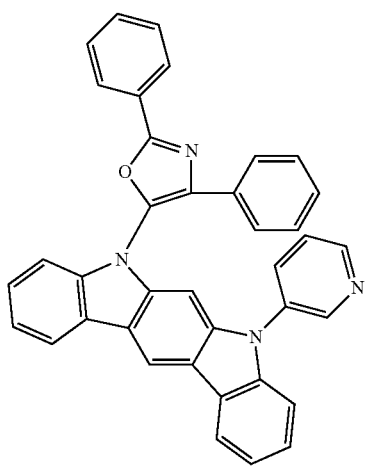
105
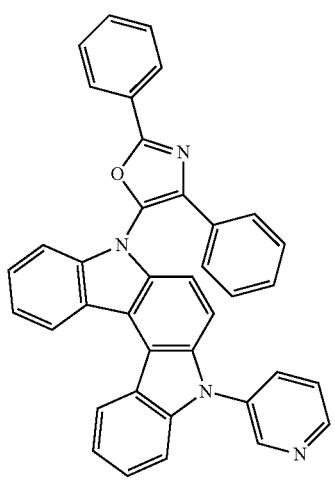
106
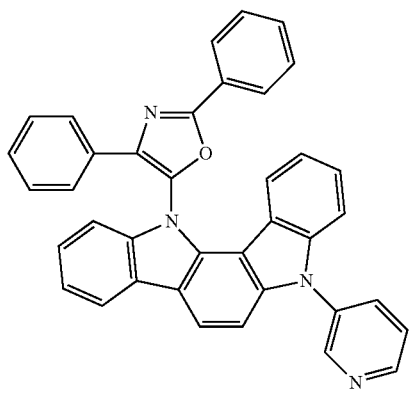
107
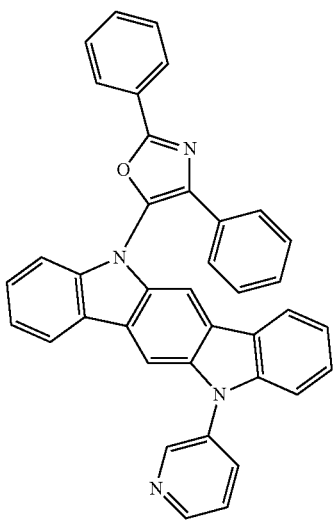
108
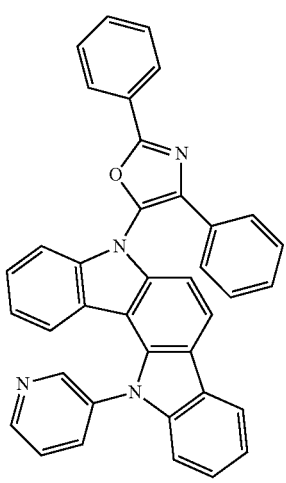
109
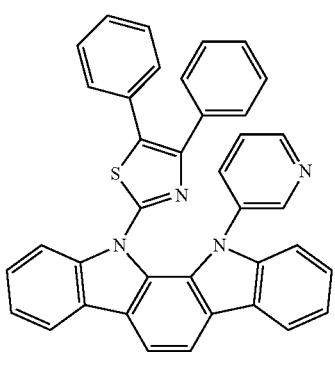

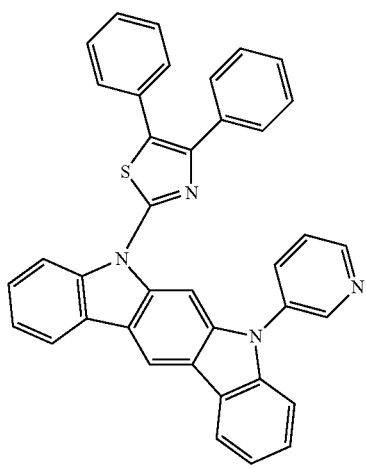
110
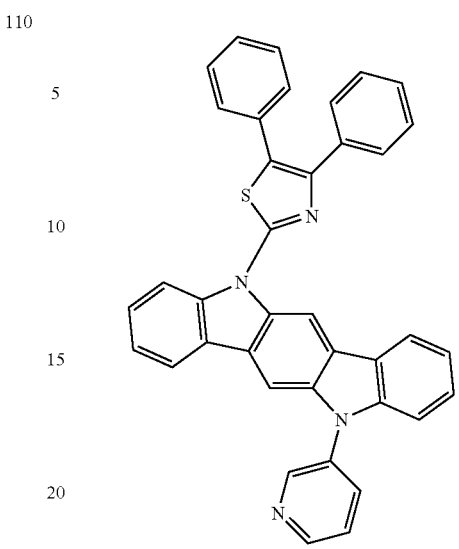
113
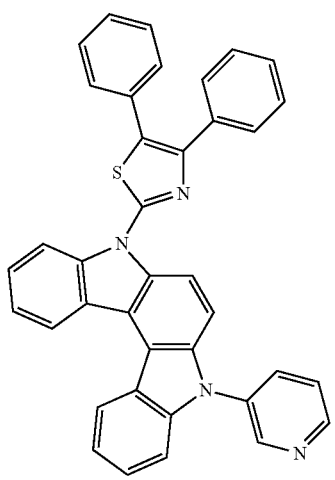
111
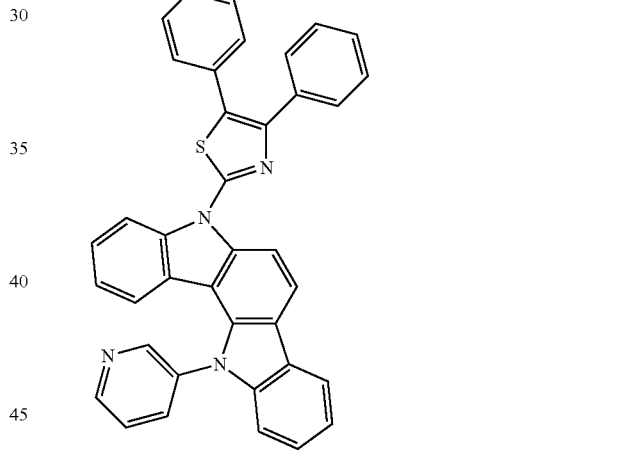
114
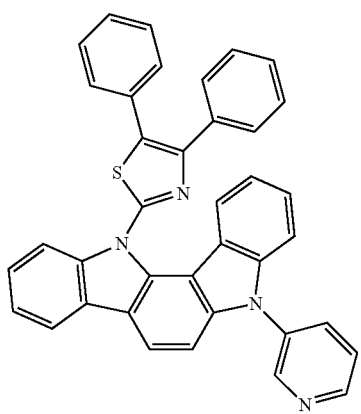
112
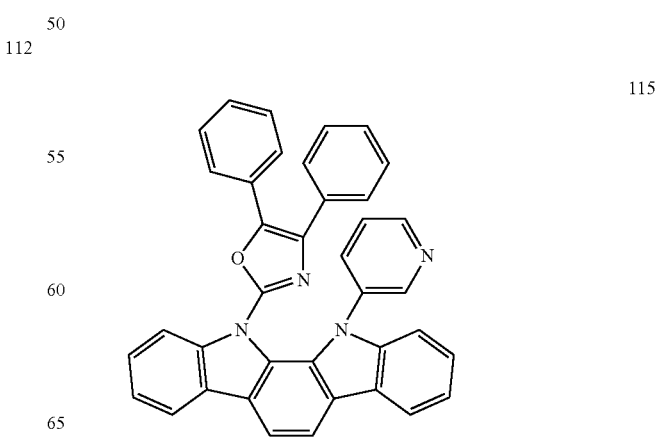
115

116
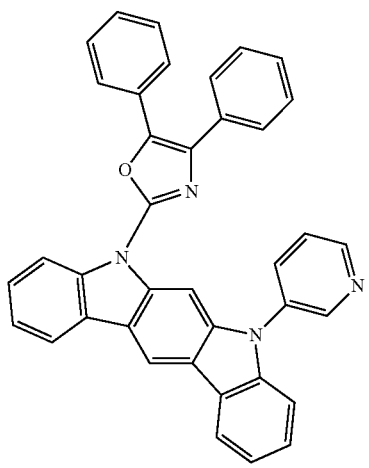
117
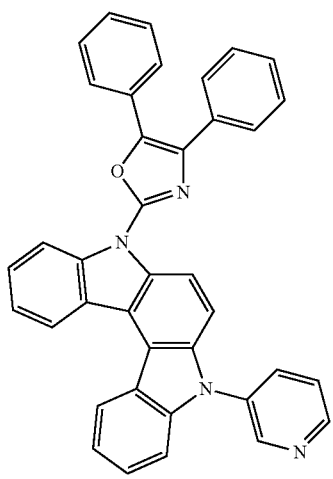
118
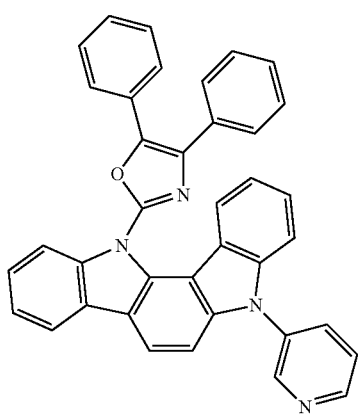
119
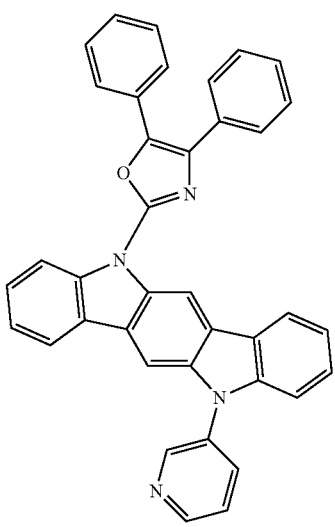
120
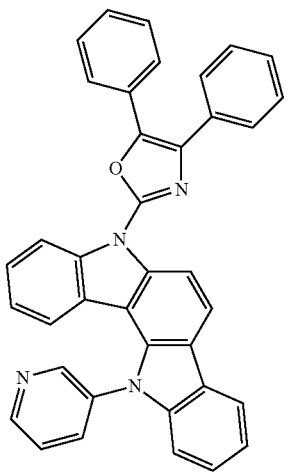
121
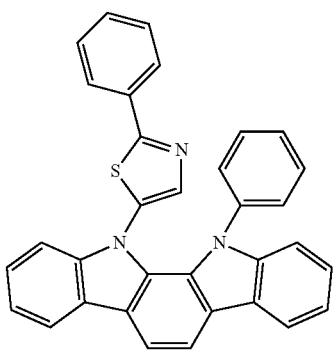

122
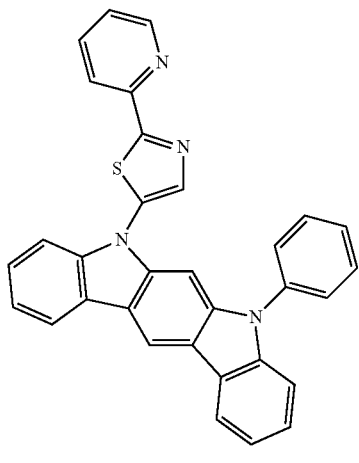
123
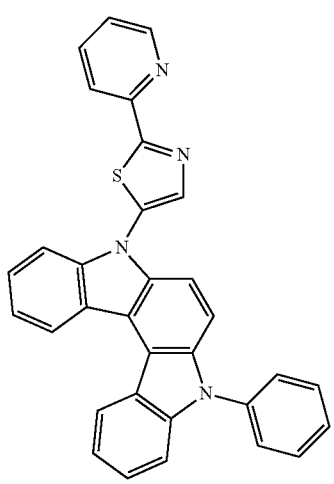
124
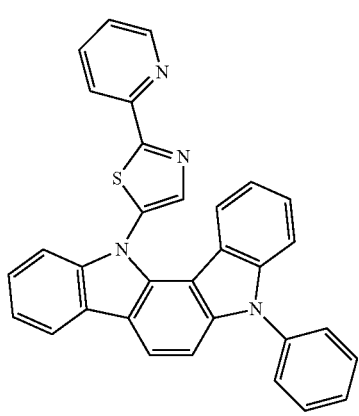
125
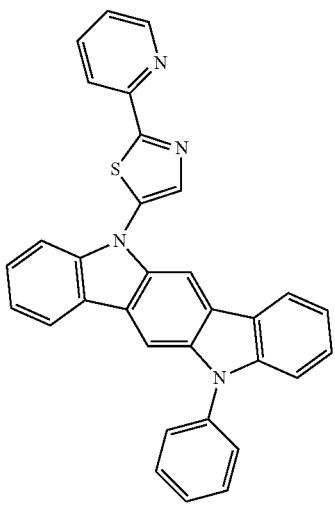
126
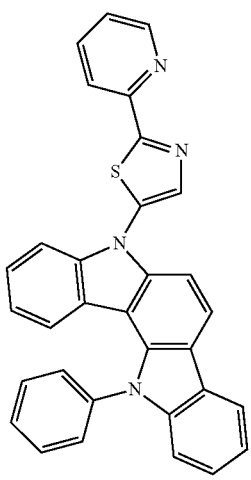
127
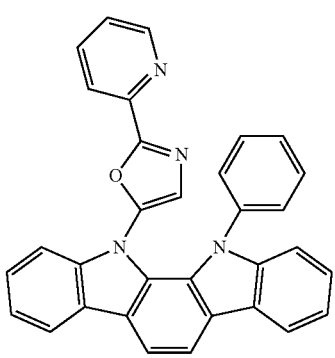

-continued
128
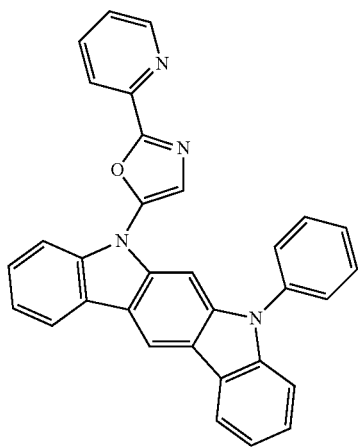
129
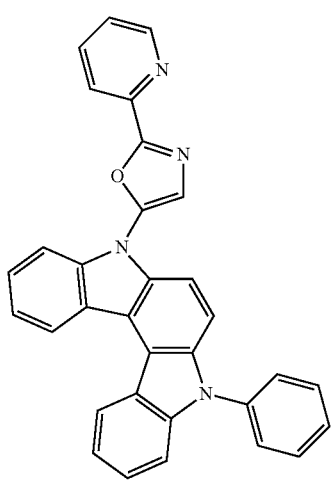
130
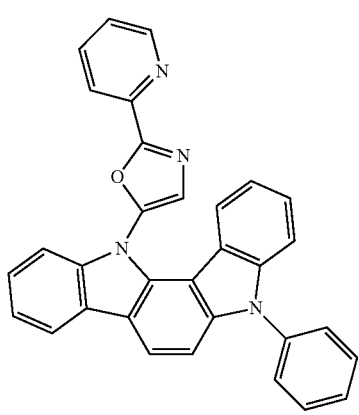
-continued
131
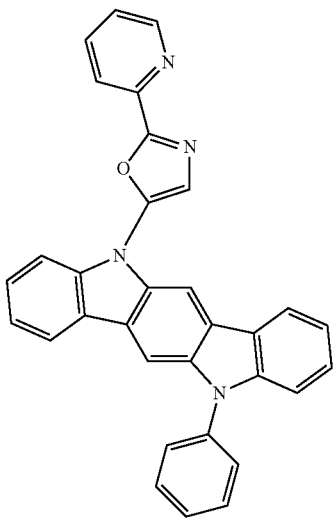
132
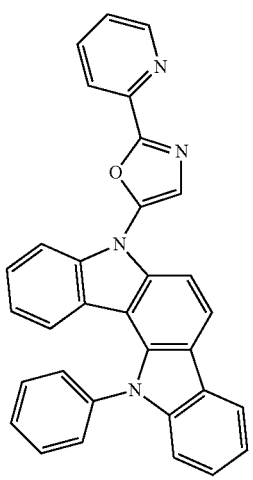
133
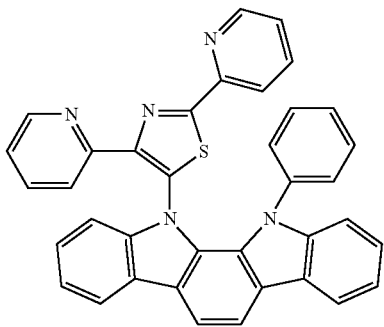

134
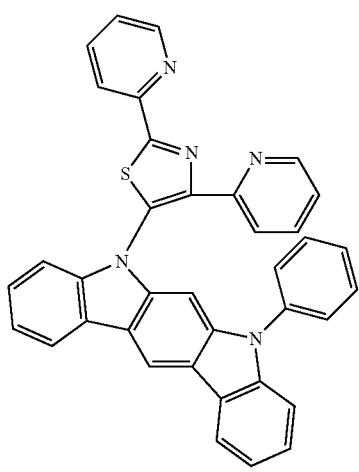
135
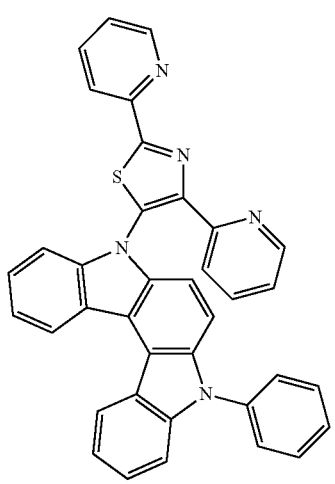
136
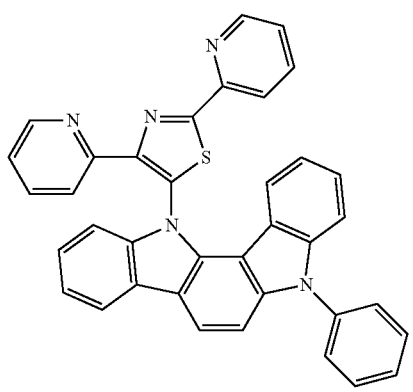
137
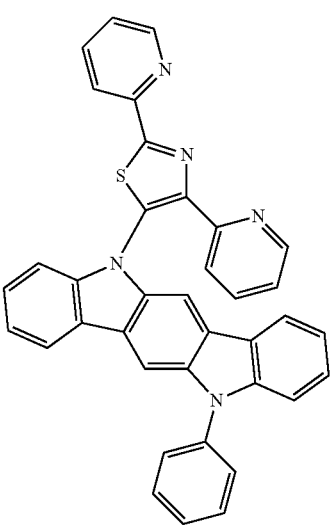
138
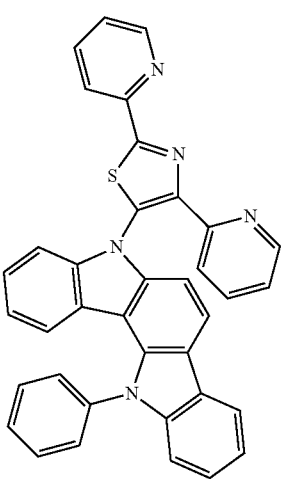
139
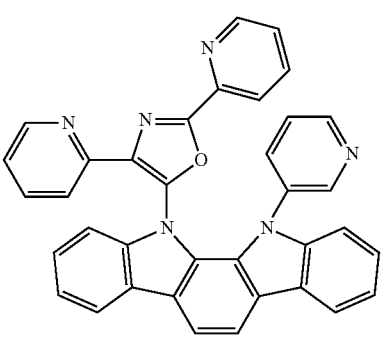

140
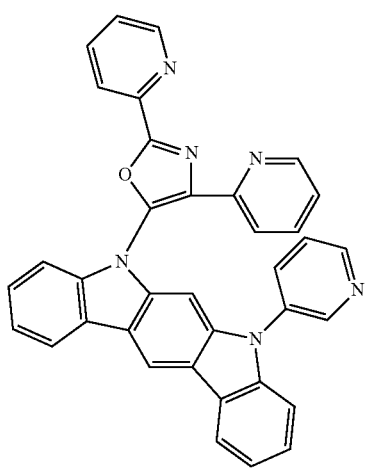
141
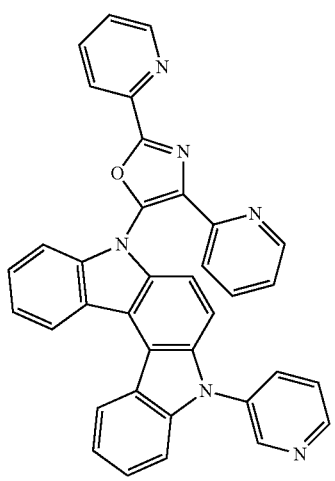
142
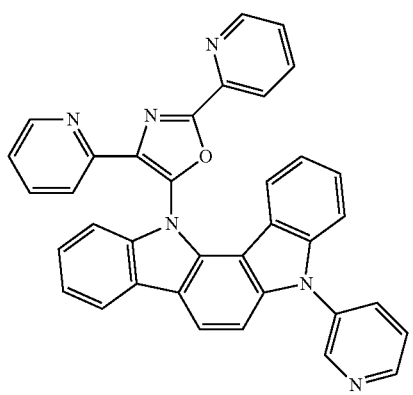
143
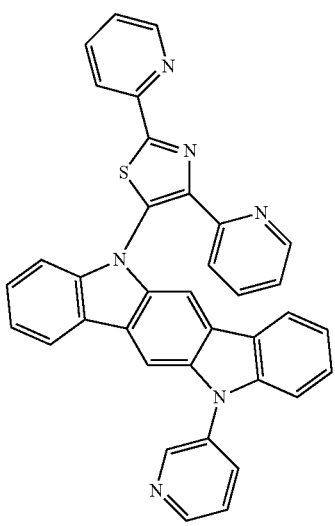
144
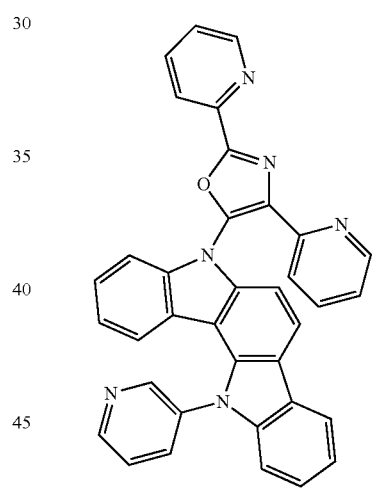
145
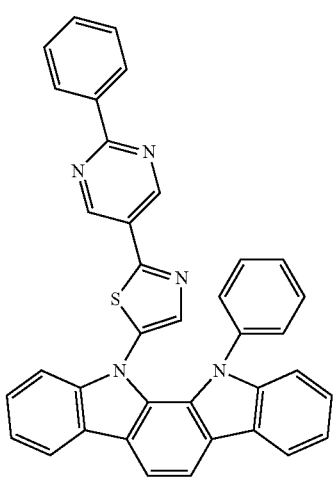

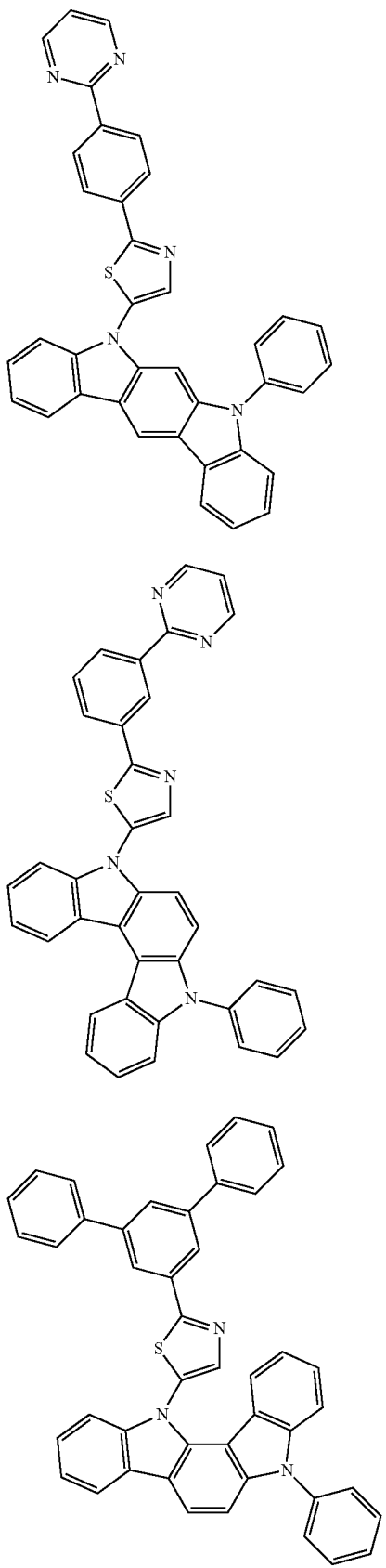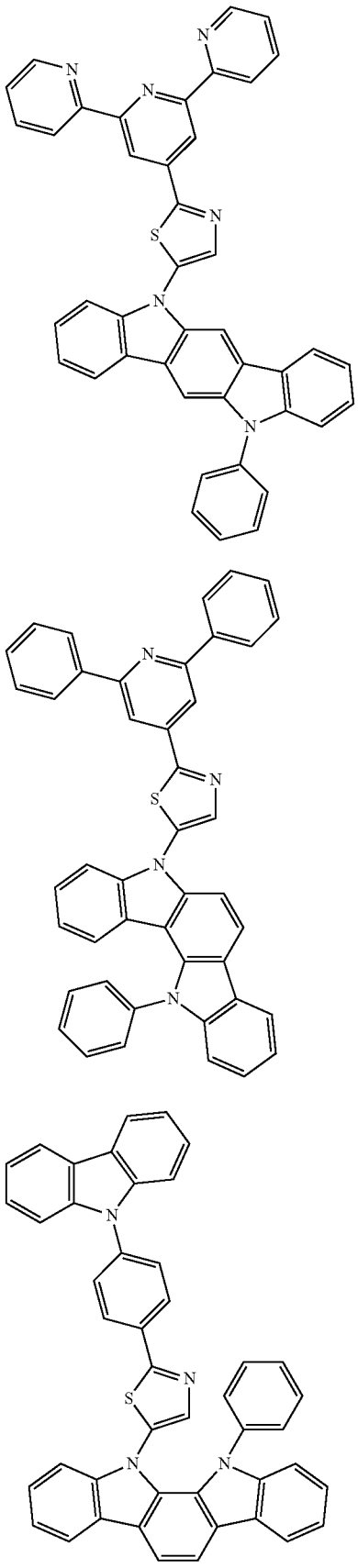

152
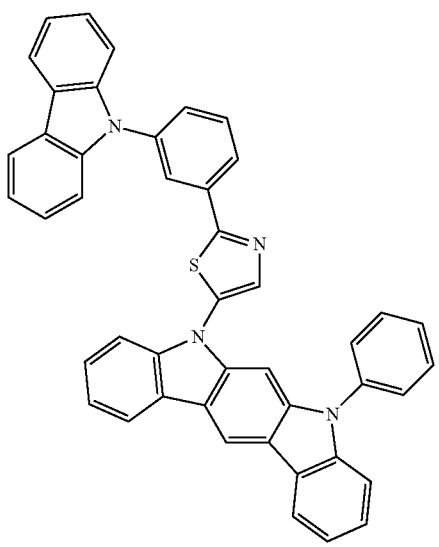
153
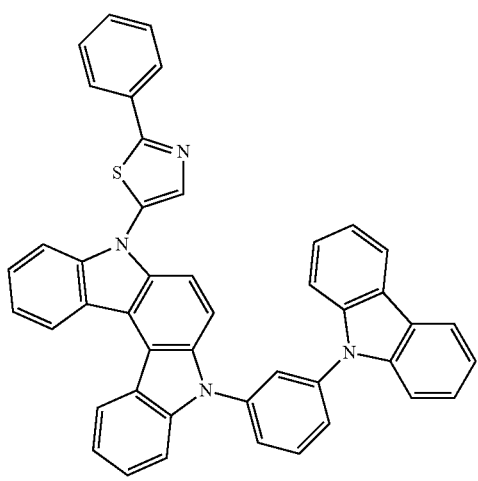
154
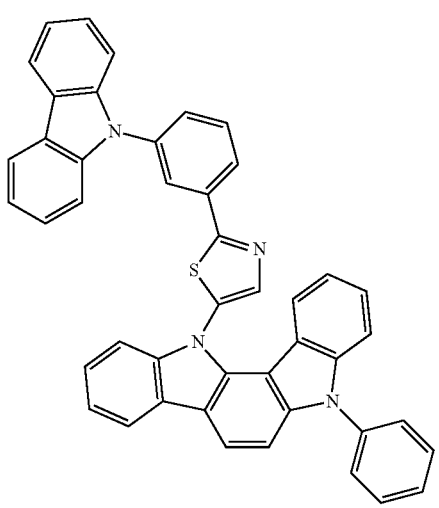
155
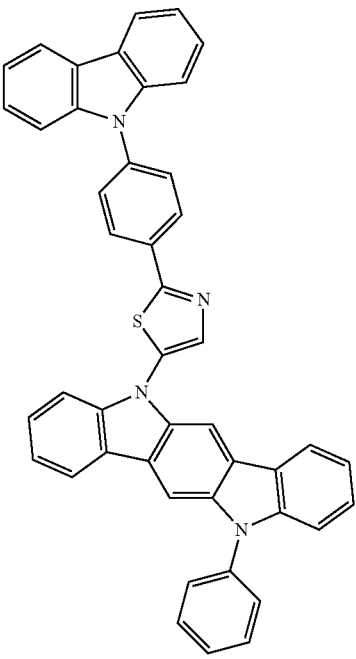
156
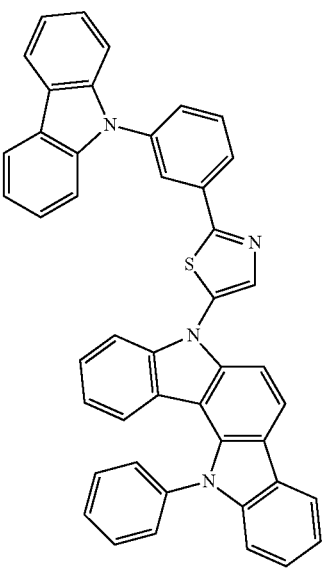

157

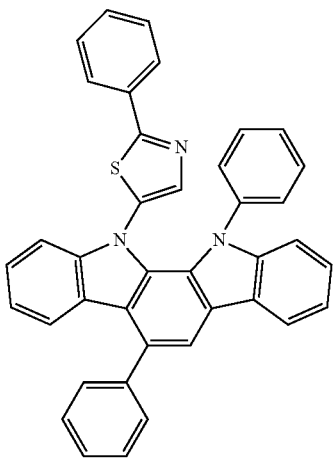

158

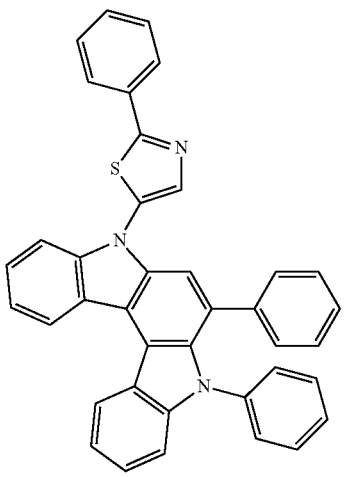

159

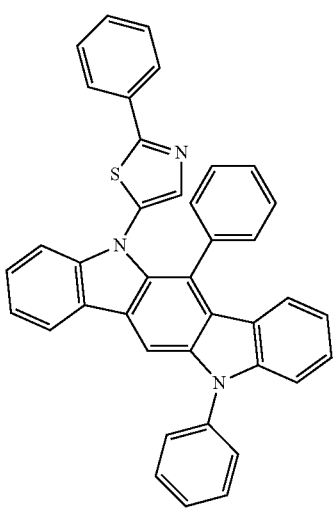

The condensed cyclic compound of Formula 1 in which an indole group is condensed into (or fused with) a carbazole group and in which a pentagonal hetero ring including a N atom and a S atom or an O atom is introduced to (or bonded to) a N atom of the carbazole group has enhancements (or advantages) in that electrons within the condensed cyclic compound (or organic molecules) may be balanced by maintaining a main skeleton of the condensed cyclic compound (or organic molecules), and accordingly may improve (or optimize) performance of the OLED. Therefore, the OLED including the condensed cyclic compound of Formula 1 may have a low driving voltage, high efficiency, high brightness, and long lifespan.

The condensed cyclic compound of Formula 1 may be synthesized by using (utilizing) any suitable organic synthesis method used in the art. A synthesis method of the condensed cyclic compound should be apparent to one of ordinary skill in the art in view of the following embodiments.

The condensed cyclic compound of Formula 1 may be used (utilized) between a pair of electrodes of an OLED. For example, the condensed cyclic compound may be included in a hole transport region, such as, for example, a hole transport layer. Accordingly, an OLED according to an embodiment of the present disclosure includes: a first electrode; a second electrode facing the first electrode; and an organic layer between the first and second electrodes and including an emission layer, the organic layer including at least one of the condensed cyclic compound.

The expression "(an organic layer) includes (or including) at least one of the condensed cyclic compound" used herein includes a case in which "(an organic layer) includes one condensed cyclic compound of Formula 1 and a case in which (an organic layer) includes two or more different condensed cyclic compounds of Formula 1".

For example, the organic layer may include only one of the condensed cyclic compound described herein. In this regard, the only one of the condensed cyclic compound may exist in an emission layer of an OLED, an electron transport layer or a hole transport layer of an OLED. In another embodiment of the present disclosure, the organic layer may include, two of the condensed cyclic compounds described herein, the two condensed cyclic compounds having different structures relative to one another. In this regard, the two different condensed cyclic compounds may exist in a same (or an identical) layer (for example, the two different condensed cyclic compounds may both be present in an emission layer), or different layers (for example, one of the two different condensed cyclic compounds may be present in an emission layer and the other of the two different condensed cyclic compounds may be present in an electron transport layer).

The organic layer may further include a hole transport region between the first electrode and the emission layer; and an electron transport region between the emission layer and the second electrode. The electron transport region may include at least one selected from a hole blocking layer, an electron transport layer, and an electron injection layer. The hole transport region may include at least one selected from an electron blocking layer, a hole transport layer, and a hole injection layer.

The emission layer may include the condensed cyclic compound of Formula 1 above.

The electron transport region may include the condensed cyclic compound of Formula 1 above. For example, the electron transport region may include the electron transport layer including the condensed cyclic compound of Formula 1.

The expression "organic layer" used herein refers to a single layer and/or a plurality of layers between the first and second electrodes of an OLED. A material of the "the organic layer" is not limited to an organic material. For example, the organic layer may include inorganic materials or compounds in addition to organic materials or compounds.

The accompanying drawing is a schematic view of an OLED 10 according to an embodiment of the present disclosure. The OLED 10 includes a substrate 11, a first electrode 13, an organic layer 15, and a second electrode 17.

Hereinafter, the structure of an OLED according to an embodiment of the present disclosure and a method of manufacturing an OLED, according to an embodiment of the present disclosure, will be described in connection with the accompanying drawing.

The substrate 11 may be a glass substrate or a transparent plastic substrate, each with excellent mechanical strength, thermal stability, transparency, surface smoothness, ease of handling, and water repellency.

The first electrode 13 may be formed by depositing or sputtering a material for forming the first electrode 13 on the substrate 11. When the first electrode 13 is an anode, the material for the first electrode 13 may be selected from materials with a high work function to allow holes to be easily injected. The first electrode 13 may be a reflective electrode or a transmissive electrode. The material for the first electrode may be a transparent and highly conductive material, and examples of such a material include indium tin oxide (ITO), indium zinc oxide (IZO), tin oxide ($SnO_2$), and zinc oxide (ZnO). When the first electrode 13 is a semi-transmissive electrode or a reflective electrode, a material for forming the first electrode 13 may include at least one selected from magnesium (Mg), aluminum (Al), aluminum-lithium (Al—Li), calcium (Ca), magnesium-indium (Mg—In), and magnesium-silver (Mg—Ag).

The first electrode 13 may have a single-layer structure, or a multi-layer structure including two or more layers. For example, the first electrode 110 may have a three-layered structure of ITO/Ag/ITO, but the structure of the first electrode 120 is not limited thereto.

The organic layer 15 is on the first electrode 13. The organic layer 15 may include an emission layer.

The organic layer 15 may further include a hole transport region between the first electrode 13 and the emission layer, and an electron transport region between the emission layer and the second electrode 17.

The hole transport region may include at least one selected from a hole injection layer (HIL), a hole transport layer (HTL), a buffer layer, and an electron blocking layer (EBL), and the electron transport region may include at least one selected from a hole blocking layer (HBL), an electron transport layer (ETL), and an electron injection layer (EIL), but the hole transport region and the electron transport region are not limited thereto.

The hole transport region may have a single-layered structure formed of a single material, a single-layered structure formed of different materials, or a multi-layered structure having a plurality of layers formed of different materials.

For example, the hole transport region may have a single-layered structure formed of different materials, or a structure of HIL/HTL, a structure of HIL/HTL/buffer layer, a structure of HIL/buffer layer, a structure of HTL/buffer layer, or a structure of HIL/HTL/EBL, but the structures are not limited thereto.

When the hole transport region includes a HIL, the HIL may be formed on the first electrode 13 by using (utilizing) various suitable methods, such as vacuum deposition, spin coating, casting, a Langmuir-Blodgett (LB) method, ink-jet printing, laser-printing, or laser-induced thermal imaging (LITI)

When a HIL is formed by vacuum deposition, for example, the vacuum deposition may be performed at a deposition temperature of about 100° C. to about 500° C., at a vacuum degree of about $10^{-8}$ to about $10^{-3}$ torr, and at a deposition rate of about 0.01 to about 100 Å/sec in consideration of a composition of the compound to be deposited for the HIL, and the structure of the HIL to be formed.

When a HIL is formed by spin coating, the spin coating may be performed at a coating rate of about 2,000 rpm to about 5,000 rpm, and at a temperature of about 80° C. to 200° C. in consideration of a composition of the compound to be deposited for the HIL, and the structure of the HIL to be formed.

When the hole transport region includes a HTL, the HTL may be formed on the first electrode 13 or the HIL by using (utilizing) various methods, such as vacuum deposition, spin coating, casting, an LB method, ink-jet printing, laser-printing, or LITI. When the HTL is formed by vacuum deposition or spin coating, deposition and coating conditions for the HTL may be determined by referring to the deposition and coating conditions for the HIL.

The hole transport region may include at least one selected from the condensed cyclic compound of Formula 1, m-MTDATA, TDATA, 2-TNATA, NPB, 13-NPB, TPD, Spiro-TPD, Spiro-NPB, α-NPD, TAPC, HMTPD, 4,4',4"-tris(N-carbazolyl)triphenylamine (TCTA), polyaniline/dodecylbenzenesulfonic acid (PANI/DBSA), poly(3,4-ethylenedioxythiophene)/poly(4-styrenesulfonate) (PEDOT/PSS), polyaniline/camphor sulfonicacid (PANI/CSA), polyaniline/poly(4-styrenesulfonate) (PANI/PSS), a compound represented by Formula 201, and a compound represented by Formula 202:

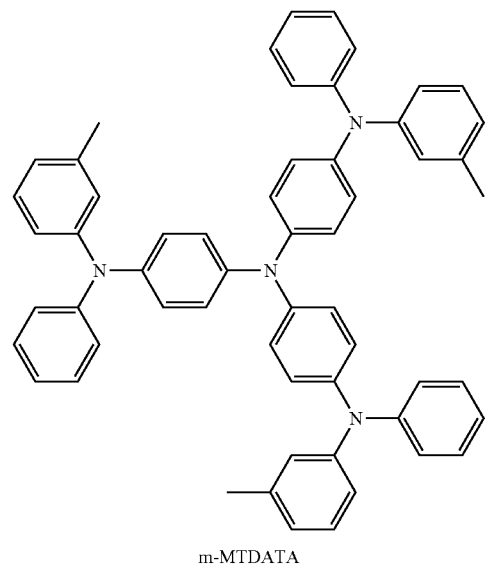

m-MTDATA

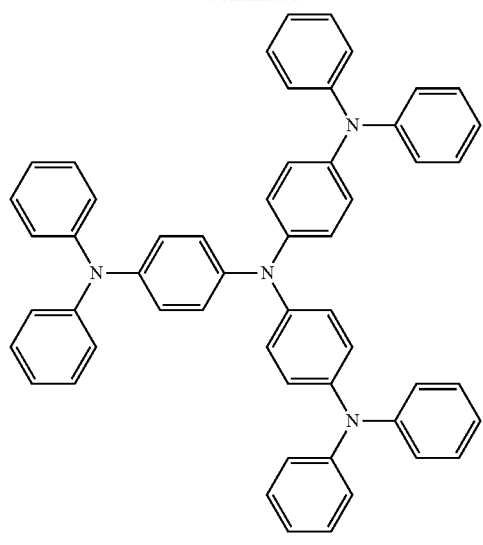
TDATA
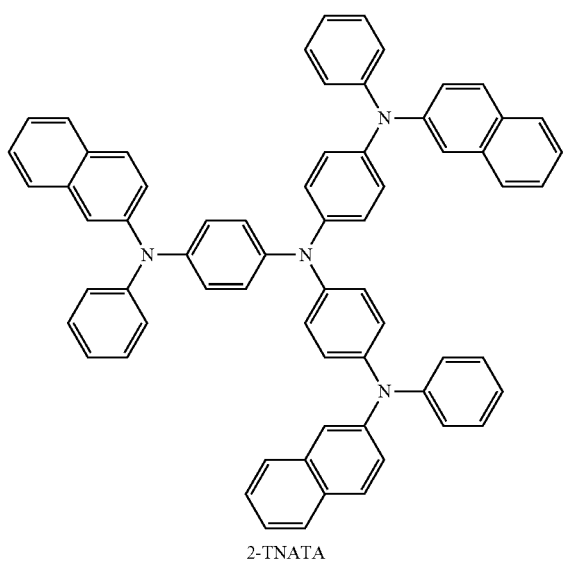
2-TNATA
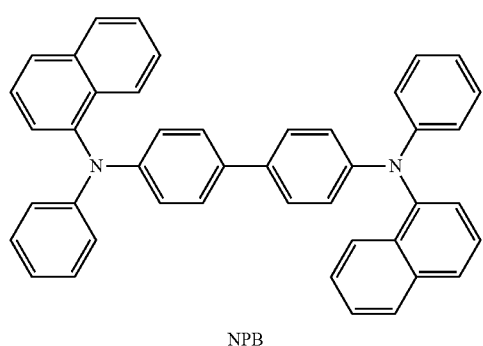
NPB
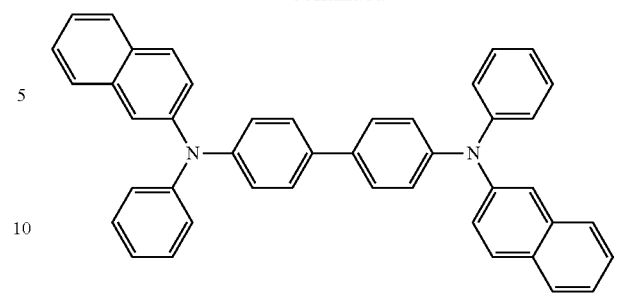
β-NPB
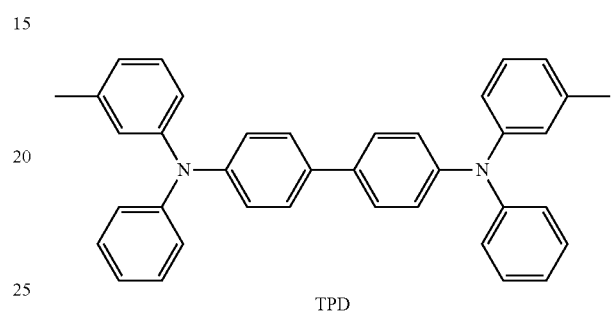
TPD
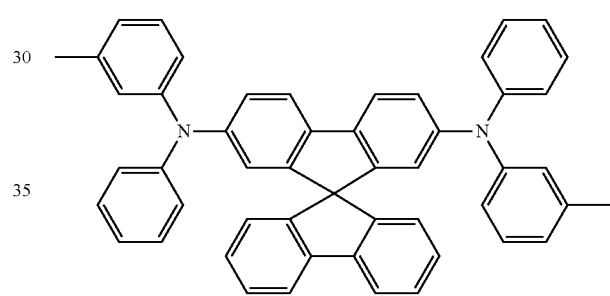
spiro-TBD
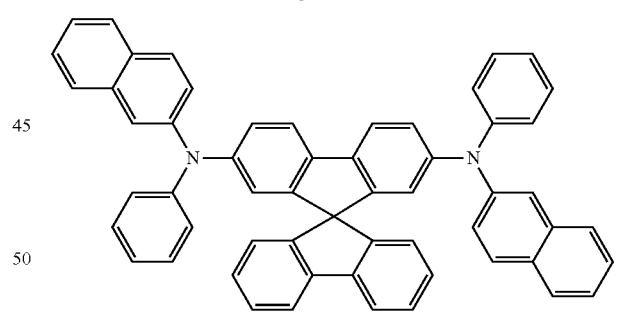
spiro-NPB
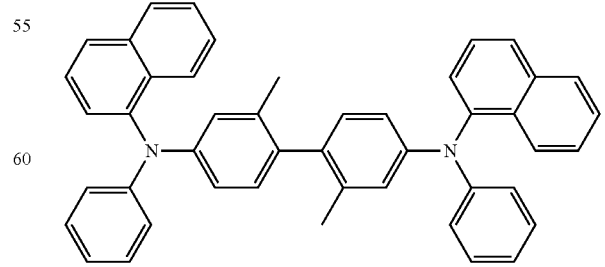
α-NPD -continued

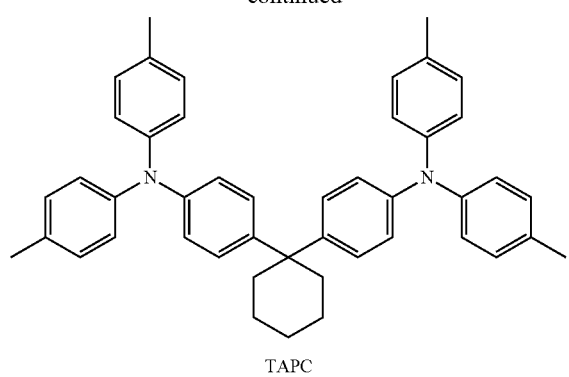
TAPC

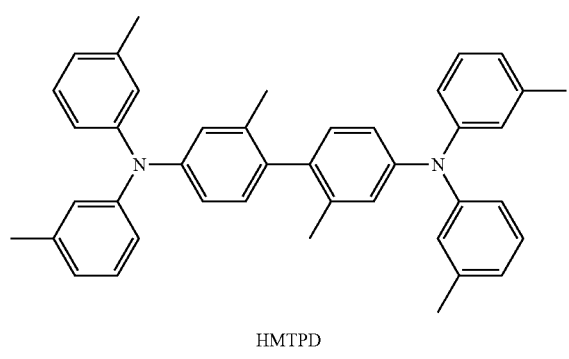
HMTPD

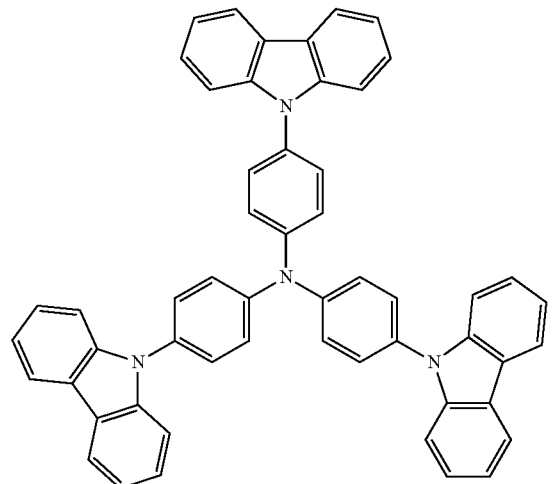
TCTA

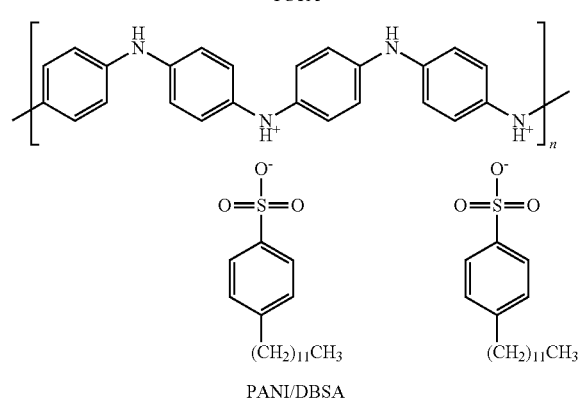
PANI/DBSA

-continued

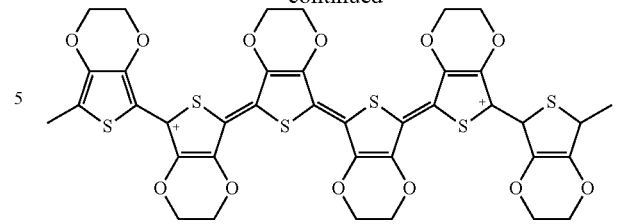
PEDOT/PSS

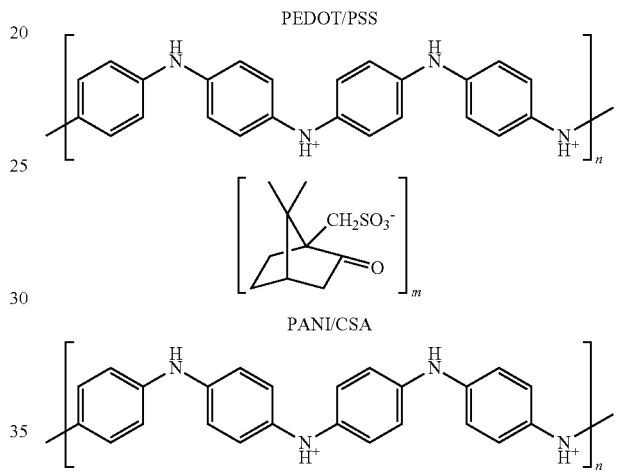
PANI/CSA

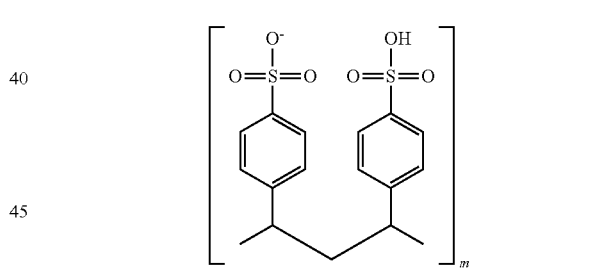
PANI/PSS

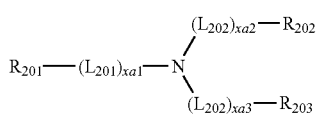

Formula 201

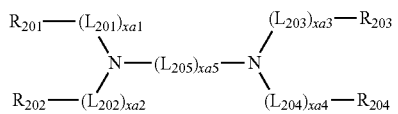

Formula 202 where in Formulae 201 and 202, $L_{201}$ to $L_{205}$ may be each independently selected from a substituted or unsubstituted $C_3$-$C_{10}$ cycloalkylene group, a substituted or unsubstituted $C_3$-$C_{10}$ heterocycloalkylene group, a substituted or unsubstituted $C_3$-$C_{10}$ cycloalkenylene group, a substituted or unsubstituted $C_3$-$C_{10}$ heterocycloalkenylene group, a substituted or unsubstituted $C_6$-$C_{60}$ arylene group, a substituted or unsubstituted $C_2$-$C_{60}$ heteroarylene group, and a substituted or unsubstituted divalent $C_6$-$C_{60}$ non-aromatic condensed polycyclic group;

xa1 to xa4 may be each independently selected from 0, 1, 2, and 3;

xa5 may be selected from 1, 2, 3, 4, and 5; and $R_{201}$ to $R_{204}$ may be each independently selected from a substituted or unsubstituted $C_3$-$C_{10}$ cycloalkyl group, a substituted or unsubstituted $C_3$-$C_{10}$ heterocycloalkyl group, a substituted or unsubstituted $C_3$-$C_{10}$ cycloalkenyl group, a substituted or unsubstituted $C_3$-$C_{10}$ heterocycloalkenyl group, a substituted or unsubstituted $C_6$-$C_{60}$ aryl group, a substituted or unsubstituted $C_2$-$C_{60}$ heteroaryl group, and a substituted or unsubstituted a monovalent $C_6$-$C_{30}$ non-aromatic condensed polycyclic group.

For example, in Formulae 201 and 202, $L_{201}$ to $L_{205}$ may be each independently selected from:

a phenyl group, a naphthyl group, a fluorenyl group, a spiro-fluorenyl group, a benzofluorenyl group, a dibenzofluorenyl group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, an isoindolyl group, a quinolinyl group, an isoquinolinyl group, a quinoxalinyl group, a quinazolinyl group, a carbazolyl group, and a triazinyl group;

xa1 to xa4 may be each independently 0, 1, or 2;

xa5 may be 1, 2, or 3;

$R_{201}$ to $R_{204}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group.

For example, the compound of Formula 201 may be represented by Formula 201A.

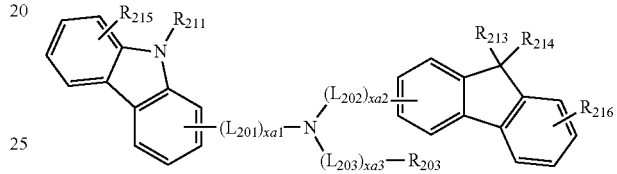

Formula 201A

For example, the compound of Formula 201 may be represented by Formula 201A-1, but the present disclosure is not limited thereto:

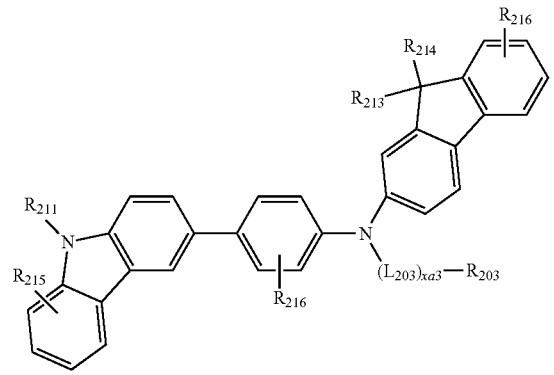

Formula 201A-1

For example, the compound of Formula 202 may be represented by Formula 202A, but the present disclosure is not limited thereto:

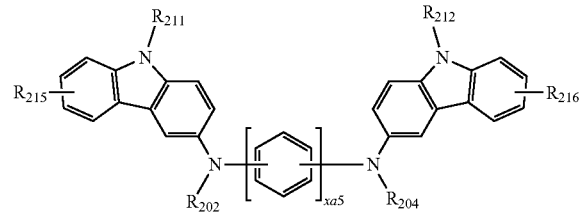

Formula 202A where in Formulae 201A, 201A-1, and 202A, $L_{201}$ to $L_{203}$, xa1 to xa3, xa5, and $R_{202}$ to $R_{204}$ may be understood by referring to the description thereof provided herein with respect to Formulae 201 and 202, and $R_{211}$ may be understood by referring to the description provided herein for $R_{203}$ with respect to Formulae 201 and 202, and where $R_{213}$ to $R_{216}$ may be each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{60}$ alkyl group, a $C_2$-$C_{60}$ alkenyl group, a $C_2$-$C_{60}$ alkynyl group, a $C_1$-$C_{60}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{60}$ aryl group, a $C_6$-$C_{60}$ aryloxy group, a $C_6$-$C_{60}$ arylthio group, a $C_2$-$C_{60}$ heteroaryl group, and a $C_6$-$C_{60}$ non-aromatic condensed polycyclic group.

For example, in Formulae 201A, 201A-1, and 202A, $L_{201}$ to $L_{203}$ may be each independently selected from:

a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group; and a phenylene group, a naphthylene group, a fluorenylene group, a spiro-fluorenylene group, a benzofluorenylene group, a dibenzofluorenylene group, a phenanthrenylene group, an anthracenylene group, a pyrenylene group, a chrysenylene group, a pyridinylene group, a pyrazinylene group, a pyrimidinylene group, a pyridazinylene group, a quinolinylene group, an isoquinolinylene group, a quinoxalinylene group, a quinazolinylene group, a carbazolylene group, and a triazinylene group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xa1 to xa3 may be each independently 0 or 1;

$R_{203}$, $R_{211}$, and $R_{212}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{213}$ and $R_{214}$ may be each independently selected from:

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

$R_{215}$ and $R_{216}$ may be each independently selected from:

a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, and a phosphoric acid group or a salt thereof;

a $C_1$-$C_{20}$ alkyl group and a $C_1$-$C_{20}$ alkoxy group;

a $C_1$-$C_{20}$ alkyl group and a $C_1$-$C_{20}$ alkoxy group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and xa5 may 1 or 2.

In Formulae 201A and 201A-1, $R_{213}$ and $R_{214}$ may, optionally, bind to each other (e.g., combine) to form a saturated or unsaturated ring.

The compound of 201 and the compound of 202 may include Compounds HT1 to HT20, but the present disclosure is not limited thereto.

HT1

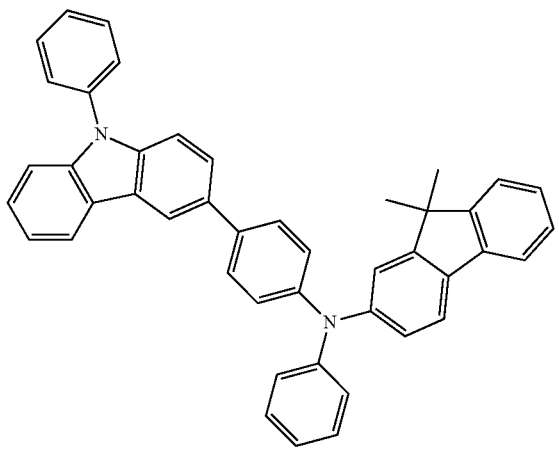

HT2

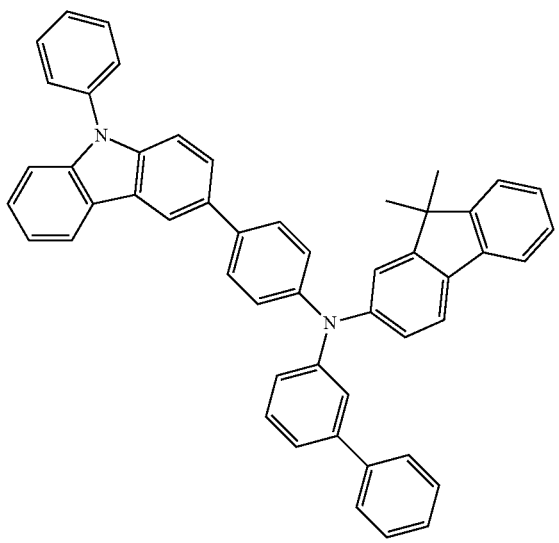

HT3

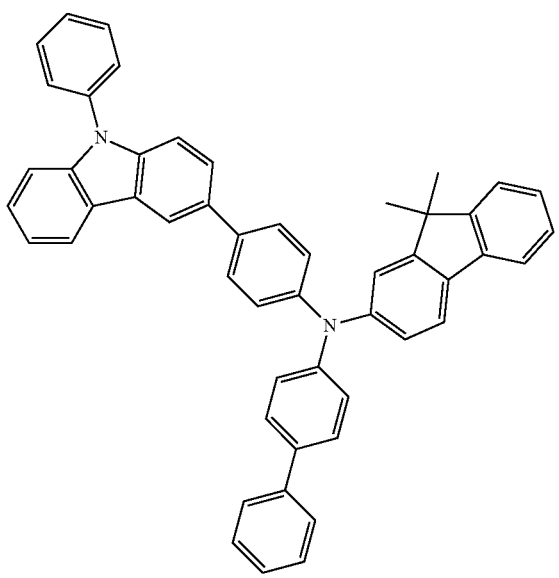

HT4
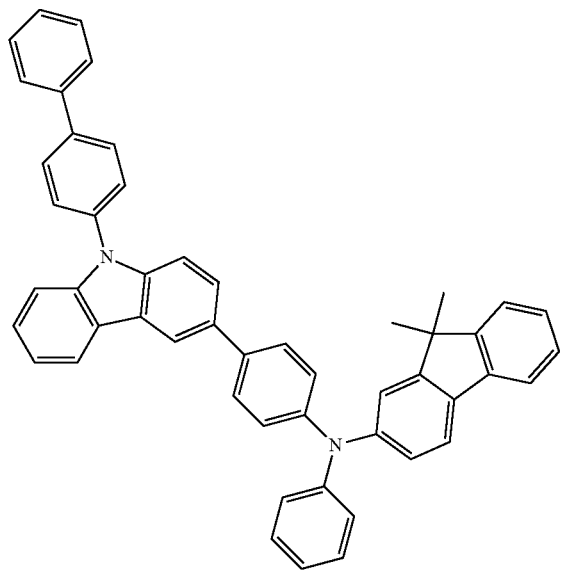
HT5
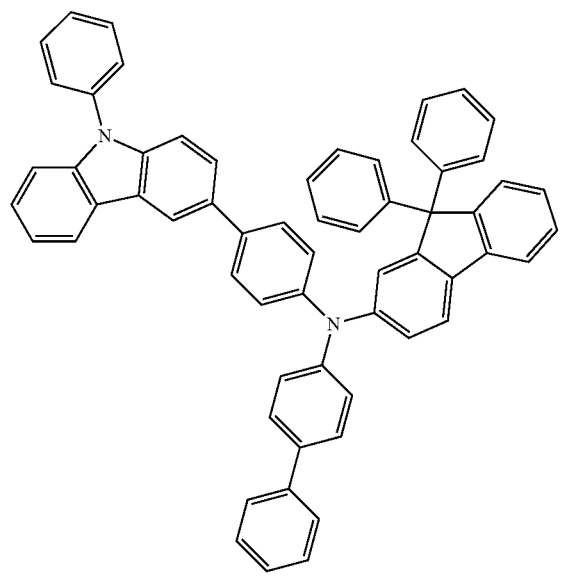
HT6
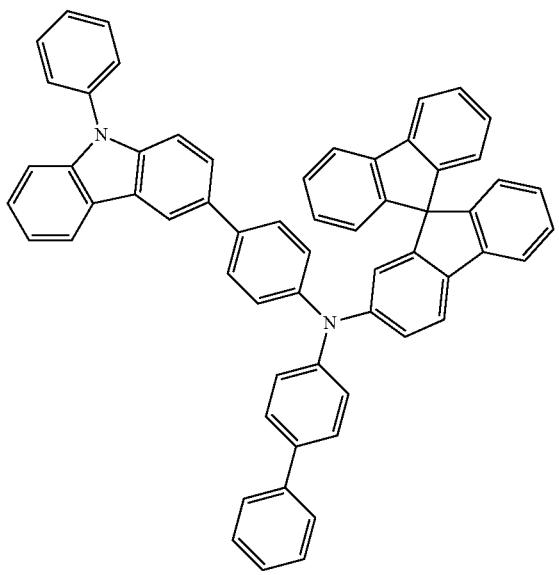
HT7
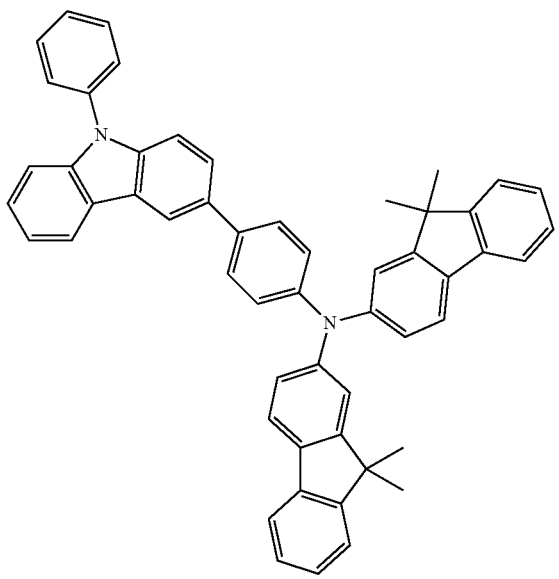

-continued
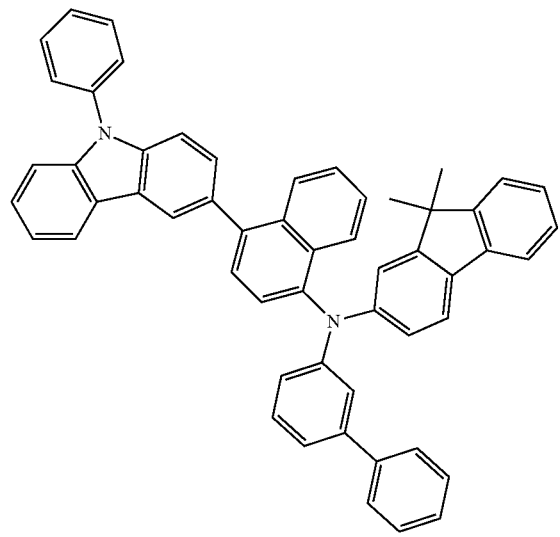
HT8
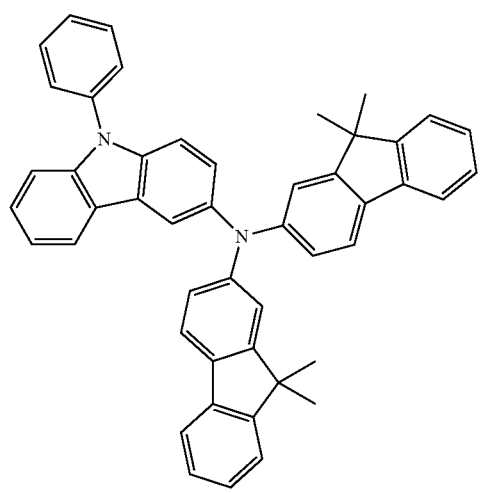
HT9
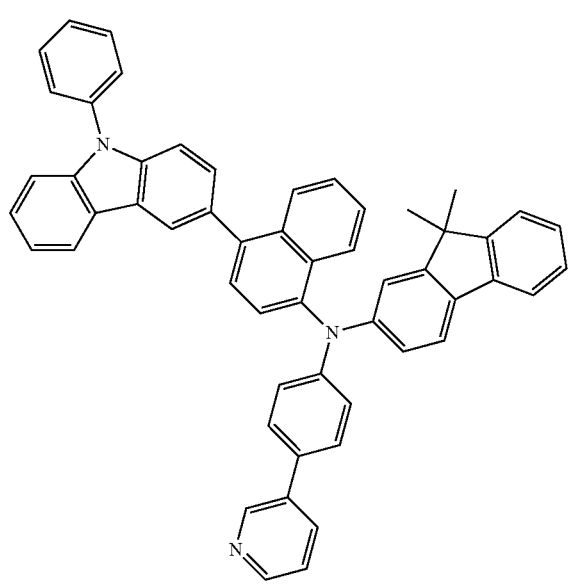
HT10
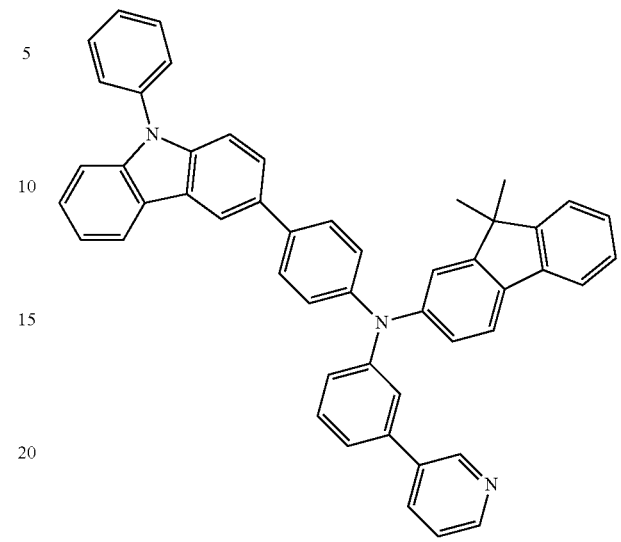
HT11
HT12
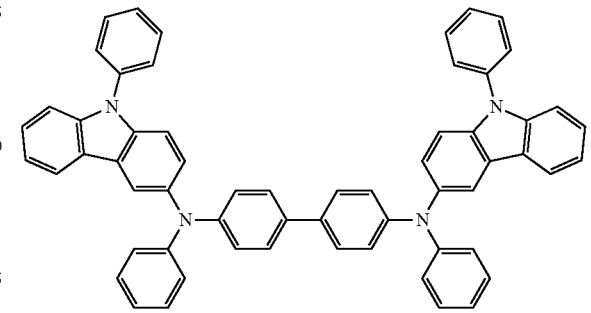
HT13

-continued

HT14
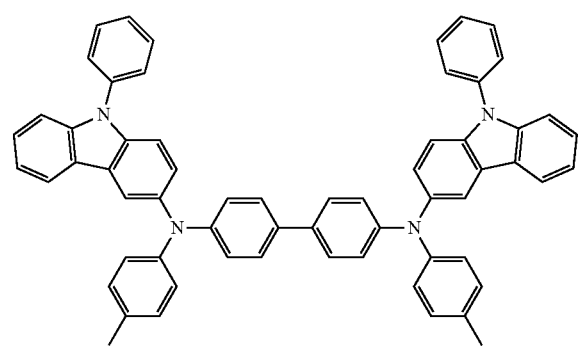

HT15
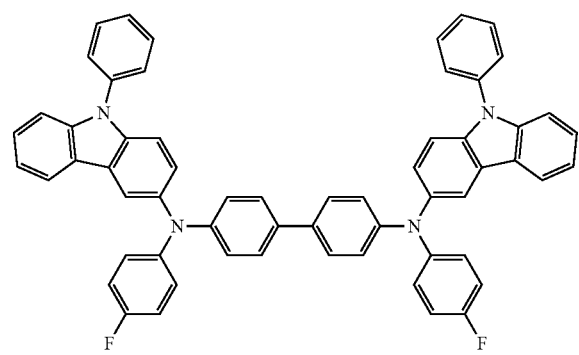

HT16
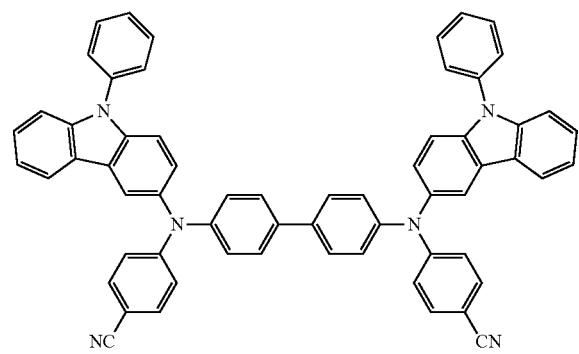

HT17
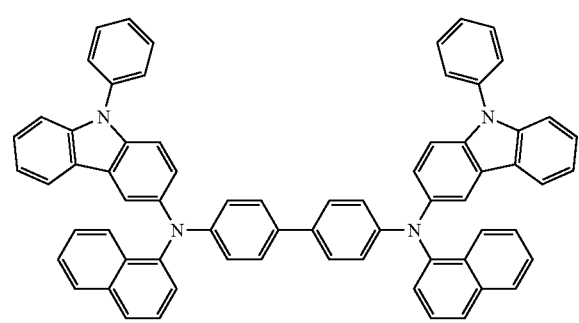

-continued

HT18
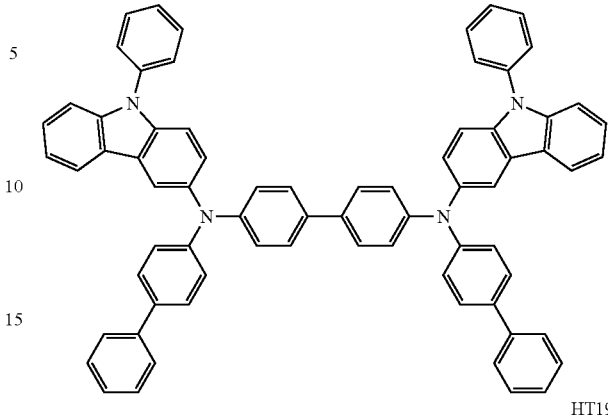

HT19
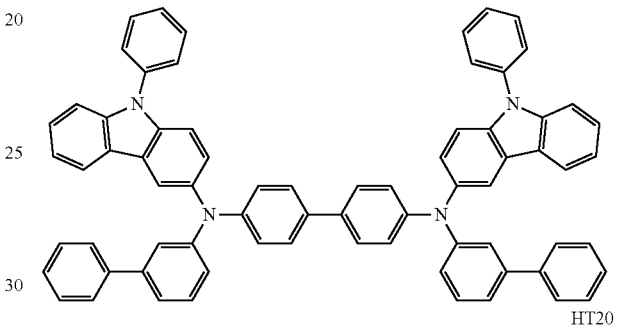

HT20
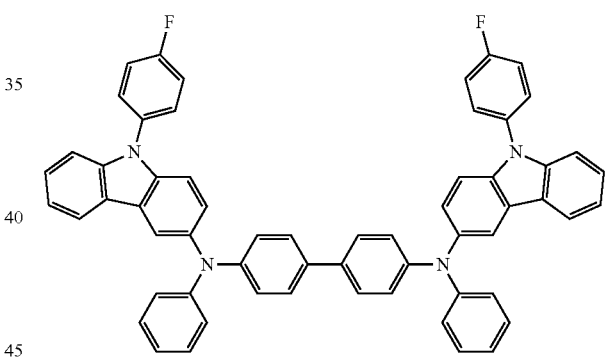

A thickness of the hole transport region may be in a range of about 100 Å to about 10,000 Å, for example, about 100 Å to about 1,000 Å. When the hole transport region includes a HIL and a HTL, a thickness of the HIL may be in a range of about 100 Å to about 10,000 Å, for example, about 100 Å to about 1,000 Å, and a thickness of the HTL may be in a range of about 50 Å to about 2,000 Å, for example, about 100 Å to about 1,500 Å. When the thicknesses of the hole transport region, the HIL, and the HTL are within any of the foregoing ranges, satisfactory hole transporting characteristics may be obtained without a substantial increase in driving voltage.

The hole transport region may further include, in addition to the foregoing materials, a charge-generation material for the improvement of conductive properties. The charge-generation material may be homogeneously or non-homogeneously dispersed in the hole transport region.

The charge-generation material may be, for example, a p-dopant. The p-dopant may be one of a quinone derivative, a metal oxide, and a cyano group-containing compound, but is not limited thereto. For example, non-limiting examples of the p-dopant include a quinone derivative, such as tetracyanoquinonedimethane (TCNQ) or 2,3,5,6-tetrafluoro-tetracyano-1,4-benzoquinonedimethane (F4-TCNQ); a metal oxide, such as a tungsten oxide or a molybdenum oxide, and HATCN, but are not limited thereto.

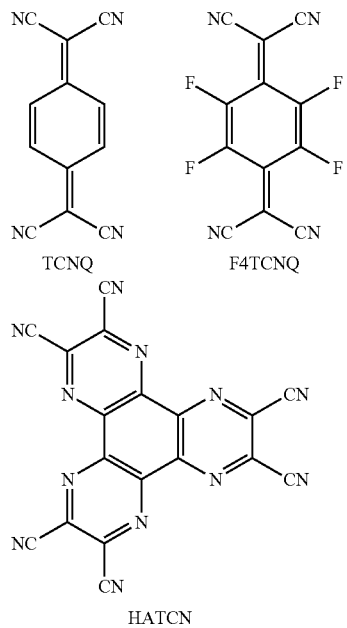

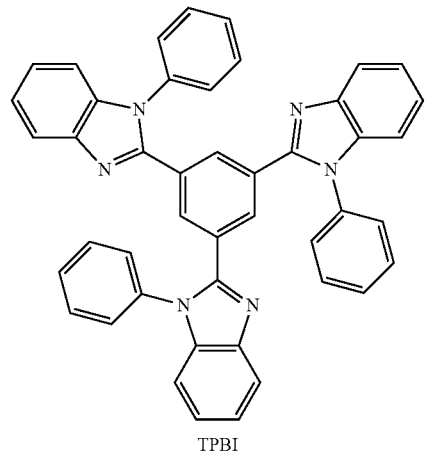

TPBI

The hole transport region may further include, in addition to the HIL and the HTL, at least one selected from a buffer layer and an EBL. The buffer layer may compensate for an optical resonance distance according to a wavelength of light emitted from the emission layer, and thus, a light-emission efficiency of a formed OLED may be improved. For use as a material of the buffer layer, materials of the hole transport region may be used (utilized). The EBL prevents (or reduces) injection of electrons from the electron transport region.

An emission layer is formed on the first electrode 13 or the hole transport region by using (utilizing) various suitable methods, such as vacuum deposition, spin coating, casting, an LB method, ink-jet printing, laser-printing, or LITI. When the emission layer is formed by vacuum deposition or spin coating, deposition and coating conditions for the emission layer may be determined by referring to the deposition and coating conditions described herein for the HIL.

When the OLED 10 is a full color OLED, the emission layer may be patterned into a red emission layer, a green emission layer, and a blue emission layer, according to a sub-pixel. In some embodiments, the emission layer may have a stacked structure of a red emission layer, a green emission layer, and a blue emission layer, or may include a red-light emission material, a green-light emission material, and a blue-light emission material, which are mixed with each other in a single layer, to emit white light.

The emission layer may include a host and a dopant.

The host may include at least one selected from the compound of Formula 1, TPBi, TBADN, ADN, CBP, CDBP, and TCP illustrated:

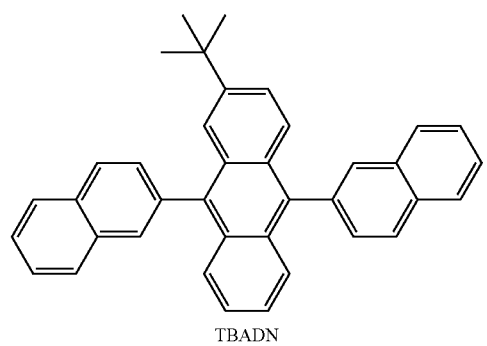

TBADN

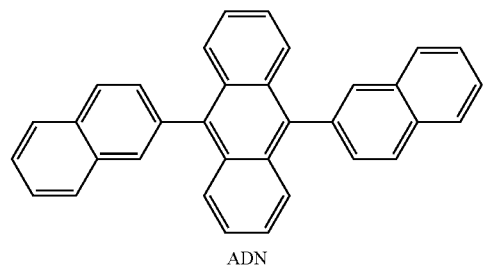

ADN

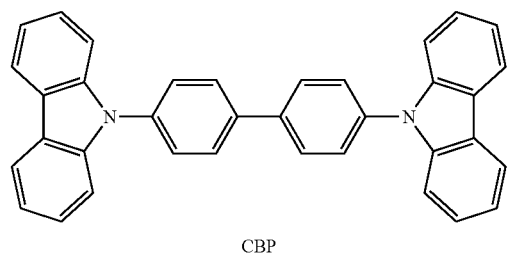

CBP

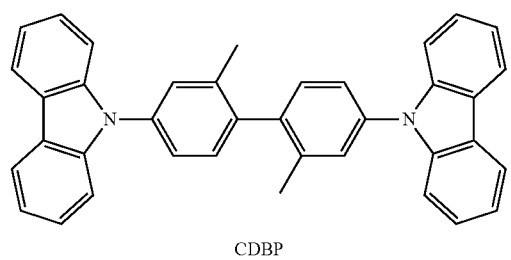

CDBP

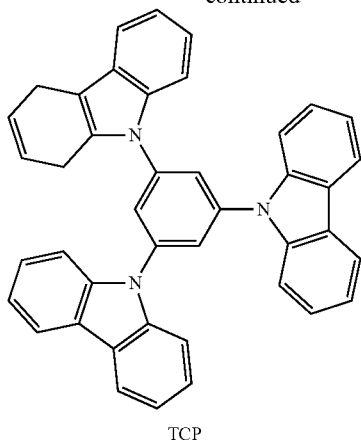

TCP

According to another embodiment of the present disclosure, the host may include a compound represented by Formula 301.

Ar$_{301}$-[(L$_{301}$)$_{xb1}$-R$_{301}$]$_{xb2}$    Formula 301 where in Formula 301, Ar$_{301}$ may be:

a naphthalene, a heptalene, a fluorenene, a spiro-fluorene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene;

a naphthalene, a heptalene, a fluorenene, a spiro-fluorene, a benzofluorenene, a dibenzofluorenene, a phenalene, a phenanthrene, an anthracene, a fluoranthene, a triphenylene, a pyrene, a chrysene, a naphthacene, a picene, a perylene, a pentaphene, and an indenoanthracene, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{60}$ alkyl group, a C$_2$-C$_{60}$ alkenyl group, a C$_2$-C$_{60}$ alkynyl group, a C$_1$-C$_{60}$ alkoxy group, a C$_3$-C$_{10}$ cycloalkyl group, a C$_3$-C$_{10}$ heterocycloalkyl group, a C$_3$-C$_{10}$ cycloalkenyl group, a C$_3$-C$_{10}$ heterocycloalkenyl group, a C$_6$-C$_{60}$ aryl group, a C$_6$-C$_{60}$ aryloxy group, a C$_6$-C$_{60}$ arylthio group, a C$_2$-C$_{60}$ heteroaryl group, a monovalent C$_2$-C$_{60}$ non-aromatic condensed polycyclic group, and —Si(Q$_{301}$)(Q$_{302}$)(Q$_{303}$) (where Q$_{301}$ to Q$_{303}$ may be each independently selected from a hydrogen atom, a C$_1$-C$_{60}$ alkyl group, a C$_2$-C$_{60}$ alkenyl group, a C$_6$-C$_{60}$ aryl group, and a C$_2$-C$_{60}$ heteroaryl group);

L$_{301}$ may be understood by referring to the description provided herein for L$_{201}$ with respect to Formulae 201 and 202;

R$_{301}$ may be selected from:
a C$_1$-C$_{20}$ alkyl group and a C$_1$-C$_{20}$alkoxy group;
a C$_1$-C$_{20}$ alkyl group and a C$_1$-C$_{20}$alkoxy group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbozoyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbozoyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xb1 may be selected from 0, 1, 2, and 3; and
xb2 may be selected from 1, 2, 3, and 4.

For example, in Formula 301
L$_{301}$ may be selected from:
a phenyl group, a naphthyl group, a fluorenyl group, a spiro-fluorenyl group, a benzofluorenyl group, a dibenzofluorenyl group, a phenanthrenylene group, an anthracenylene group, a pyrenylene group and a chrysenylene group; and a phenyl group, a naphthyl group, a fluorenyl group, a spiro-fluorenyl group, a benzofluorenyl group, a dibenzofluorenyl group, a phenanthrenylene group, an anthracenylene group, a pyrenylene group and a chrysenylene group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a C$_1$-C$_{20}$ alkyl group, a C$_1$-C$_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and R$_{301}$ may be selected from:
a C$_1$-C$_{20}$ alkyl group and a C$_1$-C$_{20}$ alkoxy group;
a C$_1$-C$_{20}$ alkyl group and a C$_1$-C$_{20}$alkoxy group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group;

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, and a chrysenyl group, but they are not limited thereto.

For example, the host may include a compound represented by Formula 301A:

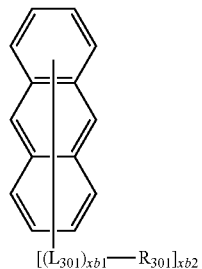

Formula 301A $[(L_{301})_{xb1}\text{—}R_{301}]_{xb2}$

Substituents of Formula 301A are as those described above with respect to Formula 301.

The compound of Formula 301 may include at least one selected from Compounds H1 to H42, but the present disclosure is not limited thereto:

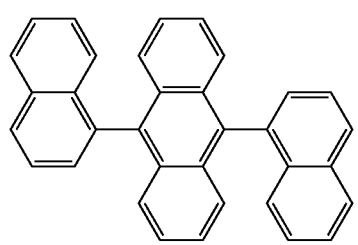

H1

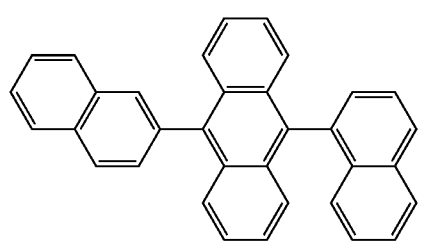

H2

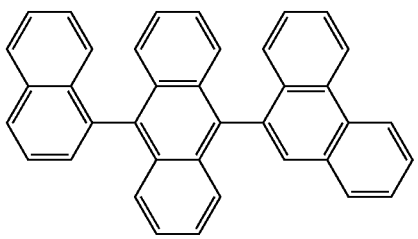

H3

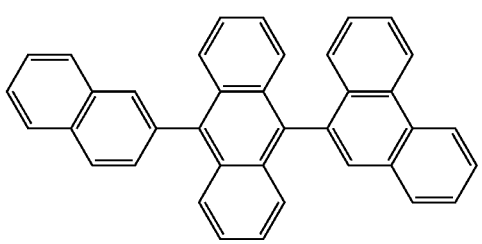

H4

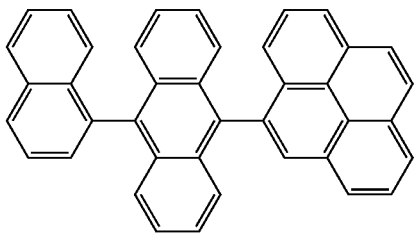

H5

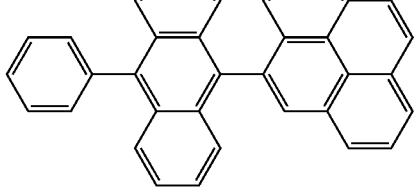

H6

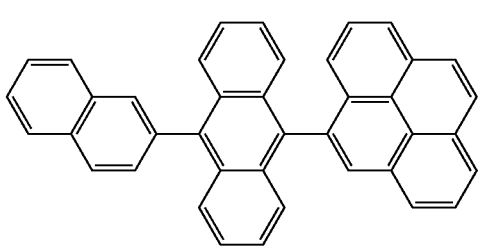

H7

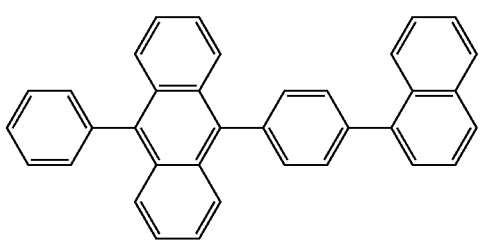

H8

-continued
H9
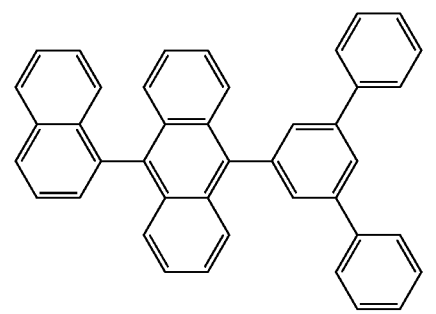
H10
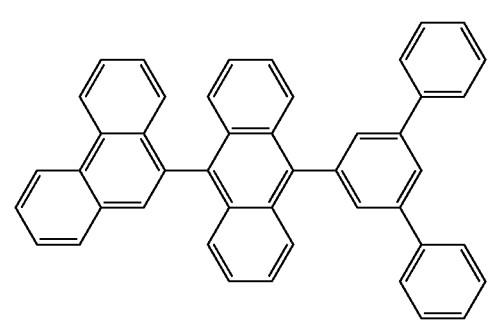
H11
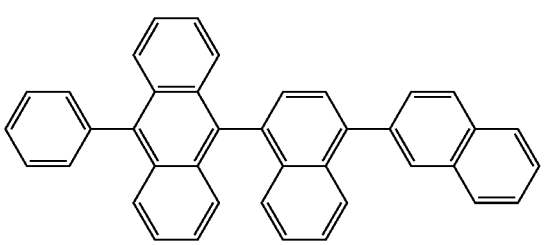
H12
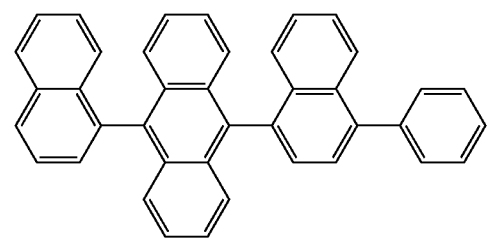
H13
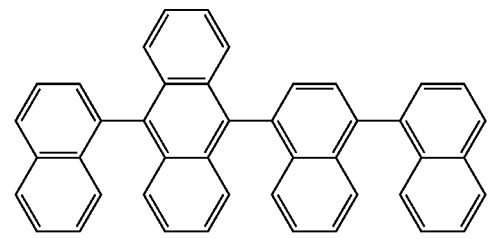
H14
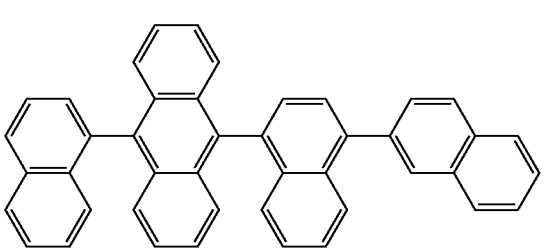
-continued
H15
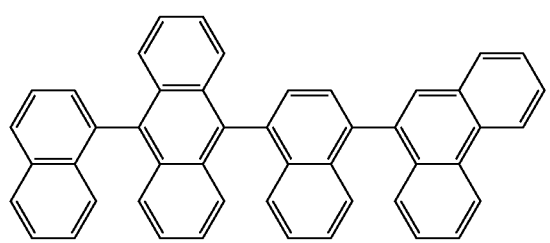
H16
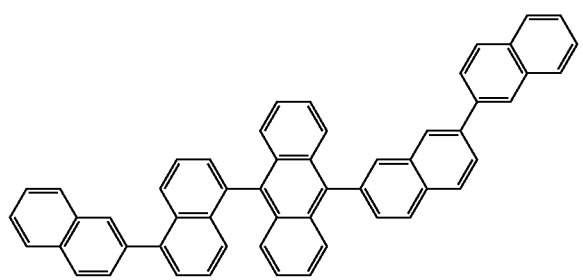
H17
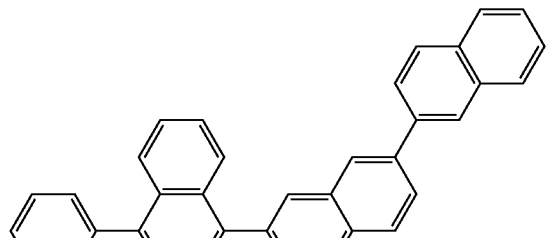
H18
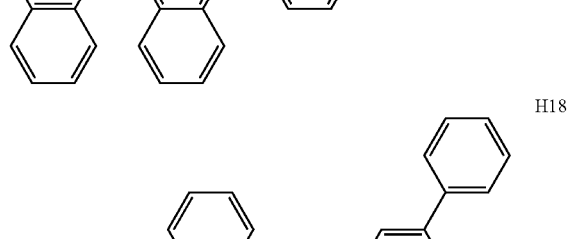
H19
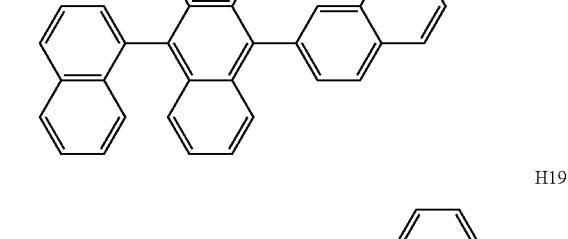
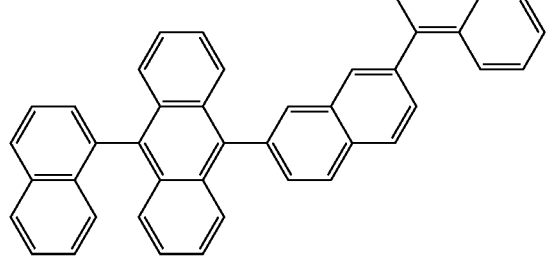

H20
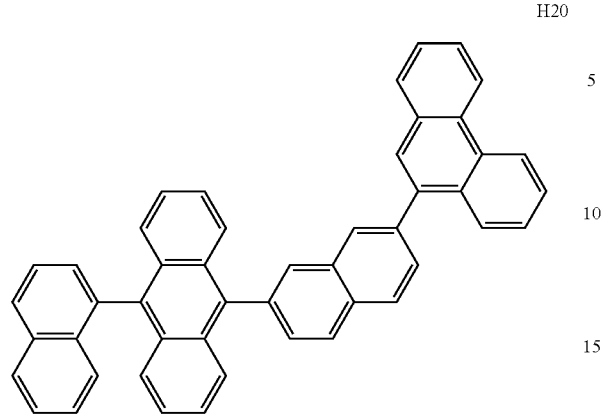
H21
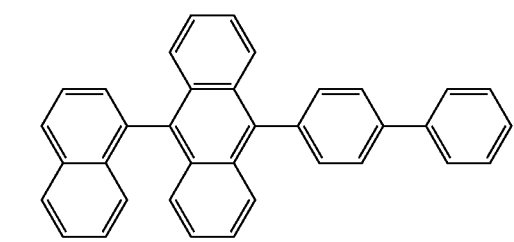
H22
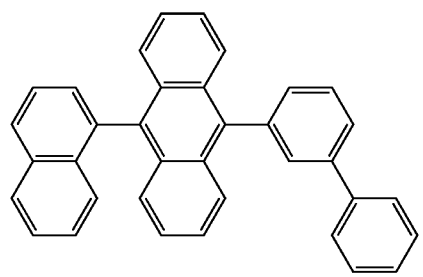
H23
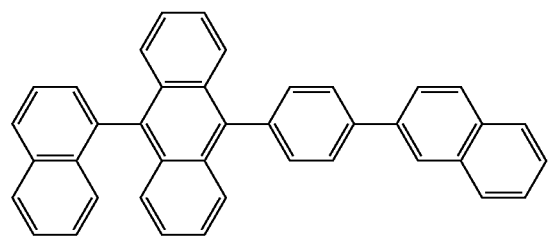
H24
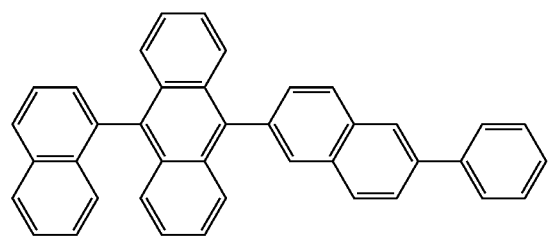
H25
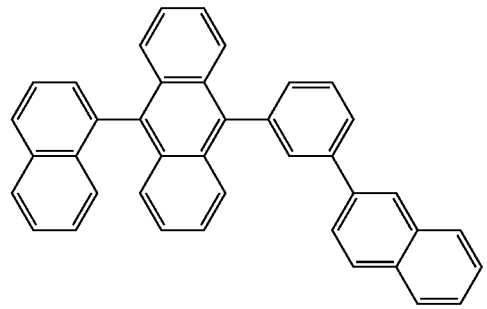
H26
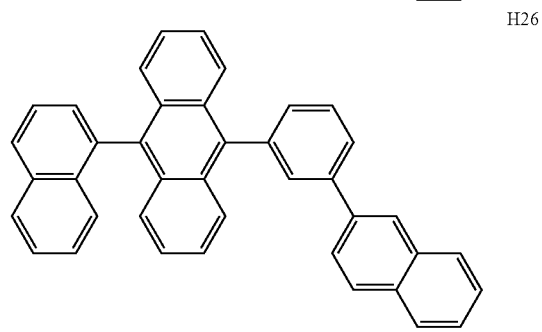
H27
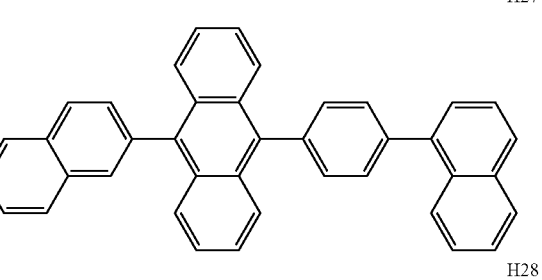
H28
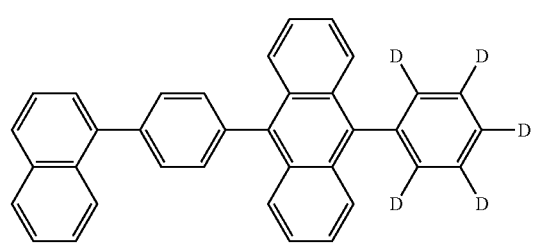
H29
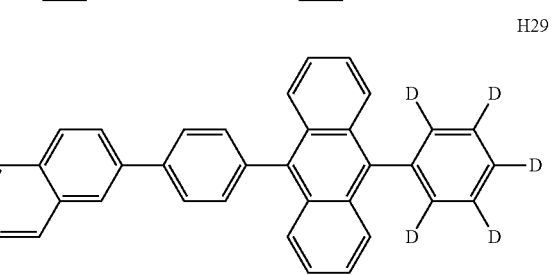
H30
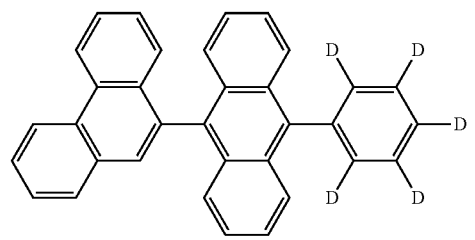

H31
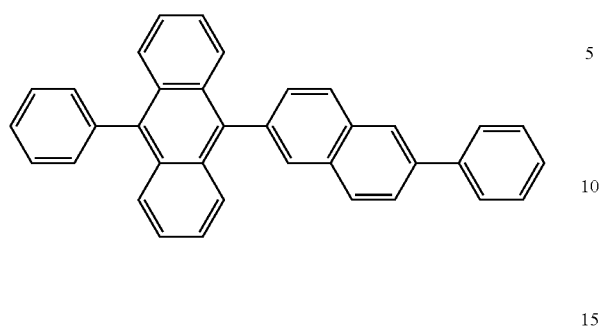
H32
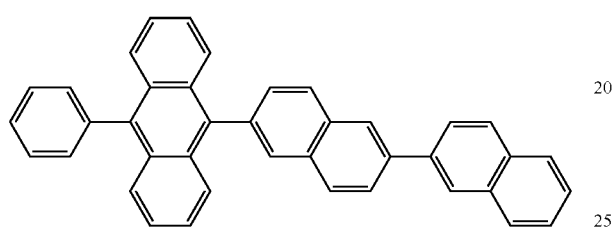
H33
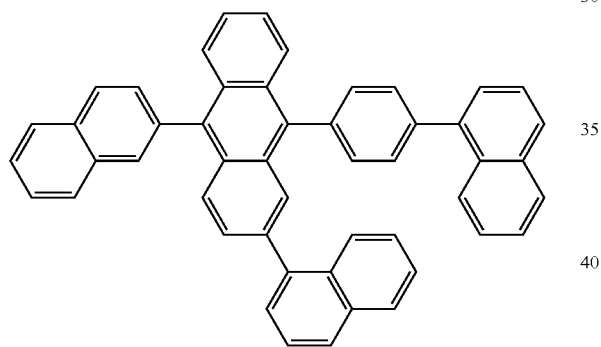
H34
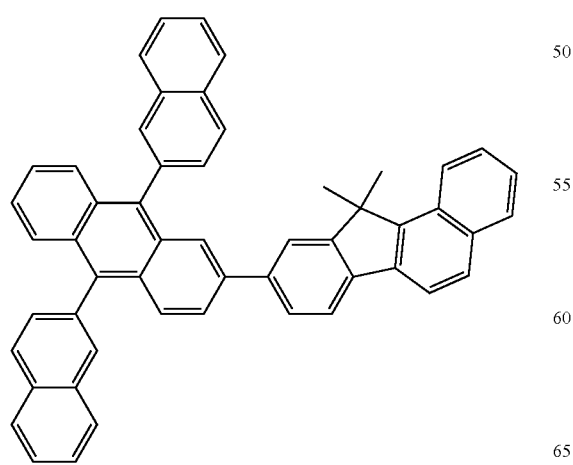
H35
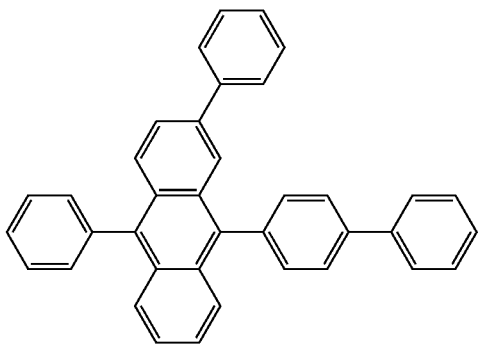
H36
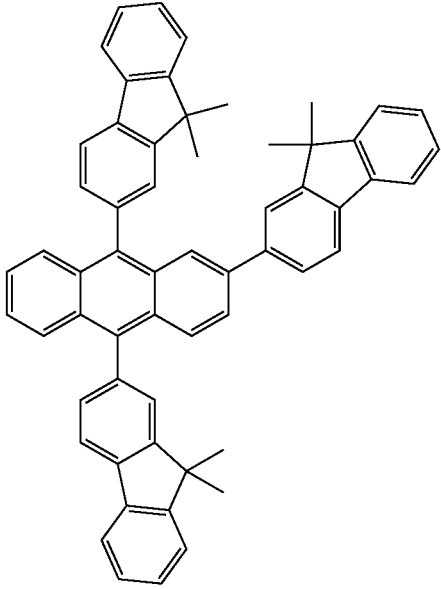
H37
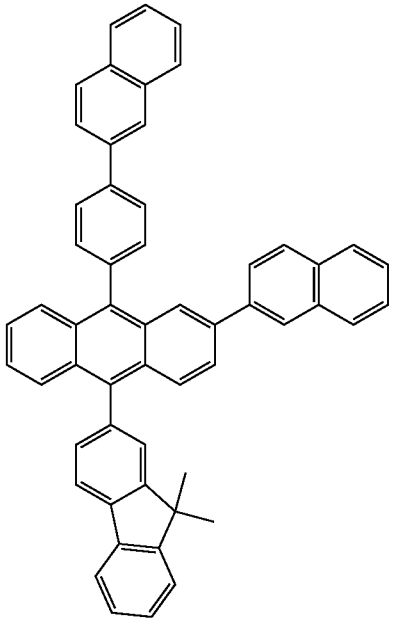

H38
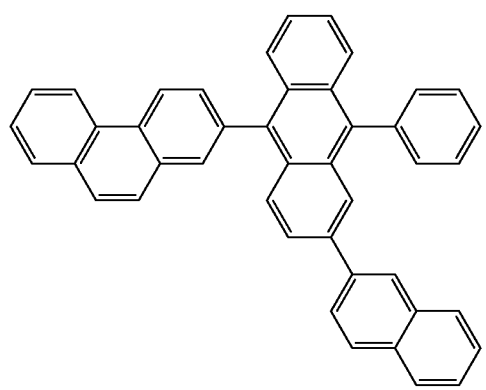
H39
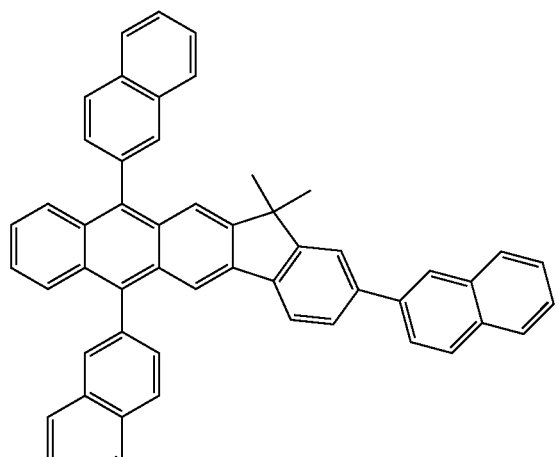
H40
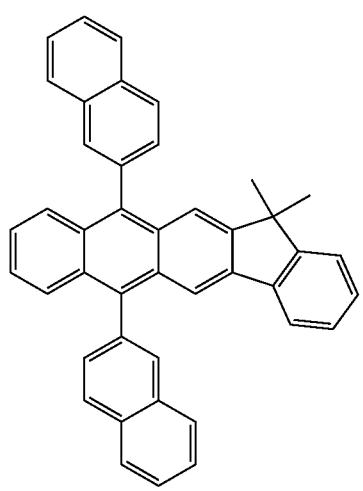
H41
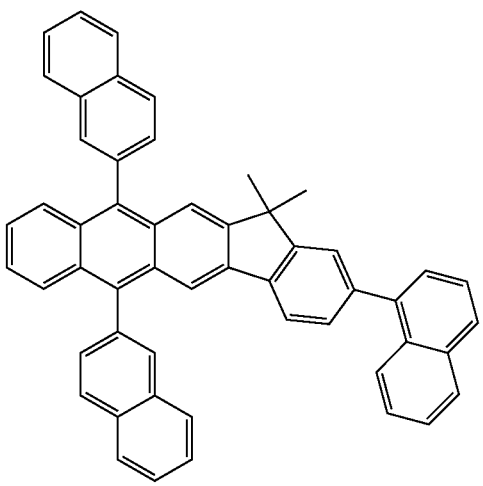
H42
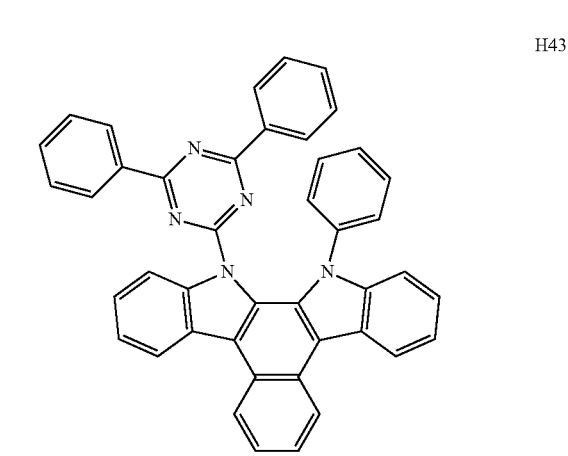
According to another embodiment of the present disclosure, the host may include at least one selected from Compounds H43 to H49, but the host is not limited thereto:
H43

H44

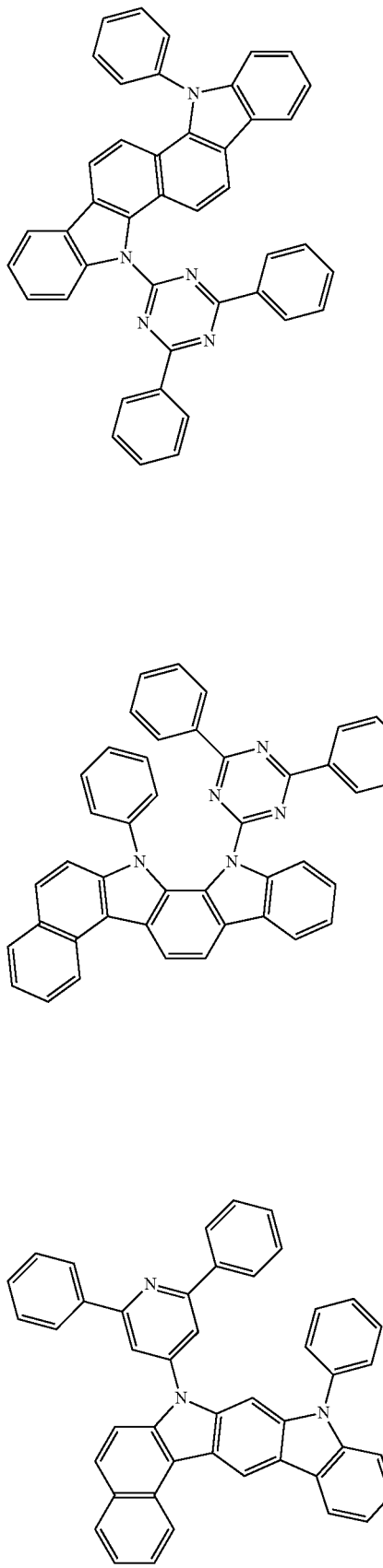

H45

H46

H47

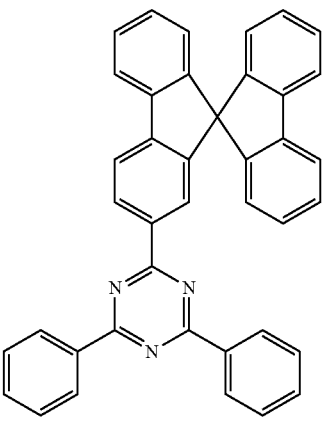

H48

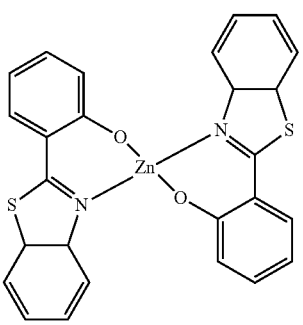

H49

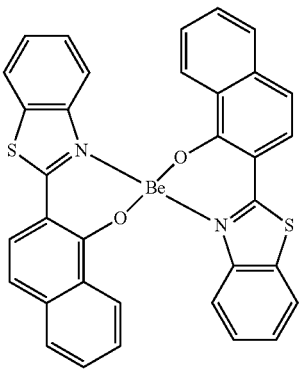

The dopant may be any suitable dopant generally used in the art. The dopant may include at least one selected from a fluorescent dopant and a phosphorescent dopant. The phosphorescent dopant may include an organometallic complex containing a combination of two or more of iridium (Ir), platinum (Pt), osmium (Os), rhenium (Re), titanium (Ti), zirconium (Zr), and hafnium (Hf), but the present disclosure is not limited thereto.

Meanwhile, as a suitable blue dopant, the following compounds, such as $F_2$Irpic bis[3,5-difluoro-2-(2-pyridyl)phenyl](picolinato)iridium (III), $(F_2ppy)_2$Ir(tmd), Ir(dfppz)$_3$, 4,4'-bis(2,2'-diphenylethen-1-yl)biphenyl (DPVBi), and 4,4'-bis[4-(diphenylamino)styryl]biphenyl (DPAVBi), or 2,5,8,11-tetra-tert-butyl perylene (TBPe) may be used, but the blue dopant is not limited thereto.

101
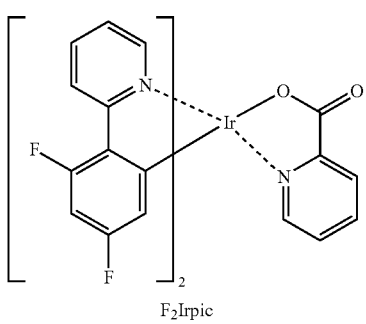
F₂Irpic
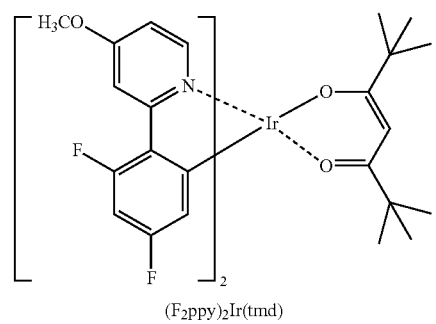
(F₂ppy)₂Ir(tmd)
102
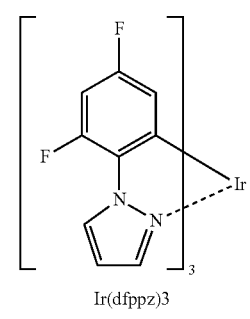
Ir(dfppz)3
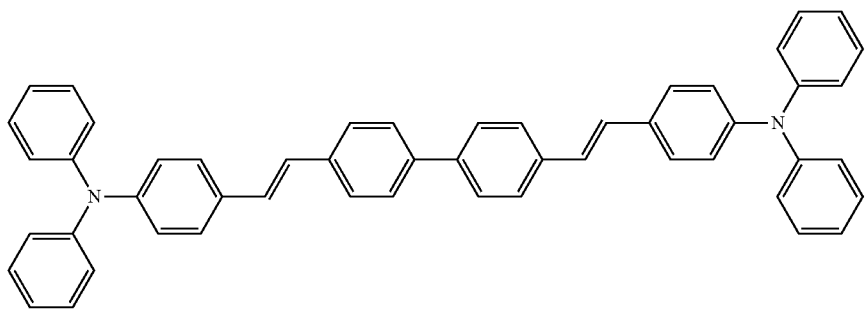
DPAVBi
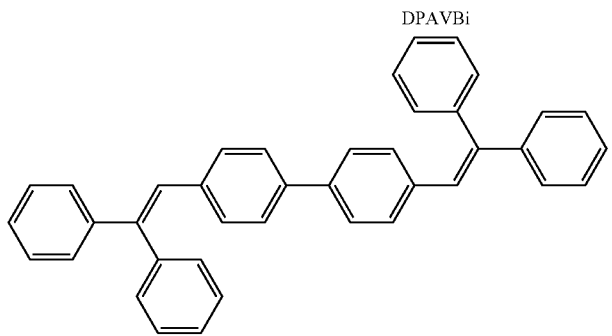
DPABi
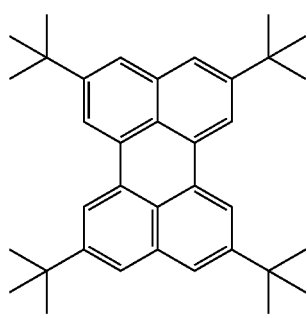
TPBe
In some embodiments, as a suitable blue dopant, any of the following compounds may be used, but the blue dopant is not limited thereto.
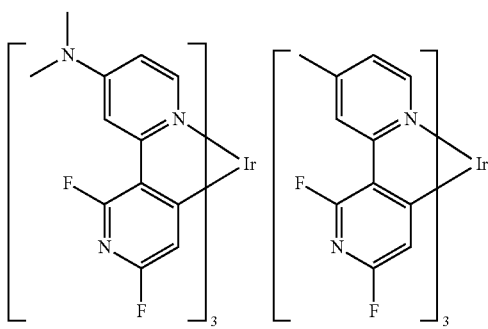
-continued
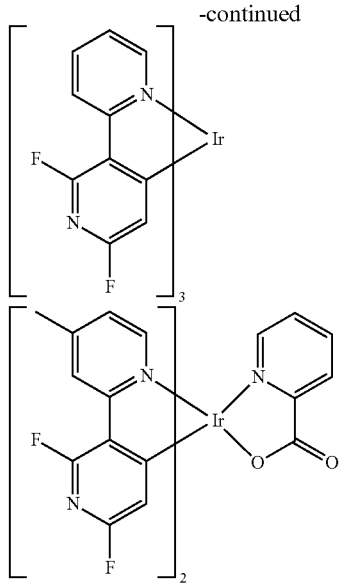

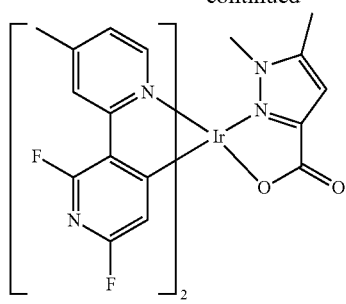

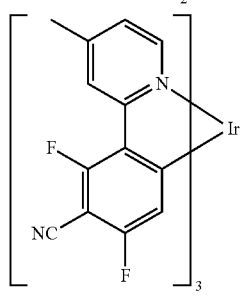

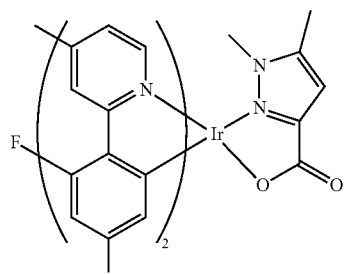

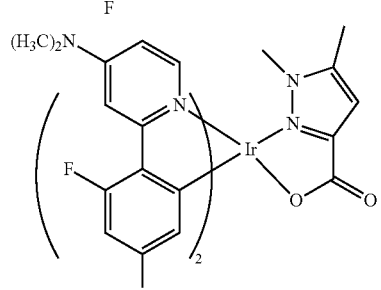

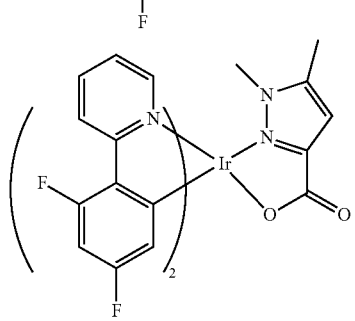

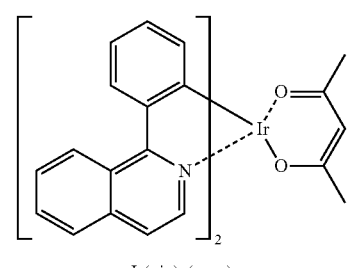

Ir(piq)₂(acac)

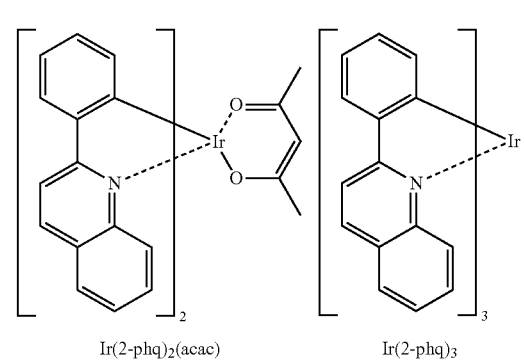

Ir(2-phq)₂(acac)　　　Ir(2-phq)₃

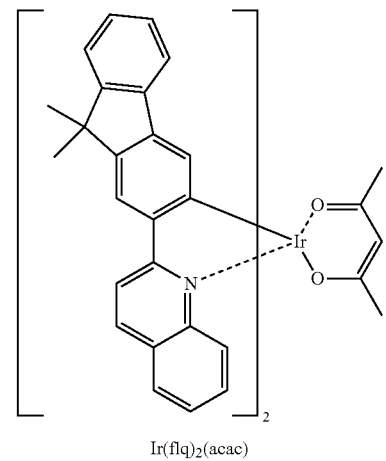

Ir(flq)₂(acac)

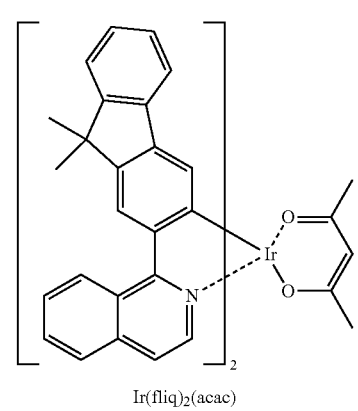

Ir(fliq)₂(acac)

Meanwhile, as a suitable red dopant, the following compounds, such as Pt(II) octaethylporphine (PtOEP), tris(2-phenylisoquinoline)iridium (Ir(piq)₃), bis(2-(2'-benzothienyl)-pyridinato-N,C3')iridium (acetylacetonate) (Btp₂Ir(acac), 4-(dicyanomethylene)-2-methyl-6-[p-(dimethylamino)styryl]-4H-pyran (DCM), or 4-(dicyanomethylene)-2-tert-butyl-6-(1,1,7,7,-tetramethyl-julolidyl-9-enyl)-4H-pyran (DCJTB), may be used, but the red dopant is not limited thereto.

-continued

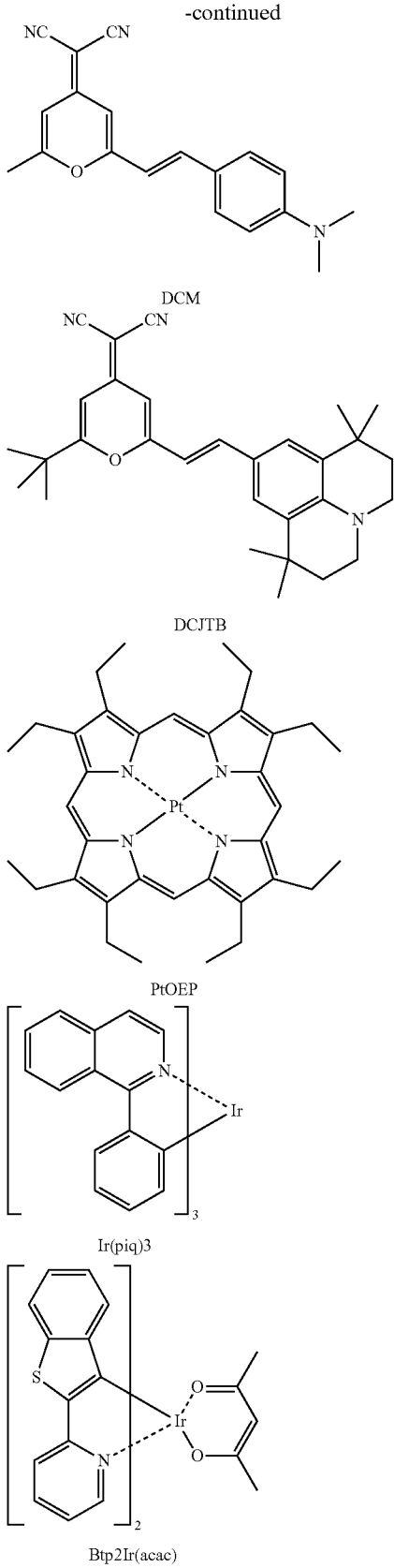

In some embodiments, as a suitable green dopant, the following compounds, such as tris(2-phenylpyridine) iridium (Ir(ppy)₃), bis(2-phenylpyridine)(acetylacetonato) iridium (III) (Ir(ppy)₂(acac)), tris(2-(4-tolyl)phenylpiridine) iridium (Ir(mppy)₃), or 10-(2-benzothiazolyl)-1,1,7,7-tetramethyl-2,3,6,7-tetrahydro-1H,5H,11H-[1]benzopyrano[6,7,81]-quinolizin-11-one (C545T), may be used, but the green dopant is not limited thereto.

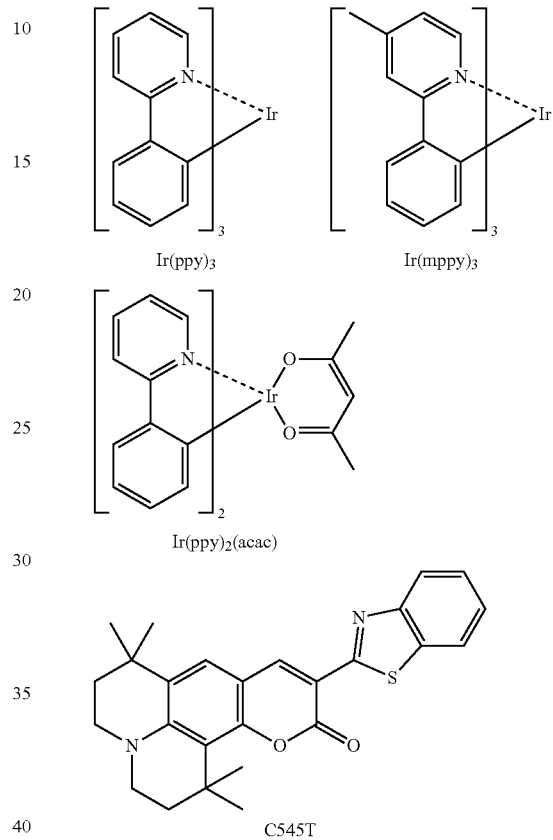

In some other embodiments, the dopant included in the emission layer may be any one of Pt-complexes D1-D50, but the dopant is not limited thereto:

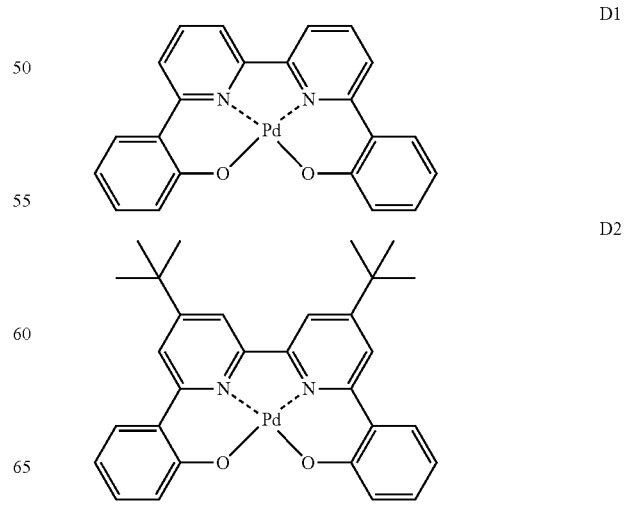

D3 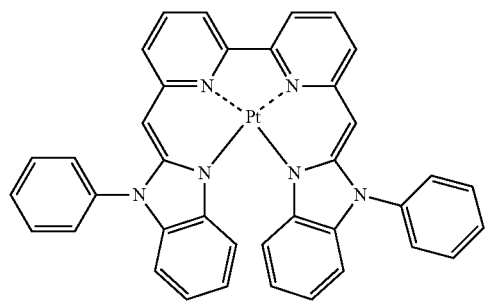
D4 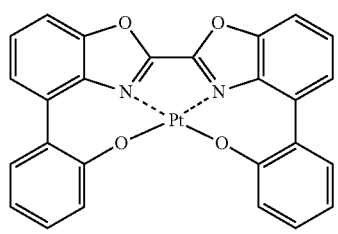
D5 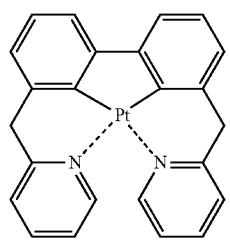
D6 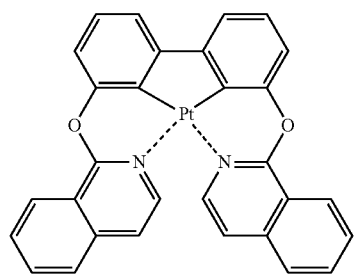
D7 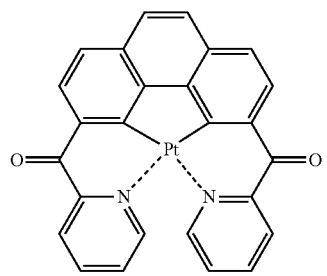
D8 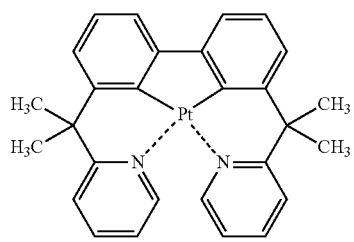
D9 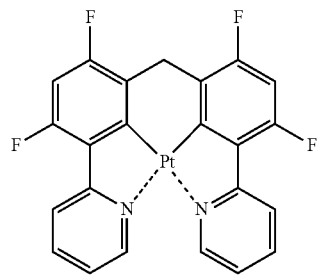
D10 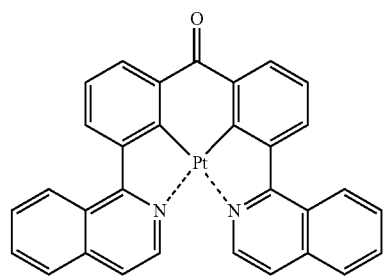
D11 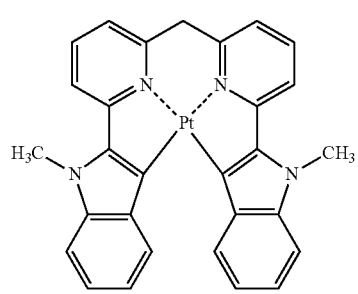
D12 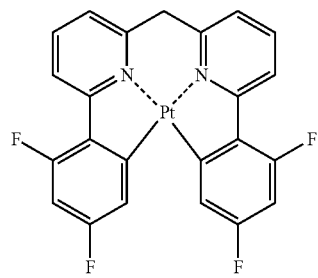
D13 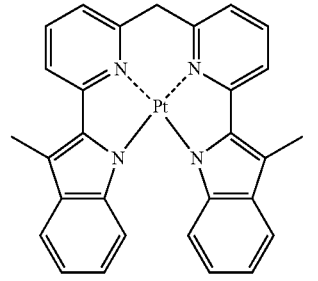

-continued
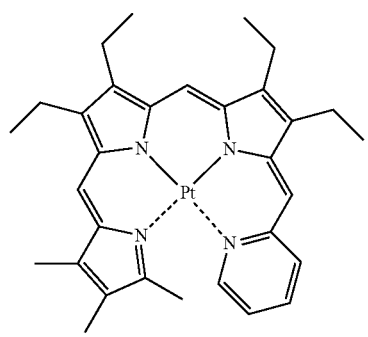
D14
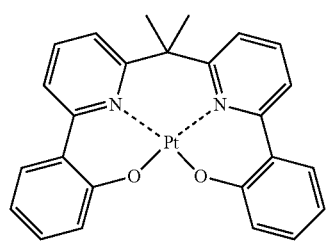
D15
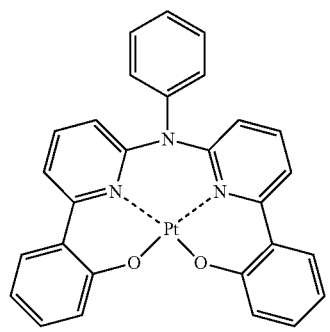
D16
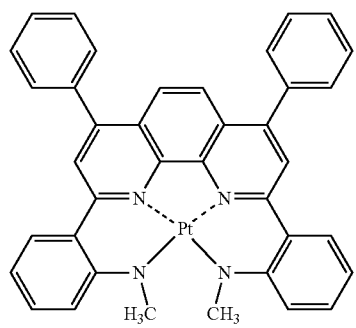
D17
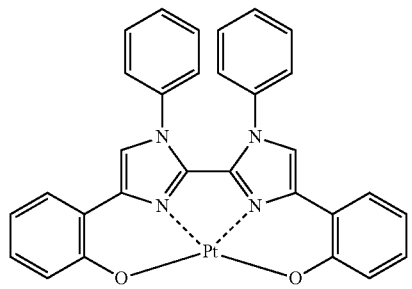
D18
-continued
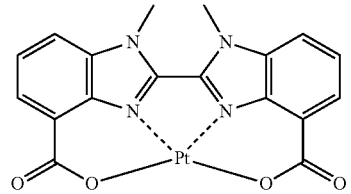
D19
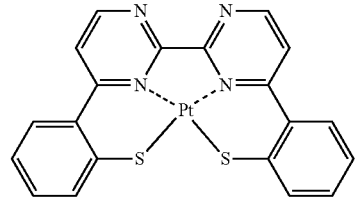
D20
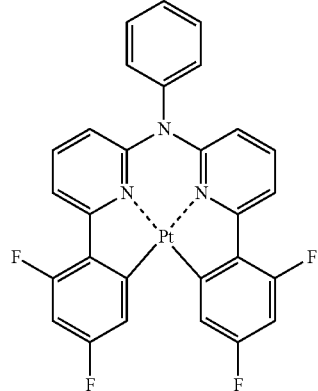
D21
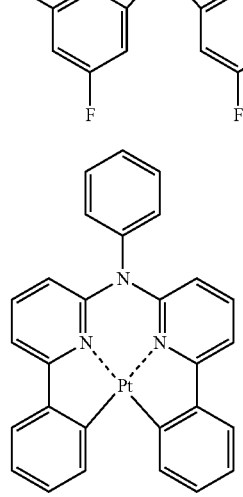
D22
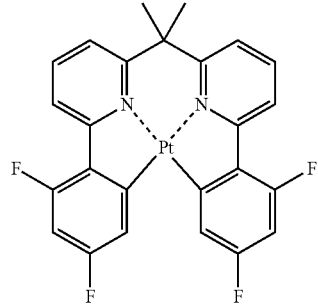
D23

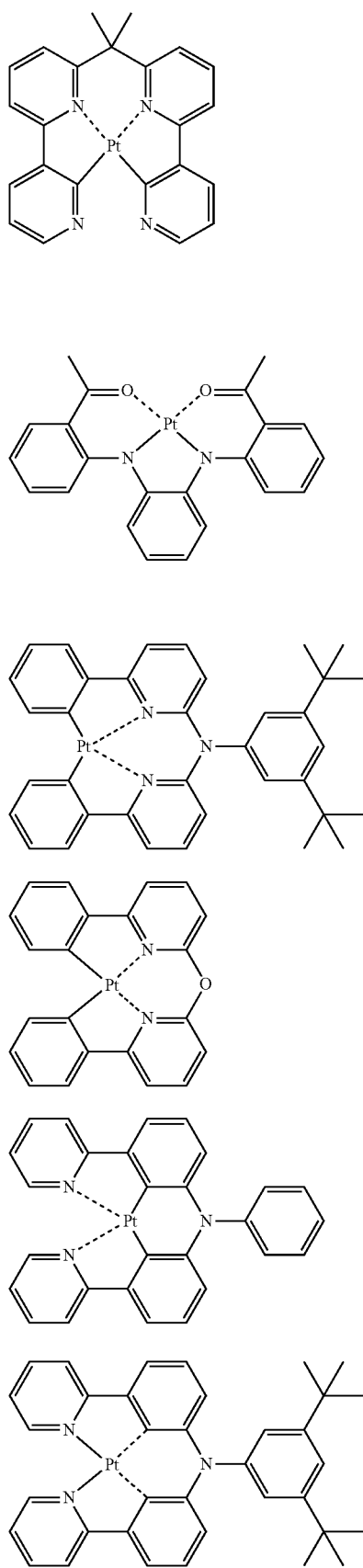
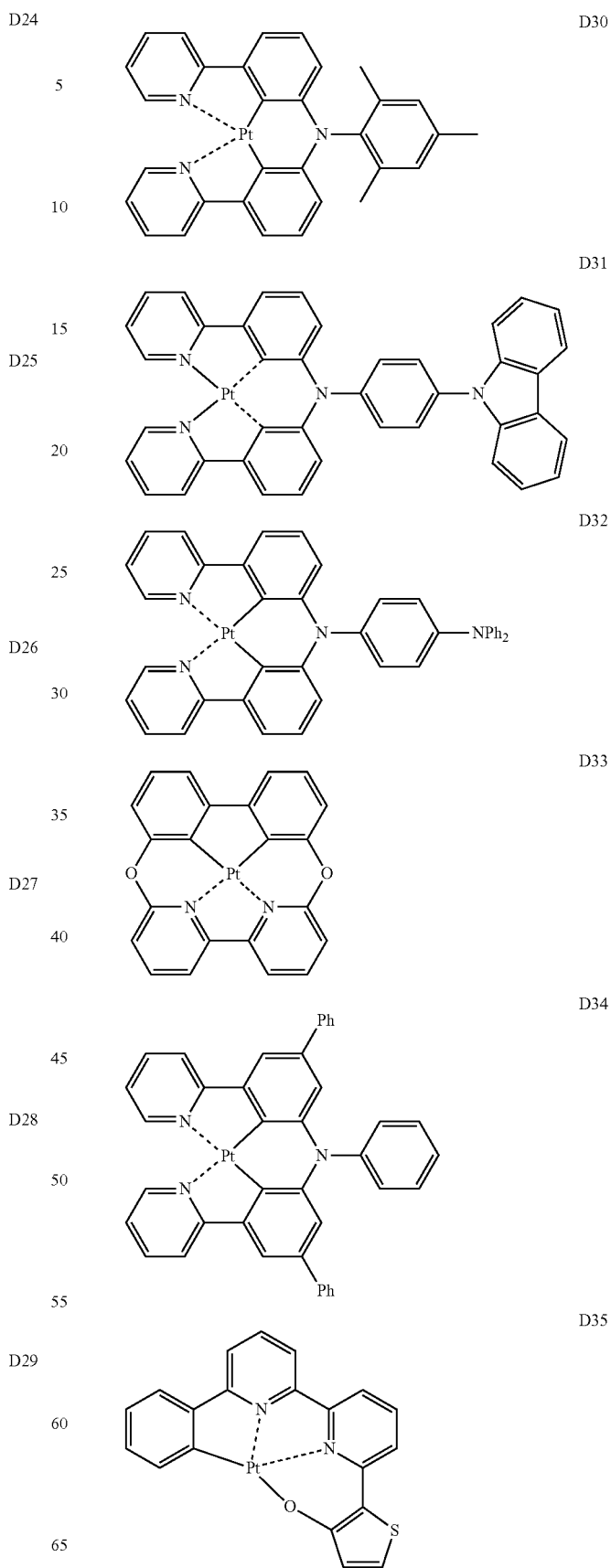

D36
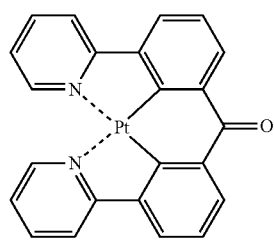
D37
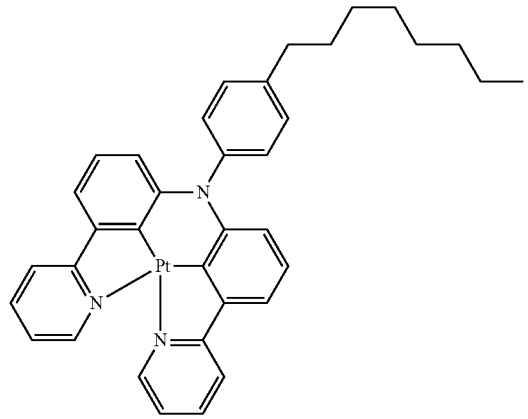
D38
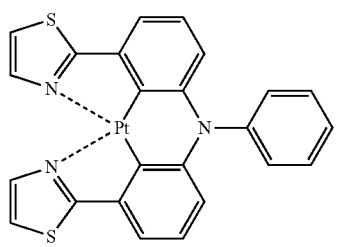
D39
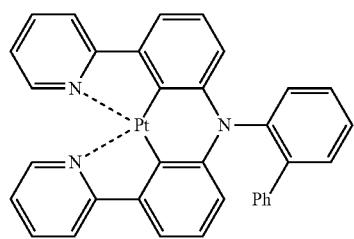
D40
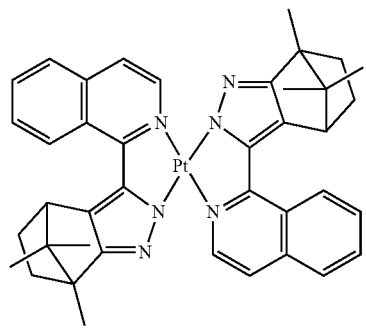
D41
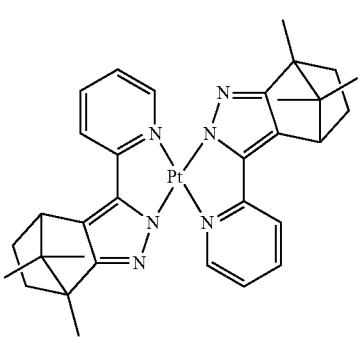
D42
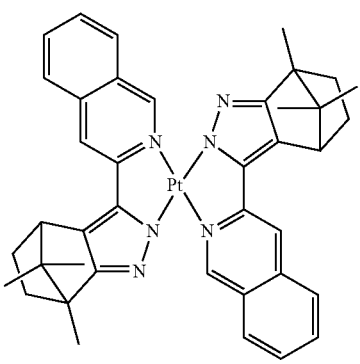
D43
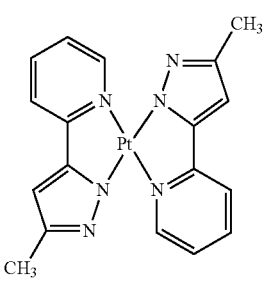
D44
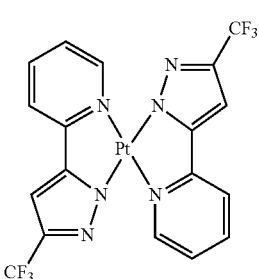
D45
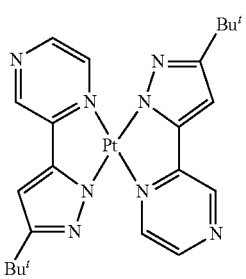

-continued
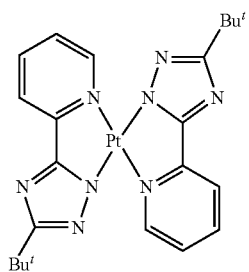
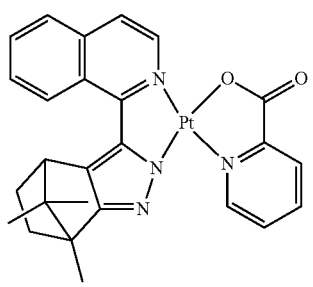
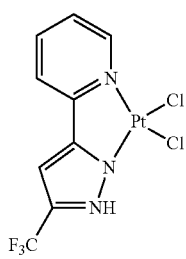
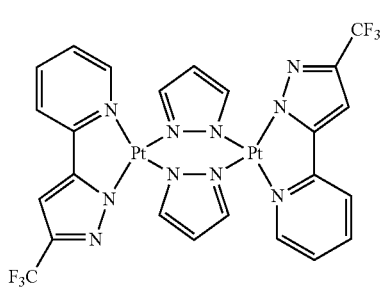
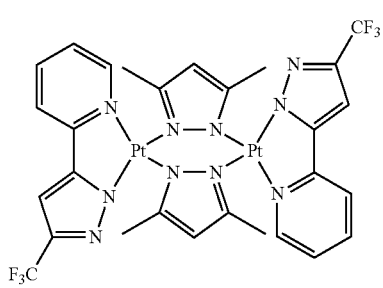
In addition, the dopant included in the emission layer may be any one of Os-complexes shown below, but the dopant is not limited thereto:
D46
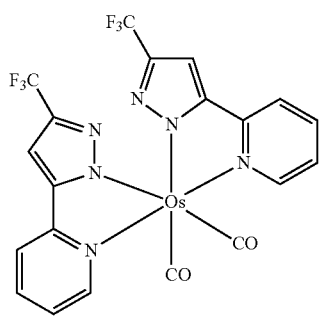
Os(fppz)$_2$(CO)$_2$
D47
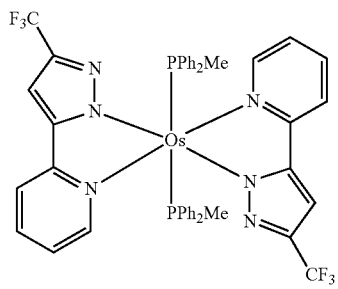
Os(fppz)$_2$(PPh$_2$Me)$_2$
D48
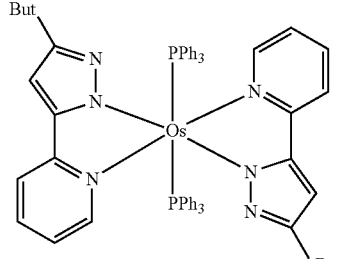
Os(bppz)$_2$(PPh$_3$)$_2$
D49
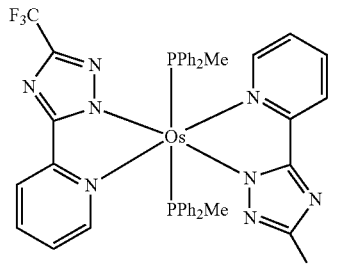
Os(fptz)$_2$(PPh$_2$Me)$_2$
D50
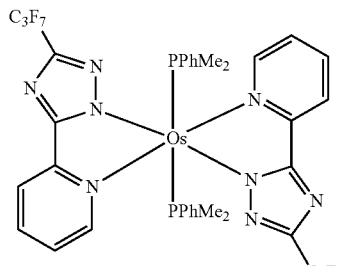
Os(hptz)$_2$(PPhMe$_2$)$_2$ An amount of the dopant in the emission layer may be, in general, in a range of about 0.01 to about 15 parts by weight based on 100 parts by weight of the host, but the dopant is not limited thereto.

A thickness of the emission layer may be in a range of about 100 Å to about 1,000 Å, for example, about 200 Å to about 600 Å. When the thickness of the emission layer is within any of the foregoing ranges, excellent light-emission characteristics may be obtained without a substantial increase in driving voltage.

Then, an electron transport region may be on the emission layer.

The electron transport region may include at least one selected from a HBL, an electron transport layer (ETL), and an EIL, but the electron transport region is not limited thereto.

For example, the electron transport region may have a structure of ETL/EIL or a structure of HBL/ETL/EIL, where layers of each structure are sequentially stacked from the emission layer in the stated order, but the electron transport region is not limited thereto.

According to an embodiment of the present disclosure, the organic layer 15 of the OLED includes an electron transport region between the emission layer and the second electrode 17, where the electron transport region includes the condensed cyclic compound of Formula 1.

The electron transport region may include a HBL. The HBL may be formed, when the emission layer includes a phosphorescent dopant, to prevent (or reduce) diffusion of excitons or holes into an electron transport layer.

When the electron transport region may include a HBL, the HBL may be formed on the emission layer by using various methods, such as vacuum deposition, spin coating casting, an LB method, ink-jet printing, laser-printing, or LITI. When the hole blocking layer is formed by vacuum deposition or spin coating, deposition and coating conditions for the HBL may be determined by referring to the deposition and coating conditions described herein with respect to the HIL.

The HBL may include, for example, at least one selected from BCP and Bphen, but the HBL is not limited thereto.

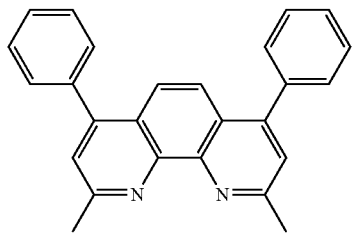

BCP

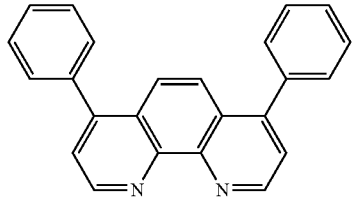

Bphen

A thickness of the HBL may be in a range of about 20 Å to about 1,000 Å, for example, about 30 Å to about 300 Å. When the thickness of the HBL is within any of the foregoing ranges, the HBL may have excellent hole blocking characteristics without a substantial increase in driving voltage.

The electron transport region may include an ETL. The ETL may be formed on the emission layer or the HBL by using various methods, such as vacuum deposition, spin coating casting, an LB method, ink-jet printing, laser-printing, or LITI. When an ETL is formed by vacuum deposition or spin coating, deposition and coating conditions for the ETL may be determined by referring to the deposition and coating conditions described herein with respect to the HIL.

The ETL may further include, in addition to the condensed cyclic compound of Formula 1, at least one selected from BCP, Bphen, and Alq$_3$, Balq, TAZ, and NTAZ, which are illustrated below.

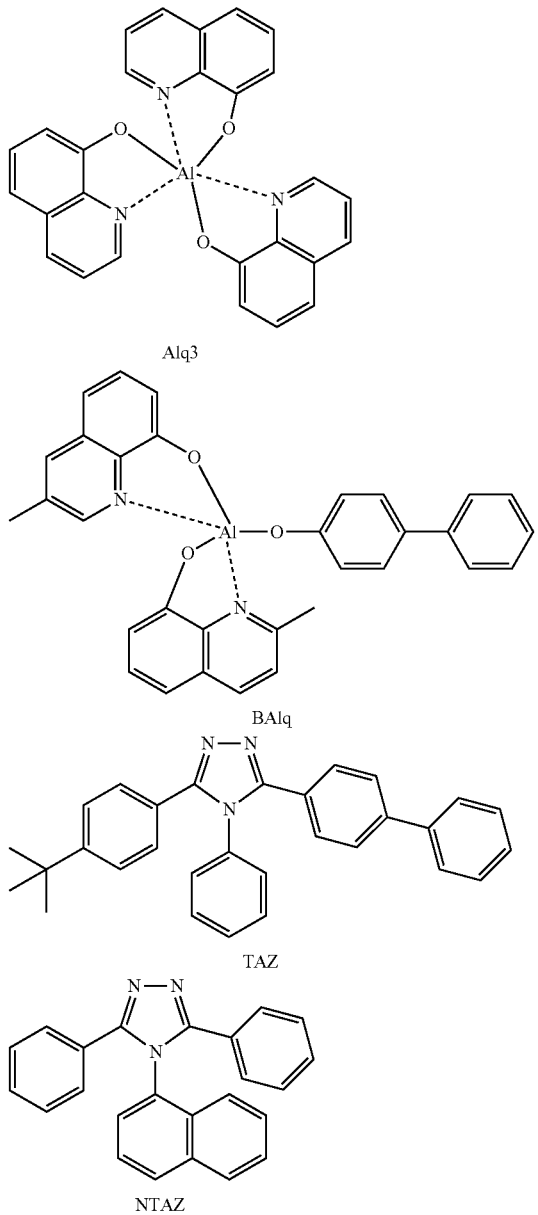

In some embodiments, the ETL may include at least one selected from compounds represented by Formula 601:

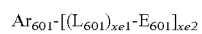

where in Formula 601,

Ar$_{601}$ may be may be understood by referring to the description provided herein for Ar$_{301}$ with respect to Formula 301;

$L_{601}$ may be may be understood by referring to the description provided herein for $L_{201}$ with respect to Formulae 201 and 202; and $E_{601}$ may be selected from a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group, a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a pentalenyl group, an indenyl group, a naphthyl group, an azulenyl group, a heptalenyl group, an indacenyl group, an acenaphthyl group, a fluorenyl group, a spiro-fluorenyl group, a benzofluorenyl group, a dibenzofluorenyl group, a phenalenyl group, a phenanthrenyl group, an anthracenyl group, a fluoranthenyl group, a triphenylenyl group, a pyrenyl group, a chrysenyl group, a naphthacenyl group, an picenyl group, a perylenyl group, a pentaphenyl group, a hexacenyl group, a pentacenyl group, a rubicenyl group, a coronenyl group, an ovalenyl group, a pyrrolyl group, a thiophenyl group, a furanyl group, an imidazolyl group, a pyrazolyl group, a thiazolyl group, an isothiazolyl group, an oxazolyl group, an isoxazolyl group, a pyridinyl group, a pyrazinyl group, a pyrimidinyl group, a pyridazinyl group, an isoindolyl group, an indolyl group, an indazolyl group, a purinyl group, a quinolinyl group, an isoquinolinyl group, a benzoquinolinyl group, a phthalazinyl group, a naphthyridinyl group, a quinoxalinyl group, a quinazolinyl group, a cinnolinyl group, a carbazolyl group, a phenanthridinyl group, an acridinyl group; a phenanthrolinyl group, a phenazinyl group, a benzoimidazolyl group, a benzofuranyl group, a benzothiophenyl group, an isobenzothiazolyl group, a benzooxazolyl group, an isobenzooxazolyl group, a triazolyl group, a tetrazolyl group, an oxadiazolyl group, a triazinyl group, a dibenzofuranyl group, a dibenzothiophenyl group, a benzocarbazolyl group, and a dibenzocarbazolyl group; and xe1 may be selected from 0, 1, 2, and 3;

xe2 may be selected from 1, 2, 3, and 4.

In some other embodiments, the ETL may include at least one compound represented by Formula 602:

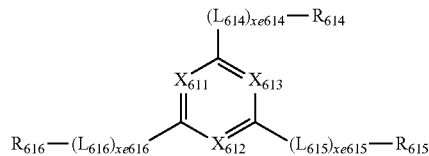

Formula 602 where in Formula 602, $X_{611}$ may be N or C-$(L_{611})_{xe611}$-$R_{611}$, $X_{612}$ may be N or C-$(L_{612})_{xe612}$-$R_{612}$, $X_{613}$ may be N or C-$(L_{613})_{xe613}$-$R_{613}$, at least one of $X_{611}$ to $X_{613}$ may be N; and $L_{611}$ to $L_{616}$ may be each understood by referring to a detailed description thereof provided herein for $L_{201}$ with respect to Formulae 201 and 202;

$R_{611}$ to $R_{616}$ may be each independently selected from:

a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group; and a phenyl group, a naphthyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{20}$ alkyl group, a $C_1$-$C_{20}$ alkoxy group, a phenyl group, a naphthyl group, an azulenyl group, a fluorenyl group, a spiro-fluorenyl group, a benzofluorenyl group, a dibenzofluorenyl group, a phenanthrenyl group, an anthracenyl group, a pyrenyl group, a chrysenyl group, a pyridinyl group, a pyrazinyl group, a pyrimidinyl group, a pyridazinyl group, a quinolinyl group, an isoquinolinyl group, a quinoxalinyl group, a quinazolinyl group, a carbazolyl group, and a triazinyl group;

xe611 to xe616 may be each independently selected from 0, 1, 2, and 3.

The compound of Formula 601 and the compound of Formula 602 may include at least one selected from Compounds ET1 to ET15.

ET1
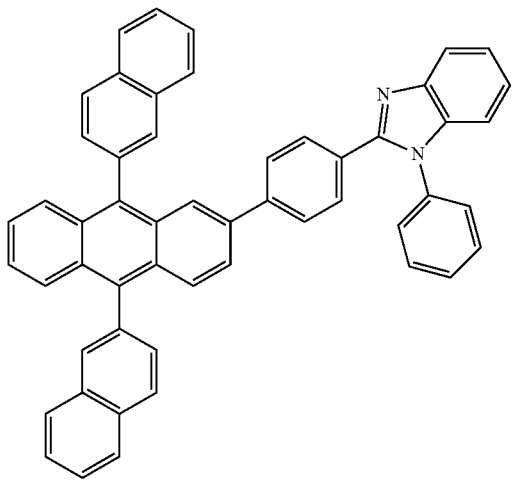
ET2
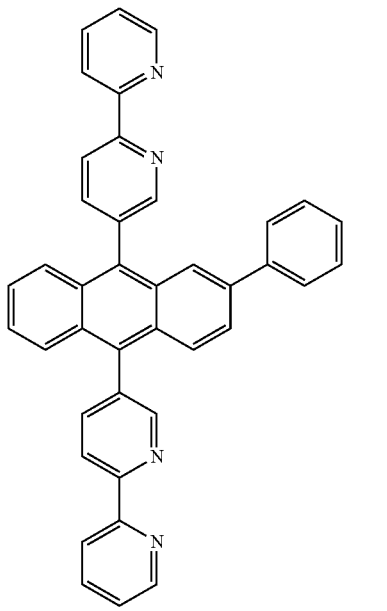
ET3
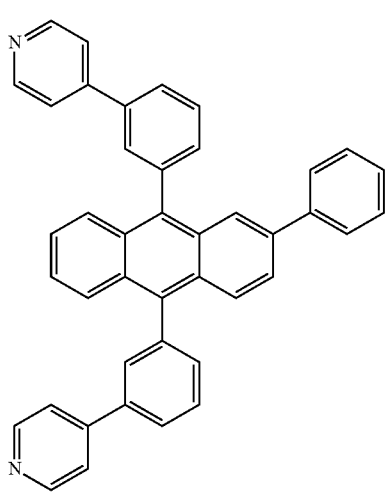
ET4
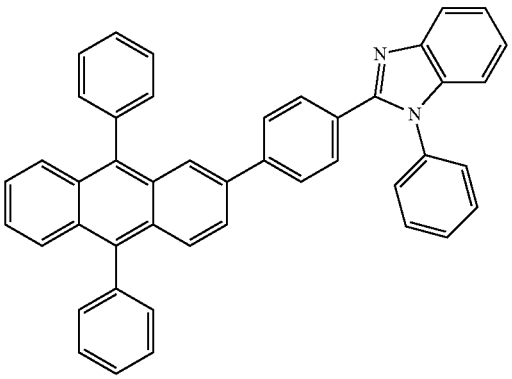
ET5
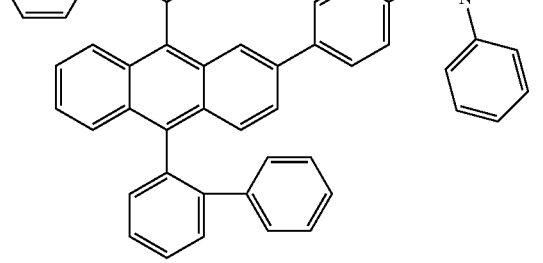
ET6
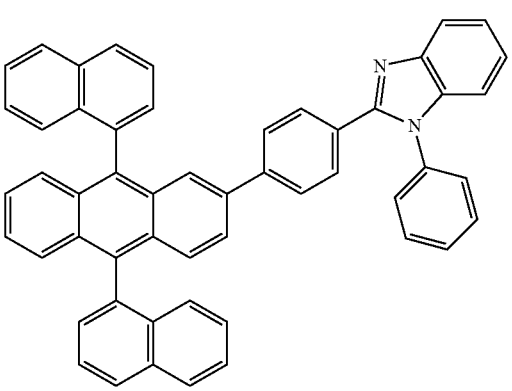

ET7
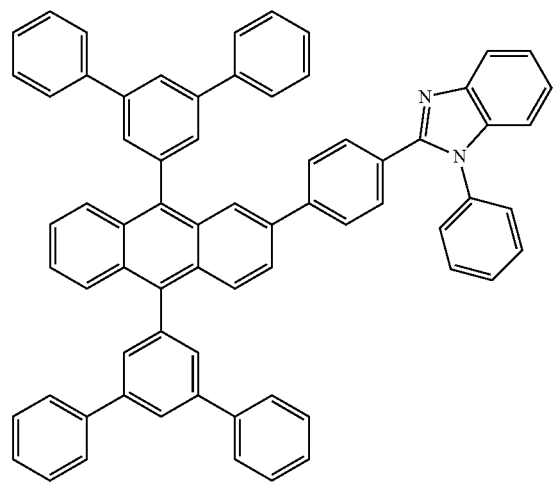
ET8
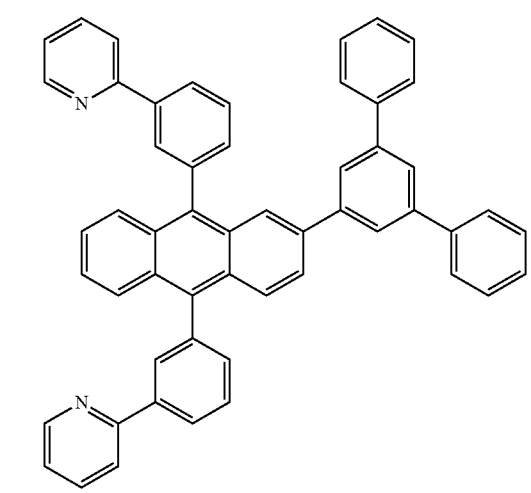
ET9
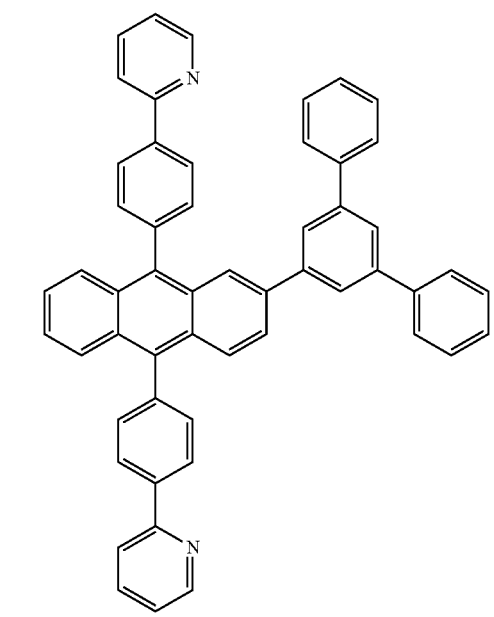
ET10
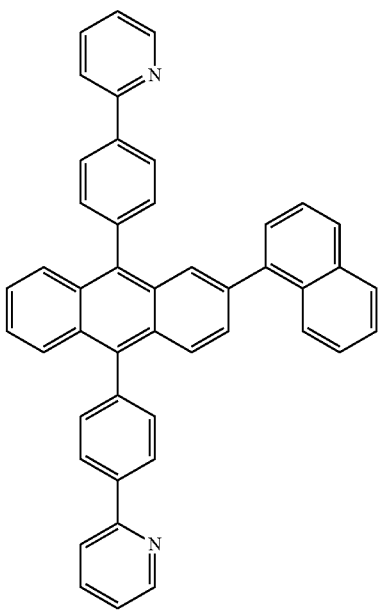
ET11
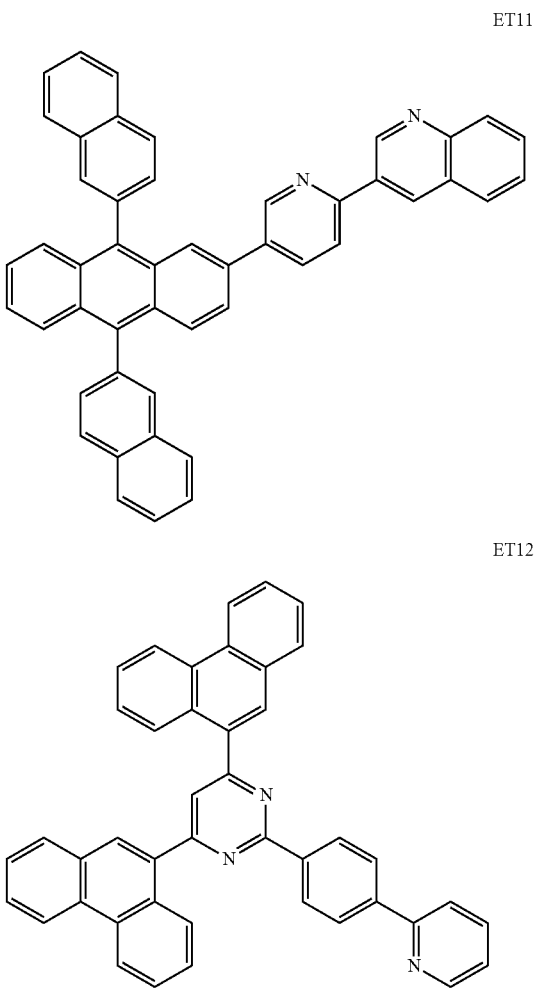
ET12
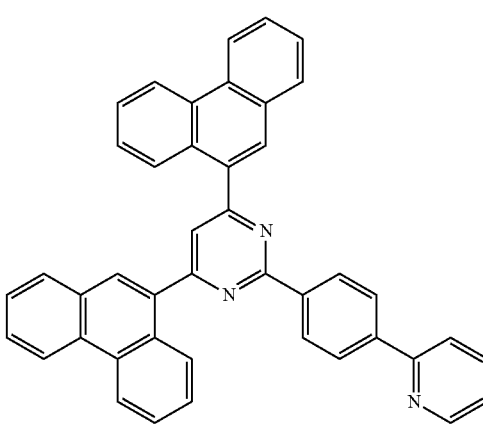

-continued

ET13

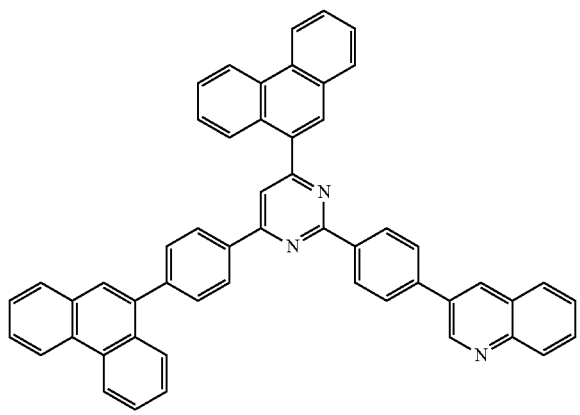

ET14

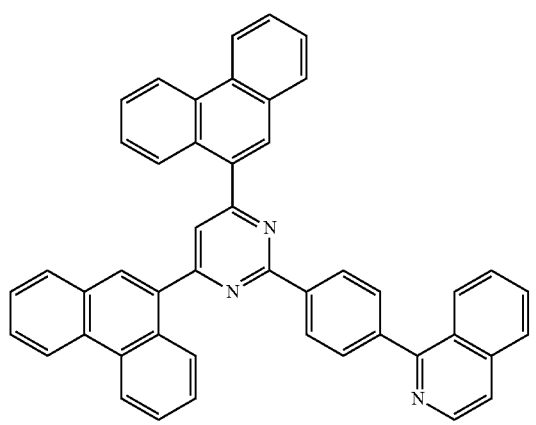

ET15

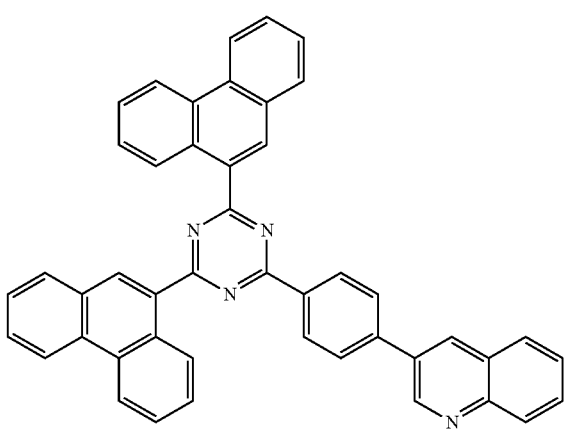

A thickness of the ETL may be in a range of about 100 Å to about 1,000 Å, for example, about 150 Å to about 500 Å. When the thickness of the ETL is within any of the foregoing ranges, the ETL may have satisfactory electron transportation characteristics without a substantial increase in driving voltage.

The ETL may further include, in addition to the materials described above, a metal-containing material.

The metal-containing material may include a Li complex. The Li complex may include, for example, Compound ET-D1 (lithium quinolate, LiQ) or ET-D2.

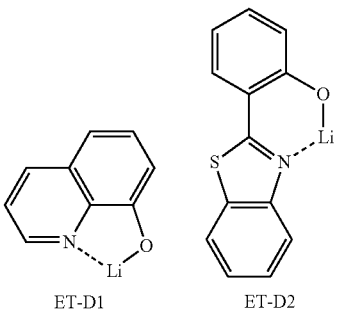

ET-D1                ET-D2

The electron transport region may include an EIL that allows electrons to be easily provided from the second electrode 17.

The EIL may be formed on the ETL by using (utilizing) various suitable methods, such as vacuum deposition, spin coating casting, an LB method, ink-jet printing, laser-printing, or LITI. When an EIL is formed by vacuum deposition or spin coating, deposition and coating conditions for the EIL may be determined by referring to the deposition and coating conditions described herein with respect to the HIL.

The EIL may include at least one selected from, LiF, NaCl, CsF, $Li_2O$, BaO, and LiQ.

A thickness of the EIL may be in a range of about 1 Å to about 100 Å, for example, about 3 Å to about 90 Å. When the thickness of the EIL is within any of the foregoing ranges, the EIL may have satisfactory electron transportation characteristics without a substantial increase in driving voltage.

The second electrode 17 is on the organic layer 15 having such a structure. The second electrode 17 may be a cathode that is an electron injection electrode, and in this regard, a material for forming the second electrode 17 may be a material having a low work function, and such a material may be a metal, an alloy, an electrically conductive compound, or a mixture thereof. Examples of the second electrode 17 include lithium (Li), magnesium (Mg), aluminum (Al), aluminum-lithium (Al—Li), calcium (Ca), magnesium-indium (Mg—In), or magnesium-silver (Mg—Ag). According to another embodiment of the present disclosure, the material for forming the second electrode 190 may be ITO or IZO. The second electrode 17 may be a reflective electrode, a semi-transmissive electrode, or a transmissive electrode.

The OLED has been described with reference to the accompanying drawing, but the OLED is not limited thereto. For example, the OLED of the accompanying drawing includes the substrate 11 that is disposed at the bottom of the first electrode 13, but optionally, the substrate 11 may be disposed on top of the second electrode 17.

The term "alkyl group" as used herein refers to a linear or branched aliphatic hydrocarbon monovalent group, and examples thereof include a methyl group, an ethyl group, a propyl group, an isobutyl group, a sec-a butyl group, a ter-butyl group, a pentyl group, an iso-amyl group, and a hexyl group. The term "alkylene group" as used herein refers to a divalent group having substantially the same structure as the alkyl group except that the alkylene group is a divalent group instead of a monovalent group.

The term "alkoxy group" as used herein refers to a monovalent group represented by $OA_{101}$ (where $A_{101}$ is the $C_1$-$C_{30}$ alkyl group), and examples thereof include a methoxy group, an ethoxy group, and an isopropyloxy group.

The term "alkenyl group" as used herein refers to a hydrocarbon group formed by substituting at least one carbon double bond in the main chain (e.g., middle) or terminal end of the alkyl group, and examples thereof include an ethenyl group, a propenyl group and a butenyl group. The term "alkenylene group" as used herein refers to a divalent group having substantially the same structure as the alkenyl group except that the alkenylene group is a divalent group instead of a monovalent group.

The term "alkynyl group" as used herein refers to a hydrocarbon group formed by substituting at least one carbon triple bond in the main chain (e.g., middle) or terminal end of the alkyl group, and examples thereof include an ethynyl group and a propynyl group. The term "alkynylene group" as used herein refers to a divalent group having substantially the same structure as the alkynyl group except that the alkynylene group is a divalent group instead of a monovalent group.

The term "cycloalkyl group" as used herein refers to a monovalent saturated hydrocarbon monocyclic group, and examples thereof include a cyclopropyl group, a cyclobutyl group, a cyclopentyl group, a cyclohexyl group, and a cycloheptyl group. The term "cycloalkylene group" as used herein refers to a divalent group having substantially the same structure as the cycloalkyl group except that the cycloalkylene group is a divalent group instead of a monovalent group.

The term "heterocycloalkyl group" as used herein refers to a monovalent monocyclic group having at least one heteroatom selected from N, O, P, and S as a ring-forming atom, and examples thereof include a tetrahydrofuranyl group and a tetrahydrothiophenyl group. The term "heterocycloalkylene group" as used herein refers to a divalent group having substantially the same structure as the heterocycloalkyl group except that the heterocycloalkylene group is a divalent group instead of a monovalent group.

The term "cycloalkenyl group" as used herein refers to a monovalent monocyclic group that has at least one double bond in the ring thereof and does not have aromaticity (e.g., is not aromatic), and examples thereof include a cyclopentenyl group, a cyclohexenyl group, and a cycloheptenyl group. The term "cycloalkenylene group" as used herein refers to a divalent group having substantially the same structure as the cycloalkenyl group except that the cycloalkenylene group is a divalent group instead of a monovalent group.

The term "heterocycloalkenyl group" as used herein refers to a monovalent monocyclic group that has at least one heteroatom selected from N, O, P, and S as a ring-forming atom, and at least one double bond in its ring. Examples of the heterocycloalkenyl group include a 2,3-hydrofuranyl group and a 2,3-hydrothiophenyl group. The term "heterocycloalkenylene group" as used herein refers to a divalent group having substantially the same structure as the heterocycloalkenyl group except that the heterocycloalkenylene group is a divalent group instead of a monovalent group.

The term "aryl group" as used herein refers to a monovalent group having a carbocyclic aromatic system, and the term "arylene group" as used herein refers to a divalent group having a carbocyclic aromatic system. Examples of the aryl group include a phenyl group, a naphthyl group, an anthracenyl group, a phenanthrenyl group, a pyrenyl group, and a chrysenyl group. When the aryl group and the arylene group each include two or more rings, the rings may be fused to each other.

The term "heteroaryl group" as used herein refers to a monovalent group having a carbocyclic aromatic system that has at least one heteroatom selected from N, O, P, and S as a ring-forming atom. The term "heteroarylene group" as used herein refers to a divalent group having a carbocyclic aromatic system that has at least one heteroatom selected from N, O, P, and S as a ring-forming atom. Examples of the heteroaryl group include a pyridinyl group, a pyrimidinyl group, a pyrazinyl group, a pyridazinyl group, a triazinyl group, a quinolinyl group, and an isoquinolinyl group. When the heteroaryl group and the heteroarylene group each include two or more rings, the rings may be fused to each other.

The term "aryloxy group" as used herein refers to —OA$_{102}$ (where, A$_{102}$ is the aryl group), and the term "arylthio group" as used herein refers to —SA$_{103}$ (where, A$_{103}$ is the aryl group).

A monovalent non-aromatic condensed polycyclic group used herein refers to a monovalent group that has two or more rings condensed to each other, and non-aromaticity in the entire molecular structure. The monovalent non-aromatic condensed polycyclic group includes i) only carbon atoms as a ring-forming atom, or ii) a heteroatom selected from N, O, P, and S, other than carbon atoms, as a ring forming atom. Examples of the monovalent non-aromatic condensed polycyclic group include a heptalenyl group and a triquinacenyl group. The term "divalent non-aromatic condensed polycyclic group" as used herein refers to a divalent group having substantially the same structure as the monovalent non-aromatic condensed polycyclic group except that the divalent non-aromatic condensed polycyclic group is a divalent group instead of a monovalent group.

Regarding the expression $C_m$-$C_n$ (m<n) as used herein, m and n indicate the number of carbon atoms. For example, a $C_1$-$C_{10}$ alkyl group refers to an alkyl group having 1 to 10 carbon atoms, and a $C_6$-$C_{30}$ aryl group refers to an aryl group having 6 to 30 carbon atoms.

The term "Ph" as used herein refers to a phenyl group, the term "Me" as used herein refers to a methyl group, the term "Et" as used herein refers to an ethyl group, and the term "ter-Bu" or "Bu$^t$" as used herein refers to tert-butyl.

Hereinafter, an organic light-emitting diode according to an embodiment of the present disclosure will be described with reference to Synthesis Examples and Examples. The wording "B was used instead of A" as used in describing the Synthesis Examples means that a molar equivalent of A was identical (or substantially identical) to a molar equivalent of B.

SYNTHESIS EXAMPLE

Synthesis Example 1: Synthesis of Compound 1

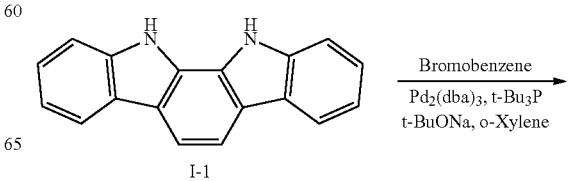

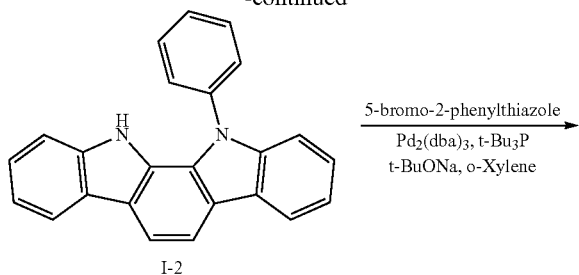

Synthesis of Intermediate I-2

178.6 mg (0.20 mmol) of Pd$_2$(dba)$_3$ and 78.9 mg (0.39 mmol) of t-Bu$_3$P were dissolved in 50 mL of o-xylene, and then, the resultant mixture was stirred at room temperature for 10 minutes. 5 g (19.51 mmol) of 11,12-dihydroindolo[2,3-a]carbazole (Intermediate I-1), 3.37 g (21.46 mmol) of bromobenzene, and 1.12 g (11.71 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.35 g (yield: 83%) of Intermediate I-2 (11-pheny-11,12-dihydroindolo[2,3-a]carbazol).

EI-MS, m/e, 332.13 (calculated value), 332.19 (measured value).

Synthesis of Compound 1

137.7 mg (0.15 mmol) of Pd$_2$(dba)$_3$ and 60.8 mg (0.30 mmol) of t-Bu$_3$P were dissolved in 50 mL of o-xylene, and then, the resultant mixture was stirred at room temperature for 10 minutes. Here, 5 g (15.04 mmol) of Intermediate I-2, 3.97 g (16.54 mmol) of 5-bromo-2-phenyl phenyithiazole, and 0.867 mg (9.03 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.84 g (yield: 79%) of Compound 1 (2-phenyl-5-(12-phenylindolo[2,3-a]carbazole-11(12H)-yl)thiazole).

1H NMR (300 MHz, CDCl3), d (ppm): 8.02-7.95 (1H, s), 7.74-7.58 (7H, m), 7.57-7.50 (2H, m), 7.43-7.34 (5H, m), 7.34-7.27 (1H, m), 7.26-7.14 (3H, m), 7.13-7.06 (2H, m).

EI-MS, m/e, 491.15 (calculated value), 491.17 (measured value).

Synthesis Example 2: Synthesis of Compound 7

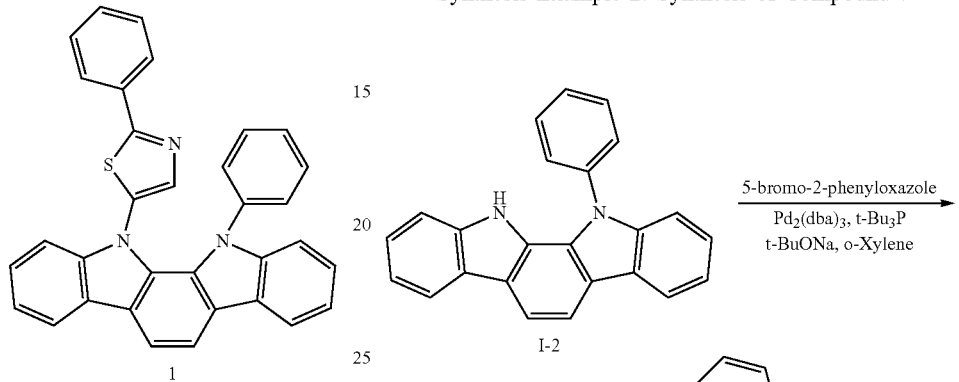

Synthesis of Compound 7

137.7 mg (0.15 mmol) of Pd$_2$(dba)$_3$ and 60.8 mg (0.30 mmol) of t-Bu$_3$P were dissolved in 50 mL of o-xylene, and then, the resultant mixture was stirred at room temperature for 10 minutes. Here, 5 g (15.04 mmol) of Intermediate I-2, 3.71 g (16.55 mmol) of 5-bromo-2-phenyloxazole, and 0.867 mg (9.03 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 6.12 g (yield 86%) of Compound 7 (2-phenyl-5-(12-phenylindolo[2,3-a]carbazole-11(12H)-yl)oxazole).

1H NMR (300 MHz, CDCl3), d (ppm): 7.72-7.68 (1H, d), 7.68-7.64 (2H, m), 7.63-7.58 (3H, m), 7.54-7.48 (2H, m), 7.46-7.37 (4H, m), 7.37-7.29 (3H, m), 7.21-7.04 (6H, m).

EI-MS, m/e, 475.17 (calculated value), 475.21 (measured value)

Synthesis Example 3: Synthesis of Compound 59

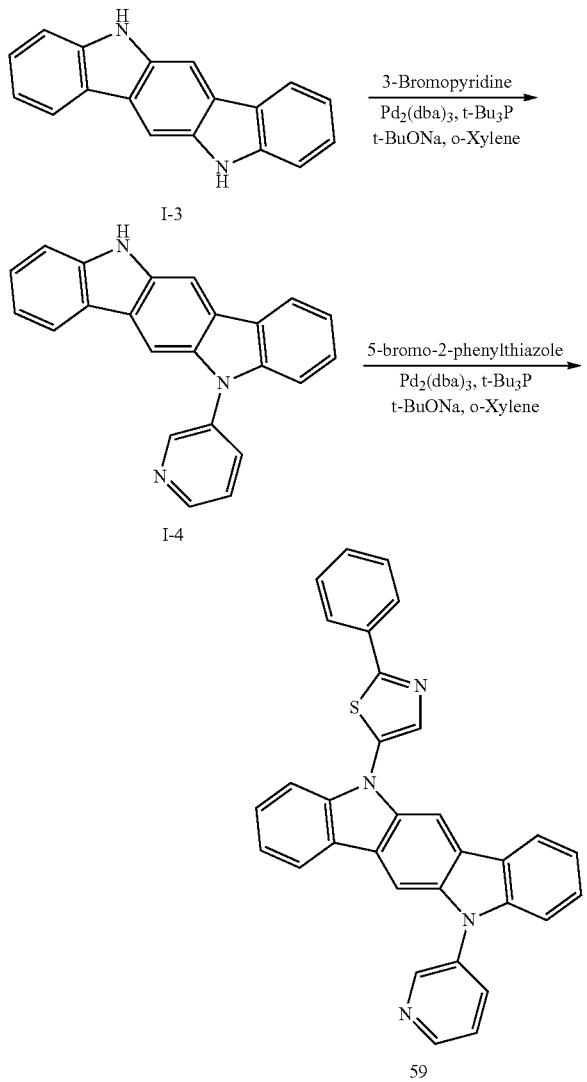

I-3

I-4

59

Synthesis of Intermediate I-4

178.6 mg (0.20 mmol) of Pd$_2$(dba)$_3$ and 78.9 mg (0.39 mmol) of t-Bu$_3$P were dissolved in 50 mL of o-xylene, and then, the resultant mixture was stirred at room temperature for 10 minutes. Here, 5 g (19.51 mmol) of 5,11-dihydroindolo[3,2-b]carbazole (Intermediate I-3), 3.39 g (21.46 mmol) of 3-bromopyridine, and 1.12 g (11.71 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.10 g (yield: 78%) of Intermediate I-4 (5-(pyridine-3-yl)-5,11-dihydroindolo[3,2-b]carbazol).

EI-MS, m/e, 332.13 (calculated value), 332.15 (measured value).

Synthesis of Compound 59

137.3 mg (0.15 mmol) of Pd$_2$(dba)$_3$ and 60.7 mg (0.30 mmol) of t-Bu3P were dissolved in 50 mL of o-xylene, and then, the resultant mixture was stirred at room temperature for 10 minutes. Here, 5 g (15.00 mmol) of Intermediate I-4, 3.96 g (16.50 mmol) of 5-bromo-2-phenylthiazole, and 0.864 mg (9.00 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 6.02 g (yield: 81%) of Compound 59 (2-phenyl-5-(11-(pyridine-3-yl)indolo[3,2-b]carbazole-5 (11H)-yl)thiazole).

1H NMR (300 MHz, CDCl3), d (ppm): 9.28-9.17 (1H, s), 8.63-8.53 (1H, m), 8.36-8.27 (1H, s), 8.03-7.92 (2H, m), 7.85-7.79 (1H, s), 7.75-7.69 (2H, m), 7.68-7.60 (3H, m), 7.58-7.51 (1H, m), 7.51-7.44 (1H, t), 7.44-7.37 (2H, t), 7.37-7.28 (1H, m), 7.22-7.14 (2H, m), 7.14-7.05 (2H, m).

EI-MS, m/e, 492.14 (calculated value), 492.19 (measured value).

Synthesis Example 4: Synthesis of Compound 101

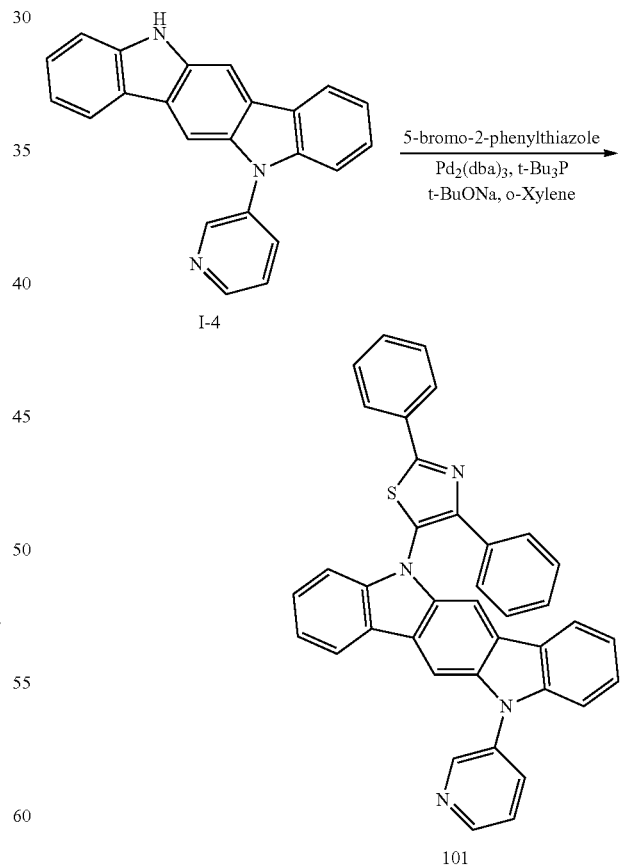

I-4

101

Synthesis of Compound 101

137.3 mg (0.15 mmol) of Pd$_2$(dba)$_3$ and 60.7 mg (0.30 mmol) of t-Bu3P were dissolved in 50 mL of o-xylene, and then, the resultant mixture was stirred at room temperature for 10 minutes. Here, 5 g (15.00 mmol) of Intermediate I-4, 5.22 g (16.50 mmol) of 5-bromo-2,4-diphenylthiazole, and 0.864 mg (9.00 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 6.77 g (yield: 79%) of Compound 101 (2,4-diphenyl-5-(11-(pyridine-3-yl)indolo[3,2-b]carbazole-5(11H)-yl)thiazole).

1H NMR (300 MHz, CDCl3), d (ppm): 9.13-9.05 (1H, m), 8.58-8.49 (1H, m), 8.21-8.10 (1H, s), 8.00-7.90 (2H, m), 7.84-7.70 (7H, m), 7.66-7.58 (1H, m), 7.52-7.36 (6H, m), 7.35-7.15 (5H, m).

EI-MS, m/e, 568.17 (calculated value), 568.20 (measured value).

Synthesis Example 5: Synthesis Compound 29

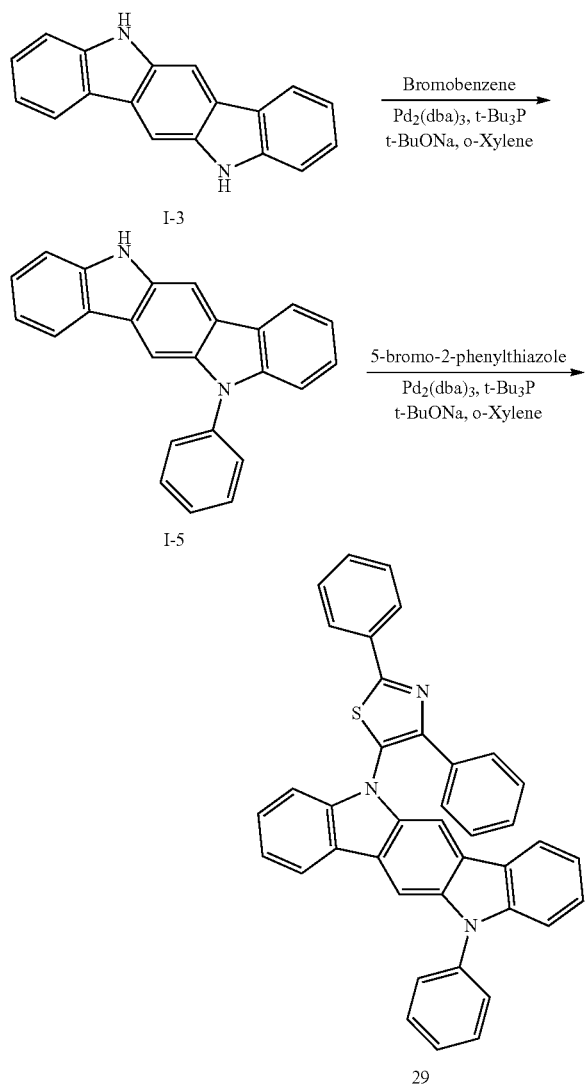

Synthesis of Intermediate I-5

178.6 mg (0.20 mmol) of Pd2(dba)3 and 78.9 mg (0.39 mmol) of t-Bu3P were dissolved in 50 mL of o-xylene, and then, the resultant mixture was stirred at room temperature for 10 minutes. Here, 5 g (19.51 mmol) of 5,11-dihydroindolo[3,2-b]carbazole (Intermediate I-3), 3.37 g (21.46 mmol) of bromobenzene, and 1.12 g (11.71 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.62 g (yield: 87%) of Intermediate I-5 (5-phenyl-5,11-dihydroindolo[3,2-b]carbazol).

EI-MS, m/e, 332.13 (calculated value), 332.18 (measured value).

Synthesis of Compound 29

137.7 mg (0.15 mmol) of Pd2(dba)3 and 60.8 mg (0.30 mmol) of t-Bu3P were dissolved 50 mL of o-xylene, and then, the resultant mixture was stirred at room temperature for 10 minutes. Here, 5 g (15.04 mmol) of Intermediate I-5, 5.23 g (16.55 mmol) of 5-bromo-2,4-diphenylthiazole, and 0.867 mg (9.03 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 7.32 g (yield: 86%) of Compound 29 (2,4-diphenyl-5-(11-phenylindolo[3,2-b]carbazole-5(11H)-yl)thiazole).

1H NMR (300 MHz, CDCl3), d (ppm): 8.09-8.05 (1H, s), 7.83-7.78 (1H, s), 7.77-7.73 (2H, s), 7.73-7.68 (2H, m), 7.64-7.53 (6H, m), 7.50-7.41 (6H, m), 7.40-7.34 (1H, m), 7.31-7.11 (6H, m).

EI-MS, m/e, 567.18 (calculated value), 567.21 (measured value).

Synthesis Example 6: Synthesis of Compound 155

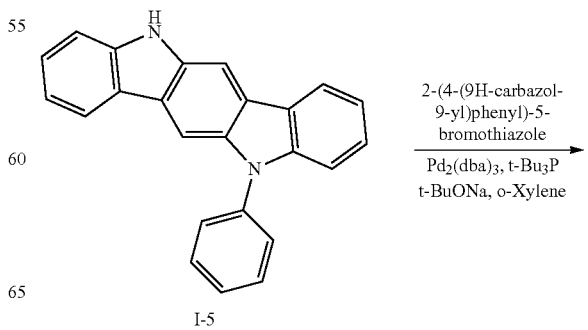

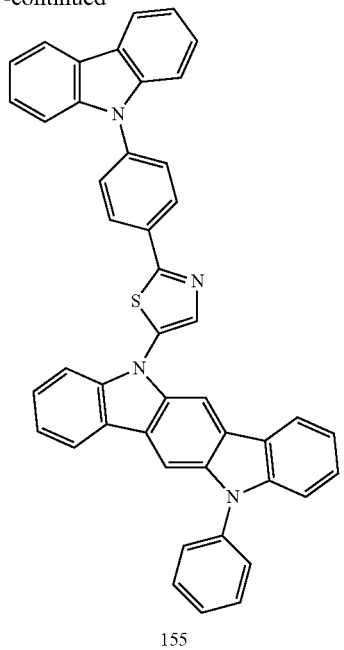

155

Synthesis of Compound 155

137.7 mg (0.15 mmol) of Pd$_2$(dba)$_3$ and 60.8 mg (0.30 mmol) of t-Bu$_3$P were dissolved in 50 mL of o-xylene, and then, the resultant mixture was stirred at room temperature for 10 minutes. Here, 5 g (15.00 mmol) of Intermediate I-5, 6.71 g (16.55 mmol) of 2-(4-(9H-carbazol-9-yl)phenyl)-5-bromotiazole, and 0.867 mg (9.03 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 7.58 g (yield: 77%) of Compound 155 (2-(4-(9H-carbazol-9-yl)phenyl)-5-(11-phenylindolo[3,2-b]carbazole-5(11H)-yl)thiazole).

1H NMR (300 MHz, CDCl3), d (ppm): 8.32-8.27 (1H, s), 8.03-7.99 (1H, s), 7.86-7.83 (1H, s), 7.82-7.72 (7H, m), 7.70-7.64 (3H, m), 7.64-7.59 (2H, m), 7.56-7.50 (2H, m), 7.49-7.42 (2H, t), 7.31-7.14 (9H, m).

EI-MS, m/e, 656.20 (calculated value), 656.25 (measured value).

Synthesis Example 7: Synthesis of Compound 159

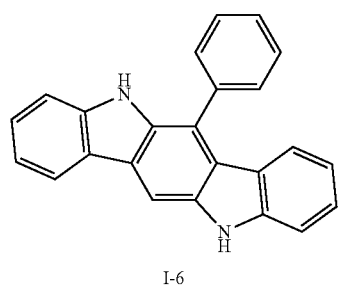

I-6

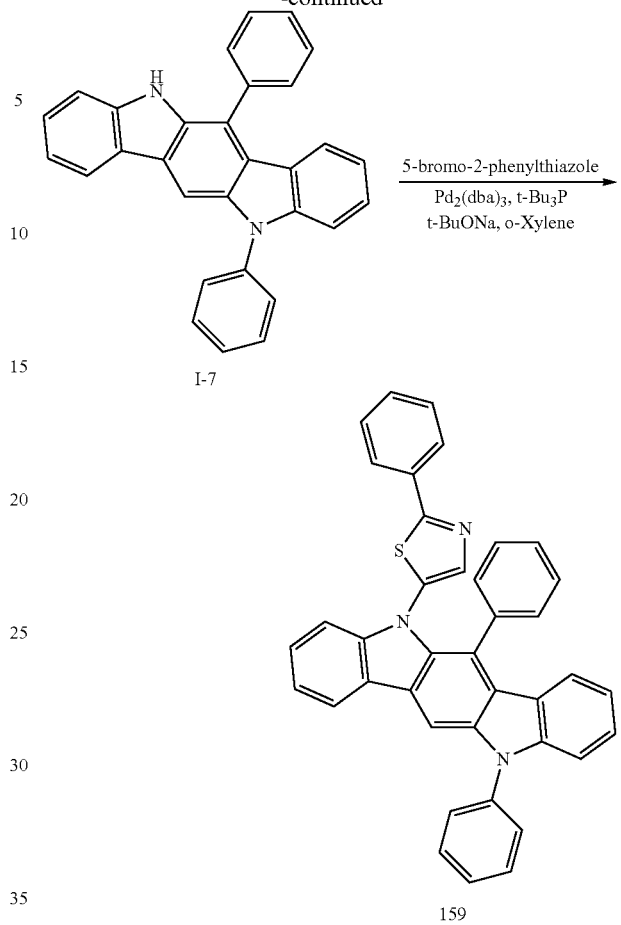

I-7

159

Synthesis of Intermediate I-7

178.6 mg (0.20 mmol) of Pd$_2$(dba)$_3$ and 78.9 mg (0.39 mmol) of t-Bu$_3$P were dissolved in 50 mL of o-xylene, and then, the resultant mixture was stirred at room temperature for 10 minutes. Here, 5 g (15.04 mmol) of 6-phenyl-5,11-dihydroindolo[3,2-b]carbazole (Intermediate I-6), 2.60 g (16.55 mmol) of bromobenzene, and 867 mg (9.03 mmol) of t-BuONa were added thereto, the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.14 g (yield: 84%) of Intermediate I-7 (5,12-diphenyl-5,11-dihydroindolo[3,2-b]carbazol).

EI-MS, m/e, 408.16 (calculated value), 408.21 (measured value).

Synthesis of Compound 159

112.1 mg (0.12 mmol) of Pd$_2$(dba)$_3$ and 49.5 mg (0.24 mmol) of t-Bu$_3$P were dissolved in 50 mL of o-xylene, and then, the resultant mixture was stirred at room temperature for 10 minutes. Here, 5 g (12.24 mmol) of Intermediate I-7, 3.23 g (13.46 mmol) of 5-bromo-2-phenylthiazole, and 0.706 mg (7.34 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.25 g (yield: 76%) of Compound 159 (5-(6,11-diphenylindolo[3,2-b]carbazole-5(11H)-yl)-2-phenylthiazole).

1H NMR (300 MHz, CDCl3), d (ppm): 8.08-8.03 (1H, s), 7.95-7.90 (1H, s), 7.82-7.75 (3H, m), 7.14-7.08 (1H, m), 7.64-7.59 (3H, m), 7.69-7.64 (3H, m), 7.58-7.43 (7H, m), 7.33-7.21 (3H, m), 7.42-7.34 (2H, m), 7.21-7.15 (1H, m).

EI-MS, m/e, 567.18 (calculated value), 567.23 (measured value)

Synthesis Example 8: Synthesis of Compound 70

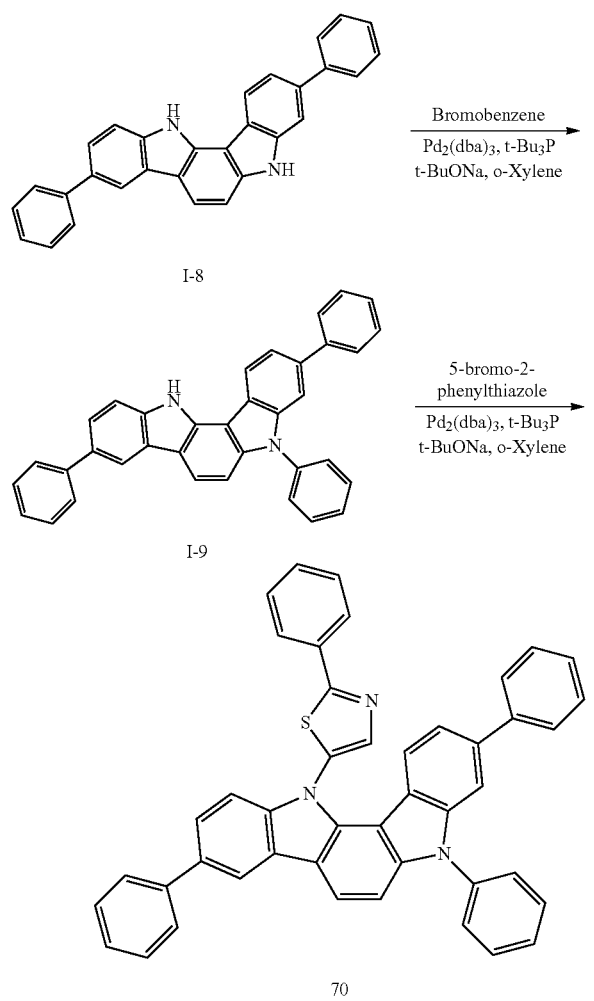

Synthesis of Intermediate I-9

112.0 mg (0.12 mmol) of Pd$_2$(dba)$_3$ and 49.5 mg (0.24 mmol) of t-Bu$_3$P were dissolved in 50 mL of o-xylene, and then, the resultant mixture was stirred at room temperature for 10 minutes. Here, 5 g (12.24 mmol) of 3,9-diphenyl-5,12-dihydroindolo[3,2-a]carbazole (Intermediate I-8), 2.11 g (13.46 mmol) of bromobenzene, and 706 mg (7.34 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 2.87 g (yield: 48%) of Intermediate I-9 (3,5,9-triphenyl-5,12-dihydroindolo[3,2-a]carbazol).

EI-MS, m/e, 484.19 (calculated value), 484.23 (measured value).

Synthesis of Compound 70

94.5 mg (0.10 mmol) of Pd$_2$(dba)$_3$ and 41.7 mg (0.21 mmol) of t-Bu$_3$P were dissolved in 50 mL of o-xylene, and then, the resultant mixture was stirred at room temperature for 10 minutes. Here, 5 g (10.32 mmol) of Intermediate I-9, 2.73 g (11.35 mmol) of 5-bromo-2-phenylthiazole, and 0.595 mg (6.19 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.42 g (yield: 82%) of Compound 70 (2-phenyl-5-(3,5,9-triphenylindolo[3,2-a]carbazole-12(5H)-yl)thiazole).

1H NMR (300 MHz, CDCl3), d (ppm): 8.28-8.23 (1H, m), 8.16-8.10 (2H, m), 8.04-7.99 (1H, d), 7.97-7.94 (1H, s), 7.93-7.88 (1H, d), 7.74-7.65 (6H, m), 7.65-7.60 (3H, m), 7.56-7.51 (2H, m), 7.51-7.43 (8H, m), 7.42-7.33 (3H, m), 7.33-7.26 (1H, m).

EI-MS, m/e, 643.21 (calculated value), 643.25 (measured value).

Synthesis Example 9: Synthesis of Compound 88

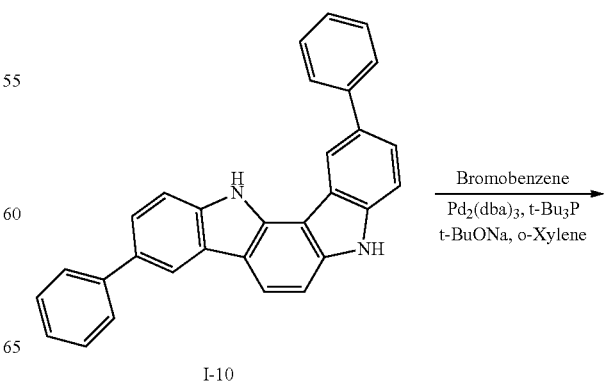

Synthesis of Intermediate I-11

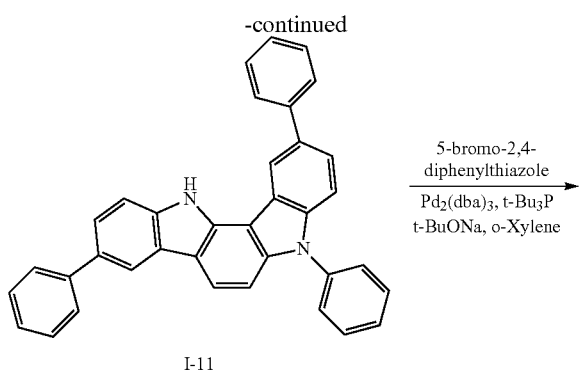

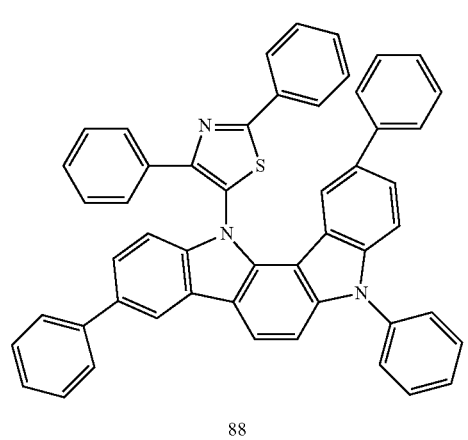

112.0 mg (0.12 mmol) of Pd₂(dba)₃ and 49.5 mg (0.24 mmol) of t-Bu₃P were dissolved in 50 mL of o-xylene, and then, the resultant mixture was stirred at room temperature for 10 minutes. Here, 5 g (12.24 mmol) of 2,9-diphenyl-5, 12-dihydroindolo[3,2-a]carbazole (Intermediate I-10), 2.11 g (13.46 mmol) of bromobenzene, and 706 mg (7.34 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 3.14 g (yield: 53%) of Intermediate I-11 (2,5,9-triphenyl-5,12-dihydroindolo[3,2-a]carbazol).

EI-MS, m/e, 484.19 (calculated value), 484.22 (measured value).

Synthesis of Compound 88

94.5 mg (0.10 mmol) of Pd₂(dba)₃ and 41.7 mg (0.21 mmol) of t-Bu₃P were dissolved in 50 mL of o-xylene, and then, the resultant mixture was stirred at room temperature for 10 minutes. Here, 5 g (10.32 mmol) of Intermediate I-11, 3.59 g (11.35 mmol) of 5-bromo-2,4-diphenylthiazole, and 0.595 mg (6.19 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.14 g (yield: 69%) of Compound 88 (2,4-diphenyl-5-(2,5,9-triphenylindolo[3,2-a]carbazole-12 (5H)-yl)thiazole).

1H NMR (300 MHz, CDCl3), d (ppm): 8.74-8.65 (1H, m), 8.27-8.21 (1H, m), 7.94-7.87 (2H, m), 7.87-7.81 (3H, m), 7.78-7.70 (4H, m), 7.69-7.58 (5H, m), 7.56-7.51 (1H, m), 7.51-7.43 (11H, m), 7.42-7.34 (4H, m), 7.33-7.26 (1H, m).

EI-MS, m/e, 719.24 (calculated value), 719.28 (measured value)

Synthesis Example 10: Synthesis of Compound 112

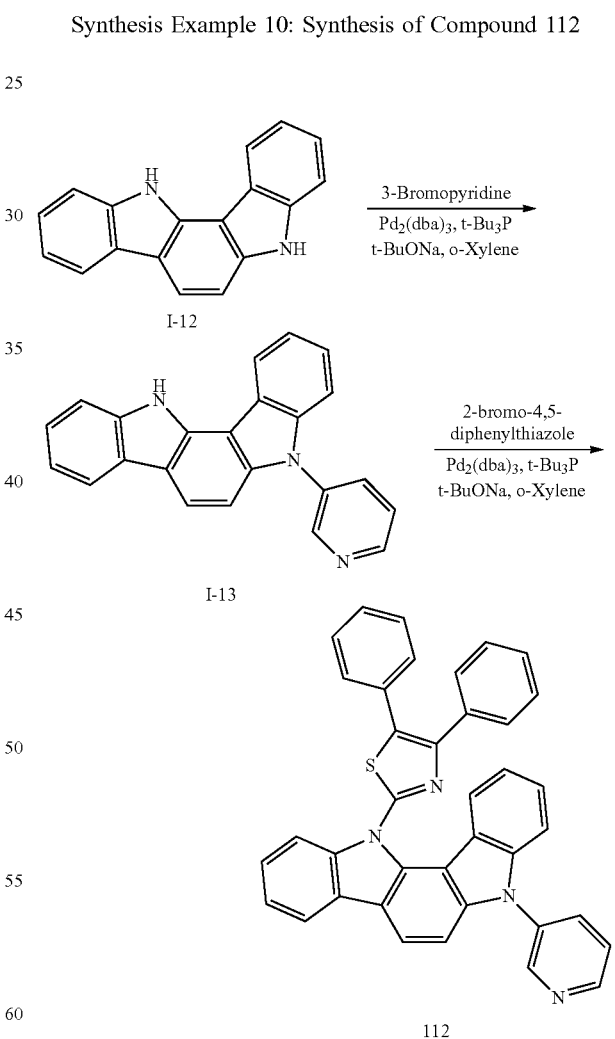

Synthesis of Intermediate I-13

178.6 mg (0.20 mmol) of Pd₂(dba)₃ and 78.9 mg (0.39 mmol) of t-Bu₃P were dissolved in 50 mL of o-xylene, and then, the resultant mixture was stirred at room temperature for 10 minutes. Here, 5 g (19.51 mmol) of 5,12-dihydroindolo[3,2-a]carbazole (Intermediate I-12), 3.39 g (21.46 mmol) of 3-bromopyridine, and 1.12 g (11.71 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 3.43 g (yield: 53%) of Intermediate I-13 (5-(pyridine-3-yl)-5,12-dihydroindolo[3,2-a]carbazol).

EI-MS, m/e, 333.13 (calculated value), 333.14 (measured value).

Synthesis of Compound 112

137.3 mg (0.15 mmol) of $Pd_2(dba)_3$ and 60.7 mg (0.30 mmol) of $t-Bu_3P$ were dissolved in 50 mL of o-xylene, and then, the resultant mixture was stirred at room temperature for 10 minutes. Here, 5 g (15.00 mmol) of Intermediate I-13, 5.22 g (16.50 mmol) of 2-bromo-4,5-diphenylthiazole, and 0.864 mg (9.00 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 6.23 g (yield: 73%) of Compound 112 (4,5-diphenyl-2-(5-(pyridine-3-yl)indolo[3,2-a]carbazole-12(5H)-yl)thiazole).

1H NMR (300 MHz, CDCl3), d (ppm): 9.15-9.07 (1H, m), 8.59-8.51 (1H, m), 8.02-7.94 (1H, m), 7.92-7.86 (1H, m), 7.86-7.82 (1H, d), 7.82-7.74 (2H, m), 7.71-7.66 (2H, m), 7.66-7.61 (2H, m), 7.61-7.56 (1H, m), 7.51-7.33 (8H, m), 7.31-7.23 (1H, m), 7.22-7.14 (2H, m), 7.13-7.04 (1H, m).

EI-MS, m/e, 568.17 (calculated value), 568.20 (measured value).

Synthesis Example 11: Synthesis of Compound 133

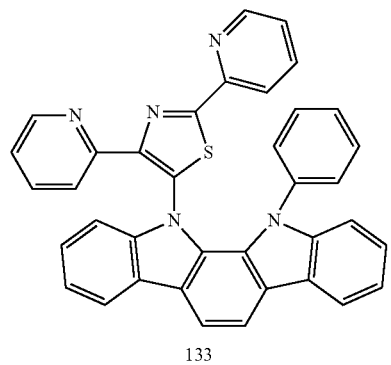

133

Synthesis of Compound 133

137.7 mg (0.15 mmol) of $Pd_2(dba)_3$ and 60.8 mg (0.30 mmol) of $t-Bu_3P$ dissolved in 50 mL of o-xylene, and then, the resultant mixture was stirred at room temperature for 10 minutes. Here, 5 g (15.04 mmol) Intermediate I-2, 5.26 g (16.54 mmol) of 5-bromo-2,4-di(pyridine-2-yl)thiazole, and 0.867 mg (9.03 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 6.48 g (yield: 76%) of Compound 133 (5-(12-phenylindolo[2,3-a]carbazole-11(12H)-yl)-2,4-di(pyridine-2-yl)thiazole).

1H NMR (300 MHz, CDCl3), d (ppm): 8.78-8.71 (2H, m), 7.97-7.88 (2H, m), 7.86-7.76 (5H, m), 7.75-7.69 (1H, m), 7.69-7.63 (2H, m), 7.59-7.53 (1H, m), 7.52-7.39 (5H, m), 7.30-7.13 (5H, m).

EI-MS, m/e, 569.17 (calculated value), 569.22 (measured value).

Synthesis Example 12: Synthesis of Compound 149

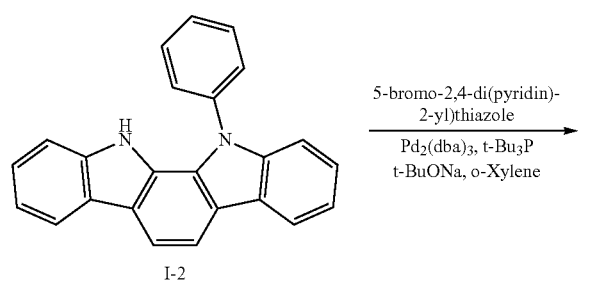

I-2

5-bromo-2,4-di(pyridin-2-yl)thiazole
$Pd_2(dba)_3$, $t-Bu_3P$
t-BuONa, o-Xylene
→

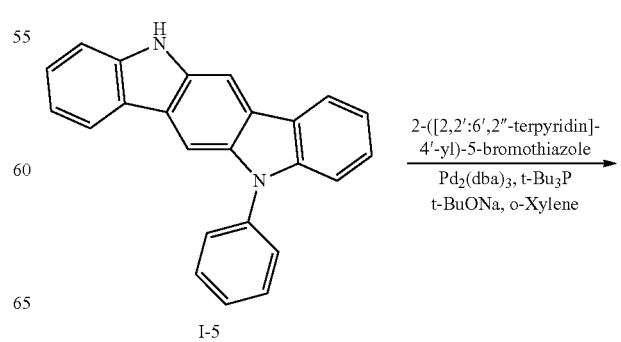

I-5

2-([2,2':6',2''-terpyridin]-4'-yl)-5-bromothiazole
$Pd_2(dba)_3$, $t-Bu_3P$
t-BuONa, o-Xylene
→

-continued

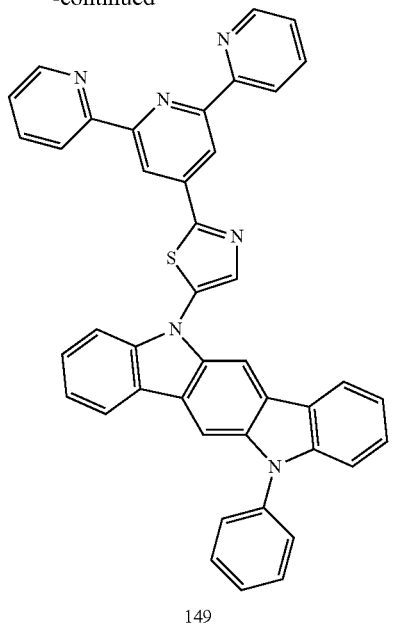

149

Synthesis of Compound 149

137.7 mg (0.15 mmol) of $Pd_2(dba)_3$ and 60.8 mg (0.30 mmol) of $t-Bu_3P$ were dissolved in 50 mL of o-xylene, and then, the resultant mixture was stirred at room temperature for 10 minutes. Here, 5 g (15.04 mmol) of Intermediate I-5, 6.54 g (16.55 mmol) of 2-([2,2':6',2''-terpyridine]-4'-yl)-5-bromothiazole, and 0.867 mg (9.03 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 8.19 g (yield: 84%) of Compound 149 (2-([2,2':6',2''-terpyridine]-4'-yl)-5-(11-phenylindolo[3,2-b]carbazole-5(11H)-yl)thiazole).

1H NMR (300 MHz, CDCl3), d (ppm): 8.74-8.69 (2H, s), 8.67-8.61 (3H, m), 8.47-8.40 (2H, m), 8.08-8.03 (1H, s), 7.91-7.87 (1H, s), 7.86-7.76 (3H, m), 7.74-7.65 (3H, m), 7.65-7.60 (2H, m), 7.50-7.43 (2H, t), 7.33-7.25 (3H, m), 7.24-7.16 (4H, m).

EI-MS, m/e, 646.19 (calculated value), 646.25 (measured value).

Synthesis Example 13: Synthesis of Compound 152

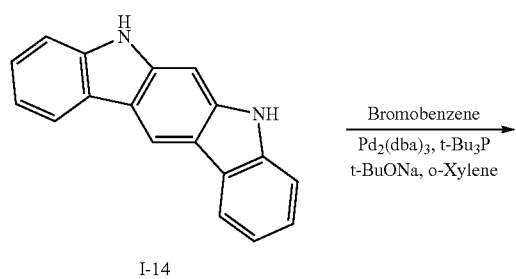

I-14

Bromobenzene
$\xrightarrow{Pd_2(dba)_3, t-Bu_3P}_{t-BuONa, o-Xylene}$ 2-(3-(9H-carbazol-9-yl)phenyl)-5-bromothiazole
$\xrightarrow{Pd_2(dba)_3, t-Bu_3P}_{t-BuONa, o-Xylene}$

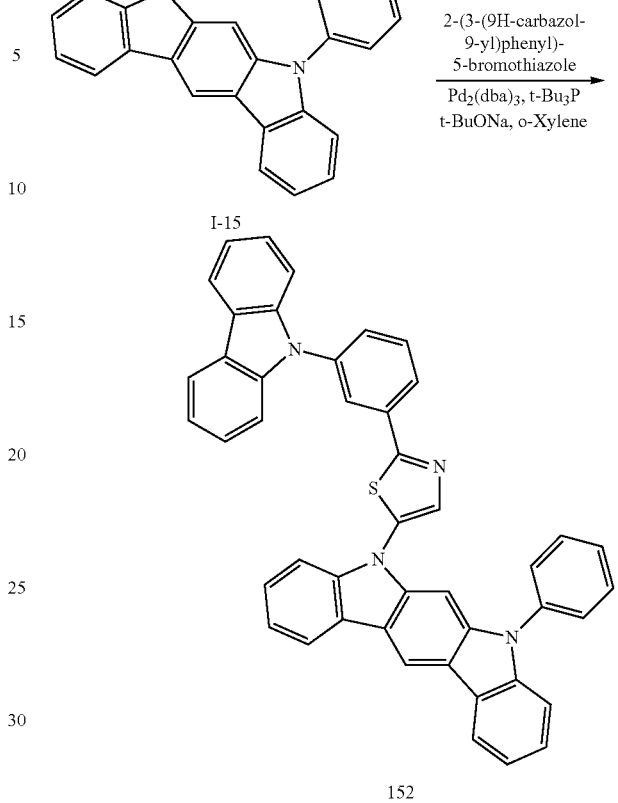

Synthesis of Intermediate I-15

178.6 mg (0.20 mmol) of $Pd_2(dba)_3$ and 78.9 mg (0.39 mmol) of $t-Bu_3P$ were dissolved 50 mL of o-xylene, and then, the resultant mixture was stirred at room temperature for 10 minutes. Here, 5 g (19.51 mmol) of 5,7-dihydroindolo[2,3-b]carbazole (Intermediate I-14), 3.37 g (21.46 mmol) of bromobenzene, and 1.12 g (11.71 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 5.72 g (yield: 88%) of Intermediate I-15 (5-phenyl-5,7-dihydroindolo[2,3-b]carbazol).

EI-MS, m/e, 332.13 (calculated value), 332.17 (measured value).

Synthesis of Compound 152

137.7 mg (0.15 mmol) of $Pd_2(dba)_3$ and 60.8 mg (0.30 mmol) of $t-Bu_3P$ were dissolved 50 mL of o-xylene, and then, the resultant mixture was stirred at room temperature for 10 minutes. Here, 5 g (15.04 mmol) of Intermediate I-15, 6.71 g (16.55 mmol) of 2-(3-(9H-carbazol-9-yl)phenyl)-5-bromothiazole, and 0.867 mg (9.03 mmol) of t-BuONa were added thereto, and the resultant solution was stirred under reflux at a temperature of 160° C. for 48 hours. After completing (or substantially completing) the reaction, 20 mL of cold distilled water was added to the reaction solution, and then an extraction was performed thereon by using (utilizing) ethyl acetate. An organic layer obtained therefrom was dried by using (utilizing) magnesium sulfate, and then, was dried and filtered to remove a solvent therefrom, and the obtained residual was separation-purified by using (utilizing) column chromatography to obtain 8.12 g (yield: 82%) of Compound 152 (2-(3-(9H-carbazol-9-yl)phenyl)-5-(7-phenylindolo[2,3-b]carbazole-5(7H)-yl)thiazole).

1H NMR (300 MHz, CDCl3), d (ppm): 8.38-8.32 (1H, s), 8.10-8.05 (1H, m), 7.98-7.94 (1H, s), 7.90-7.83 (3H, m), 7.82-7.75 (3H, m), 7.71-7.65 (4H, m), 7.65-7.58 (4H, m), 7.50-7.43 (2H, t), 7.36-7.13 (9H, m).

EI-MS, m/e, 656.20 (calculated value), 656.25 (measured value).

Additional compounds were synthesized according to synthesis pathways and synthesis methods substantially the same as those described above by using (utilizing) appropriate intermediates. The additional synthesized compounds were identified by $^1$H NMR and MS/FAB as shown in Table 1.

Synthesis methods for compounds other than the compounds shown in Table 1 should be apparent to one of ordinary skill in the art by referring to the synthesis methods and source materials of the Synthesis Examples above.

TABLE 1

| Compound | $^1$H NMR (CDCl$_3$, 300 MHz) | MS/FAB measured value | MS/FAB calculated value |
|---|---|---|---|
| 2 | 8.23-8.17 (1H, s), 7.90-7.86 (1H, s), 7.81-7.76 (1H, s), 7.70-7.59 (5H, m), 7.57-7.49 (3H, m), 7.44-7.36 (4H, m), 7.34-7.27 (1H, m), 7.26-7.21 (1H, m), 7.20-7.13 (2H, m), 7.12-7.04 (2H, m). | 491.18 | 491.15 |
| 8 | 7.91-7.86 (1H, s), 7.81-7.77 (1H, s), 7.70-7.64 (3H, m), 7.63-7.58 (2H, m), 7.57-7.49 (3H, m), 7.44-7.37 (4H, m), 7.33-7.28 (1H, m), 7.26-7.13 (4H, m), 7.13-7.05 (2H, m). | 475.22 | 475.17 |
| 17 | 8.25-8.20 (1H, s), 7.99-7.94 (1H, s), 7.76-7.73 (1H, s), 7.73-7.70 (1H, m), 7.70-7.65 (2H, d), 7.65-7.59 (2H, m), 7.56-7.49 (3H, m), 7.43-7.36 (4H, m), 7.32-7.26 (1H, m), 7.26-7.14 (3H, m), 7.12-7.05 (2H, m). | 491.17 | 491.15 |
| 23 | 7.95-7.91 (1H, s), 7.76-7.72 (1H, s), 7.72-7.68 (1H, m), 7.68-7.58 (4H, m), 7.56-7.50 (3H, m), 7.44-7.36 (4H, m), 7.33-7.27 (1H, m), 7.25-7.14 (4H, m), 7.12-7.06 (2H, m). | 475.21 | 475.17 |
| 33 | 8.06-8.00 (2H, m), 7.85-7.81 (1H, d), 7.75-7.67 (4H, m), 7.65-7.62 (1H, m), 7.62-7.57 (3H, m), 7.56-7.51 (1H, d), 7.49-7.42 (6H, m), 7.41-7.33 (2H, m), 7.32-7.18 (5H, m). | 551.25 | 551.20 |
| 39 | 8.06-7.99 (2H, m), 7.99-7.95 (1H, d), 7.83-7.78 (1H, m), 7.74-7.66 (4H, m), 7.65-7.57 (3H, m), 7.55-7.51 (1H, d), 7.50-7.42 (6H, m), 7.41-7.34 (2H, m), 7.32-7.18 (5H, m). | 567.19 | 567.18 |
| 53 | 8.74-8.67 (1H, m), 8.23-8.16 (1H, s), 7.94-7.86 (2H, m), 7.82-7.77 (1H, s), 7.73-7.60 (6H, m), 7.60-7.54 (1H, m), 7.44-7.38 (2H, t), 7.38-7.27 (2H, m), 7.23-7.14 (2H, m), 7.13-7.04 (2H, m). | 492.19 | 492.14 |
| 63 | 8.74-8.67 (2H, d), 8.10-8.05 (1H, s), 7.93-7.87 (2H, m), 7.72-7.67 (1H, d), 7.66-7.56 (5H, m), 7.53-7.48 (1H, m), 7.43-7.36 (3H, t), 7.34-7.28 (1H, m), 7.23-7.08 (4H, m). | 492.19 | 492.14 |
| 123 | 8.73-8.67 (1H, m), 8.12-8.06 (1H, s), 7.94-7.86 (3H, m), 7.79-7.73 (1H, m), 7.72-7.67 (1H, d), 7.66-7.61 (1H, m), 7.56-7.48 (3H, m), 7.48-7.36 (4H, m), 7.26-7.07 (5H, m). | 492.16 | 492.14 |
| 132 | 8.73-8.66 (1H, m), 7.95-7.88 (1H, m), 7.81-7.70 (4H, m), 7.65-7.59 (3H, m), 7.58-7.52 (1H, d), 7.51-7.41 (4H, m), 7.35-7.28 (1H, m), 7.28-7.21 (3H, m), 7.21-7.14 (1H, m), 7.11-7.04 (1H, m). | 476.21 | 476.16 |
| 148 | 8.28-8.23 (2H, m), 8.21-8.17 (1H, m), 8.03-7.98 (1H, s), 7.86-7.81 (2H, d), 7.78-7.74 (2H, m), 7.72-7.65 (4H, m), 7.63-7.57 (3H, m), 7.50-7.42 (7H, m), 7.41-7.35 (2H, m), 7.32-7.26 (2H, m), 7.26-7.14 (3H, m). | 643.22 | 643.21 |

EXAMPLE

Example 1

An ITO glass substrate (a product of Corning Co., Ltd) including an ITO layer having a sheet resistance of 15 Ω/cm$^2$ (thickness of 1,200 Å) was cut to a size of 50 mm×50 mm×0.7 mm, sonicated by using (utilizing) isopropyl alcohol and pure water each for 5 minutes, and cleaned by exposure to ultraviolet rays for 30 minutes and then ozone. Then, the ITO glass substrate was mounted on a vacuum deposition apparatus.

2-TNATA was deposited on the ITO anode to form a HIL having a thickness of 600 Å, NPB was deposited on the HIL to form a HTL having a thickness of 300 Å, and then, Compound 1 (host) and Ir(piq)$_2$(acac) (dopant) were co-deposited at a weight ratio of 87:13 on the HTL to form an emission layer having a thickness of 300 Å.

Thereafter, Alq$_3$ was deposited on the emission layer to form an ETL having a thickness of 300 Å, LiF was deposited on the ETL to form an EIL having a thickness of 10 Å, and Al was deposited on the ETL to form a cathode having a thickness of 3,000 Å, thereby completing the manufacture of an OLED.

Example 2

An OLED was manufactured as in Example 1, except that in forming the emission layer, Compound 7 was used instead of Compound 1.

Example 3

An OLED was manufactured as in Example 1, except that in forming the emission layer, Compound 88 was used instead of Compound 1.

Example 4

An OLED was manufactured as in Example 1, except that in forming the emission layer, Compound 112 was used instead of Compound 1.

Example 5

An OLED was manufactured as in Example 1, except that in forming the emission layer, Compound 29 was used instead of Compound 1, and Ir(ppy)$_3$ was used instead of Ir(piq)$_2$(acac).

Example 6

An OLED was manufactured as in Example 5, except that in forming the emission layer, Compound 59 was used instead of Compound 29.

Example 7

An OLED was manufactured as in Example 5, except that in forming the emission layer, Compound 70 was used instead of Compound 29.

Example 8

An OLED was manufactured as in Example 5, except that in forming the emission layer, Compound 101 was used instead of Compound 29.

Example 9

An OLED was manufactured as in Example 1, except that in forming the emission layer, ADN and DPVBi were co-deposited at a weight ratio of 98:2 instead of Compound 1 and Ir(piq)$_2$(acac) that were co-deposited at a weight ratio of 87:13, and in forming the ETL, Compound 133 was used instead of Alq$_3$.

Example 10

An OLED was manufactured as in Example 9, except that in forming the ETL, Compound 149 was used instead of Compound 133.

Example 11

An OLED was manufactured as in Example 9, except that in forming the ETL, Alq$_3$ was as used instead of Compound 133, and in forming a HTL, Compound 152 was used instead of NPB.

Example 12

An OLED was manufactured as in Example 9, except that in forming the HTL, Compound 155 was used instead of Compound 152.

Comparative Example 1

An OLED was manufactured as in Example 1, except that in forming the emission layer, CBP was used instead of Compound 1.

Comparative Example 2

An OLED was manufactured as in Example 5, except that in forming the emission layer, Compound 401 was used instead of Compound 59.

Compound 401

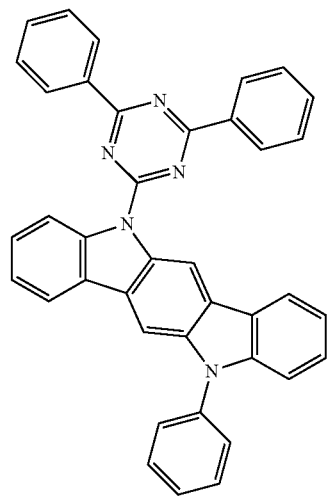

Comparative Example 3

An OLED was manufactured as in Example 9, except that in forming the ETL, Alq$_3$ was used instead of Compound 133.

Comparative Example 4

An OLED was manufactured as in Example 11, except that in forming the ETL, NPB was used instead of Compound 152.

Evaluation Example

The driving voltage and emission efficiency of the OLEDs of Examples 1 to 8 and Comparative Examples 1 and 2 were measured by using (utilizing) a Keithley SMU 236 and a brightness photometer PR650 with respect to a brightness of 1,000 cd/m$^2$, and results thereof are shown in Table 2.

TABLE 2

|  | Host | Dopant | ETL | HTL | Driving voltage (V) | Emission efficiency (cd/A) | Emission color | Brightness (cd/m$^2$) |
|---|---|---|---|---|---|---|---|---|
| Example 1 | Compound 1 | Ir(piq)$_2$(acac) | Alq$_3$ | NPB | 5.7 | 16.8 | Red | 1,000 |
| Example 2 | Compound 7 | Ir(piq)$_2$(acac) | Alq$_3$ | NPB | 6.0 | 17.5 | Red | 1,000 |
| Example 3 | Compound 88 | Ir(piq)$_2$(acac) | Alq$_3$ | NPB | 5.9 | 18.1 | Red | 1,000 |
| Example 4 | Compound 112 | Ir(piq)$_2$(acac) | Alq$_3$ | NPB | 6.1 | 17.8 | Red | 1,000 |
| Example 5 | Compound 29 | Ir(ppy)$_3$ | Alq$_3$ | NPB | 5.1 | 24.3 | Green | 1,000 |
| Example 6 | Compound 59 | Ir(ppy)$_3$ | Alq$_3$ | NPB | 5.2 | 23.8 | Green | 1,000 |
| Example 7 | Compound 70 | Ir(ppy)$_3$ | Alq$_3$ | NPB | 5.4 | 25.4 | Green | 1,000 |
| Example 8 | Compound 101 | Ir(ppy)$_3$ | Alq$_3$ | NPB | 5.5 | 23.7 | Green | 1,000 |
| Comparative Example 1 | CBP | Ir(piq)$_2$(acac) | Alq$_3$ | NPB | 7.8 | 11.1 | Red | 1,000 |
| Comparative Example 2 | Compound 401 | Ir(ppy)$_3$ | Alq$_3$ | NPB | 7.4 | 19.4 | Green | 1,000 |

The driving voltage, brightness, emission efficiency of the OLEDs of Examples 9 to 12 and Comparative Examples 3 and 4 were measured with respect to a current density of 50 mA/cm$^2$, and results thereof are shown in Table 3 with the half-lifespan of the same OLEDs. Here, the half-lifespan of the OLEDs was measured as the time taken for the OLEDs to arrive at a brightness that is 50% of the initial value of the brightness of the OLED while being operated at current density of 100 mA/cm$^2$. The measurements were made using (utilizing) a Keithley SMU 236 and a brightness photometer PR650.

TABLE 3

|  | Host | Dopant | ETL | HTL | Driving voltage (V) | Brightness (cd/m$^2$) | Emission efficiency (cd/A) | Current density (mA/cm$^2$) | Emission color | Half-lifespan (Hr) |
|---|---|---|---|---|---|---|---|---|---|---|
| Example 9 | ADN | DPVBi | Compound 133 | NPB | 6.5 | 2472 | 4.9 | 50 | Blue | 265 |
| Example 10 | ADN | DPVBi | Compound 149 | NPB | 6.2 | 2380 | 4.7 | 50 | Blue | 248 |
| Example 11 | ADN | DPVBi | Alq$_3$ | Compound 152 | 6.4 | 2375 | 4.6 | 50 | Blue | 268 |
| Example 12 | ADN | DPVBi | Alq$_3$ | Compound 155 | 6.5 | 2432 | 4.7 | 50 | Blue | 254 |
| Comparative Example 3 | ADN | DPVBi | Alq$_3$ | NPB | 7.8 | 1664 | 3.4 | 50 | Blue | 132 |
| Comparative Example 4 | ADN | DPVBi | Alq$_3$ | NPB | 7.8 | 1640 | 3.3 | 50 | Blue | 142 |

Referring to Table 2 above, it can be seen that the driving voltage and emission efficiency of the OLEDs of Examples 1 to 8 are improved relative to those of Comparative Examples 1 and 2. Referring to Table 3, it can be seen that the driving voltage, current density, brightness, emission efficiency and half-lifespan of the OLEDs of Examples 9 to 12 are improved relative to the driving voltage, current density, brightness, emission efficiency, and half-lifespan of the OLEDs of Comparative Examples 3 and 4.

As described above, according to aspects of one or more embodiments of the present disclosure, an organic light-emitting device including a condensed cyclic compound may have a low driving voltage, high efficiency, high brightness, and long lifespan It should be understood that the embodiments described herein should be considered in a descriptive sense only and not for purposes of limitation. Descriptions of features or aspects within each embodiment should typically be considered as available for other similar features or aspects in other embodiments.

While one or more embodiments of the present disclosure have been described with reference to the figures, it will be understood by those of ordinary skill in the art that various changes in form and details may be made therein without departing from the spirit and scope of the present invention as defined by the following claims, and equivalents thereof.

What is claimed is:
1. A condensed cyclic compound for an organic light-emitting device represented by Formula 1:

Formula 1

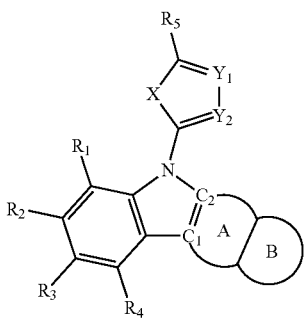

wherein in Formula 1,

X is an oxygen atom (O) or a sulfur (S) atom;

one selected from $Y_1$ and $Y_2$ is a nitrogen (N) atom and the other of $Y_1$ and $Y_2$ is a nitrogen (N) atom or —$CR_6$;

$C_1$ and $C_2$ are each a carbon (C) atom;

ring A is a benzene ring represented by Formula 1A, wherein 3 to 6 in Formula 1A are reference numbers and two of the reference numbers 3 to 6 correspond to respective carbon atoms of the ring B;

Formula 1A

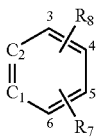

the ring B is an indole ring represented by Formula 1B, wherein 7 and 8 in Formula 1B are reference numbers, each of which corresponds to a carbon atom of the ring A;

Formula 1B $R_1$ to $R_{13}$ are each independently selected from a hydrogen atom, a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a substituted or unsubstituted $C_1$-$C_{10}$ alkyl group, a substituted or unsubstituted $C_2$-$C_{10}$ alkenyl group, a substituted or unsubstituted $C_2$-$C_{10}$ alkynyl group, a substituted or unsubstituted $C_1$-$C_{10}$ alkoxy group, a substituted or unsubstituted $C_3$-$C_{10}$ cycloalkyl group, a substituted or unsubstituted $C_3$-$C_{10}$ cycloalkenyl group, a substituted or unsubstituted $C_3$-$C_{10}$ heterocycloalkyl group, a substituted or unsubstituted $C_3$-$C_{10}$ heterocycloalkenyl group, a substituted or unsubstituted $C_6$-$C_{30}$ aryl group, a substituted or unsubstituted $C_2$-$C_{30}$ heteroaryl group, a substituted or unsubstituted $C_6$-$C_{30}$ aryloxy group, a substituted or unsubstituted $C_6$-$C_{30}$ arylthio group, a monovalent $C_6$-$C_{30}$ non-aromatic condensed polycyclic group, —$Si(Q_1)(Q_2)(Q_3)$, and —$B(Q_4)(Q_5)$, at least one substituent of the $C_1$-$C_{10}$ substituted alkyl group, the substituted $C_2$-$C_{10}$ alkenyl group, the substituted $C_2$-$C_{10}$ alkynyl group, the substituted $C_1$-$C_{10}$ alkoxy group, the substituted $C_3$-$C_{10}$ cycloalkyl group, the substituted $C_3$-$C_{10}$ cycloalkenyl group, the substituted $C_3$-$C_{10}$ heterocycloalkyl group, the substituted $C_3$-$C_{10}$ heterocycloalkenyl group, the substituted $C_6$-$C_{30}$ aryl group, the substituted $C_2$-$C_{30}$ heteroaryl group, the substituted $C_6$-$C_{30}$ aryloxy group, and the substituted $C_6$-$C_{30}$ arylthio group is selected from:

a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, and a $C_1$-$C_{30}$ alkoxy group;

a $C_1$-$C_{30}$ alkyl group, a $C_2$-$C_{30}$ alkenyl group, a $C_2$-$C_{30}$ alkynyl group, and a $C_1$-$C_{30}$ alkoxy group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —$N(Q_{11})(Q_{12})$, —$Si(Q_{13})(Q_{14})(Q_{15})$, and —$B(Q_{16})(Q_{17})$;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_2$-$C_{30}$ non-aromatic condensed polycyclic group;

a $C_3$-$C_{10}$ cycloalkyl group, a $C_3$-$C_{10}$ cycloalkenyl group, a $C_3$-$C_{10}$ heterocycloalkyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, and a monovalent $C_6$-$C_{30}$ non-aromatic condensed polycyclic group, each substituted with at least one selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, a $C_6$-$C_{30}$ aryloxy group, a $C_6$-$C_{30}$ arylthio group, a monovalent $C_6$-$C_{30}$ non-aromatic condensed polycyclic group, —$N(Q_{21})(Q_{22})$, —$Si(Q_{23})(Q_{24})(Q_{25})$, and —$B(Q_{26})(Q_{27})$; and $Si(Q_{31})(Q_{32})(Q_{33})$ and —$B(Q_{34})(Q_{35})$, and $Q_1$ to $Q_5$, $Q_{11}$ to $Q_{17}$, $Q_{21}$ to $Q_{27}$, and $Q_{31}$ to $Q_{35}$ are each independently selected from a hydrogen atom, a $C_1$-$C_{30}$ alkyl group, a $C_2$-$C_{30}$ alkenyl group, a $C_2$-$C_{30}$ alkynyl group, a $C_1$-$C_{30}$ alkoxy group, a $C_3$-$C_{10}$ cycloalkyl group, a $C_3$-$C_{10}$ heterocycloalkyl group, a $C_3$-$C_{10}$ cycloalkenyl group, a $C_3$-$C_{10}$ heterocycloalkenyl group, a $C_6$-$C_{30}$ aryl group, a $C_2$-$C_{30}$ heteroaryl group, and a monovalent $C_6$-$C_{30}$ non-aromatic condensed polycyclic group.

2. The condensed cyclic compound of claim 1, wherein the carbon atoms corresponding to the reference numbers 3 and 4 of the ring A are present in the ring B, the carbon atoms corresponding to the reference numbers 4 and 5 of the ring A, or the carbon atoms corresponding to the reference numbers 5 and 6 of the ring A.

3. The condensed cyclic compound of claim 1, wherein the rings A and B

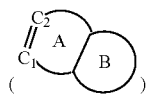

are a group represented by any one of Formulae 2A to 2F:

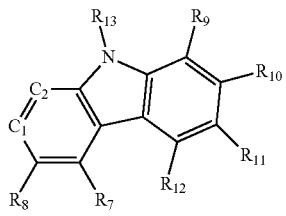
<Formula 2A>

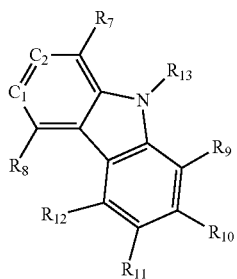
<Formula 2B>

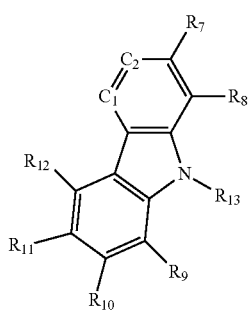
<Formula 2C>

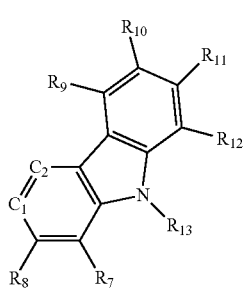
<Formula 2D>

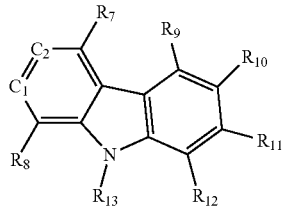
<Formula 2E>

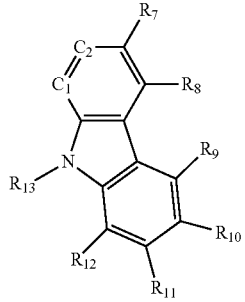
<Formula 2F> wherein in Formulae 2A to 2F, $R_7$ to $R_{13}$ are each independently selected from a hydrogen atom, a substituted or unsubstituted $C_6$-$C_{30}$ aryl group, and a substituted or unsubstituted $C_2$-$C_{30}$ heteroaryl group, at least one substituent of the substituted $C_6$-$C_{30}$ aryl group and the substituted $C_2$-$C_{30}$ heteroaryl group is selected from a $C_6$-$C_{30}$ aryl group and a $C_2$-$C_{30}$ heteroaryl group, and $R_{13}$ is not a hydrogen atom.

4. The condensed cyclic compound of claim 1, wherein $R_1$ to $R_{13}$ are each independently selected from:

a hydrogen atom, a methyl group, an ethyl group, a propyl group, a butyl group, a pentyl group, a hexyl group, a heptyl group, an octyl group, a nonyl group, a decyl group, a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl function, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spirofluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, a pyranyl group, a thiophenyl group, a thiazolyl group, an isothiazolyl group, a thiopyranyl group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group;

a methyl group, an ethyl group, a propyl group, a butyl group, a pentyl group, a hexyl group, a heptyl group, an octyl group, a nonyl group, and a decyl group, each substituted with at least one selected from a deuterium atom, a halogen atom, a hydroxyl group, a cyano group, a nitro group, and an amino group; and a phenyl group, a pentalenyl group, an indenyl group, a naphthyl group, an azulenyl group, an indacenyl group, an acenaphthyl group, a biphenyl group, a heptalenyl group, a phenalenyl group, a fluorenyl group, a phenanthrenyl group, an anthryl function, a fluoranthenyl group, a pyrenyl group, a benzofluorenyl group, a naphthacenyl group, a chrysenyl group, a triphenylenyl group, a terphenyl group, a perylenyl group, a picenyl group, a hexacenyl group, a spiro-fluorenyl group, a pyrrolyl group, a furyl group, a pyrazolyl group, an imidazolyl group, an oxazolyl group, an isoxazolyl group, a triazolyl group, a tetrazolyl group, an oxadiazolyl group, a pyridyl group, a pyrimidinyl group, a pyrazinyl group, a pyridazinyl group, a triazinyl group, pyranyl group, a thiophenyl group, a thiazolyl group, an isothiazolyl group, a thiopyranyl group, an indolyl group, an isoindolyl group, an indolizinyl group, a benzofuryl group, an isobenzofuryl group, an indazolyl group, a benzimidazolyl group, a benzoxazolyl group, a benzisoxazolyl group, an imidazopyridyl group, a purinyl group, a quinolyl group, an isoquinolyl group, a phthalazinyl group, a quinazolinyl group, a quinoxalinyl group, a naphthyridinyl group, a cinnolinyl group, a benzothiophenyl group, a benzothiazolyl group, a carbazolyl group, a benzocarbazolyl group, a pyridoindolyl group, a dibenzofuryl group, a phenanthridinyl group, a benzoquinolyl group, a phenazinyl group, a dibenzosilolyl group, a dibenzothiophenyl group, and a benzocarbazolyl group, each substituted with at least one selected from a deuterium atom, a halogen atom, a hydroxyl group, a cyano group, a nitro group, an amino group, a carboxylic acid group or a salt thereof, a sulfonic acid group or a salt thereof, and a phosphoric acid group or a salt thereof, a $C_1$-$C_{10}$ alkyl group, a $C_2$-$C_{10}$ alkenyl group, a $C_2$-$C_{10}$ alkynyl group, a $C_1$-$C_{10}$ alkoxy group, a $C_3$-$C_{10}$ cycloalkyl group, a $C_3$-$C_{10}$ heterocycloalkyl group, a $C_3$-$C_{10}$ cycloalkenyl group, $C_3$-$C_{10}$ heterocycloalkenyl group, a $C_6$-$C_{30}$ aryl group, a $C_4$-$C_{30}$ heteroaryl group, a $C_5$-$C_{30}$ aryloxy group, a $C_5$-$C_{30}$ arylthio group, and —Si($Q_{31}$)($Q_{32}$)($Q_{33}$) (wherein, $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group), wherein $R_5$ and $R_{13}$ are not hydrogen.

5. The condensed cyclic compound of claim 1, wherein $R_1$ to $R_4$ and $R_6$ to $R_{12}$ are each independently a hydrogen atom or a compound represented by one of Formulae 3A to 3C, and $R_5$ and $R_{13}$ are each independently selected from a compound represented by one of Formulae 3A to 3C:

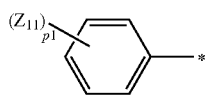
<3A>

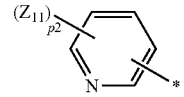
<3B>

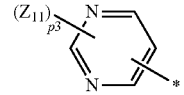
<3C> wherein in Formulae 3A to 3C, $Z_{11}$ is selected from a deuterium atom, a halogen atom, a hydroxyl group, a cyano group, a nitro group, an amino group, an amidino group, a hydrazine group, a hydrazone group, a carboxylic acid group or a salt thereof, a sulfonic acid group or a salt thereof, a phosphoric acid group or a salt thereof, a $C_1$-$C_{10}$ alkyl group, a $C_1$-$C_{10}$ alkoxy group, a $C_6$-$C_{30}$ aryl group, a $C_4$-$C_{30}$ heteroaryl group, and —Si($Q_{31}$)($Q_{32}$)($Q_{33}$) (wherein $Q_{31}$ to $Q_{33}$ are each independently selected from a hydrogen atom, a $C_1$-$C_{10}$ alkyl group, a $C_1$-$C_{10}$ alkoxy group, and a $C_6$-$C_{20}$ aryl group), p1 is selected from an integer of 1 to 5,
p2 is selected from an integer of 1 to 4,
p3 is selected from an integer of 1 to 3, and
* is a binding site.

6. The condensed cyclic compound of claim 1, wherein:
$R_1$ to $R_4$ and $R_6$ to $R_{12}$ are each independently a hydrogen atom or a compound represented by one of Formulae 4A to 4M, and $R_5$ and $R_{13}$ are each independently a compound represented by one of Formulae 4A to 4M:

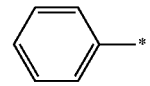
<4A>

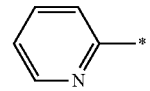
<4B>

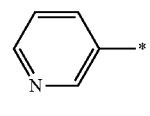
<4C>

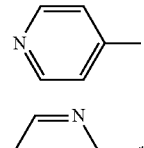
<4D>

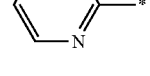
<4E>

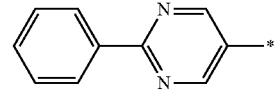
<4F>

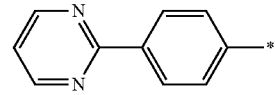
<4G>

7. The condensed cyclic compound of claim 1, wherein X is a sulfur (S) atom, $Y_1$ is a nitrogen (N) atom, and $Y_2$ is —$CR_6$.

8. The condensed cyclic compound of claim 1, wherein X is a S atom, $Y_1$ is —$CR_6$, and $Y_2$ is a N atom.

9. The condensed cyclic compound of claim 1, wherein X is an oxygen (O) atom, $Y_1$ is a N atom, and $Y_2$ is —$CR_6$.

10. The condensed cyclic compound of claim 1, wherein X is an O atom, $Y_1$ is $CR_6$, and $Y_2$ is a N atom.

11. The condensed cyclic compound of claim 1, wherein the condensed cyclic compound of Formula 1 is represented by Formulae 1-1 to 1-6:

Formula 1-5

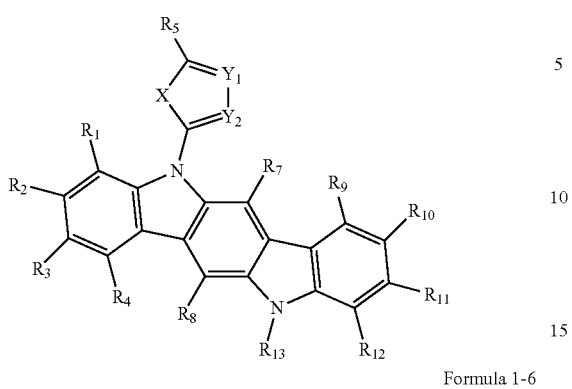

Formula 1-6

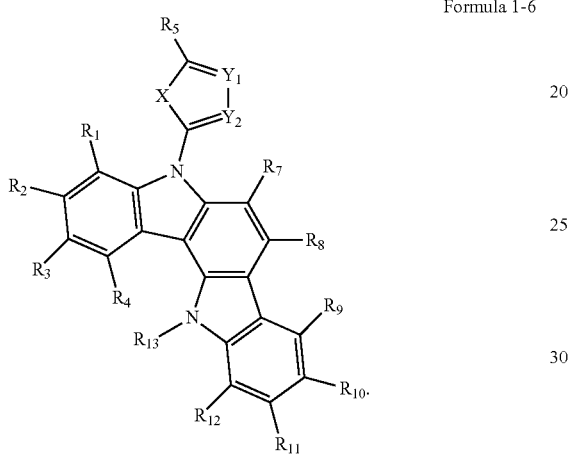

12. The condensed cyclic compound of claim 11, wherein:
$R_1$ to $R_4$ and $R_6$ to $R_{12}$ are each independently selected from a hydrogen atom, a phenyl group, a pyridyl group, and a pyrimidinyl group; a phenyl group, a pyridyl group, and a pyrimidinyl group, each substituted with at least one selected from a phenyl group, a pyridyl group, a pyrimidinyl group, and a carbazolyl group, and $R_5$ and $R_{13}$ are each independently selected from a phenyl group, a pyridyl group, and a pyrimidinyl group; a phenyl group, a pyridyl group, and a pyrimidinyl group, each substituted with at least one selected from a phenyl group, a pyridyl group, a pyrimidinyl group, and a carbazolyl group.

13. The condensed cyclic compound of claim 1, wherein the condensed cyclic compound is any one of Compounds 1 to 159:

1

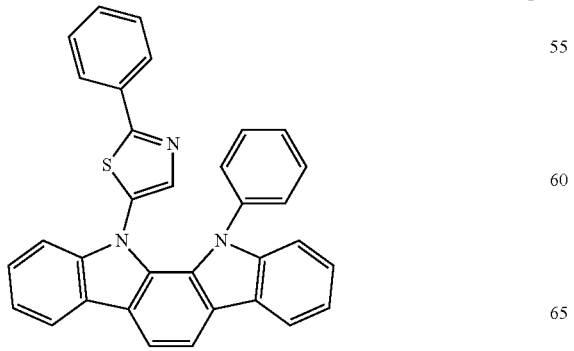

2

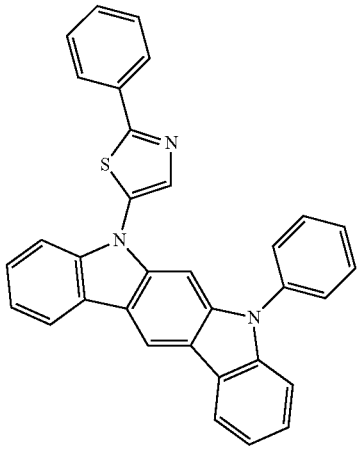

3

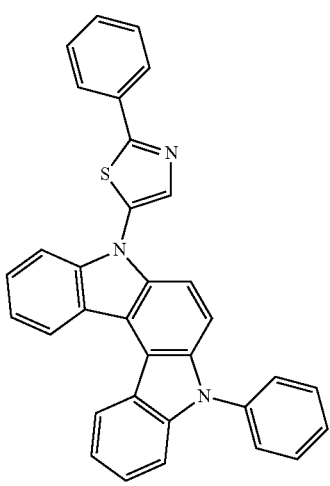

4

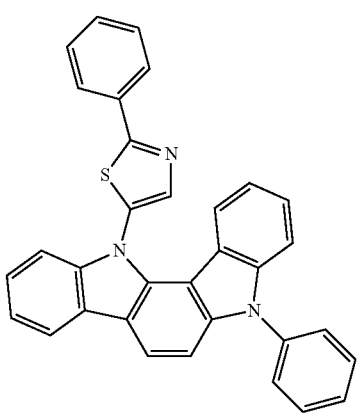

US 9,966,540 B2
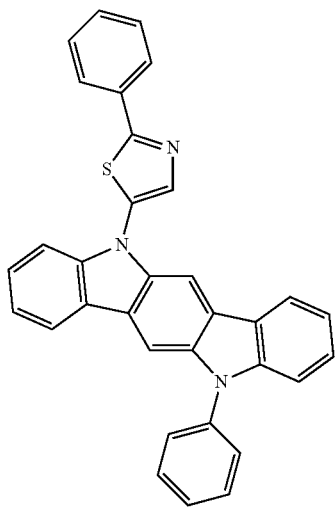
5
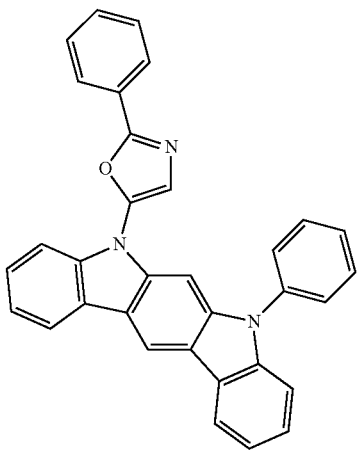
5
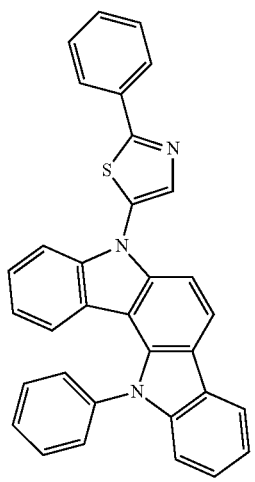
6
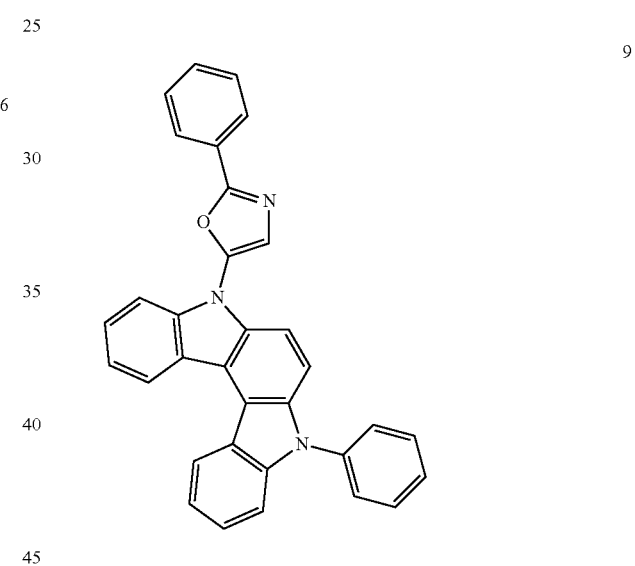
8
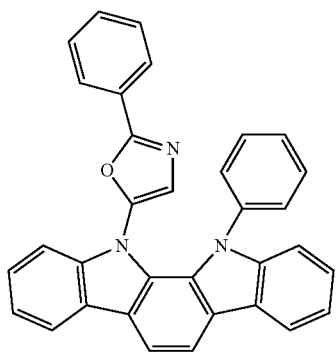
7
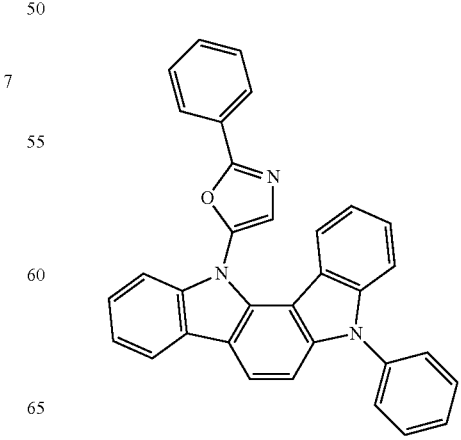
9
10

11
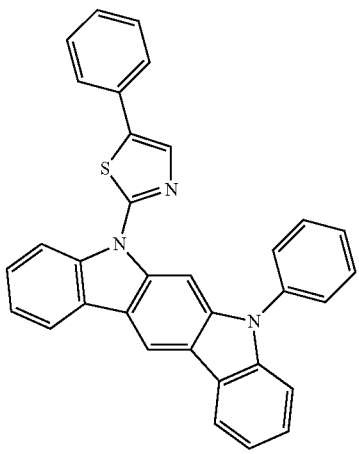
12
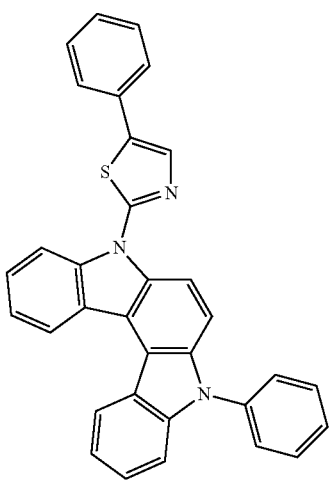
13
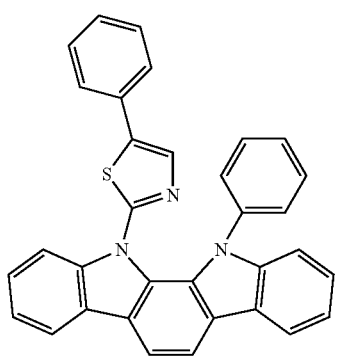
14
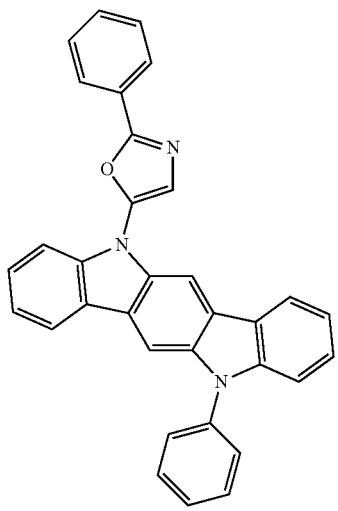
15
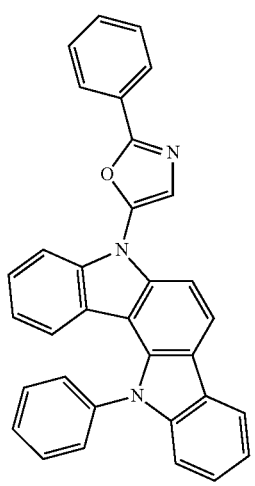
16
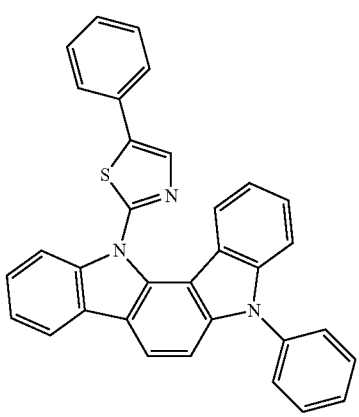

17
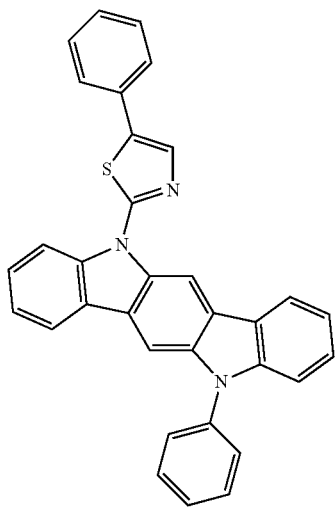
18
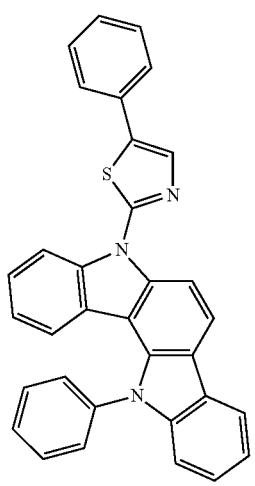
19
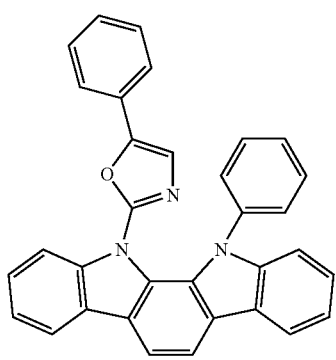
20
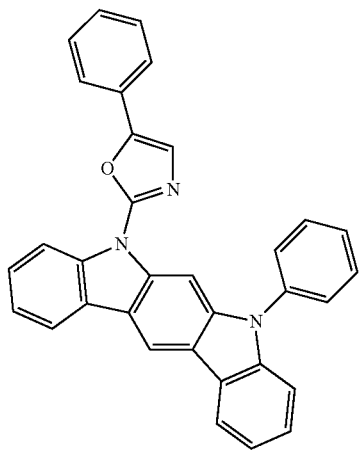
21
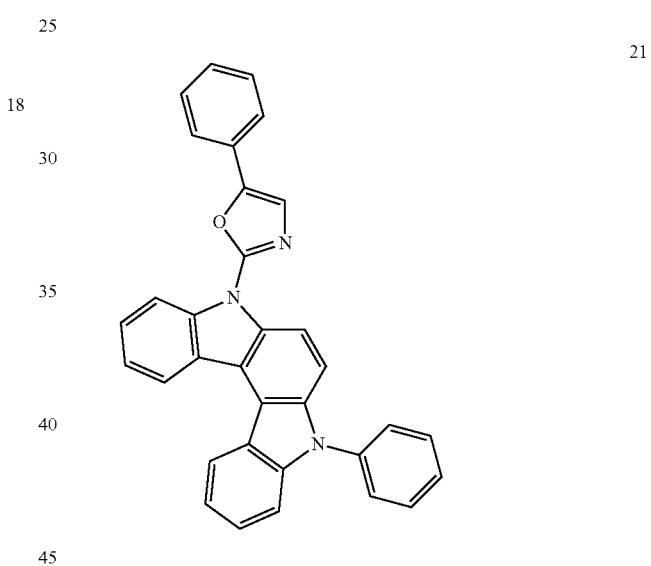
22
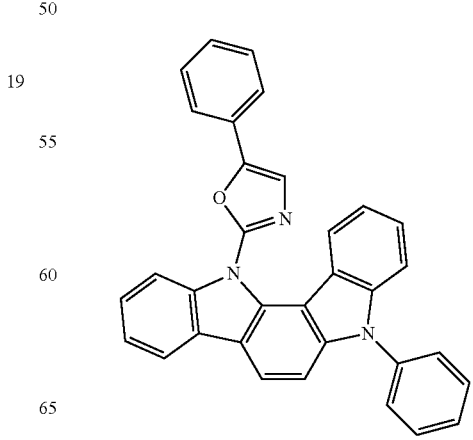

23
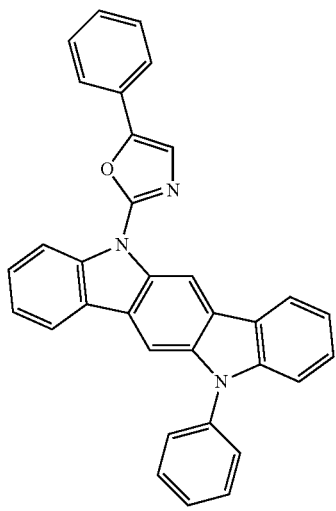
24
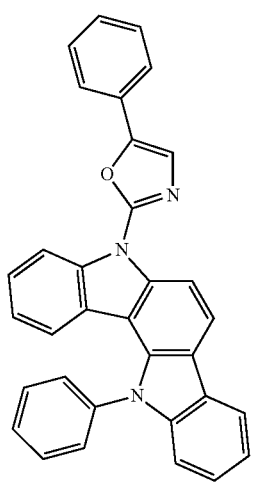
25
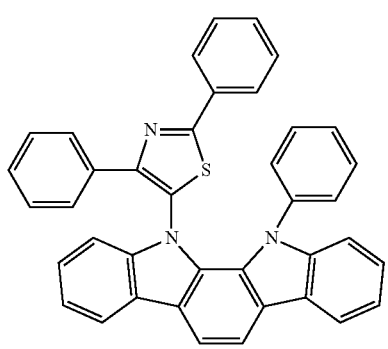
26
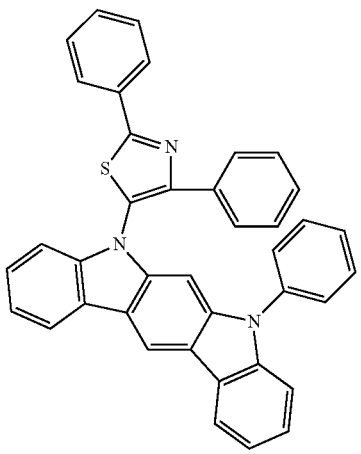
27
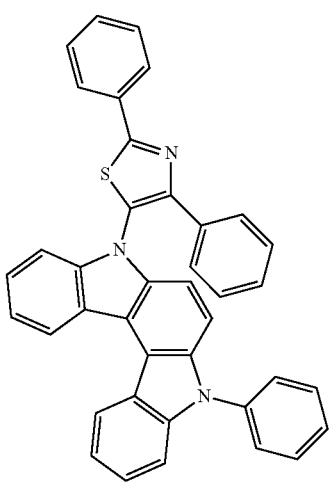
28
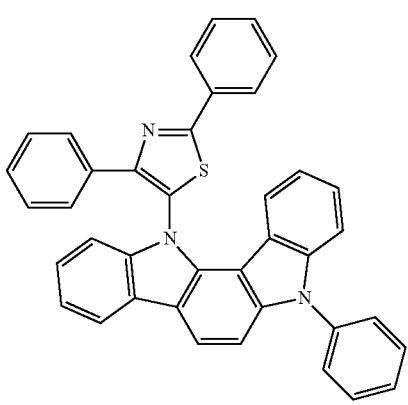

29
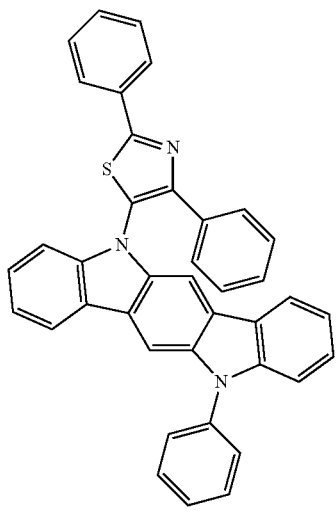
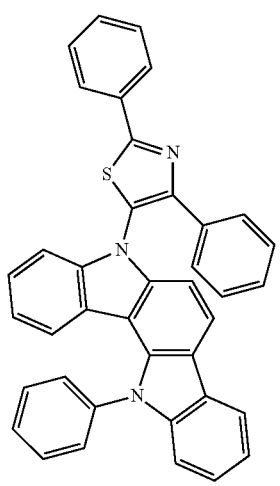
30
31
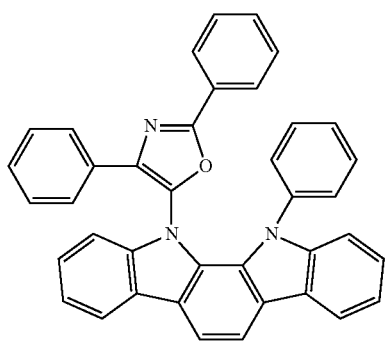
32
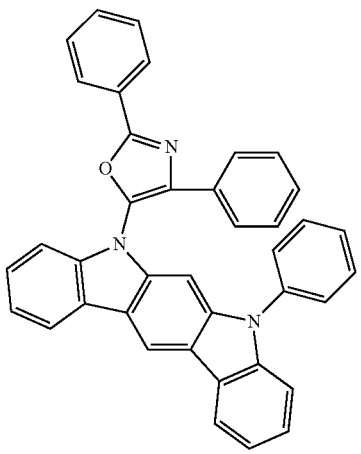
33
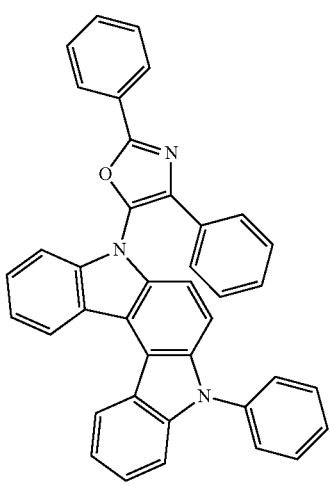
34
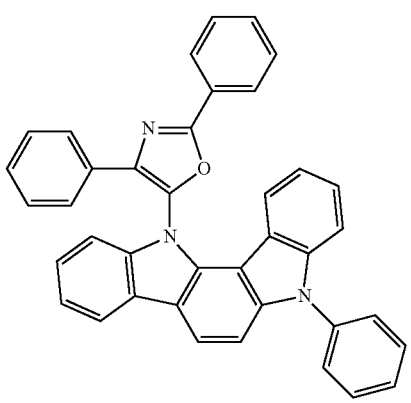

171
-continued
35
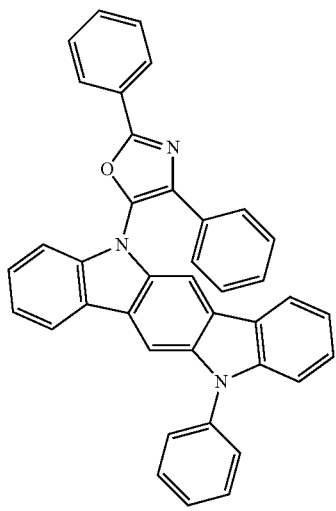
36
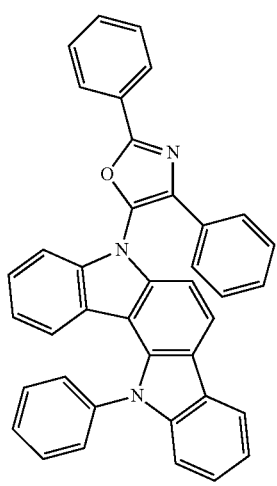
37
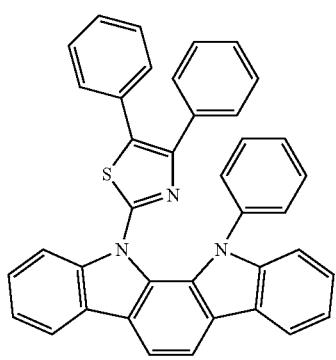
172
-continued
38
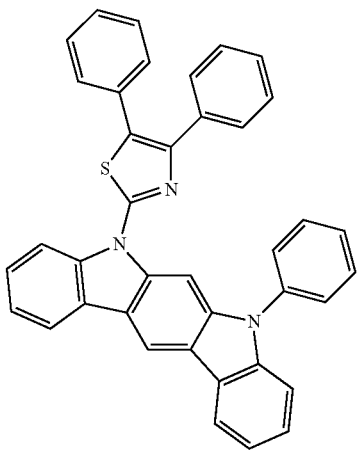
39
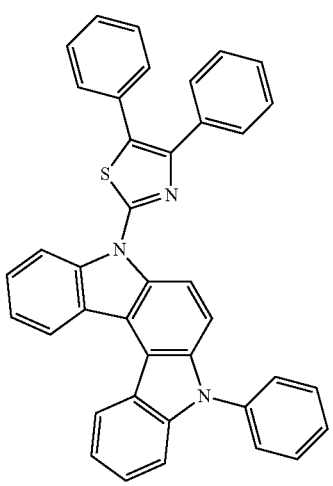
40
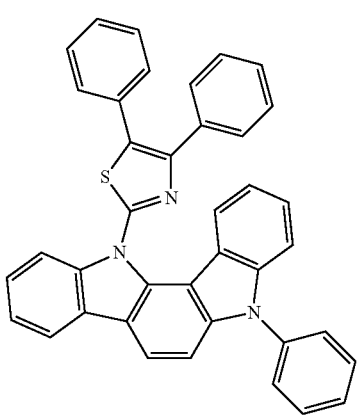

173
-continued
41
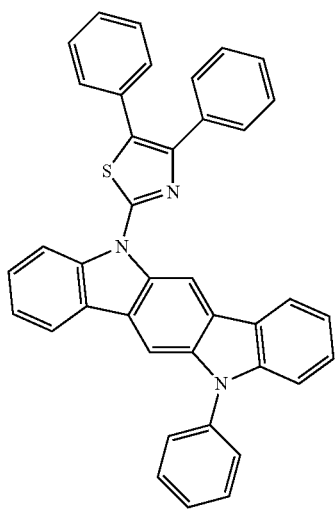
42
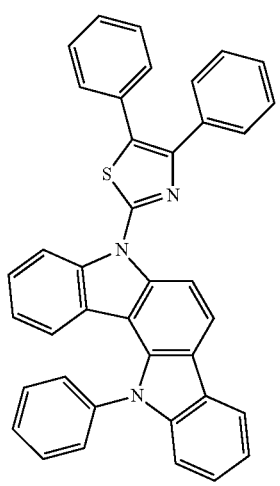
43
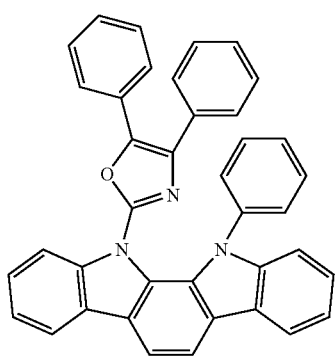
174
-continued
44
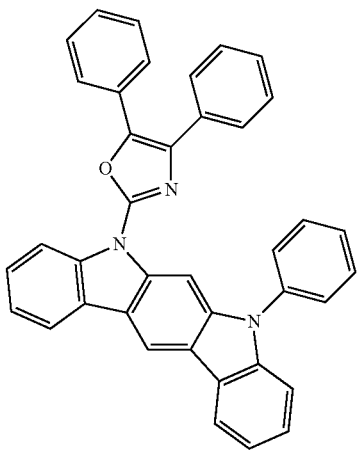
45
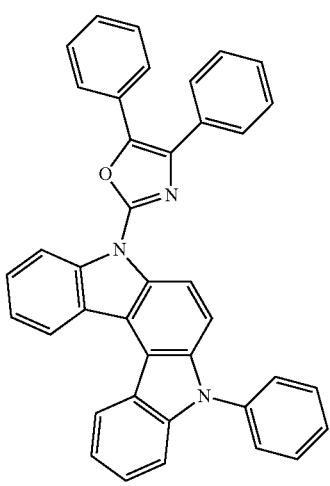
46
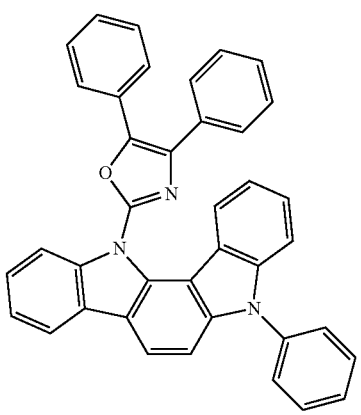

47
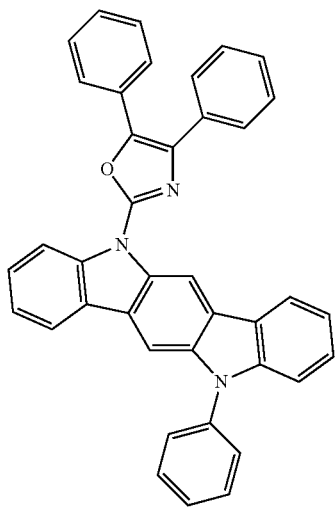
48
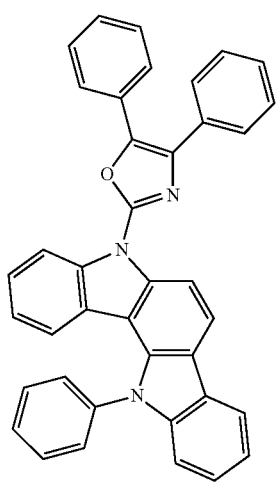
49
50
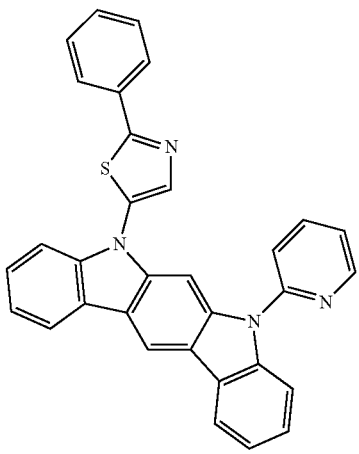
51
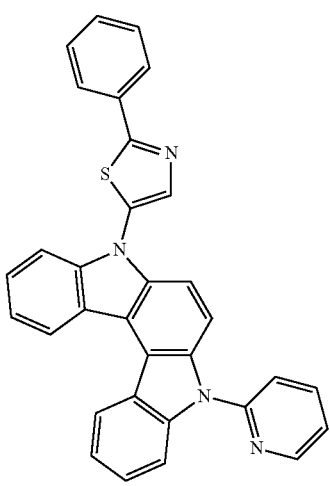
52
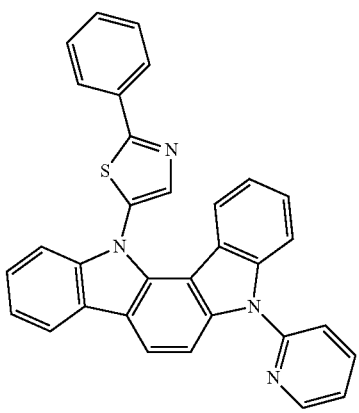

177
-continued
53
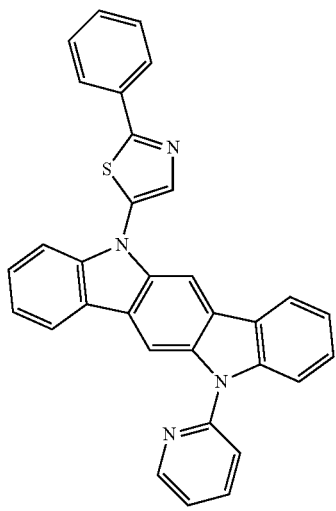
54
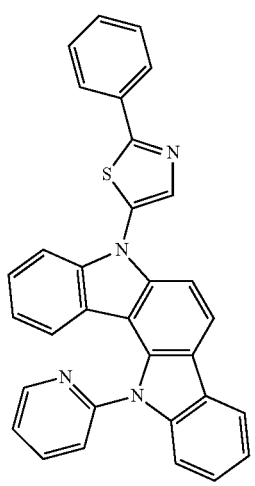
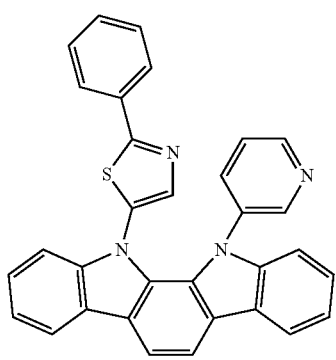
178
-continued
56
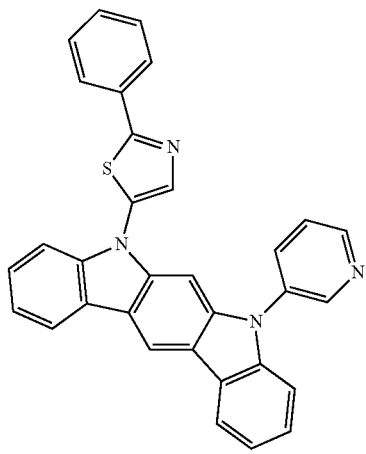
57
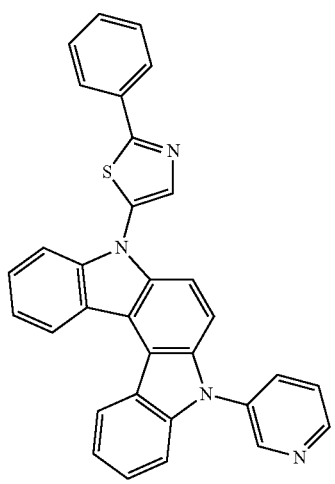
58
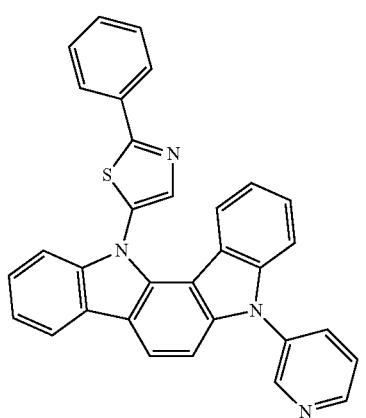

59
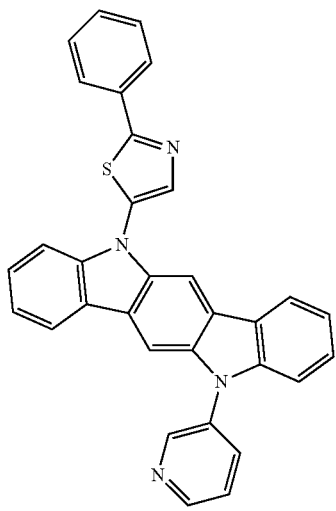
60
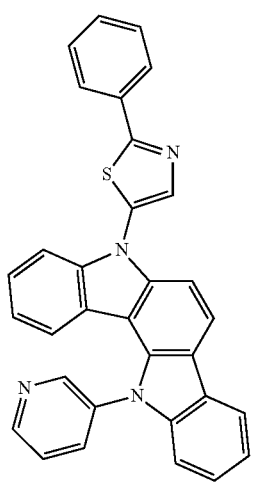
61
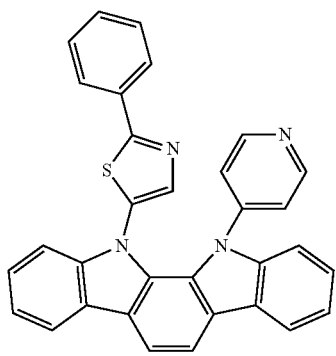
62
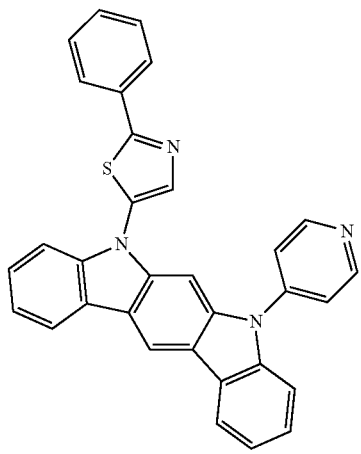
63
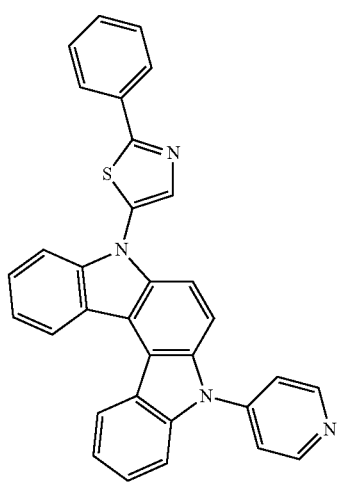
64
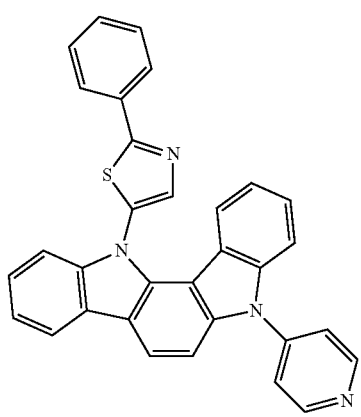

| 65 | 68 |
|---|---|
| 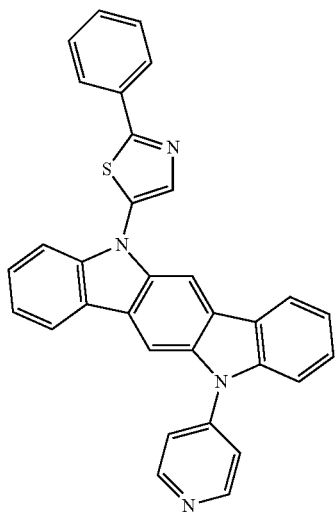 | 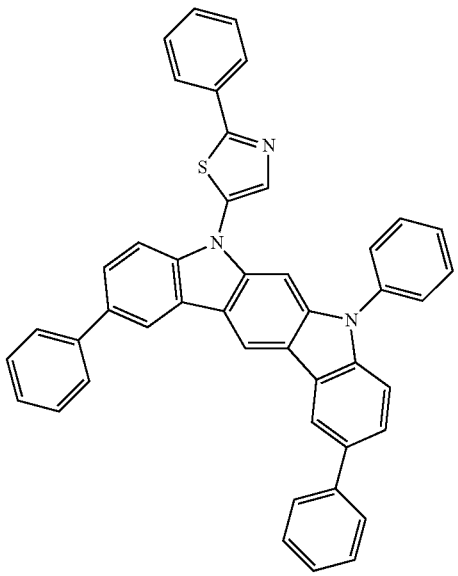 |
| 66 | 69 |
| 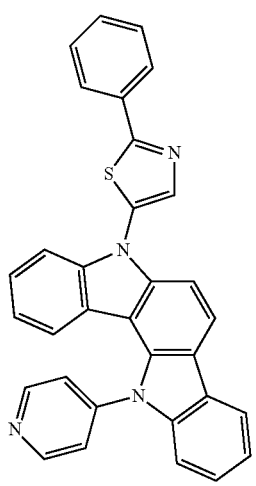 | 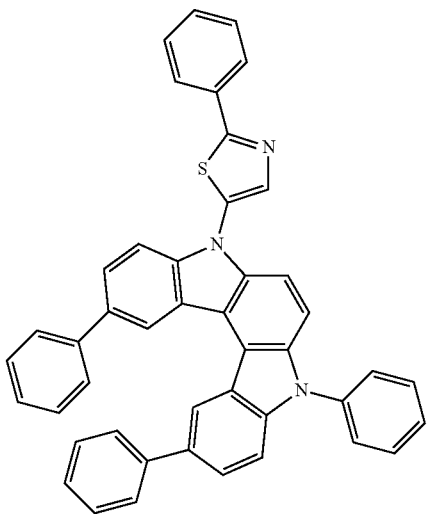 |
| 67 | 70 |
| 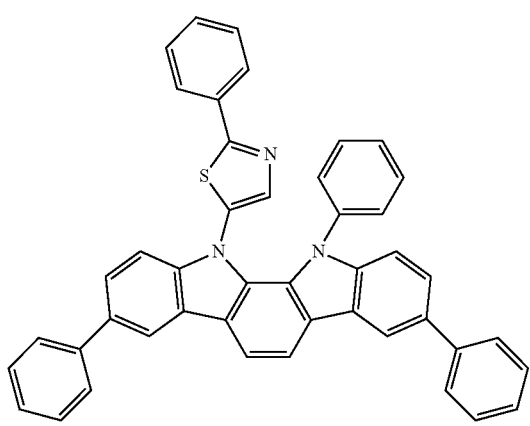 | 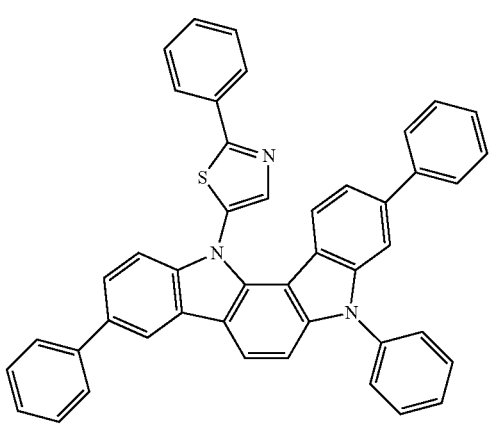 |

183
-continued
71
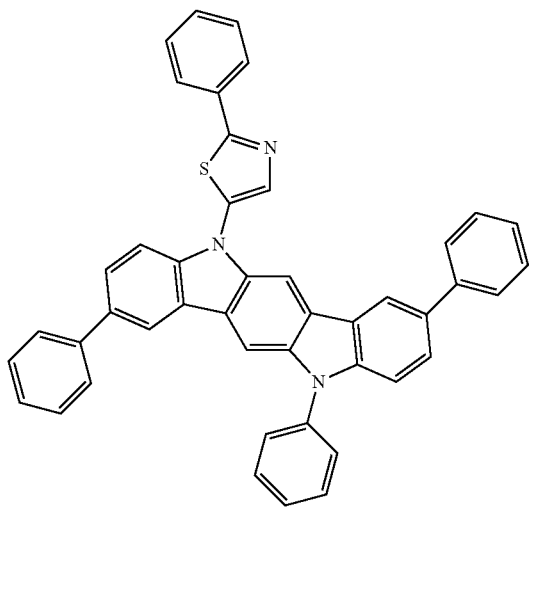
72
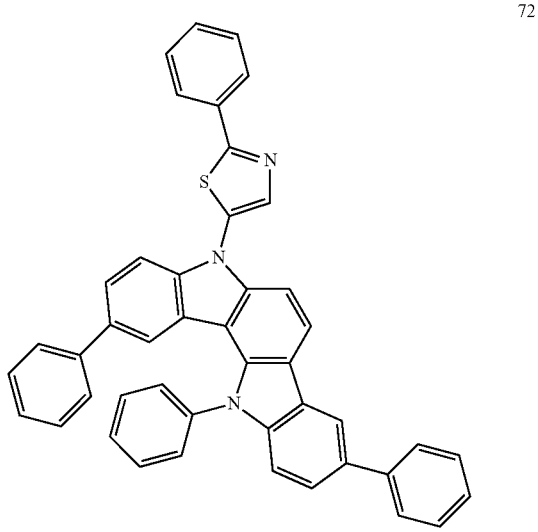
73
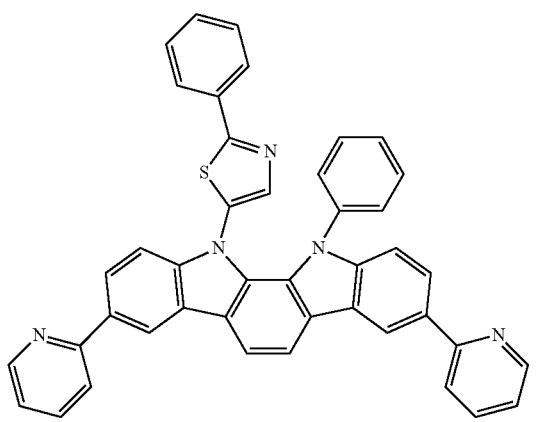
184
-continued
74
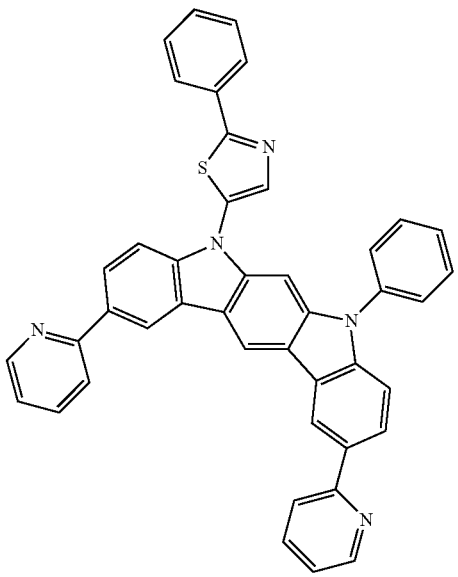
75
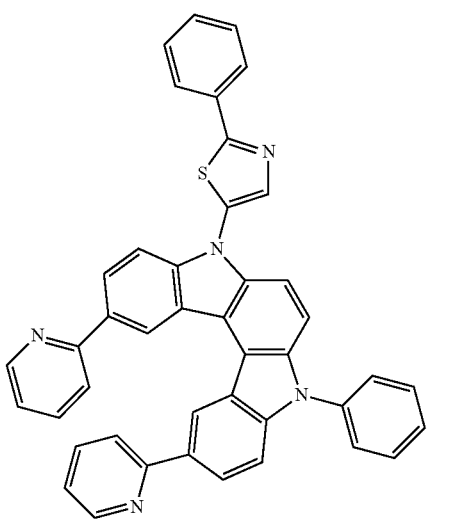
76
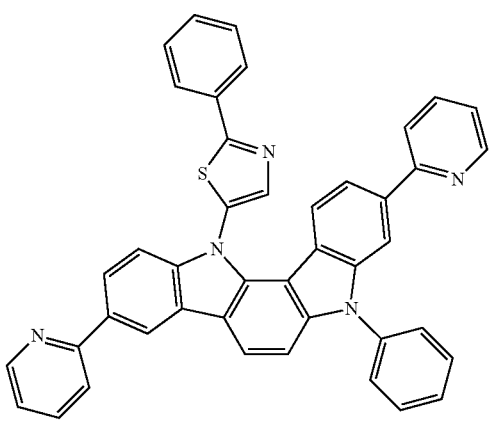

-continued
77
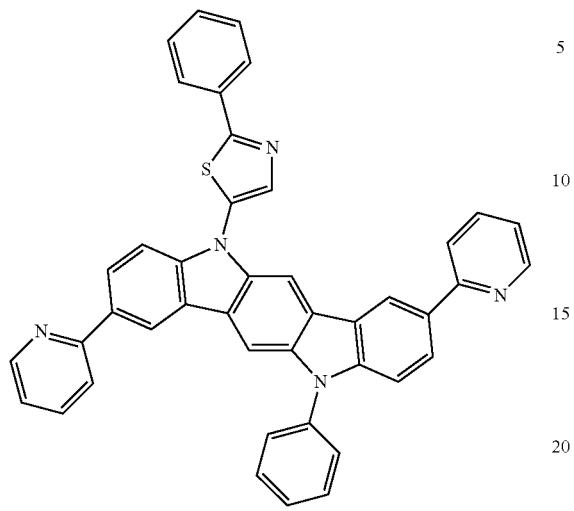
78
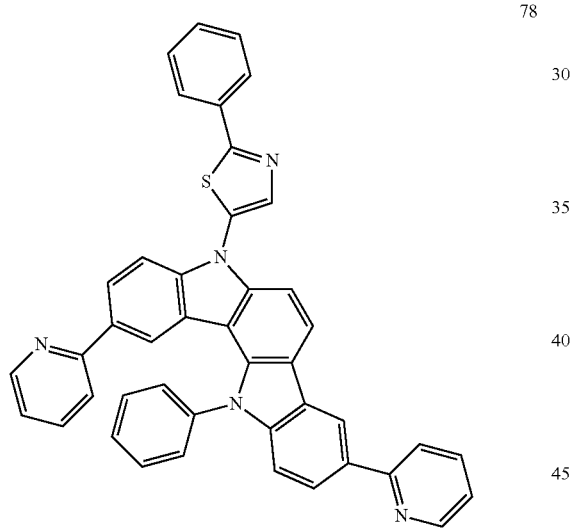
79
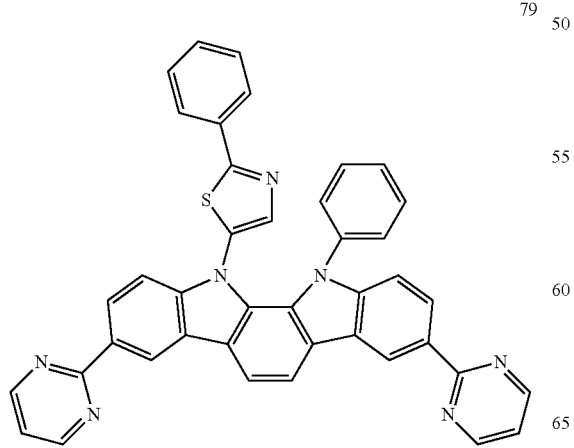
-continued
80
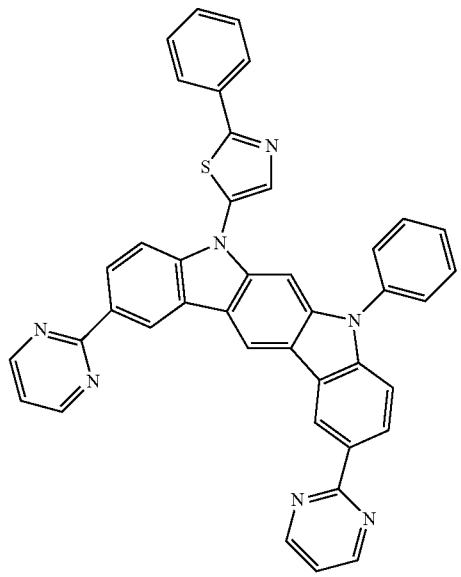
81
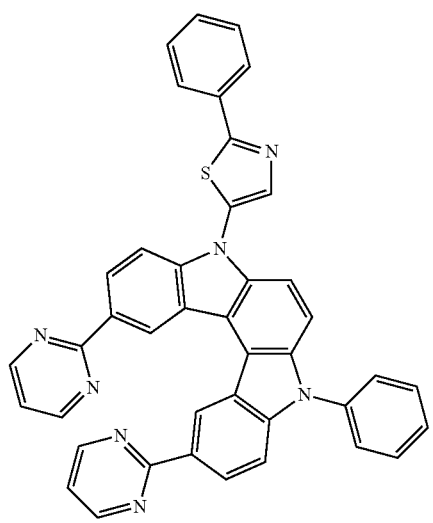
82
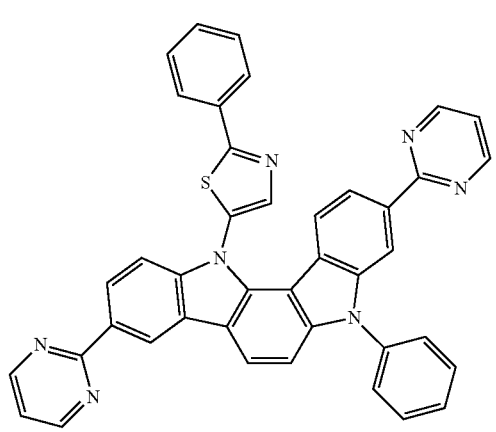

83
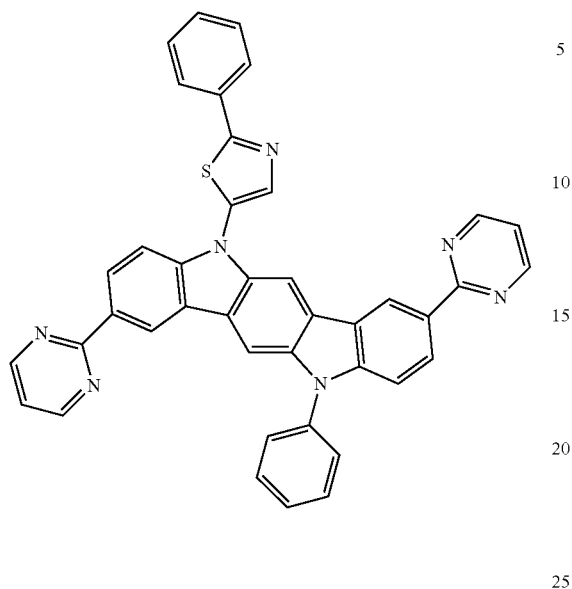
84
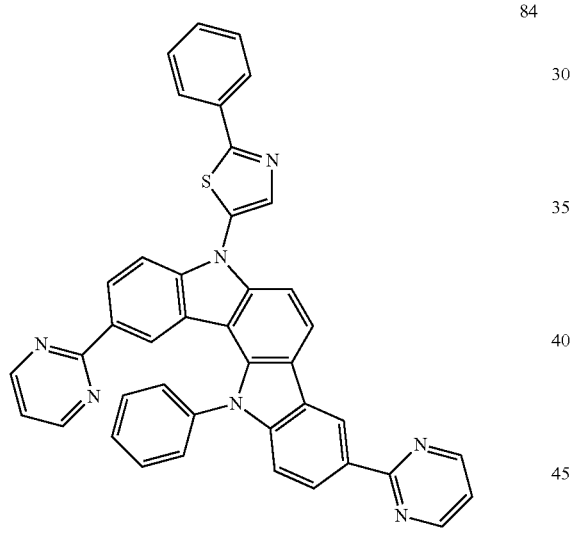
85
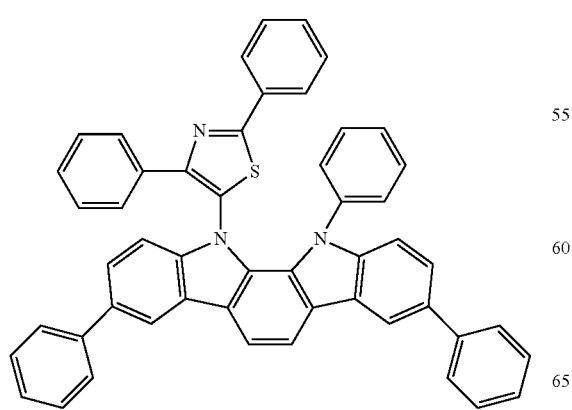
86
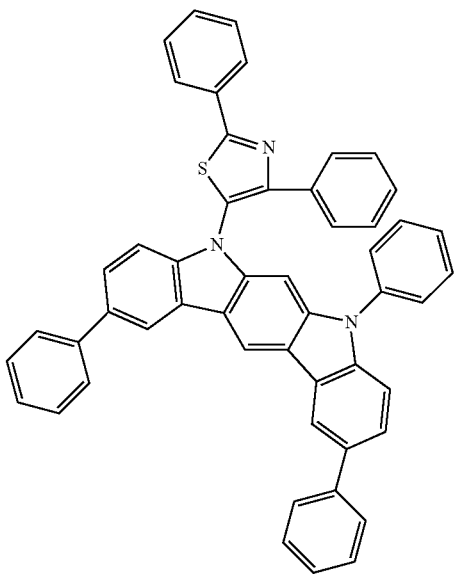
87
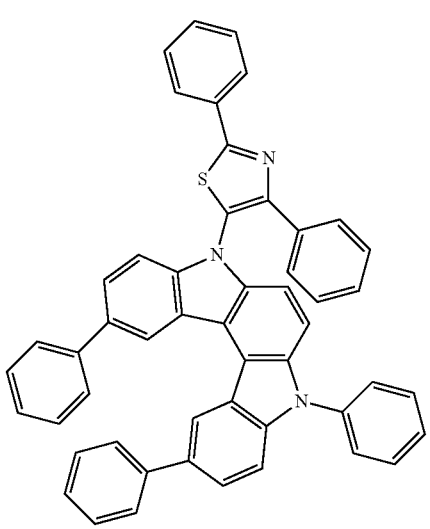
88
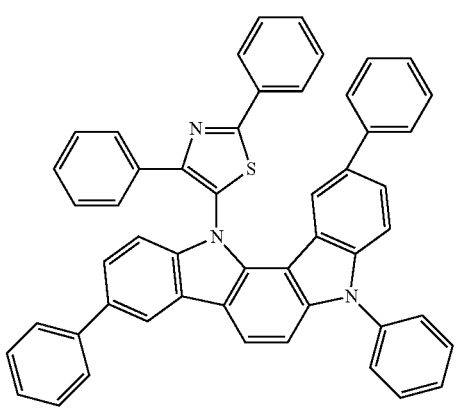

89
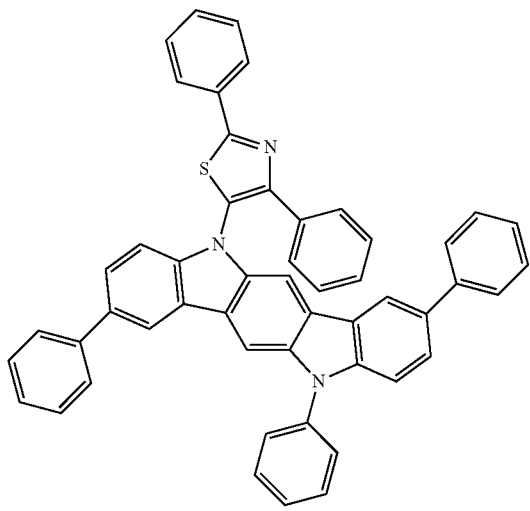
90
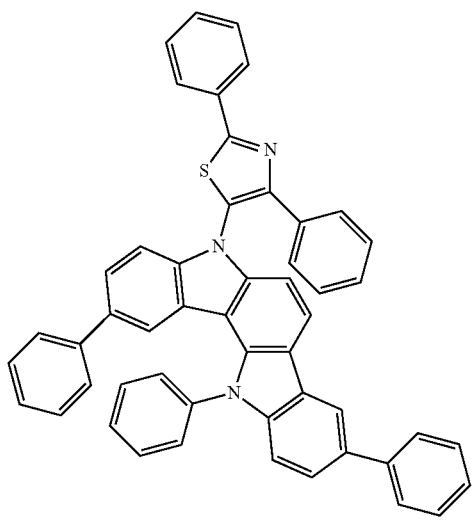
91
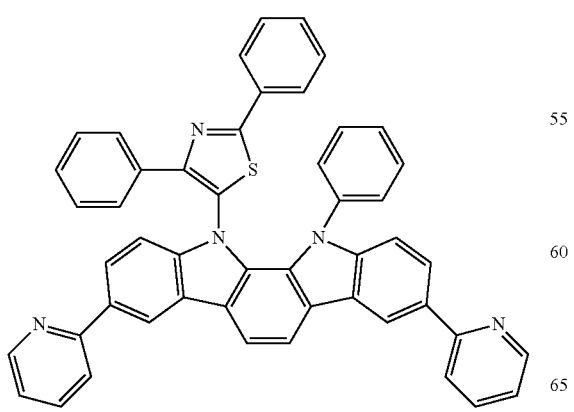
92
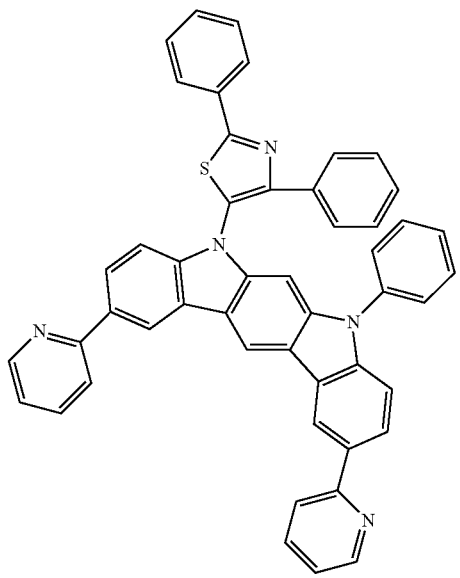
93
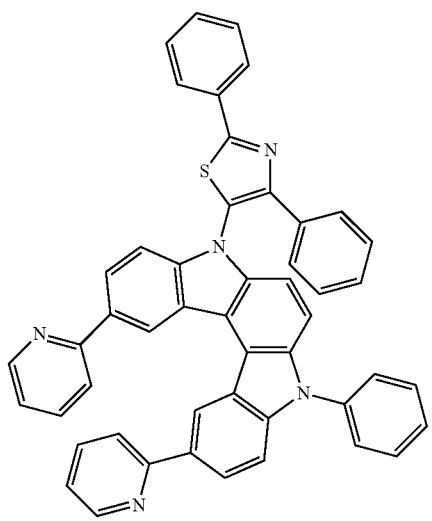
94
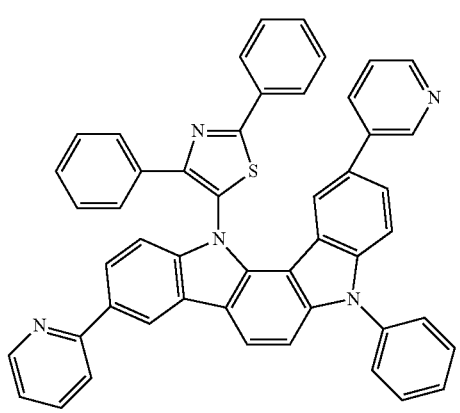

95
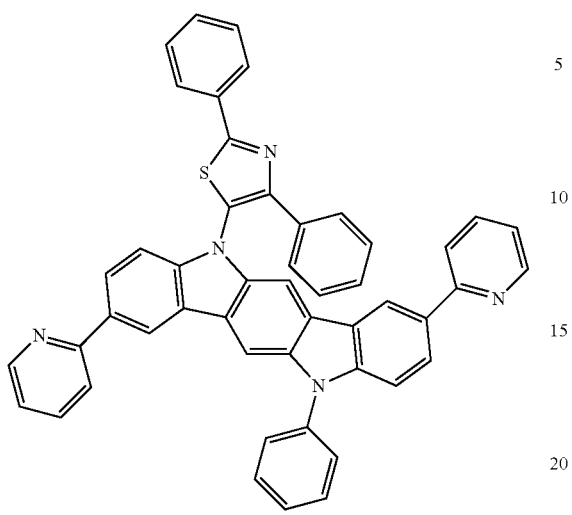
96
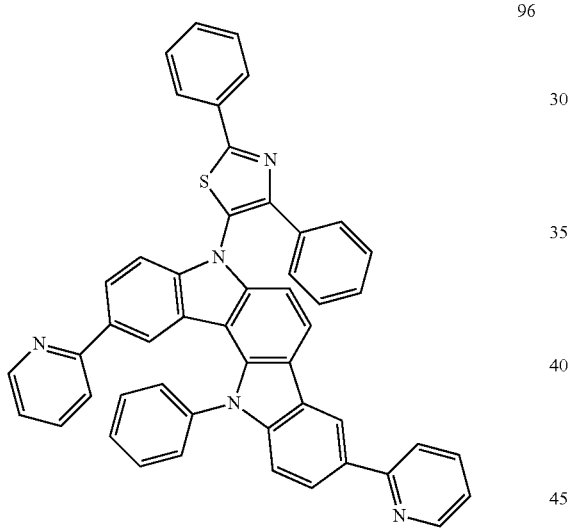
97
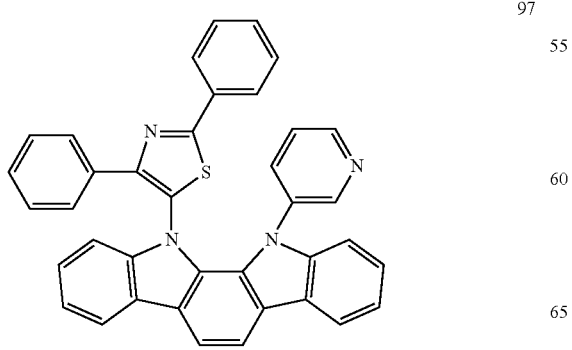
98
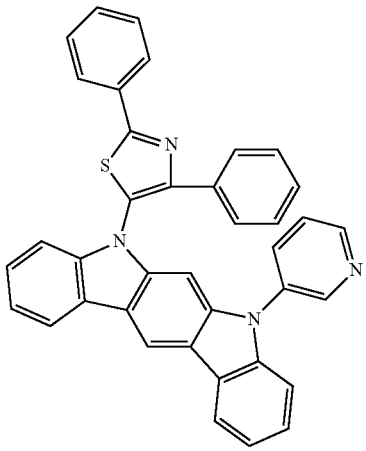
99
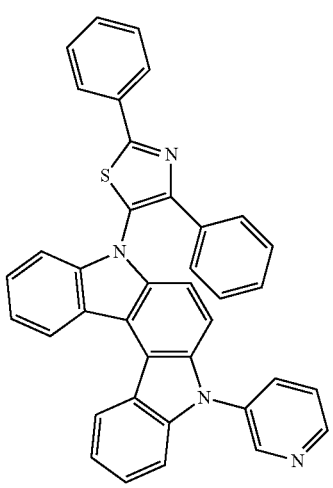
100
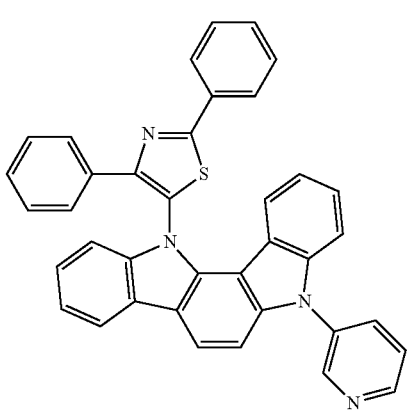

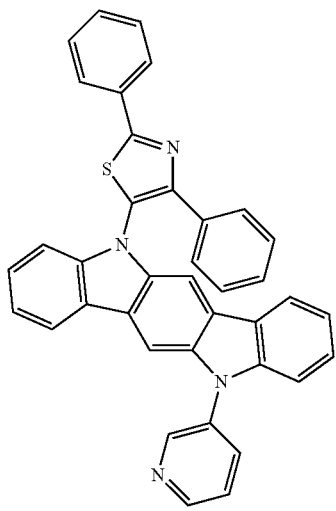
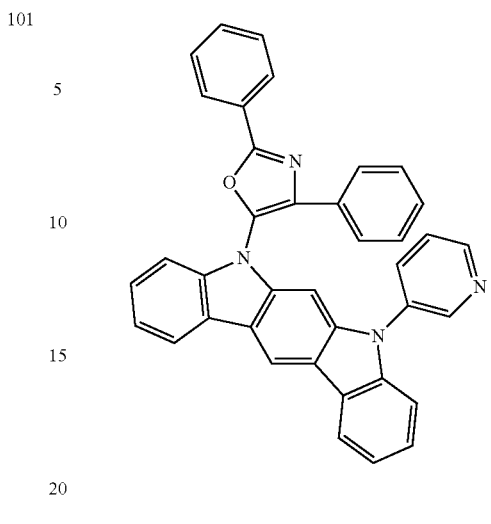
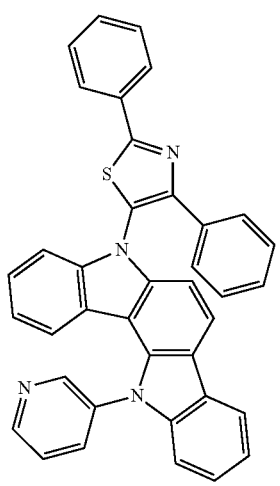
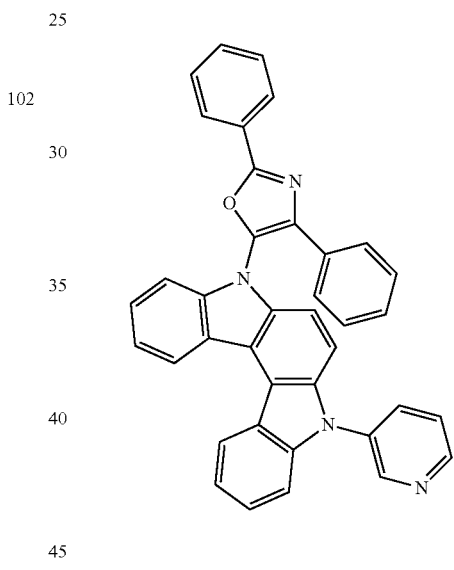
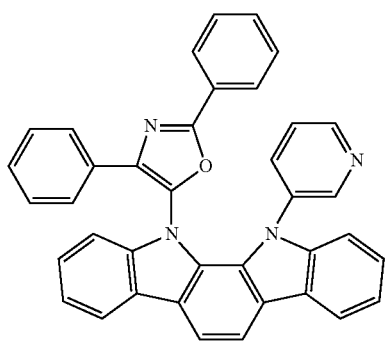
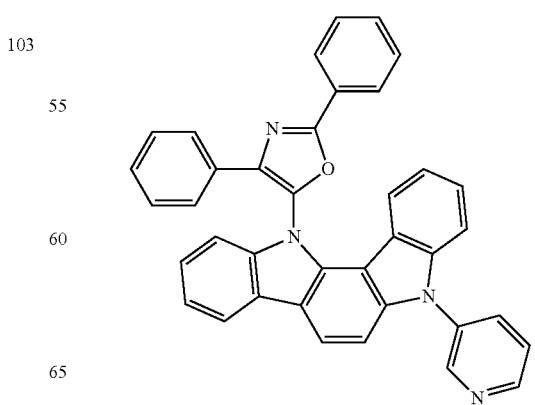

107
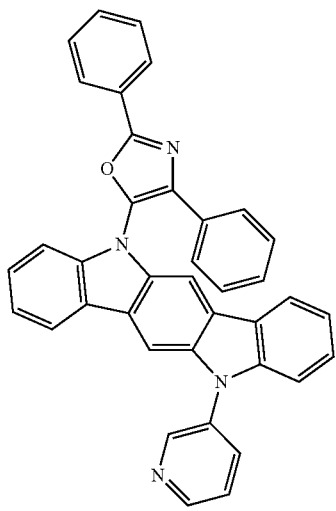
108
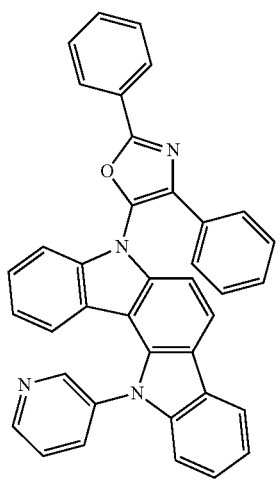
109
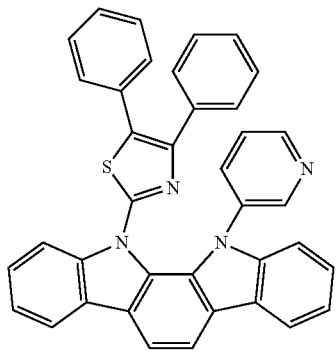
110
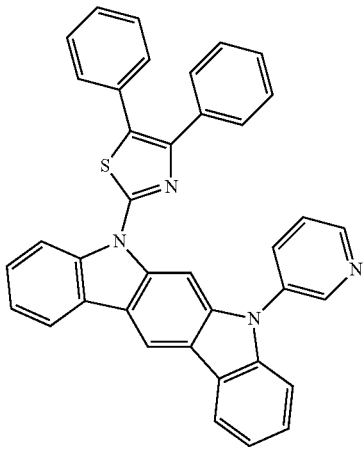
111
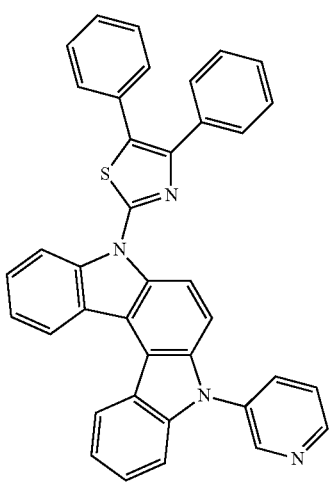
112
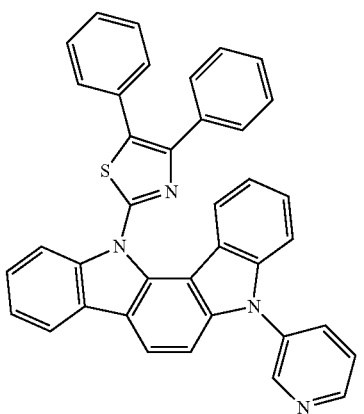

113
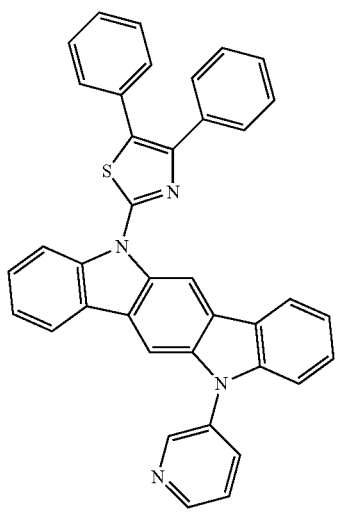
114
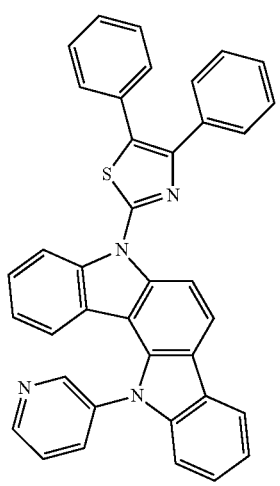
115
116
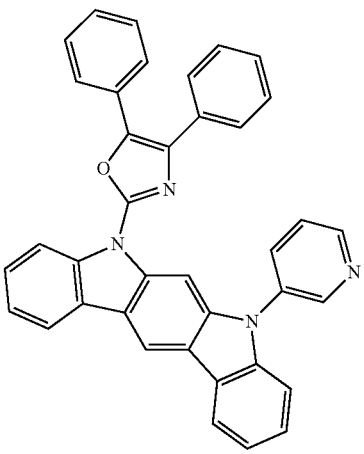
117
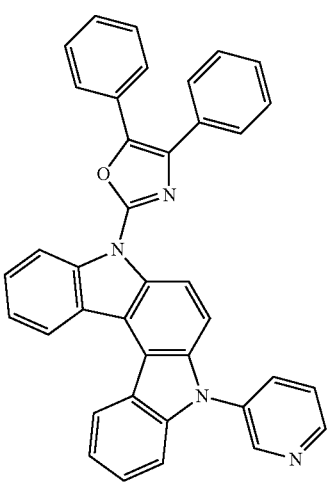
118
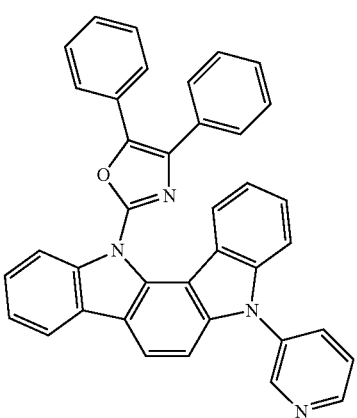

119
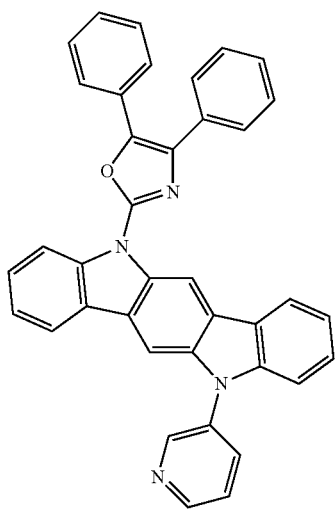
120
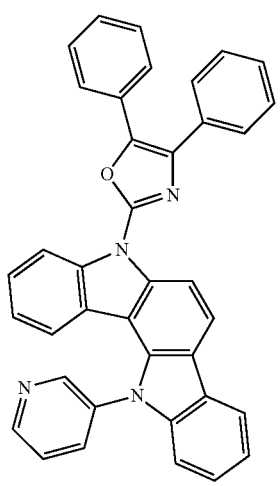
121
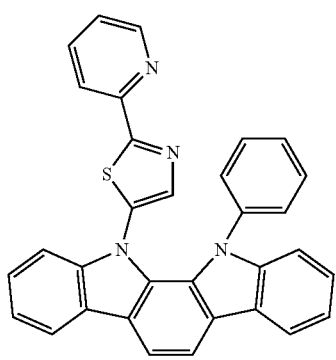
122
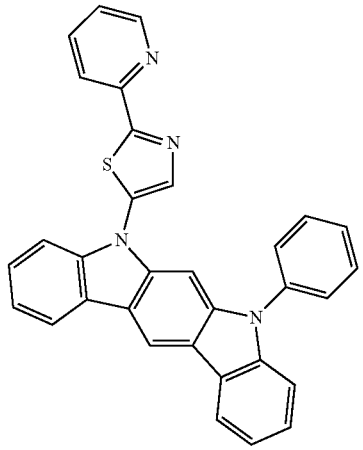
123
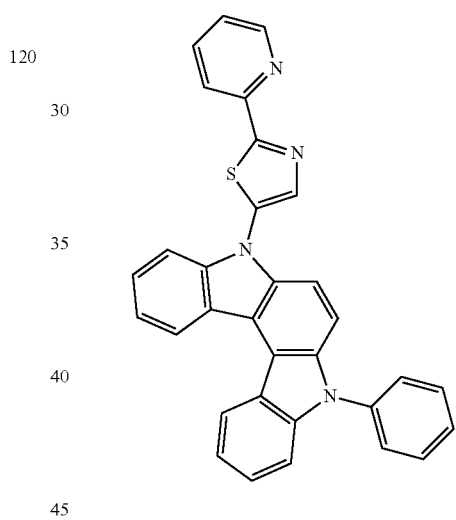
124
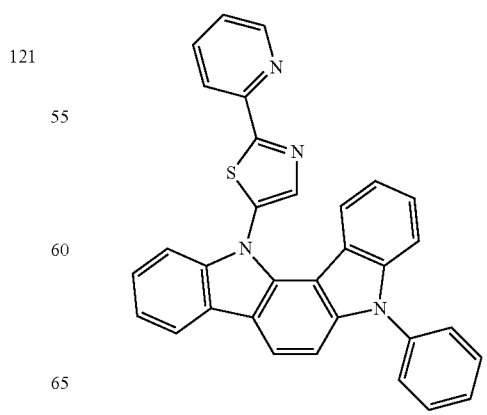

201
-continued
125
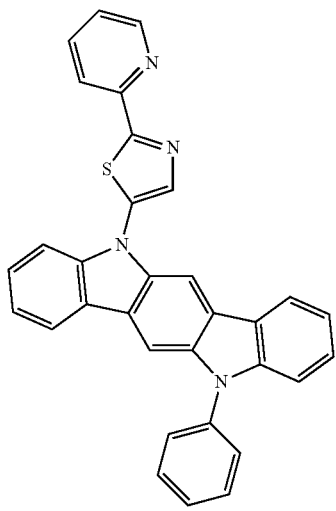
126
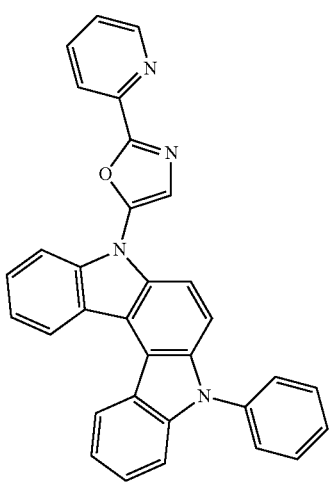
127
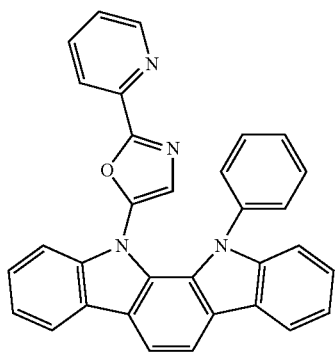
202
-continued
128
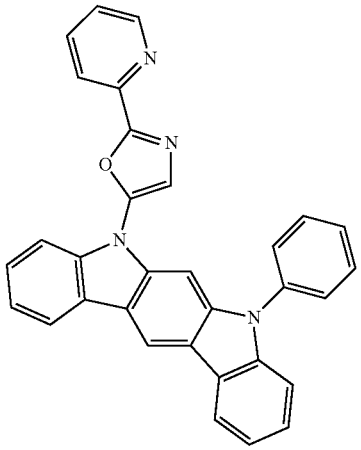
129
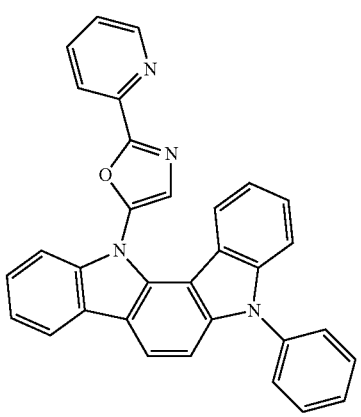
130

203
-continued
131
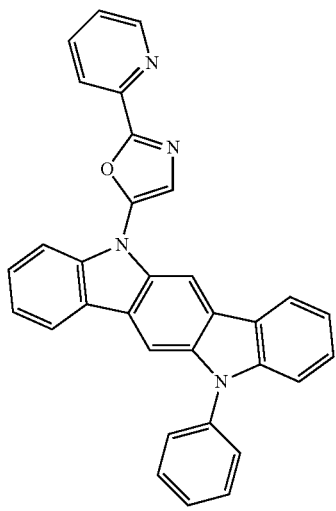
132
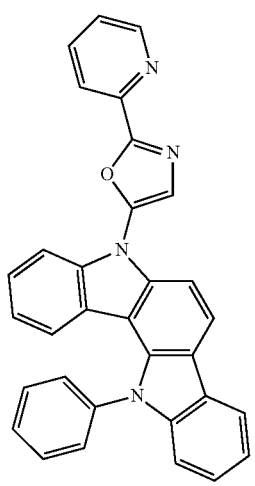
133
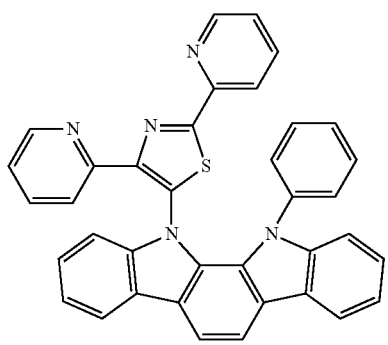
204
-continued
134
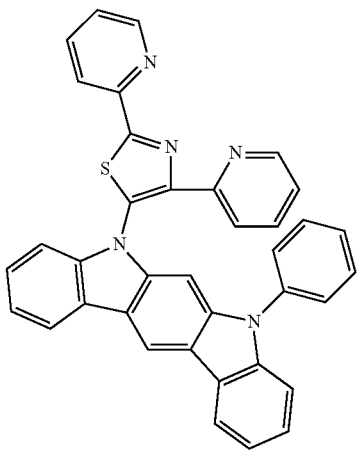
135
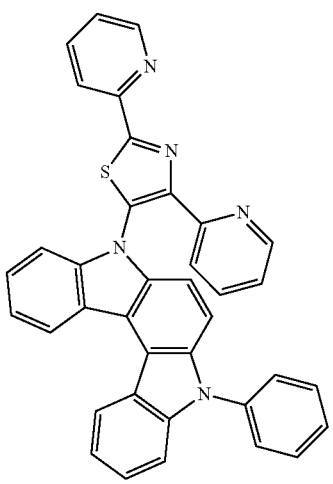
136
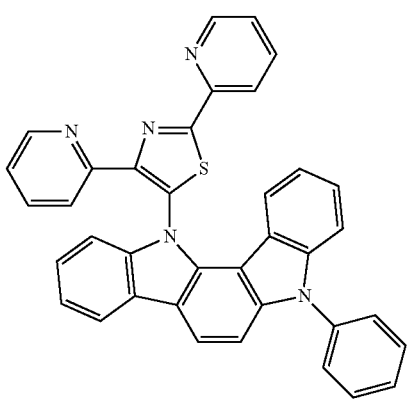

205
-continued
137
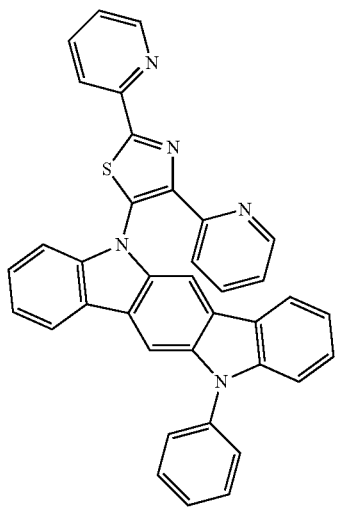
138
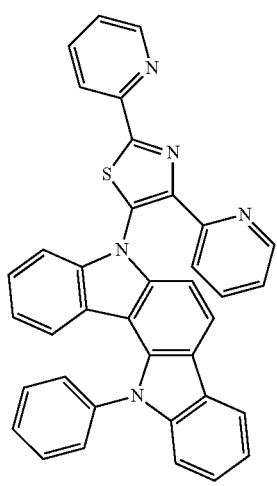
139
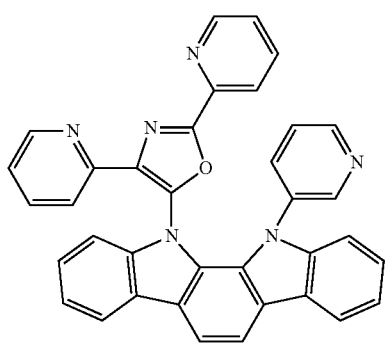
206
-continued
140
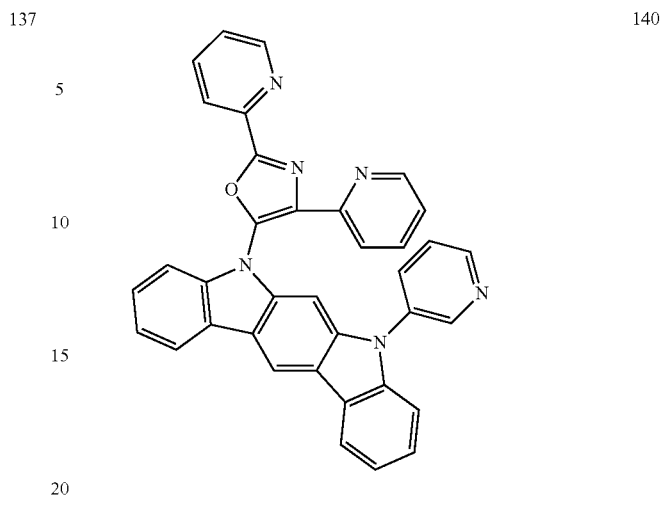
141
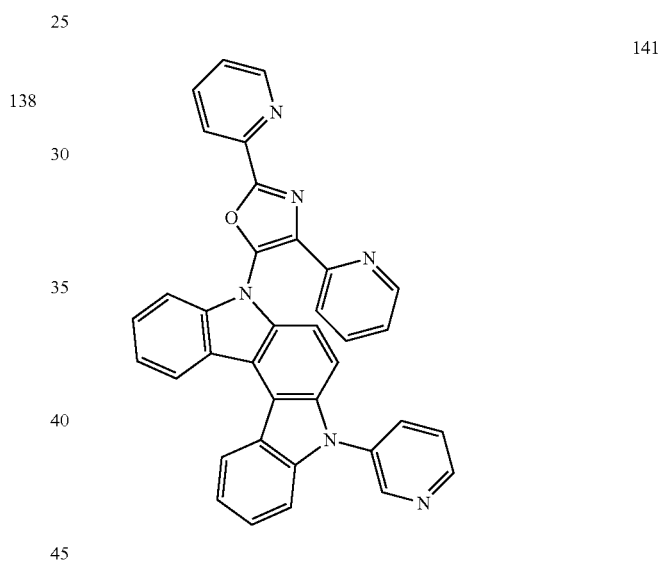
142
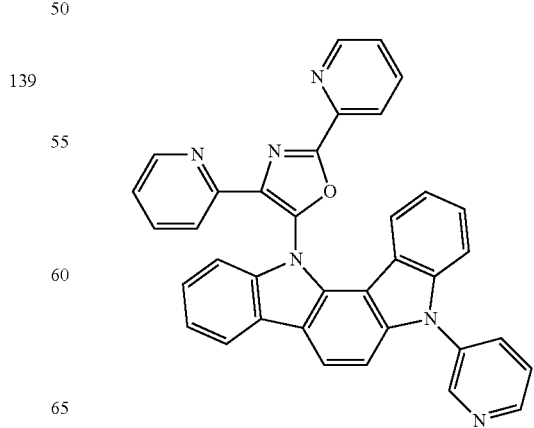

207
-continued
143
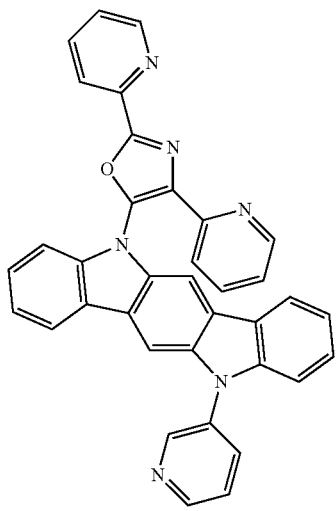
144
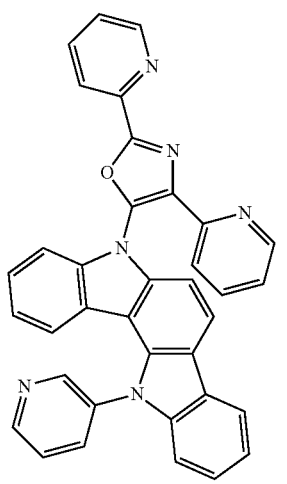
145
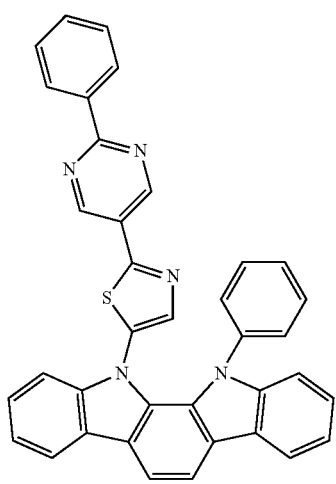
208
-continued
146
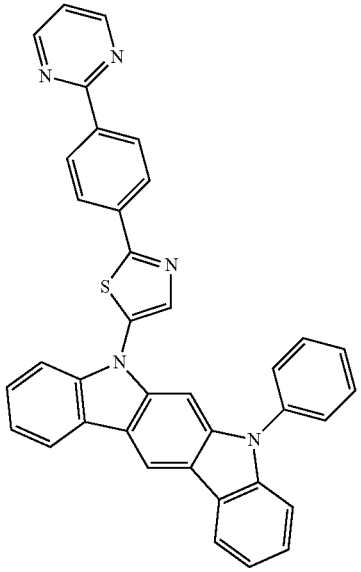
147
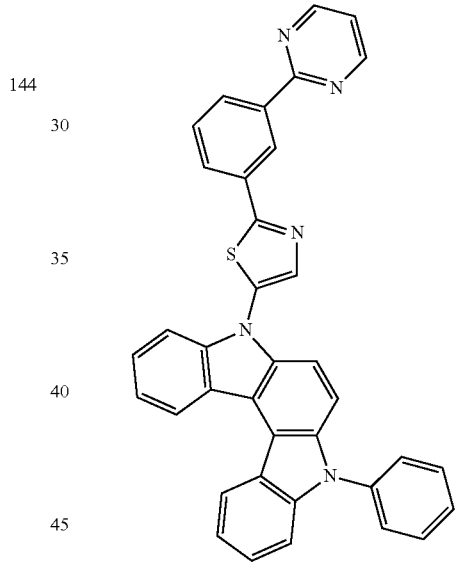
148
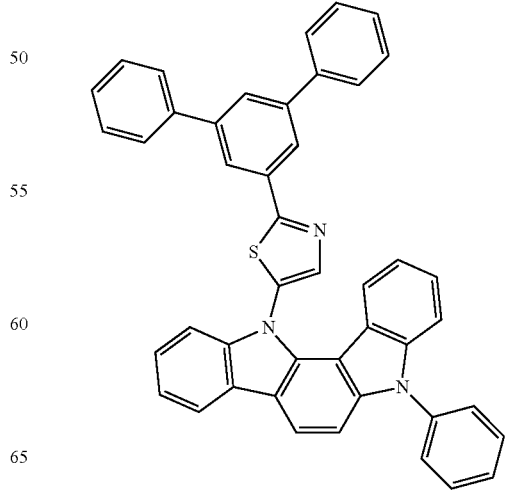

149
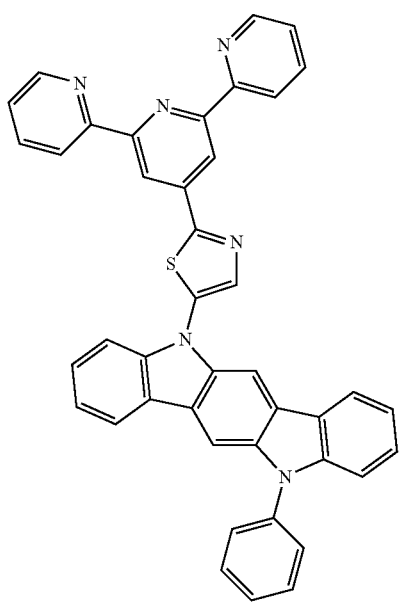
150
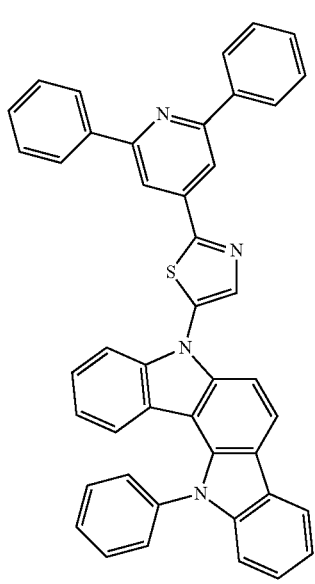
151
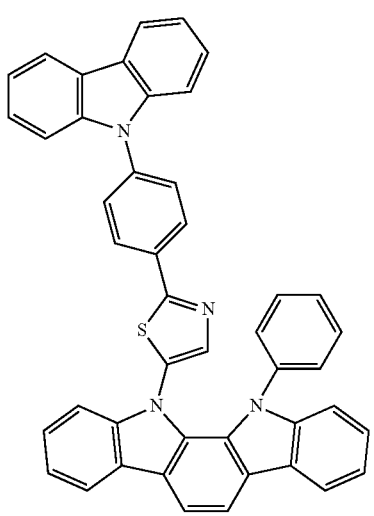
152
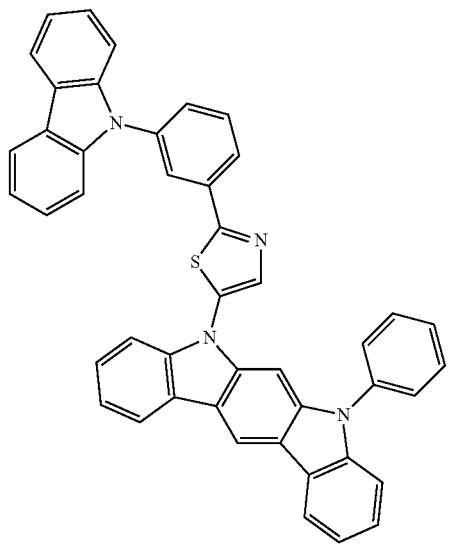
153
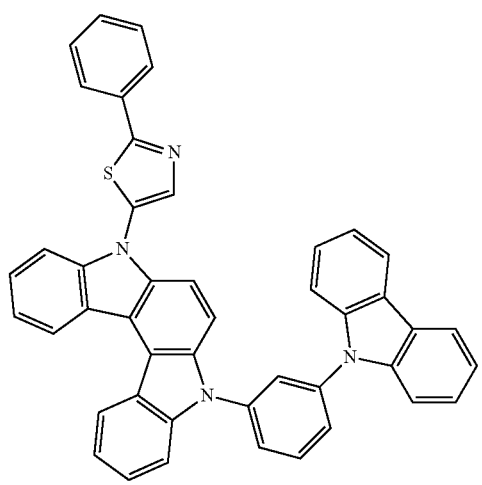
154
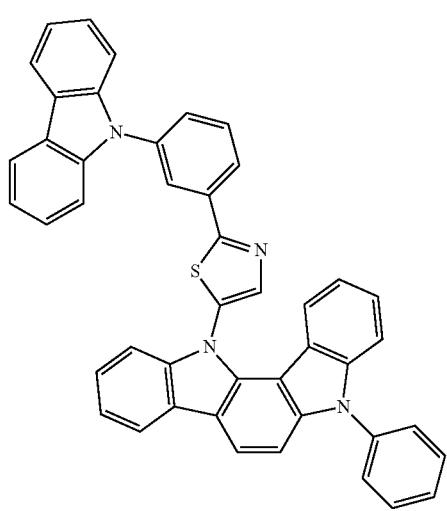

211
-continued
155
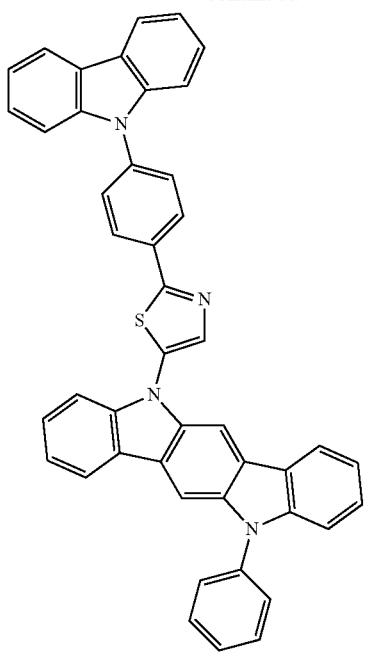
156
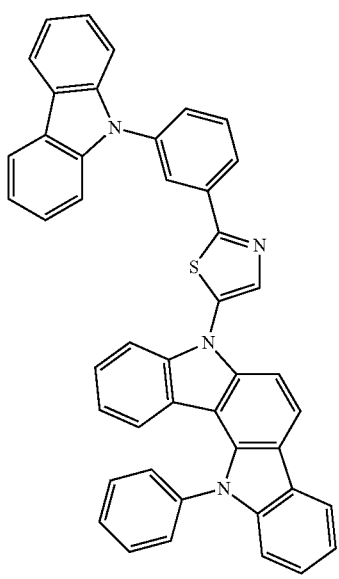
157
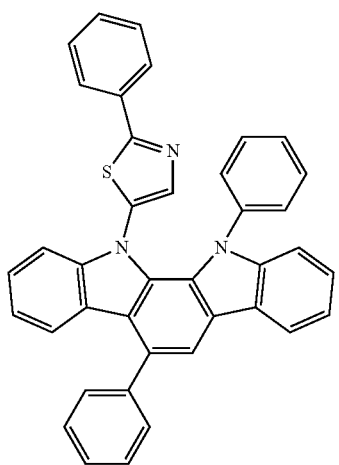
212
-continued
158
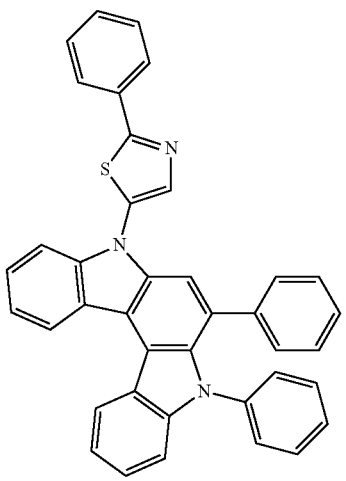
159
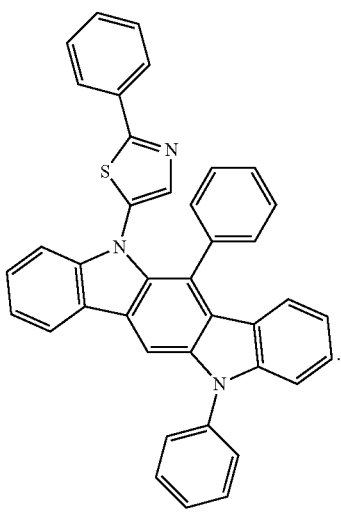
14. The condensed cyclic compound of claim 1, wherein the condensed cyclic compound is any one of Compounds 1, 7, 29, 59, 70, 88, 101, 112, 133, 149, 152, 155, and 159:
1
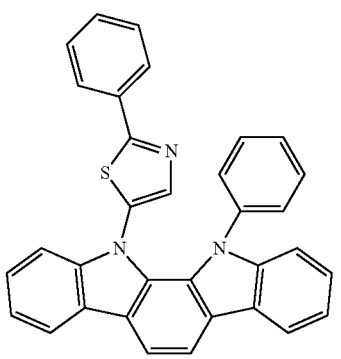

213
-continued
7
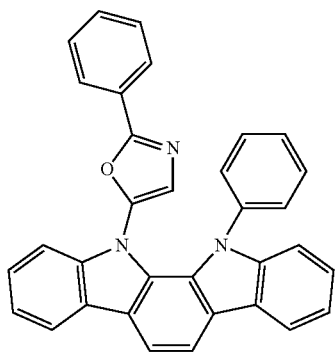
29
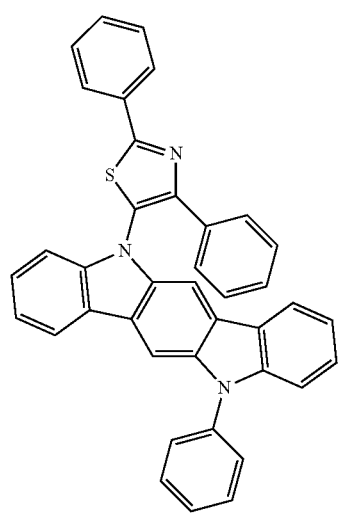
59
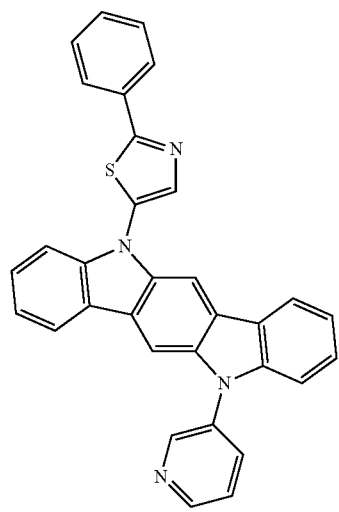
214
-continued
5
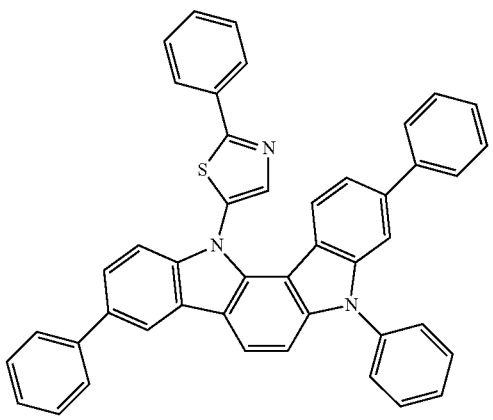
88
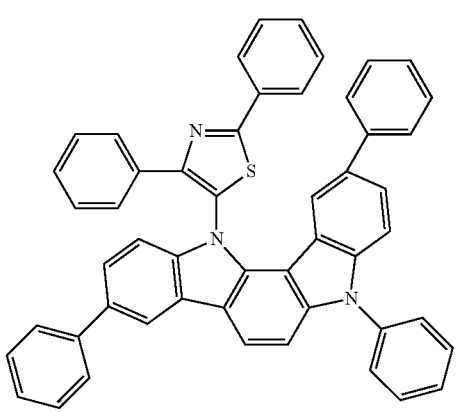
101
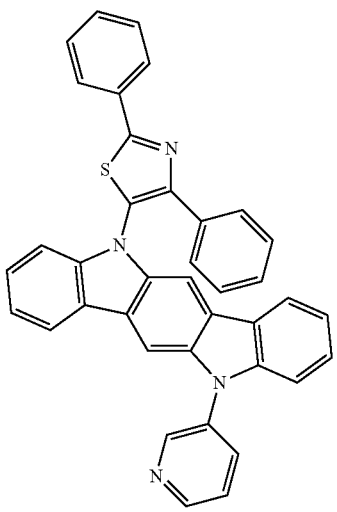

112
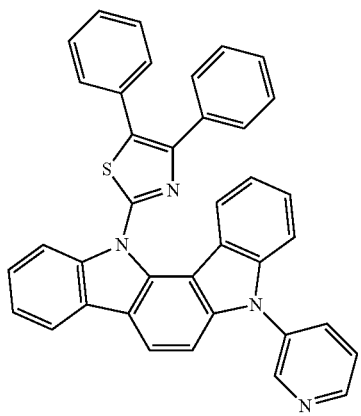
133
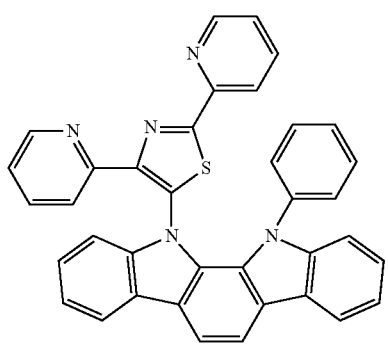
149
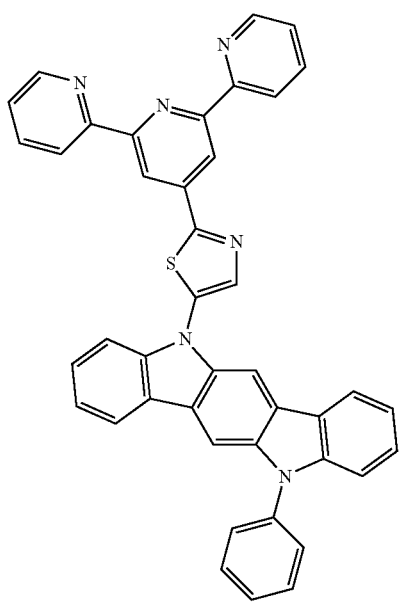
152
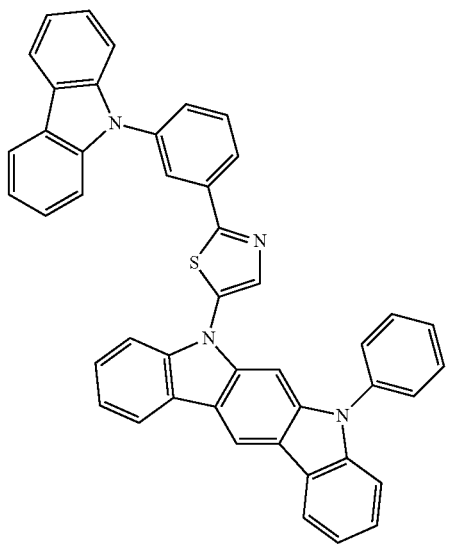
155
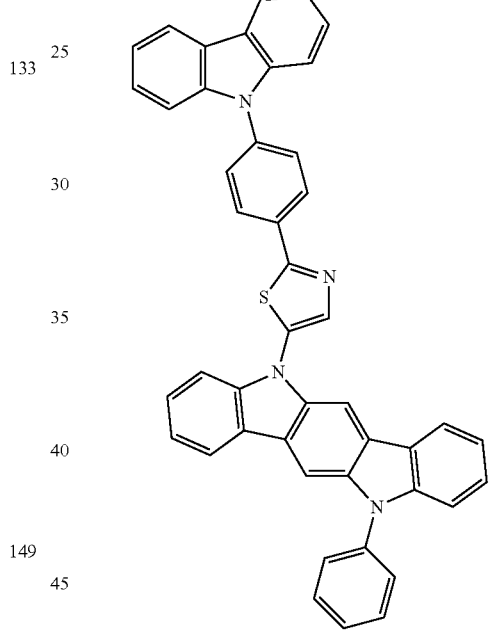
159
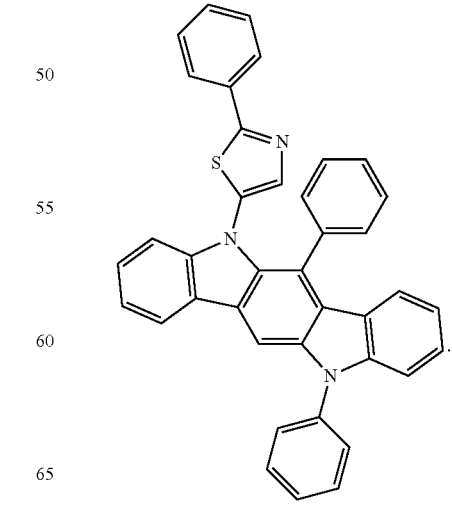

15. An organic light-emitting device comprising:
a first electrode;
a second electrode facing the first electrode; and
an organic layer between the first and second electrodes and comprising an emission layer,
wherein the organic layer comprises the condensed cyclic compound of claim 1.

16. The organic light-emitting device of claim 15, wherein the organic layer comprises:
a hole transport region between the first electrode and the emission layer; and
an electron transport region between the emission layer and the second electrode.

17. The organic light-emitting device of claim 16, wherein the electron transport region comprises at least one selected from a hole blocking layer, an electron transport layer, and an electron injection layer.

18. The organic light-emitting device of claim 16, wherein the hole transport region comprises at least one selected from an electron blocking layer, a hole transport layer, and a hole injection layer.

19. The organic light-emitting device of claim 16, wherein the emission layer comprises the condensed cyclic compound.

20. The organic light-emitting device of claim 16, wherein the electron transport region comprises the condensed cyclic compound.

* * * * *